(12) United States Patent
Firooznia et al.

(10) Patent No.: US 8,124,629 B2
(45) Date of Patent: Feb. 28, 2012

(54) NAPHTHYLACETIC ACIDS

(75) Inventors: Fariborz Firooznia, Florham Park, NJ (US); Paul Gillespie, Westfield, NJ (US); Tai-An Lin, Pequannock, NJ (US); Eric Mertz, Fair Lawn, NJ (US); Achyutharao Sidduri, Livingston, NJ (US); Sung-Sau So, Verona, NJ (US); Jenny Tan, New Providence, NJ (US); Kshitij Chhabilbhai Thakkar, Clifton, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/614,478

(22) Filed: Nov. 9, 2009

(65) Prior Publication Data

US 2010/0137250 A1    Jun. 3, 2010

Related U.S. Application Data

(60) Provisional application No. 61/115,147, filed on Nov. 17, 2008, provisional application No. 61/222,235, filed on Jul. 1, 2009.

(51) Int. Cl.
*A61K 31/44* (2006.01)
*A61K 31/192* (2006.01)
*C07D 211/54* (2006.01)
*C07C 63/64* (2006.01)

(52) U.S. Cl. ........ 514/344; 546/286; 546/290; 562/405; 514/345; 514/569

(58) Field of Classification Search ............. 546/286, 546/290; 562/405; 514/344, 345, 569
See application file for complete search history.

(56) References Cited

U.S. PATENT DOCUMENTS

| | | | |
|---|---|---|---|
| 3,899,529 | A | 8/1975 | Witzel |
| 4,371,537 | A | 2/1983 | Markley et al. |
| 4,443,462 | A | 4/1984 | Carr et al. |
| 4,868,331 | A | 9/1989 | Niewöhner et al. |
| 4,921,998 | A | 5/1990 | Niewöhner et al. |
| 5,424,481 | A | 6/1995 | Hagen et al. |
| 7,226,951 | B2 | 6/2007 | Vasudevan et al. |
| 2005/0014749 | A1 | 1/2005 | Chen et al. |
| 2006/0154965 | A1 | 7/2006 | Harris et al. |
| 2007/0161698 | A1 | 7/2007 | Chien et al. |
| 2010/0016368 | A1 | 1/2010 | Chen et al. |
| 2010/0016369 | A1 | 1/2010 | Chen et al. |
| 2010/0041713 | A1 | 2/2010 | Firooznia et al. |
| 2010/0041714 | A1 | 2/2010 | Blanc et al. |
| 2010/0041760 | A1 | 2/2010 | Blanc et al. |
| 2010/0125058 | A1 | 5/2010 | Chen et al. |
| 2010/0125061 | A1 | 5/2010 | Firooznia et al. |

FOREIGN PATENT DOCUMENTS

| | | |
|---|---|---|
| DE | 4411856 | 1/1994 |
| EP | 0242518 | 10/1987 |
| EP | 0253257 | 1/1988 |
| EP | 0405602 | 1/1991 |
| EP | 0657422 | 6/1995 |
| EP | 1505061 | 2/2005 |
| EP | 1939175 | 7/2008 |
| WO | 92/01675 | 2/1992 |
| WO | 00/16798 | 3/2000 |
| WO | 03/028755 | 4/2003 |
| WO | 2005/040114 | 5/2005 |
| WO | 2005/054232 | 6/2005 |
| WO | 2006/034418 | 3/2006 |
| WO | 2006/036664 | 4/2006 |
| WO | 2006/091674 | 8/2006 |
| WO | 2007/028132 | 3/2007 |
| WO | 2007/146136 | 12/2007 |

OTHER PUBLICATIONS

Feixas Jet Al, "Naphthalene Derivatives; a New Series of Selective Cycloxygenase-2 Inhibitors" Bioorganic & Medicinal Chemistry Letters, 11:20 (2001) 2687-2690.*
Nagata et al., FEBS Lett 459: 195-199, 1999.
Hirai et al., J Exp Med 193: 255-261, 2001.
Gervais et al., J Allergy Clin Immunol 108: 982-988 (2001).
Xue et al., J Immunol 175: 6531-6536.
Yoshimura-Uchiyama et al., Clin Exp Allergy 34:1283-1290.
Huang et al., Hum Mol Genet 13, 2691-2697, 2004.
Cosmi et al., Eur J. Immunol 30, 2972-2979, 2000.
Lee et al., Tetrahedron Lett., 32 (1991) 5255.

(Continued)

*Primary Examiner* — Kamal Saeed
*Assistant Examiner* — Janet L Coppins
(74) *Attorney, Agent, or Firm* — George W. Johnston; Dennis P. Tramaloni; Brian C. Remy

(57) ABSTRACT

The invention is concerned with the compounds of formula I:

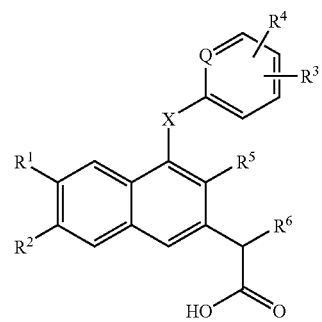

and pharmaceutically acceptable salts and esters thereof, wherein X, Q, and $R^1$-$R^6$ are defined in the detailed description and claims. In addition, the present invention relates to methods of manufacturing and using the compounds of formula I as well as pharmaceutical compositions containing such compounds. The compounds of formula I are antagonists or partial agonists at the CRTH2 receptor and may be useful in treating diseases and disorders associated with that receptor such as asthma.

32 Claims, No Drawings

OTHER PUBLICATIONS

Boger, D. L. et al., J. Org. Chem. 61 (1996) 4894-4912.
Kim, M. et al., J. Org. Chem. 69 (2004) 6945-6948.
Chan W. K., et al., J. Med. Chem. 39 (1996) 3756-3768.
Kozhinov, D. V., et al., J. Org. Chem. 69 (2004) 1378-1379.
Liu, J., et al., Org. Lett. 4 (2002) 3521-3524.
Bloomer, J. L. et al., J. Org. Chem. 58 (1993) 7906-7912.
Fuganti, C. et al., J. Chem. Res (S) 1998, 638-639.
Uno, H., et al., J. Chem. Soc., Perkin Trans. 1, 2001, 229.
Wallace, D. J. et al., Tetrahedron Lett. 43 (2002) 6987-6990.
Zupan M. et al., Bull. Chem. Soc. Jpn., 68 (1995) 1655-1660.
Wu G., et al., Synthesis 11 (2003) 1657-1660.
Thibault, M. E. et al., J. Org. Chem. 68 (2003), 8373-8378.
Schön, U. et al., Tetrahedron Lett. 46 (2005) 7111-7115.
Moseley, J. D. et al., Tetrahedron 62 (2006) 4685-4689.
Baldwin, K. P. et al., Synlett 11 (1993) 853.
Hayashi, N., et al., Org. Lett. 6 (2004) 4981-4983.
Hayashi, N. et al., Org. Lett. 7 (2005) 3093-3096.
Staas, D. D. et al., Bioorg. Med. Chem. 14 (2006) 6900.
Testaferri, L. et al., Tetrahedron 41 (1985) 1373-1384.
Li J. et al., Bioorg. Med. Chem. 13 (2005) 1805-1809.
Bargar, T. M. et al., J. Heterocyclic Chem. 22 (1985) 1583-1592.
Blizzard T. A. et al., Bioorg. Med. Chem. Lett. 14 (2004) 3861-3864.
Arnold et al., Org. Lett, 6 (2004) 3005-3007.
Ulven et al., "Targeting the prostaglandin D2 receptors DP and CRTH2 for treatment of inflammation" Current Topics in Medicinal Chemistry 6:13 (2006) 1427-1444 XP008104082.
Database Registry (online) RN 1026178-75-5 (2008) XP002547292.
Pettipher et al., "Antagonism of the prostaglandin D2 receptors DP1 and CRTH2 as an approach to treat allergic diseases." Nature Reviews Drug Discovery, vol. 6 (Apr. 2007) pp. 313-325, Nature Publishing Group.
Kostenis et al., "Emerging roles of DP and CRTH2 in allergic inflammation" Science Direct, Trends in Molecule Medicine vol. 12 No. 4, Apr. 2006, pp. 148-158, Elsevier.
Feixas J et al, "Naphthalene Derivatives; a New Series of Selective Cycloxygenase-2 Inhibitors" Bioorganic & Medicinal Chemistry Letters, 11:20 (2001) 2687-2690 XP0029995309.
Letter re: Thailand Office Action for Thai Patent Appl. No. 0901005108 (Jul. 11, 2011).
Xue, L. et al., Journal of Immunology 175:6531-6536 (2005).
Yoshimura-Uchiyama et al., Clin. Exp. Allergy 35:1283-1290 (2004).

* cited by examiner

US 8,124,629 B2

NAPHTHYLACETIC ACIDS

PRIORITY TO RELATED APPLICATIONS

This application claims the benefit of U.S. Provisional Application No. 61/115,147, filed Nov. 17, 2008 and U.S. Provisional Application No. 61/222,235, filed Jul. 1, 2009. The entire contents of the above-identified applications are hereby incorporated by reference.

BACKGROUND OF THE INVENTION

The present invention relates to novel substituted naphthalen-2-yl acetic acids, their manufacture, pharmaceutical compositions containing them and their use as CRTH2 antagonists or partial agonists. Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet.* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists or partial agonists of CRTH2 are useful for treating disorders such as asthma, allergic inflammation, allergic rhinitis, COPD, and atopic dermatitis.

SUMMARY OF THE INVENTION

The invention is concerned with the compounds of formula I:

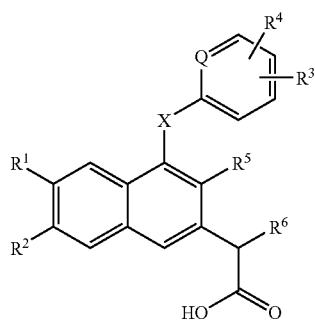

and pharmaceutically acceptable salts and esters thereof, wherein X, Q, and $R^1$-$R^6$ are defined in the detailed description and claims. In addition, the present invention relates to methods of manufacturing and using the compounds of formula I as well as pharmaceutical compositions containing such compounds. The compounds of formula I are antagonists or partial agonists at the CRTH2 receptor and may be useful in treating diseases and disorders associated with that receptor such as asthma.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^6$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen moieties (e.g., trifluoromethyl, difluoromethyl, fluoromethyl, chloromethyl, etc.). Similarly, the term "lower heterocycloalkyl substituted by lower alkyl or lower alkoxycarbonyl" refers to the fact that one or more hydrogen atoms of a lower heterocycloalkyl (as defined below) is replaced by one or more lower alkyls (e.g., 4-methyl-piperazin-1-yl, etc.) or replaced by one or more lower alkoxycarbonyls (e.g., 4-tert-butoxycarbonyl-piperazin-1-yl, 4-methoxycarbonyl-piperazin-1-yl, or 4-ethoxycarbonyl-piperazin-1-yl, etc.).

The term "optionally substituted" refers to the fact that one or more hydrogen atoms of a moiety (with one or more hydrogen atoms) can be, but does not necessarily have to be, substituted with another substituent.

The term "halogen" refers to a moiety of fluoro, chloro, bromo or iodo.

Unless otherwise indicated, the term "hydrogen" or "hydro" refers to the moiety of a hydrogen atom (—H) and not $H_2$.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "lower cycloalkyl" refers to a saturated or partly unsaturated non-aromatic hydrocarbon ring moiety having 3 to 7 carbon atoms bonded together to form a ring structure. Examples of cycloalkyls include cyclopropyl, cyclobutyl, cyclopentyl, cyclohexyl and cycloheptyl.

The term "lower alkoxy" refers to the moiety —O—R, wherein R is lower alkyl as defined previously. Examples of lower alkoxy moieties include methoxy, ethoxy, n-propoxy, isopropoxy, n-butoxy, isobutoxy, sec-butoxy and tert-butoxy.

The term "lower alkoxycarbonyl" refers to the moiety —C(O)—O—R, wherein R is lower alkyl as defined previously. Examples of lower alkoxycarbonyl moieties include methoxycarbonyl, ethoxycarbonyl, and tert-butoxycarbonyl.

The term "lower alkanesulfonylmethyl" refers to the moiety —CH$_2$—S(O)$_2$—R wherein R is lower alkyl as defined previously. An example of a lower alkanesulfonylmethyl is methanesulfonylmethyl.

The term "lower alkylamino" refers to the moiety —N(R)(H), wherein R is lower alkyl as defined previously. An example of a lower alkylamino is methylamino. The term "lower dialkylamino" refers to the moiety —N(R)(R'), wherein R and R' are lower alkyl as defined previously. An example of a lower dialkylamino is dimethylamino.

The term "N-acetyl-N-lower alkylamino" refers to the moiety —N(R)(C(O)(CH$_3$)), wherein R is lower alkyl as defined previously. An example of a N-acetyl-N-lower alkylamino is N-acetyl-N-methylamino.

The term "heteroatom" refers to nitrogen, oxygen, or sulfur.

The term "lower heterocycloalkyl" refers to a saturated or partly unsaturated non-aromatic ring moiety having 3 to 7 ring atoms bonded together to form a ring structure wherein one, two or three of the ring atoms is a heteroatom while the remaining ring atoms are carbon atoms. Examples of lower heterocycloalkyls include morpholin-4-yl, piperidin-1-yl, and piperazin-1-yl.

The term "heteroaryl" refers to an unsaturated aromatic ring moiety having 5 to 6 ring atoms bonded together to form a ring structure wherein one, two, three, or four of the ring atoms is a heteroatom while the remaining ring atoms are carbon atoms. Examples of heteroaryls include pyrazol-1-yl and tetrazol-5-yl.

Unless otherwise indicated, the term "a compound of the formula" or "a compound of formula" or "compounds of the formula" or "compounds of formula" means any compound selected from the genus of compounds as defined by the formula (Including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. The salts of the present invention may be formed by the addition of inorganic or organic bases to the acid compounds of the present invention. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention relates to the compounds of formula I:

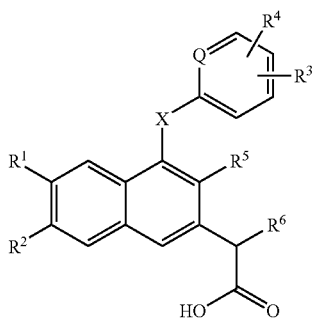

I and pharmaceutically acceptable salts and esters thereof, wherein:
Q is C(H) or N;
X is selected from the group consisting of:
    (1) C(O),
    (2) C(H)(H),
    (3) C(H)(OH),
    (4) C(F)(F),
    (5) C(H)(O—CH$_3$), and
    (6) C(H)(CH$_3$);
$R^1$ and $R^2$, independently of each other, are selected from the group consisting of:
    (1) hydrogen,
    (2) halogen,
    (3) lower alkyl optionally substituted by halogen, and
    (4) lower alkoxy,
or alternatively, $R^1$ and $R^2$ are bonded together to form methylenedioxy;
$R^3$ is selected from the group consisting of:
    (1) hydrogen,
    (2) halogen,
    (3) lower alkyl optionally substituted by halogen,
    (4) lower alkoxy, and
    (5) cyano;
$R^4$ is selected from the group consisting of:
    (1) halogen,
    (2) lower alkyl optionally substituted by halogen,
    (3) lower cycloalkyl,
    (4) lower alkoxy optionally substituted by halogen,
    (5) lower alkoxycarbonyl,
    (6) benzyloxy or benzylsulfanyl,
    (7) heteroaryl optionally substituted by lower alkyl,
    (8) cyano,
    (9) phenyl optionally substituted by methanesulfonyl,
    (10) lower alkanesulfonylmethyl, and
    (11) S(O)$_2$—R$^7$ wherein R$^7$ is selected from the group consisting of:
        (a) lower alkyl optionally substituted by halogen or phenyl,
        (b) amino,
        (c) lower alkylamino,
        (d) lower dialkylamino,
        (e) acetylamino,
        (f) N-acetyl-N-lower alkylamino,
        (g) lower heterocycloalkyl optionally substituted by a substituent selected from the group consisting of:
            (i) lower alkyl,
            (ii) phenyl optionally substituted by halogen, and
            (iii) lower alkoxycarbonyl; and
        (h) phenyl or benzyl, wherein said phenyl or benzyl is optionally substituted by halogen or trifluoromethyl; and
$R^5$ and $R^6$, independently of each other, are hydrogen or methyl.

Unless indicated otherwise, the $R^3$ and $R^4$ moieties (independently of each other) are bonded to one of the ring carbon atoms of the phenyl ring containing Q (as shown in formula I) in place of a hydrogen atom that would otherwise be bonded to that carbon atom absent being substituted by $R^3$ or $R^4$ (with the understanding, therefore, that $R^3$ and $R^4$ are not simultaneously bonded to the same carbon atom and likewise neither $R^3$ nor $R^4$ is bonded to Q when Q is N). Accordingly, unless indicated otherwise, in reference to formula I or a subgenus of formula I, the term "Q is C(H)" indicates that the carbon atom of Q when Q is C(H) may be bonded to a hydrogen atom or substituted with $R^3$ or $R^4$ in place of that hydrogen atom.

Unless indicated otherwise, the term "$R^1$ and $R^2$ are bonded together to form methylenedioxy" refers to the formation of the following structure in formula I by $R^1$ and $R^2$ as depicted below:

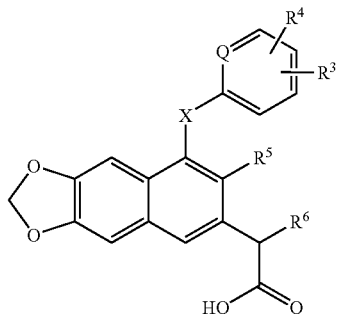

wherein X, Q, and $R^3$-$R^6$ are defined as in formula I.

Unless indicated otherwise, the genus of formula I and any subgenera thereof encompass all possible stereoisomers (i.e., (R)-enantiomers, (S)-enantiomers, diastereomers) as well as racemic and scalemic mixtures thereof.

In one embodiment the present invention is directed to the compounds of formula I or pharmaceutically acceptable salts or esters thereof wherein X is C(O), Q is C(H), and $R^4$ is $S(O)_2$—$R^7$ as depicted below in formula IA:

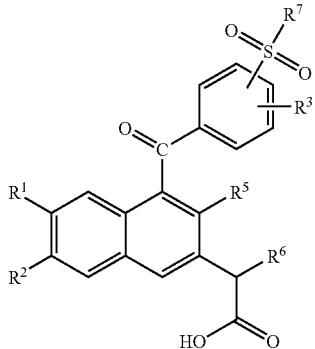

IA wherein $R^1$-$R^3$ and $R^5$-$R^7$ are defined as in formula I.

In another embodiment the present invention is directed to the compounds of formula I or pharmaceutically acceptable salts or esters thereof wherein X is C(H)(H), Q is C(H), and $R^4$ is $S(O)_2$—$R^7$ as depicted below in formula IB:

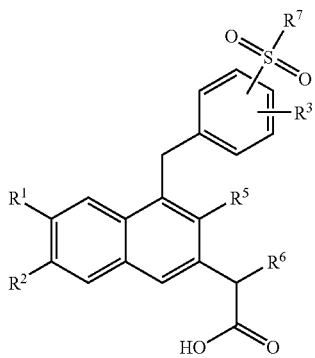

IB wherein $R^1$-$R^3$ and $R^5$-$R^7$ are defined as in formula I.

In another embodiment the present invention is directed to the compounds of formula I or pharmaceutically acceptable salts or esters thereof wherein X is C(H)(OH), Q is C(H), and $R^4$ is $S(O)_2$—$R^7$ as depicted below in formula IC:

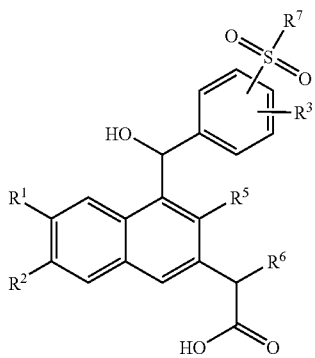

IC wherein $R^1$-$R^3$ and $R^5$-$R^7$ are defined as in formula I.

In another embodiment the present invention is directed to the compounds of formula I or pharmaceutically acceptable salts or esters thereof wherein X is C(F)(F), Q is C(H), and $R^4$ is $S(O)_2$—$R^7$ as depicted below in formula ID:

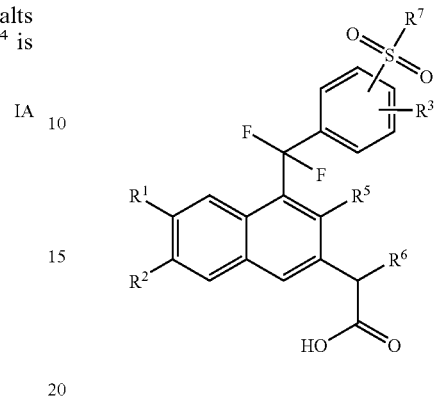

ID wherein $R^1$-$R^3$ and $R^5$-$R^7$ are defined as in formula I.

In another embodiment the present invention is directed to the compounds of formula I or pharmaceutically acceptable salts or esters thereof wherein X is C(H)(O—$CH_3$), Q is C(H), and $R^4$ is $S(O)_2$—$R^7$ as depicted below in formula IE:

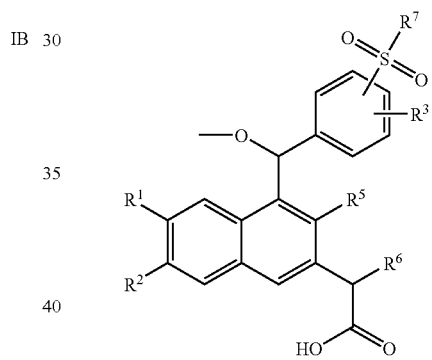

IE wherein $R^1$-$R^3$ and $R^5$-$R^7$ are defined as in formula I.

In another embodiment the present invention is directed to the compounds of formula I or pharmaceutically acceptable salts or esters thereof wherein X is C(H)(H) and $R^6$ is hydrogen as depicted below in formula IF:

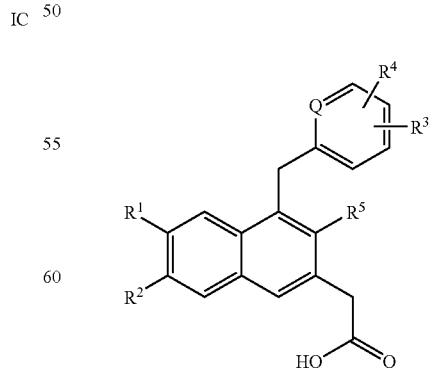

IF wherein Q, $R^1$, $R^2$, $R^3$, $R^4$ and $R^5$ are defined as in formula I.

In one embodiment the present invention is directed to the compounds of formula I or pharmaceutically acceptable salts or esters thereof wherein $R^1$ is selected from the group consisting of:
(1) hydrogen;
(2) fluoro;
(3) methyl;
(4) chloro;
(5) trifluoromethyl; and
(6) methoxy.

In a particular embodiment the present invention is directed to the compounds of formula I or pharmaceutically acceptable salts or esters thereof wherein $R^1$ is hydrogen.

In another particular embodiment the present invention is directed to the compounds of formula I or pharmaceutically acceptable salts or esters thereof wherein $R^1$ is fluoro.

In another particular embodiment the present invention is directed to the compounds of formula I or pharmaceutically acceptable salts or esters thereof wherein $R^1$ is methyl.

In another particular embodiment the present invention is directed to the compounds of formula I or pharmaceutically acceptable salts or esters thereof wherein $R^1$ is chloro.

In another particular embodiment the present invention is directed to the compounds of formula I or pharmaceutically acceptable salts or esters thereof wherein $R^1$ is trifluoromethyl.

In another particular embodiment the present invention is directed to the compounds of formula I or pharmaceutically acceptable salts or esters thereof wherein $R^1$ is methoxy.

In one embodiment the present invention is directed to the compounds of formula I or pharmaceutically acceptable salts or esters thereof wherein $R^2$ is selected from the group consisting of:
(1) hydrogen;
(2) fluoro;
(3) methyl;
(4) trifluoromethyl; and
(5) methoxy.

In a particular embodiment the present invention is directed to the compounds of formula I or pharmaceutically acceptable salts or esters thereof wherein $R^2$ is hydrogen.

In another particular embodiment the present invention is directed to the compounds of formula I or pharmaceutically acceptable salts or esters thereof wherein $R^2$ is fluoro.

In another particular embodiment the present invention is directed to the compounds of formula I or pharmaceutically acceptable salts or esters thereof wherein $R^2$ is methyl.

In another particular embodiment the present invention is directed to the compounds of formula I or pharmaceutically acceptable salts or esters thereof wherein $R^2$ is trifluoromethyl.

In another particular embodiment the present invention is directed to the compounds of formula I or pharmaceutically acceptable salts or esters thereof wherein $R^2$ is methoxy.

In another embodiment the present invention is directed to the compounds of formula I or pharmaceutically acceptable salts or esters thereof wherein $R^1$ and $R^2$ are bonded together to form methylenedioxy.

In another embodiment, the present invention is directed to the compounds of formula I or pharmaceutically acceptable salts or esters thereof wherein $R^1$ and $R^2$ are as defined previously for formula I, except that $R^1$ and $R^2$ are not both hydrogen.

In another embodiment, the present invention is directed to the compounds of formula I or pharmaceutically acceptable salts or esters thereof wherein $R^1$, $R^2$, and $R^5$ are as defined previously for formula I, except that one of $R^1$, $R^2$, or $R^5$ is not hydrogen.

In one particular embodiment the present invention is directed to the compounds of formula I or pharmaceutically acceptable salts or esters thereof wherein $R^3$ is selected from the group consisting of:
(1) hydrogen,
(2) fluoro,
(3) chloro,
(4) lower alkyl,
(5) trifluoromethyl,
(6) lower alkoxy, and
(7) cyano.

In a particular embodiment the present invention is directed to the compounds of formula I or pharmaceutically acceptable salts or esters thereof wherein $R^3$ is hydrogen.

In another particular embodiment the present invention is directed to the compounds of formula I or pharmaceutically acceptable salts or esters thereof wherein $R^3$ is fluoro.

In another particular embodiment the present invention is directed to the compounds of formula I or pharmaceutically acceptable salts or esters thereof wherein $R^3$ is chloro.

In another particular embodiment the present invention is directed to the compounds of formula I or pharmaceutically acceptable salts or esters thereof wherein $R^3$ is methyl.

In another particular embodiment the present invention is directed to the compounds of formula I or pharmaceutically acceptable salts or esters thereof wherein $R^3$ is ethyl.

In another particular embodiment the present invention is directed to the compounds of formula I or pharmaceutically acceptable salts or esters thereof wherein $R^3$ is trifluoromethyl.

In another particular embodiment the present invention is directed to the compounds of formula I or pharmaceutically acceptable salts or esters thereof wherein $R^3$ is methoxy.

In another particular embodiment the present invention is directed to the compounds of formula I or pharmaceutically acceptable salts or esters thereof wherein $R^3$ is cyano.

In one particular embodiment the present invention is directed to the compounds of formula I or pharmaceutically acceptable salts or esters thereof wherein $R^4$ is halogen.

In another particular embodiment the present invention is directed to the compounds of formula I or pharmaceutically acceptable salts or esters thereof wherein $R^4$ is cyano.

In another particular embodiment the present invention is directed to the compounds of formula I or pharmaceutically acceptable salts or esters thereof wherein $R^4$ is heteroaryl optionally substituted by lower alkyl.

In another particular embodiment the present invention is directed to the compounds of formula I or pharmaceutically acceptable salts or esters thereof wherein $R^4$ is benzyloxy or benzylsulfanyl.

In another particular embodiment the present invention is directed to the compounds of formula I or pharmaceutically acceptable salts or esters thereof wherein $R^4$ is methyl.

In another particular embodiment the present invention is directed to the compounds of formula I or pharmaceutically acceptable salts or esters thereof wherein $R^4$ is trifluoromethoxy.

In another particular embodiment the present invention is directed to the compounds of formula I or pharmaceutically acceptable salts or esters thereof wherein $R^4$ is methoxycarbonyl.

In another particular embodiment the present invention is directed to the compounds of formula I or pharmaceutically acceptable salts or esters thereof wherein $R^4$ is phenyl, wherein said phenyl is optionally substituted by methanesulfonyl.

In another particular embodiment the present invention is directed to the compounds of formula I or pharmaceutically acceptable salts or esters thereof wherein $R^4$ is lower alkanesulfonylmethyl.

In one particular embodiment the present invention is directed to the compounds of formula I or pharmaceutically acceptable salts or esters thereof wherein $R^4$ is $S(O)_2$—$R^7$ and $R^7$ is selected from the group consisting of:
(1) lower alkyl optionally substituted by halogen;
(2) amino;
(3) methylamino or ethylamino;
(4) dimethylamino or diethylamino;
(5) morpholin-4-yl;
(6) piperidin-1-yl;
(7) piperazin-1-yl;
(8) 4-methyl-piperazin-1-yl;
(9) 4-tert-butoxycarbonyl-piperazin-1-yl;
(10) 4-methoxycarbonyl-piperazin-1-yl or 4-ethoxycarbonyl-piperazin-1-yl;
(11) 4-(2-fluorophenyl)piperazin-1-yl;
(12) acetylamino or N-acetyl-N-methylamino;
(13) benzyl; and
(14) phenyl optionally substituted by halogen or trifluoromethyl.

In a particular embodiment the present invention is directed to the compounds of formula I or pharmaceutically acceptable salts or esters thereof wherein $R^4$ is $S(O)_2$—$R^7$ and $R^7$ is lower alkyl optionally substituted by halogen.

In another particular embodiment the present invention is directed to the compounds of formula I or pharmaceutically acceptable salts or esters thereof wherein $R^4$ is $S(O)_2$—$R^7$ and $R^7$ is methyl.

In another particular embodiment the present invention is directed to the compounds of formula I or pharmaceutically acceptable salts or esters thereof wherein $R^4$ is $S(O)_2$—$R^7$ and $R^7$ is trifluoromethyl.

In another particular embodiment the present invention is directed to the compounds of formula I or pharmaceutically acceptable salts or esters thereof wherein $R^4$ is $S(O)_2$—$R^7$ and $R^7$ is phenyl optionally substituted by halogen.

In another particular embodiment the present invention is directed to the compounds of formula I or pharmaceutically acceptable salts or esters thereof wherein $R^4$ is $S(O)_2$—$R^7$ and $R^7$ is benzyl.

In another particular embodiment the present invention is directed to the compounds of formula I or pharmaceutically acceptable salts or esters thereof wherein $R^4$ is $S(O)_2$—$R^7$ and $R^7$ is ethyl.

In another particular embodiment the present invention is directed to the compounds of formula I or pharmaceutically acceptable salts or esters thereof wherein $R^4$ is $S(O)_2$—$R^7$ and $R^7$ is amino.

In another particular embodiment the present invention is directed to the compounds of formula I or pharmaceutically acceptable salts or esters thereof wherein $R^4$ is $S(O)_2$—$R^7$ and $R^7$ is methylamino.

In another particular embodiment the present invention is directed to the compounds of formula I or pharmaceutically acceptable salts or esters thereof wherein $R^4$ is $S(O)_2$—$R^7$ and $R^7$ is ethylamino.

In another particular embodiment the present invention is directed to the compounds of formula I or pharmaceutically acceptable salts or esters thereof wherein $R^4$ is $S(O)_2$—$R^7$ and $R^7$ is dimethylamino.

In another particular embodiment the present invention is directed to the compounds of formula I or pharmaceutically acceptable salts or esters thereof wherein $R^4$ is $S(O)_2$—$R^7$ and $R^7$ is diethylamino.

In another particular embodiment the present invention is directed to the compounds of formula I or pharmaceutically acceptable salts or esters thereof wherein $R^4$ is $S(O)_2$—$R^7$ and $R^7$ is morpholin-4-yl.

In another particular embodiment the present invention is directed to the compounds of formula I or pharmaceutically acceptable salts or esters thereof wherein $R^4$ is $S(O)_2$—$R^7$ and $R^7$ is piperidin-1-yl.

In another particular embodiment the present invention is directed to the compounds of formula I or pharmaceutically acceptable salts or esters thereof wherein $R^4$ is $S(O)_2$—$R^7$ and $R^7$ is piperazin-1-yl.

In another particular embodiment the present invention is directed to the compounds of formula I or pharmaceutically acceptable salts or esters thereof wherein $R^4$ is $S(O)_2$—$R^7$ and $R^7$ is 4-methyl-piperazin-1-yl.

In another particular embodiment the present invention is directed to the compounds of formula I or pharmaceutically acceptable salts or esters thereof wherein $R^4$ is $S(O)_2$—$R^7$ and $R^7$ is 4-tert-butoxycarbonyl-piperazin-1-yl, 4-ethoxycarbonyl-piperazin-1-yl or 4-methoxycarbonyl-piperazin-1-yl.

In another particular embodiment the present invention is directed to the compounds of formula I or pharmaceutically acceptable salts or esters thereof wherein $R^4$ is $S(O)_2$—$R^7$ and $R^7$ is 4-(2-fluorophenyl)piperazin-1-yl.

In another particular embodiment the present invention is directed to the compounds of formula I or pharmaceutically acceptable salts or esters thereof wherein $R^4$ is $S(O)_2$—$R^7$ and $R^7$ is acetylamino or N-acetyl-N-methylamino.

In another particular embodiment the present invention is directed to the compounds of formula I or pharmaceutically acceptable salts or esters thereof wherein $R^4$ is $S(O)_2$—$R^7$ and $R^7$ is phenyl.

In another particular embodiment the present invention is directed to the compounds of formula I or pharmaceutically acceptable salts or esters thereof wherein $R^4$ is $S(O)_2$—$R^7$ and $R^7$ is phenyl substituted by chloro or fluoro.

In another particular embodiment the present invention is directed to the compounds of formula I or pharmaceutically acceptable salts or esters thereof wherein $R^4$ is $S(O)_2$—$R^7$ and $R^7$ is phenyl substituted by trifluoromethyl.

In one particular embodiment the present invention is directed to the compounds of formula I or pharmaceutically acceptable salts or esters thereof wherein $R^5$ is hydrogen.

In another particular embodiment the present invention is directed to the compounds of formula I or pharmaceutically acceptable salts or esters thereof wherein $R^5$ is methyl.

In one particular embodiment the present invention is directed to the compounds of formula I or pharmaceutically acceptable salts or esters thereof wherein $R^6$ is hydrogen.

In another particular embodiment the present invention is directed to the compounds of formula I or pharmaceutically acceptable salts or esters thereof wherein $R^6$ is methyl.

Positions of the $R^3$ and $R^4$ moieties on the phenyl ring in formula I are indicated by the following numbered positions (2, 3, 4, 5, and 6) as indicated below:

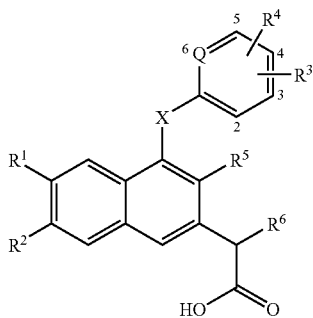

with the understanding herein that neither $R^3$ nor $R^4$ is bonded to Q when Q is N.

In one particular embodiment the present invention is directed to the compounds of formula I or pharmaceutically acceptable salts or esters thereof wherein the $R^3$ moiety is bonded to positions 2, 3, 5, or 6 and the $R^4$ moiety is bonded to position 4 on the phenyl ring in formula I.

In another more particular embodiment, $R^3$ is bonded to positions 2 or 6 and $R^4$ is bonded to position 4 on the phenyl ring in formula I.

In another specific embodiment, $R^3$ is bonded to positions 3 or 5 and $R^4$ is bonded to position 4 on the phenyl ring in formula I.

In more specific embodiments, the present invention is directed to a compound of formula I selected from the group consisting of:

[4-(4-Dimethylsulfamoyl-benzoyl)-naphthalen-2-yl]-acetic acid;
[6-Fluoro-4-(4-sulfamoyl-benzoyl)-naphthalen-2-yl]-acetic acid;
[4-(4-Sulfamoyl-benzoyl)-naphthalen-2-yl]-acetic acid;
[4-(2-Chloro-4-ethanesulfonyl-benzoyl)-6-fluoro-naphthalen-2-yl]-acetic acid;
{4-[4-(3-Chloro-benzenesulfonyl)-benzoyl]-6-fluoro-naphthalen-2-yl}-acetic acid;
[6-Fluoro-4-(4-methanesulfonyl-benzoyl)naphthalen-2-yl]-acetic acid;
[4-(4-Methanesulfonyl-benzoyl)-6-methoxy-naphthalen-2-yl]-acetic acid;
[4-(4-Methanesulfonyl-benzoyl)naphthalen-2-yl]-acetic acid;
[7-Fluoro-4-(4-methanesulfonyl-benzoyl)naphthalen-2-yl]-acetic acid;
[6-Fluoro-4-(4-methanesulfonyl-2-methyl-benzoyl)-naphthalen-2-yl]-acetic acid;
[6,7-Difluoro-4-(4-methanesulfonyl-benzoyl)-naphthalen-2-yl]-acetic acid;
[8-(4-Methanesulfonyl-benzoyl)-naphtho[2,3-d][1,3]dioxol-6-yl]-acetic acid;
[4-(2-Chloro-4-methanesulfonyl-benzoyl)-6-fluoro-naphthalen-2-yl]-acetic acid;
[4-(4-Methanesulfonyl-benzoyl)-7-methoxy-naphthalen-2-yl]-acetic acid;
[6-Fluoro-4-(3-methanesulfonyl-benzoyl)naphthalen-2-yl]-acetic acid;
[4-(3-Methanesulfonyl-benzoyl)naphthalen-2-yl]-acetic acid;
[8-(3-Methanesulfonyl-benzoyl)-naphtho[2,3-d][1,3]dioxol-6-yl]-acetic acid;
[4-(4-Ethanesulfonyl-benzoyl)-6-fluoro-naphthalen-2-yl]-acetic acid;
[4-(4-Dimethylsulfamoyl-benzoyl)-6-fluoro-naphthalen-2-yl]-acetic acid;
[6-Fluoro-4-(4-methylsulfamoyl-benzoyl)naphthalen-2-yl]-acetic acid;
{6-Fluoro-4-[4-(morpholine-4-sulfonyl)-benzoyl]-naphthalen-2-yl}-acetic acid;
[6-Fluoro-4-(2-fluoro-4-methanesulfonyl-benzoyl)-naphthalen-2-yl]-acetic acid;
[6-Fluoro-4-(4-methanesulfonyl-3-trifluoromethyl-benzoyl)-naphthalen-2-yl]-acetic acid;
[4-(3-Ethyl-4-methanesulfonyl-benzoyl)-6-fluoro-naphthalen-2-yl]-acetic acid;
[4-(4-Ethanesulfonyl-2-methyl-benzoyl)-6-fluoro-naphthalen-2-yl]-acetic acid;
{6-Fluoro-4-[4-(piperidine-1-sulfonyl)-benzoyl]-naphthalen-2-yl}-acetic acid;
[4-(4-Diethylsulfamoyl-benzoyl)-6-fluoro-naphthalen-2-yl]-acetic acid;
{6-Fluoro-4-[2-methyl-4-(morpholine-4-sulfonyl)-benzoyl]-naphthalen-2-yl}-acetic acid;
[4-(4-Dimethylsulfamoyl-2-methyl-benzoyl)-6-fluoro-naphthalen-2-yl]-acetic acid;
[6-Fluoro-4-(2-methyl-4-methylsulfonyl-benzoyl)-naphthalen-2-yl]-acetic acid;
(6-Fluoro-4-{4-[4-(2-fluoro-phenyl)-piperazine-1-sulfonyl]-benzoyl}-naphthalen-2-yl)-acetic acid;
[6-Chloro-4-(4-methanesulfonyl-benzoyl)naphthalen-2-yl]-acetic acid;
[4-(4-Methanesulfonyl-benzoyl)-6-methyl-naphthalen-2-yl]-acetic acid;
[4-(4-Methanesulfonyl-benzoyl)-6-trifluoromethyl-naphthalen-2-yl]-acetic acid;
[6-Chloro-4-(3-methanesulfonyl-benzoyl)naphthalen-2-yl]-acetic acid;
[6-Fluoro-4-(4-fluoro-3-methanesulfonyl-benzoyl)-naphthalen-2-yl]-acetic acid;
[6-Fluoro-4-(4-methanesulfonyl-benzoyl)-3-methyl-naphthalen-2-yl]-acetic acid;
[6-Chloro-4-(4-methanesulfonyl-benzoyl)-3-methyl-naphthalen-2-yl]-acetic acid;
[4-(4-Ethanesulfonyl-benzoyl)-6-fluoro-3-methyl-naphthalen-2-yl]-acetic acid;
2-[6-Fluoro-4-(4-methanesulfonyl-benzoyl)-naphthalen-2-yl]-propionic acid;
[4-(4-Methanesulfonyl-benzyl)-6-methyl-naphthalen-2-yl]-acetic acid;
[4-(4-Methanesulfonyl-benzyl)-6-trifluoromethyl-naphthalen-2-yl]-acetic acid;
[4-(4-Methanesulfonyl-benzyl)-7-trifluoromethyl-naphthalen-2-yl]-acetic acid;
[6-Fluoro-4-(4-methanesulfonyl-benzyl)naphthalen-2-yl]-acetic acid;
[6-Fluoro-4-(4-methanesulfonyl-2-methyl-benzyl)-naphthalen-2-yl]-acetic acid;
[6-Fluoro-4-(4-methanesulfonyl-3-trifluoromethyl-benzyl)-naphthalen-2-yl]-acetic acid;
[4-(4-Ethanesulfonyl-2-methyl-benzyl)-6-fluoro-naphthalen-2-yl]-acetic acid;
[4-(4-Dimethylsulfamoyl-benzyl)-6-fluoro-naphthalen-2-yl]-acetic acid;
[4-(4-Ethanesulfonyl-benzyl)-6-fluoro-naphthalen-2-yl]-acetic acid;
[6-Fluoro-4-(4-methylsulfamoyl-benzyl)naphthalen-2-yl]-acetic acid;
[6-Fluoro-4-(4-methanesulfonyl-benzyl)-3-methyl-naphthalen-2-yl]-acetic acid;

[6-Fluoro-4-(3-methanesulfonyl-benzyl)-3-methyl-naphthalen-2-yl]-acetic acid;
[6-Fluoro-3-methyl-4-(4-trifluoromethanesulfonyl-benzyl)-naphthalen-2-yl]-acetic acid;
[6-Fluoro-3-methyl-4-(3-trifluoromethanesulfonyl-benzyl)-naphthalen-2-yl]-acetic acid;
[6-Fluoro-3-methyl-4-(4-phenylmethanesulfonyl-benzyl)-naphthalen-2-yl]-acetic acid;
[4-(4-Ethanesulfonyl-benzyl)-6-fluoro-3-methyl-naphthalen-2-yl]-acetic acid;
{4-[(2-Chloro-4-methanesulfonyl-phenyl)-hydroxy-methyl]-6-fluoro-naphthalen-2-yl}-acetic acid;
{4-[Hydroxy-(4-methanesulfonyl-phenyl)-methyl]-6-methyl-naphthalen-2-yl}-acetic acid;
{6-Chloro-4-[hydroxy-(4-methanesulfonyl-phenyl)-methyl]-naphthalen-2-yl}-acetic acid;
{6-Fluoro-4-[hydroxy-(4-methanesulfonyl-2-methyl-phenyl)-methyl]-naphthalen-2-yl}-acetic acid;
{6-Fluoro-4-[hydroxy-(4-methanesulfonyl-phenyl)-methyl]-naphthalen-2-yl}-acetic acid;
{4-[Hydroxy-(4-methanesulfonyl-phenyl)-methyl]-naphthalen-2-yl}-acetic acid;
{4-[(4-Ethanesulfonyl-phenyl)-hydroxy-methyl]-6-fluoro-naphthalen-2-yl}-acetic acid;
{4-[(4-Ethanesulfonyl-2-methyl-phenyl)-hydroxy-methyl]-6-fluoro-naphthalen-2-yl}-acetic acid;
{4-[(2-Chloro-4-methanesulfonyl-phenyl)-difluoro-methyl]-6-fluoro-naphthalen-2-yl}-acetic acid;
{4-[Difluoro-(4-methanesulfonyl-phenyl)-methyl]-6-fluoro-naphthalen-2-yl}-acetic acid;
{4-[(4-Ethanesulfonyl-phenyl)-difluoro-methyl]-6-fluoro-naphthalen-2-yl}-acetic acid;
{6-Fluoro-4-[(4-methanesulfonyl-phenyl)-methoxy-methyl]-naphthalen-2-yl}-acetic acid;
{6-Fluoro-4-[hydroxy-(4-methanesulfonyl-phenyl)-methyl]-3-methyl-naphthalen-2-yl}-acetic acid;
(6-Fluoro-4-{hydroxy-[4-(morpholine-4-sulfonyl)-phenyl]-methyl}-naphthalen-2-yl)-acetic acid;
{6-Fluoro-4-[hydroxy-(4-methylsulfamoyl-phenyl)-methyl]-naphthalen-2-yl}-acetic acid;
{6-Fluoro-4-[4-(piperazine-1-sulfonyl)-benzoyl]-naphthalen-2-yl}-acetic acid;
4-[4-(3-Carboxymethyl-7-fluoro-naphthalene-1-carbonyl)-benzenesulfonyl]-piperazine-1-carboxylic acid ethyl ester;
4-[4-(3-Carboxymethyl-7-fluoro-naphthalene-1-carbonyl)-benzenesulfonyl]-piperazine-1-carboxylic acid tert-butyl ester;
{6-Fluoro-4-[4-(4-methyl-piperazine-1-sulfonyl)-benzoyl]-naphthalen-2-yl}-acetic acid;
[4-(2-Benzenesulfonyl-benzyl)-6-fluoro-3-methyl-naphthalen-2-yl]-acetic acid;
[4-(4-Benzenesulfonyl-benzyl)-6-fluoro-3-methyl-naphthalen-2-yl]-acetic acid;
[6-Fluoro-3-methyl-4-(4-pyrazol-1-yl-benzyl)-naphthalen-2-yl]-acetic acid;
{6-Fluoro-3-methyl-4-[3-(1-methyl-1H-tetrazol-5-yl)-benzyl]-naphthalen-2-yl}-acetic acid;
[4-(3-Cyano-benzyl)-6-Fluoro-3-methyl-naphthalen-2-yl]-acetic acid;
[4-(4-Cyano-benzyl)-6-Fluoro-3-methyl-naphthalen-2-yl]-acetic acid;
[6-Fluoro-3-methyl-4-(4-methyl-benzyl)-naphthalen-2-yl]-acetic acid;
[4-(4-Benzyloxy-benzyl)-6-fluoro-3-methyl-naphthalen-2-yl]-acetic acid;
[4-(4-Bromo-benzyl)-6-fluoro-3-methyl-naphthalen-2-yl]-acetic acid;
[4-(3-Chloro-benzyl)-6-fluoro-3-methyl-naphthalen-2-yl]-acetic acid;
[6-Fluoro-4-(4-fluoro-benzyl)-3-methyl-naphthalen-2-yl]-acetic acid;
[6-Fluoro-3-methyl-4-(4-trifluoromethoxy-benzyl)-naphthalen-2-yl]-acetic acid;
3-(3-Carboxymethyl-7-fluoro-2-methyl-naphthalen-1-ylmethyl)-benzoic acid methyl ester;
{6-Fluoro-3-methyl-4-[4-(1-methyl-1H-tetrazol-5-yl)-benzyl]-naphthalen-2-yl}-acetic acid;
[6-Fluoro-3-methyl-4-(4-pyrimidin-5-yl-benzyl)-naphthalen-2-yl]-acetic acid;
[6-Fluoro-4-(4'-methanesulfonyl-biphenyl-4-ylmethyl)-3-methyl-naphthalen-2-yl]-acetic acid;
[4-(4-Benzylsulfanyl-benzyl)-6-fluoro-3-methyl-naphthalen-2-yl]-acetic acid;
[6-Chloro-4-(4-methanesulfonyl-benzyl)-3-methyl-naphthalen-2-yl]-acetic acid;
[6-Chloro-4-(4-methanesulfonylmethyl-benzyl)-3-methyl-naphthalen-2-yl]-acetic acid;
[4-(4-Methanesulfonyl-benzoyl)-7-trifluoromethyl-naphthalen-2-yl]-acetic acid;

and any pharmaceutically acceptable salt or ester thereof.

General Synthesis of Compounds According to the Invention

The compounds of the present invention can be prepared by any conventional means. Suitable processes for synthesizing these compounds are provided in the examples. Generally, compounds of formula I can be prepared according to the schemes illustrated below. Unless otherwise indicated, the variables X and $R^1$-$R^7$ are defined in the same manner as defined previously for the genus of formula I.

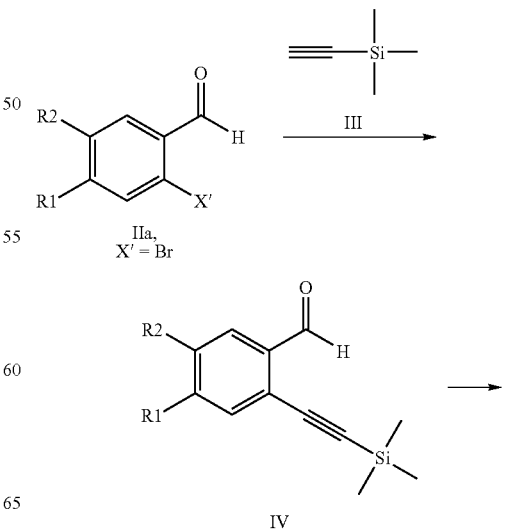

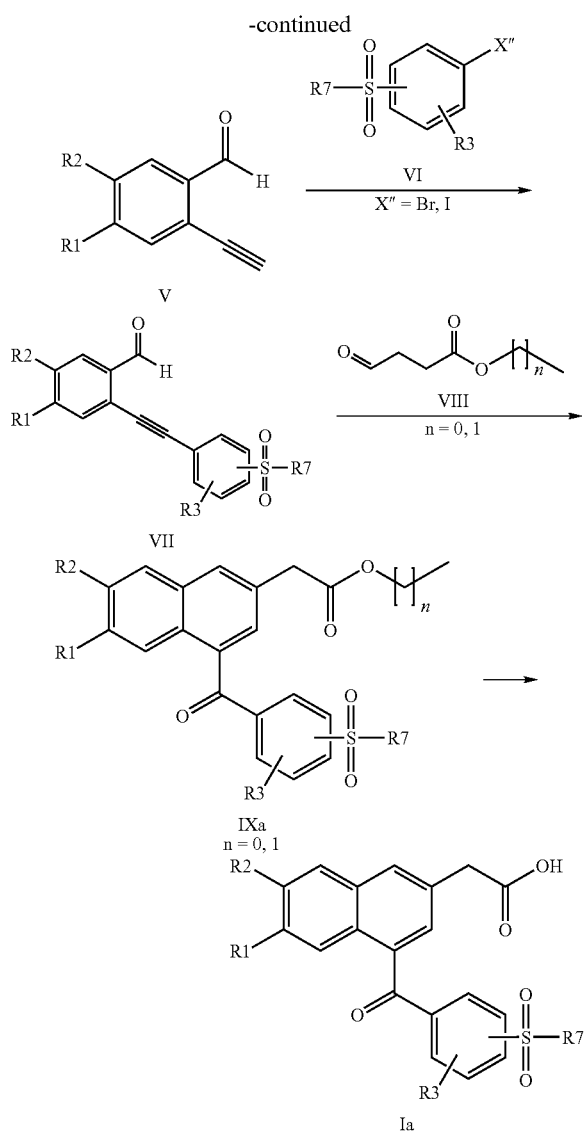

Compounds of interest Ia can be prepared according to Scheme 1. Starting with 2-bromo-benzaldehydes IIa and trimethylsilylacetylene (III), Sonogashira coupling generates 2-trimethylsilanylethynyl benzaldehydes IV. Removal of the trimethylsilanyl group in compounds IV gives the terminal acetylenes V, which can be treated with the aryl bromides or iodides VI under Sonogashira coupling conditions to give intermediates VII. Benzannulation reactions of o-alkynylbenzaldehydes VII with 4-oxo-butyric acid esters VIII catalyzed by gold(III) bromide forms the naphthalenyl derivatives IXa. Hydrolysis of esters IXa produces compounds of interest Ia.

In the first step of this sequence, the intermediates IV can be produced by coupling reactions between the appropriately substituted 2-bromo-benzaldehydes IIa and trimethylsilylacetylene (III) in the presence of a palladium catalyst such as tetrakis(triphenylphosphine)palladium(0) or bis(triphenylphosphine)palladium(II) chloride, and a copper(I) catalyst such as copper(I) iodide. The reactions can be carried out in the presence of a base such as triethylamine or diisopropylethylamine, in an inert solvent such as tetrahydrofuran (THF), acetonitrile, N,N-dimethylformamide, hexane, ethyl acetate, toluene, dichloromethane, or mixtures thereof, at a temperature between room temperature and 80° C. (or the reflux temperature) for several hours. Alternatively, the reactions can be carried out at 80° C. to 150° C. for shorter reaction times under microwave irradiation.

Removal of the trimethylsilanyl group of compounds IV to give the terminal acetylenes V can be conveniently achieved using potassium fluoride or tetrabutylammonium fluoride in a suitable solvent such as water, tetrahydrofuran, N,N-dimethylformamide, dimethyl sulfoxide, methanol, or mixtures thereof, at room temperature for several hours. Alternatively, a base such as potassium carbonate or potassium hydroxide, can be used. The reactions can be carried out in a suitable solvent such as methanol, tetrahydrofuran, water, or mixtures thereof, at room temperature for several hours.

Intermediates VII can be obtained by Sonogashira coupling reactions between the terminal acetylenes V and aryl bromides or iodides VI, in similar fashion to the first step described above. Typically, the reactions are carried out in the presence of a palladium catalyst such as tetrakis(triphenylphosphine)palladium(0) or bis(triphenylphosphine)palladium(II) chloride, and a copper(I) catalyst such as copper(I) iodide, as well as a base such as triethylamine or diisopropylethylamine. The reactions can take place in an inert solvent such as tetrahydrofuran, acetonitrile, N,N-dimethylformamide, hexane, ethyl acetate, toluene, dichloromethane or mixtures thereof, at a temperature between room temperature and 80° C. (or the reflux temperature) for several hours. Alternatively, the reactions can be carried out at 80° C. to 150° C. for shorter reaction times under microwave irradiation.

The naphthylacetic acid esters IXa can be formed via benzannulation reactions between o-alkynylbenzaldehydes VII and 4-oxo-butyric acid methyl ester (or ethyl ester) (VIII) in the presence of a gold catalyst such as gold(III) bromide in a suitable inert solvent such as tetrahydrofuran, 1,4-dioxane, 1,2-dichloroethane, or mixtures thereof, at a temperature between 60° C. and 100° C. (or reflux temperature) for several hours (Asao, N., Aikawa, H., Yamamoto, Y., *J. Am. Chem. Soc.* 126 (2004) 7458).

In some examples, the compounds of interest Ia could be isolated as a significant side product in the gold (III) catalyzed benzannulation reactions between VII and VIII. Presumably, ester compounds IXa formed in the benzannulation reactions undergo hydrolysis in the presence of the gold (III) bromide catalyst and trace amounts of water in the reaction mixture.

Hydrolysis of esters IXa to give the compounds of interest Ia can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

Alternatively, the key intermediates VII described above can be synthesized according to Scheme 2 illustrated below, and then utilized to prepare compounds of interest Ia as previously outlined in Scheme 1.

Scheme 2

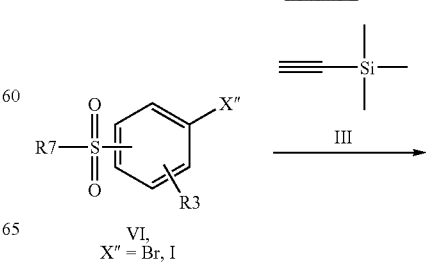

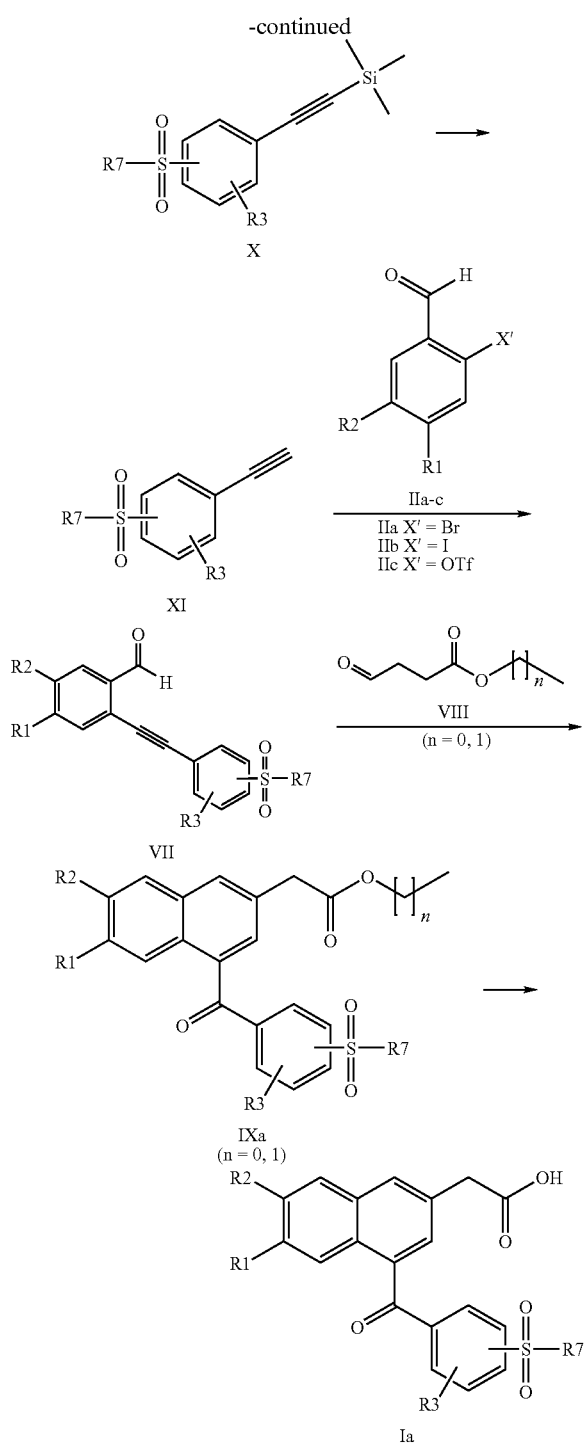

In this process, trimethylsilylacetylene (III) is first coupled onto the aryl rings bearing R3 via Sonogashira reactions with aryl bromides or iodides VI. Removal of the trimethylsilanyl group of compounds X gives intermediates XI, which are further coupled with substituted benzaldehydes IIa-c (X'=Br, I or OTf) to generate intermediates VII. Subsequently, intermediates VII are transformed into compounds of interest Ia via benzannulation reactions, followed by hydrolysis of the resulting esters.

Sonogashira coupling reactions between aryl bromides or iodides VI and trimethylsilylacetylene (III) to give compounds X can be achieved in the presence of a palladium catalyst such as tetrakis(triphenylphosphine)palladium(0) or bis(triphenylphosphine)palladium(II) chloride, and a copper (I) catalyst such as copper(I) iodide. The reactions can be carried out in the presence of a base such as triethylamine or diisopropylethylamine, in an inert solvent such as tetrahydrofuran, acetonitrile, N,N-dimethylformamide, hexane, ethyl acetate, toluene, dichloromethane, or mixtures thereof, at a temperature between room temperature and 80° C. (or the reflux temperature) for several hours. Alternatively, the reactions can be carried out at 80° C. to 150° C. for shorter reaction times under microwave irradiation.

Removal of the trimethylsilanyl group of compounds X to give the terminal acetylenes XI can be conveniently carried out using potassium fluoride or tetrabutylammonium fluoride in a solvent such as water, tetrahydrofuran, N,N-dimethylformamide, dimethyl sulfoxide, methanol, or mixtures thereof, at room temperature for several hours. Alternatively, a base such as potassium carbonate or potassium hydroxide can be used. The reactions can be carried out in a suitable solvent such as methanol, tetrahydrofuran, water, or mixtures thereof, at room temperature for several hours.

Intermediates VII can be obtained by Sonogashira coupling reactions between the terminal acetylenes XI and substituted benzaldehydes IIa-c, in a manner similar to the first step described above. Typically, the reactions are carried out in the presence of a palladium catalyst such as tetrakis(triphenylphosphine)palladium(0) or bis(triphenylphosphine)palladium(II) chloride, and a copper(I) catalyst such as copper(I) iodide, as well as a base such as triethylamine or diisopropylethylamine. The reactions can be done in an inert solvent such as tetrahydrofuran, acetonitrile, N,N-dimethylformamide, hexane, ethyl acetate, toluene, or mixtures thereof, at a temperature between room temperature and 80° C. (or the reflux temperature) for several hours. Alternatively, the reactions can be carried out at 80° C. to 150° C. for shorter reaction times under microwave irradiation.

Intermediates VII are then transformed to compounds of interest Ia as previously described in Scheme 1, via benzannulation reactions to produce esters IXa, followed by ester hydrolysis.

Scheme 3

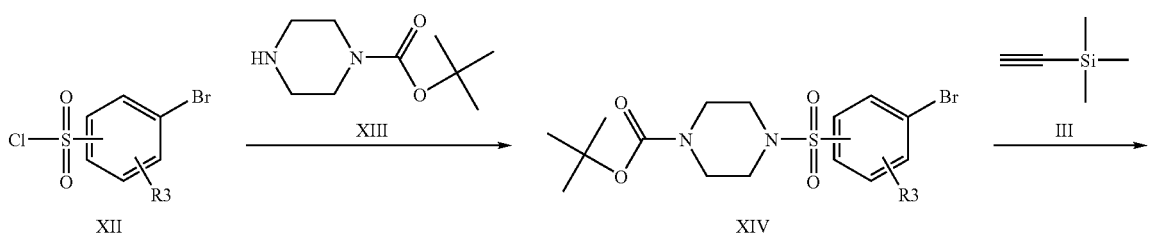

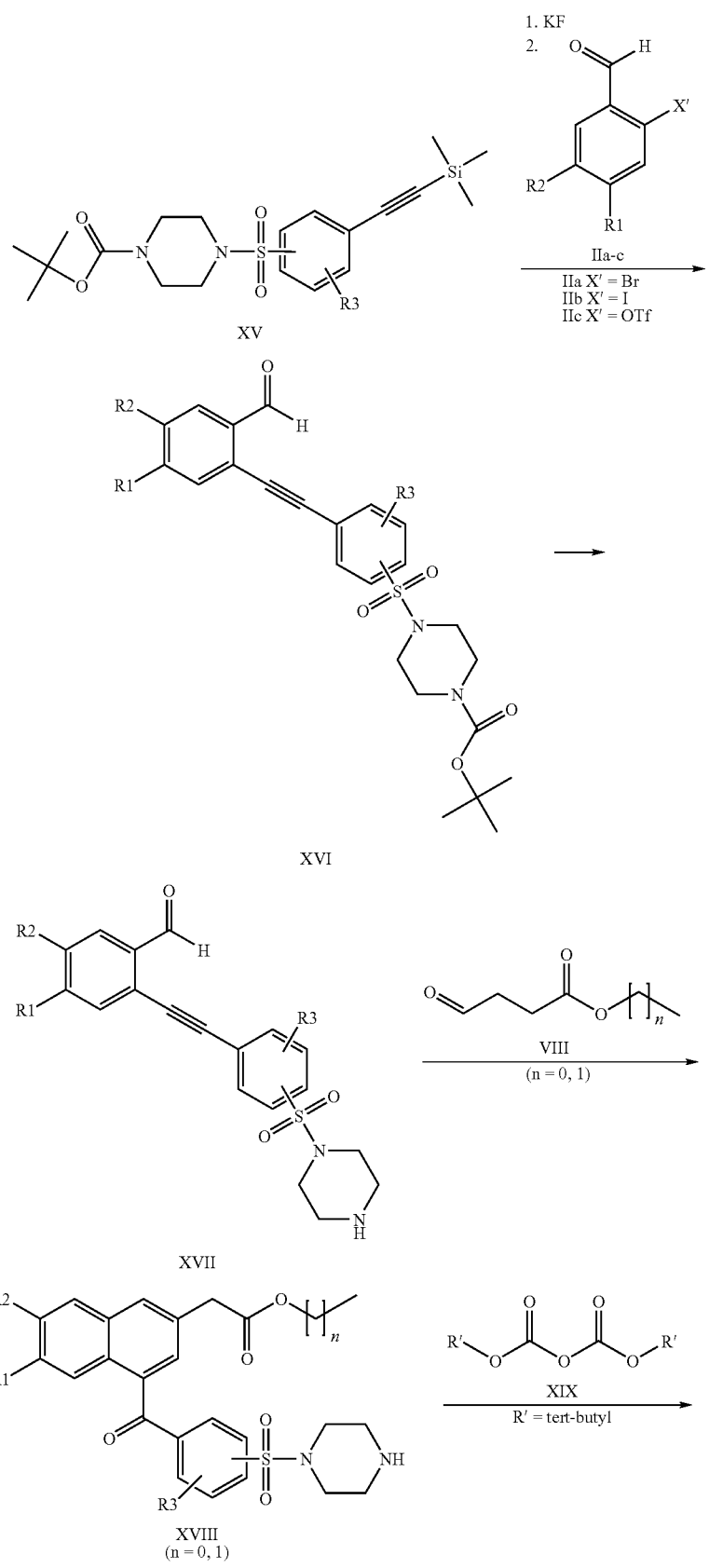

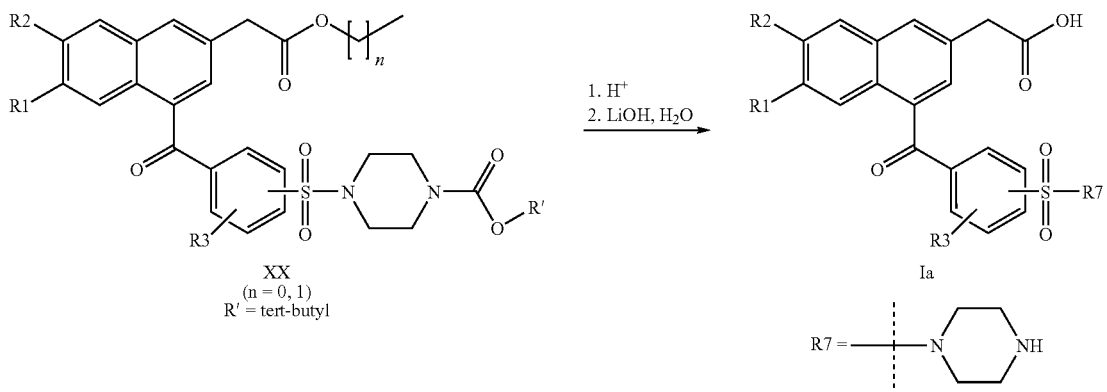

For the specific case where R7 is a piperazin-1-yl substituent, an alternative synthesis may be used as outlined in Scheme 3. Sulfonylation of N-(tert-butoxycarbonyl)-piperazine XIII with sulfonyl chlorides XII affords the corresponding sulfonamides of structure XIV. Trimethylsilylacetylene (III) can be coupled with XIV via Sonogashira reactions to give acetylenes XV. Removal of the trimethylsilanyl group of compounds XV followed by in situ coupling with substituted benzaldehydes IIa-c (X'=Br, I or OTf) generates intermediates XVI. Removal of the tert-butoxycarbonyl group in XVI provides intermediates XVII. Subsequently, intermediates XVII undergo benzannulation reactions giving intermediates XVIII. To facilitate purification of compounds where R7 is a piperazin-1-yl moiety, the crude esters XVIII may be converted to the tert-butyl carbamates XX through a reaction with dicarbonate XIX (R'=tert-butyl). Removal of the tert-butyl carbamate group followed by ester hydrolysis affords the compounds of interest Ia.

Sulfonylation of N-(tert-butoxycarbonyl)-piperazine XIII with sulfonyl chlorides XII to give sulfonamides XIV can be readily accomplished using methods well known to someone skilled in the art. The reaction is typically carried out in the presence of a base such as diisopropylethylamine, triethylamine, or pyridine in a suitable inert solvent such as dichloromethane, acetonitrile, 1,4-dioxane, tetrahydrofuran, or mixtures thereof, at 0° C. to room temperature for several hours.

Sonogashira coupling reactions between aryl bromides XIV and trimethylsilylacetylene (III) to give compounds XV can be achieved in the presence of a palladium catalyst such as tetrakis(triphenylphosphine)palladium(0) or bis(triphenylphosphine)palladium(II) chloride, and a copper(I) catalyst such as copper(I) iodide. The reactions can be carried out in the presence of a base such as triethylamine or diisopropylethylamine, in an inert solvent such as tetrahydrofuran, acetonitrile, N,N-dimethylformamide, hexane, ethyl acetate, toluene, dichloromethane, or mixtures thereof, at a temperature between room temperature and 80° C. (or the reflux temperature) for several hours.

Removal of the trimethylsilanyl group of compounds XV and subsequent Sonogashira coupling with the substituted benzaldehydes IIa-c can occur in the presence of potassium fluoride, a palladium catalyst such as tetrakis(triphenylphosphine)-palladium(0) or bis(triphenylphosphine)palladium (II) chloride, a copper(I) catalyst such as copper(I) iodide, as well as a base such as triethylamine or diisopropylethylamine. The reactions can be performed neat (without solvent) or in an inert solvent such as tetrahydrofuran, acetonitrile, N,N-dimethylformamide, hexane, ethyl acetate, toluene, or mixtures thereof, at a temperature between room temperature and 80° C. (or the reflux temperature) for several hours.

Removal of the tert-butoxycarbonyl group in XVI to give intermediates XVII can be readily achieved in the presence of an acid such as trifluoroacetic acid or hydrochloric acid in a solvent such as dichloromethane, dioxane, methanol, acetonitrile, or mixtures thereof, at a temperature between 0° C. and room temperature for several hours.

Intermediates XVII are then transformed into compounds XVIII as previously described in Scheme 1, via gold (III) catalyzed benzannulation reactions with VIII.

Carbamates XX can be obtained through a reaction of compound XVIII with XIX (R'=tert-butyl) in the presence of an amine base such as diisopropylethylamine, triethylamine or pyridine in a suitable inert solvent such as dichloromethane, acetonitrile, 1,4-dioxane, N,N,-dimethylformamide, tetrahydrofuran, or mixtures thereof, at 0° C. to room temperature for several hours.

Removal of the tert-butoxycarbonyl group in XX can be readily achieved in the presence of an acid such as trifluoroacetic acid or hydrochloric acid in a solvent such as dichloromethane, dioxane, methanol, acetonitrile, or mixtures thereof, at a temperature between 0° C. and room temperature for several hours. Subsequently, ester hydrolysis to give the compounds of interest Ia can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

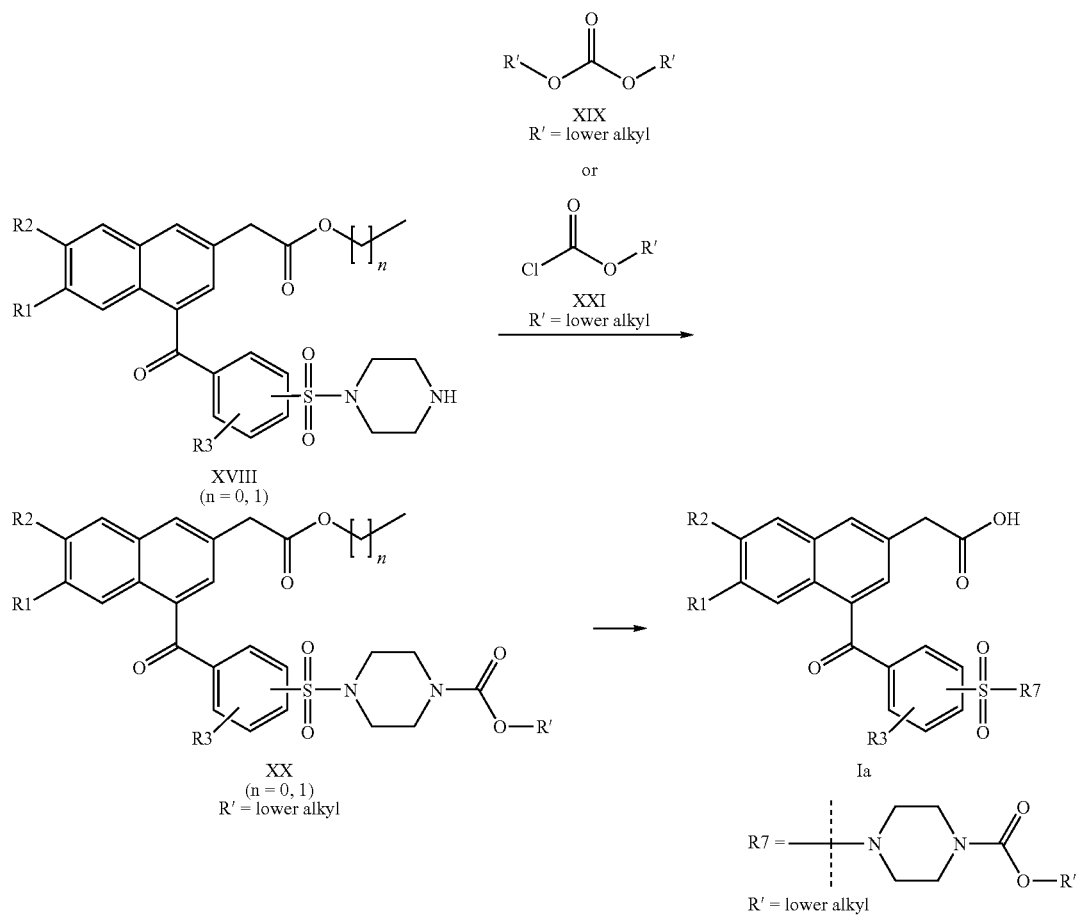

Scheme 4

For the specific case where R7 is a 4-(lower alkoxycarbonyl)-piperazin-1-yl substituent, an alternative synthesis may be used as outlined in Scheme 4. Starting with intermediates XVIII, which can be synthesized according to Scheme 3, carbamate formation affords intermediate XX. Subsequently, compounds of interest Ia are obtained from XX through ester hydrolysis reactions.

The carbamate intermediates XX can be obtained readily by reacting XVIII with a lower alkyl chloroformate (XXI), such as ethyl chloroformate or methyl chloroformate, in the presence of an amine base such as diisopropylethylamine, triethylamine or pyridine in a suitable inert solvent such as dichloromethane, acetonitrile, 1,4-dioxane, N,N,-dimethylformamide, tetrahydrofuran, or mixtures thereof, at 0° C. to room temperature for several hours. Alternatively, intermediates XX can be obtained through a reaction of XVIII with a lower alkyl dicarbonate (XIX), such as di-tert-butyl dicarbonate, in the presence of an amine base such as diisopropylethylamine, triethylamine or pyridine in a suitable inert solvent such as dichloromethane, acetonitrile, 1,4-dioxane, N,N,-dimethylformamide, tetrahydrofuran, or mixtures thereof, at 0° C. to room temperature for several hours.

Hydrolysis of esters XX to give the compounds of interest Ia can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

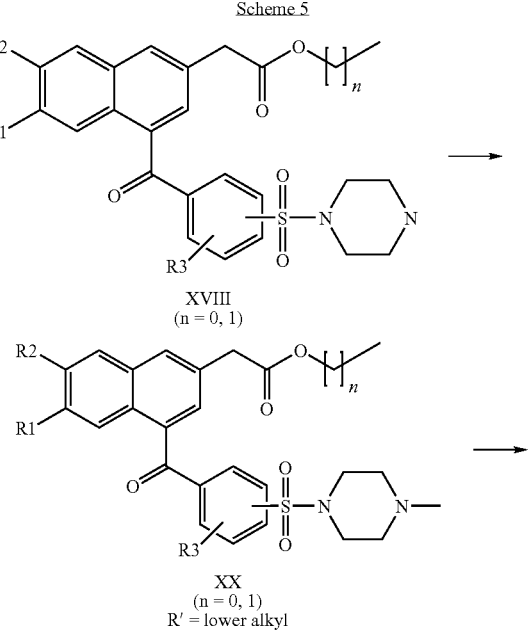

Scheme 5

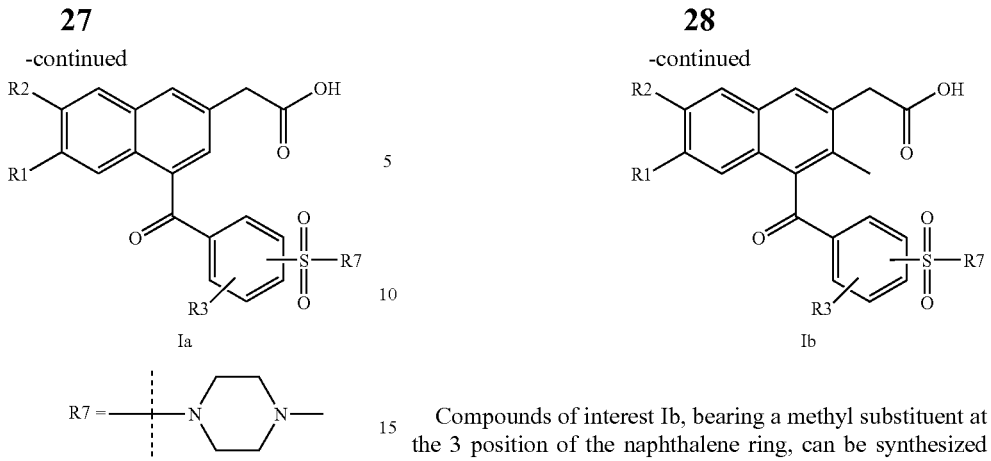

For the specific case where R7 is a 4-methyl-piperazin-1-yl substituent, an alternative synthesis can be utilized according to Scheme 5. A reductive alkylation reaction of intermediates XVIII furnishes the (4-methyl-piperazin-1-yl)sulfonyl compounds XXII. Subsequently, compounds of interest Ia are obtained through hydrolysis of the ester group in XXII.

The (4-methyl-piperazin-1-yl)sulfonyl intermediates XXII can be readily obtained from compounds XVIII in the presence of formaldehyde and an appropriate reducing agent such as sodium cyanoborohydride or sodium triacetoxyborohydride. The reactions can be carried out in solvents such as acetonitrile, methanol, tetrahydrofuran, or methylene chloride at temperatures between 0° C. and room temperature for several hours.

Hydrolysis of intermediates XXII to give the compounds of interest Ia can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

Compounds of interest Ib, bearing a methyl substituent at the 3 position of the naphthalene ring, can be synthesized according to Scheme 6, which differs from Scheme 1 and Scheme 2 only in the carbonyl compounds used in the benzannulation step. The 3-substituted naphthalenyl derivatives IXb can be obtained via gold(III) bromide catalyzed benzannulations between o-alkynylbenzaldehydes VII and esters XXIII. Basic hydrolysis of IXb yields the compounds of interest Ib.

The esters IXb can be formed via annulation reactions between o-alkynylbenzaldehydes VII and esters XXIII in the presence of a gold catalyst such as gold(III) bromide in a suitable inert solvent such as tetrahydrofuran, 1,4-dioxane, 1,2-dichloroethane, or mixtures thereof, at a temperature between 60° C. and 100° C. (or the reflux temperature) for several hours.

Hydrolysis of ester compounds IXb to give the compounds of interest Ib can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

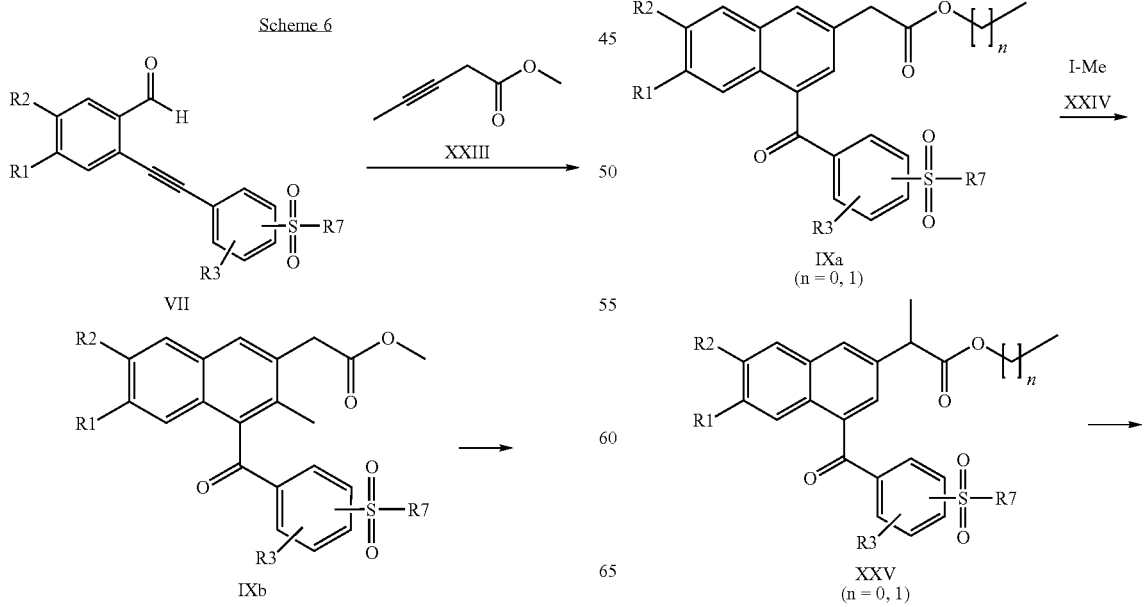

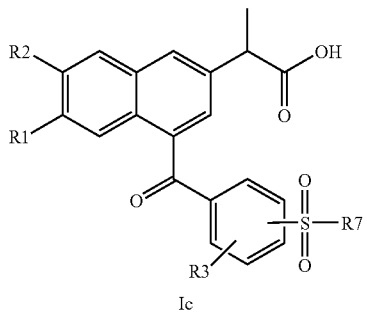

Compounds of interest Ic, with a methyl substitution on the acetic acid chain, can be prepared according to Scheme 7, by methylation reactions of compounds IXa with methyl iodide (XXIV) under basic conditions to give intermediates XXV, followed by ester hydrolysis reactions.

Methylation of compounds IXa (prepared as outlined in Schemes 1 or 2) can be achieved using methods that are well known to one skilled in the art. For example, the reactions can be carried out in a two step sequence by first deprotonating the benzylic methylene using a strong base such as lithium diisopropylamide (LDA) to generate an enolate, then alkylating the enolate with methyl iodide. The reactions can be performed in an aprotic solvent such as tetrahydrofuran, toluene, dimethoxyethane (DME), hexane, hexamethylphosphoramide (HMPA), or mixtures thereof, under an inert atmosphere at a low temperature such as −78° C.

Hydrolysis of esters XXV to give the compounds of interest Ic can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

Scheme 8

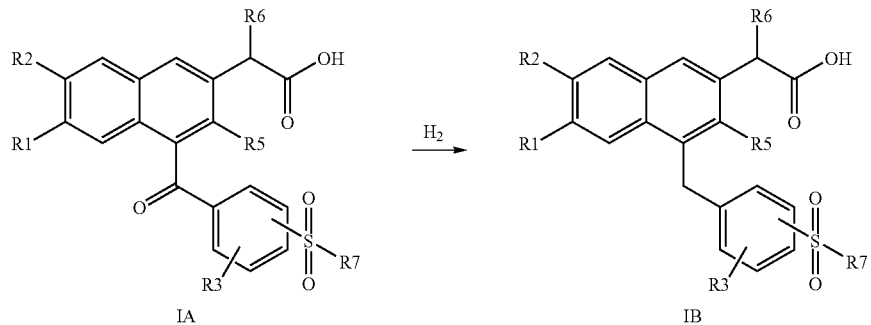

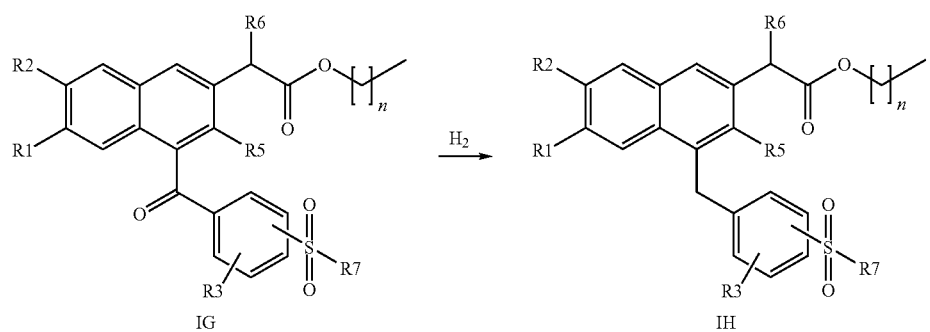

Compounds of interest IB can be generated from IA by palladium catalyzed hydrogenation as shown in Scheme 8. Alternatively, IB can be obtained by hydrogenation of the keto esters IG to the intermediates IH followed by ester hydrolysis.

Conversion of the ketones IA to compounds IB, or the keto esters IG to the intermediates IH, can be achieved by exhaustive hydrogenation reactions in the presence of 10% palladium on carbon under an atmospheric or higher pressure of hydrogen in an alcohol solvent such as ethanol or methanol at about room temperature or mildly elevated temperatures for several hours. The reactions can be carried out in an atmospheric hydrogenation apparatus, under a balloon of hydrogen gas, in a Parr hydrogenator, or in a continuous-flow hydrogenation reactor (e.g. H-Cube).

Hydrolysis of ester compounds IH to give the compounds of interest IB can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

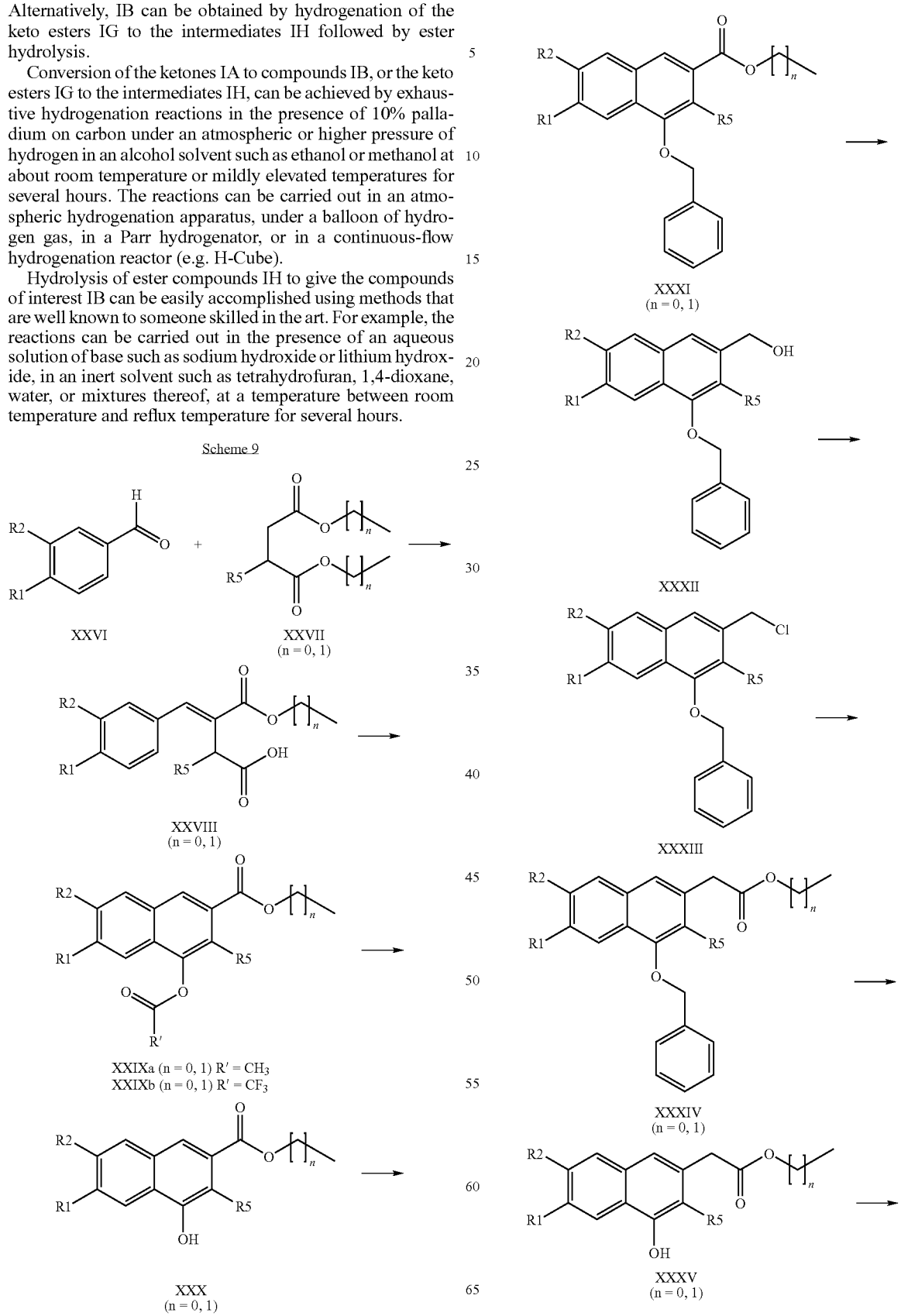

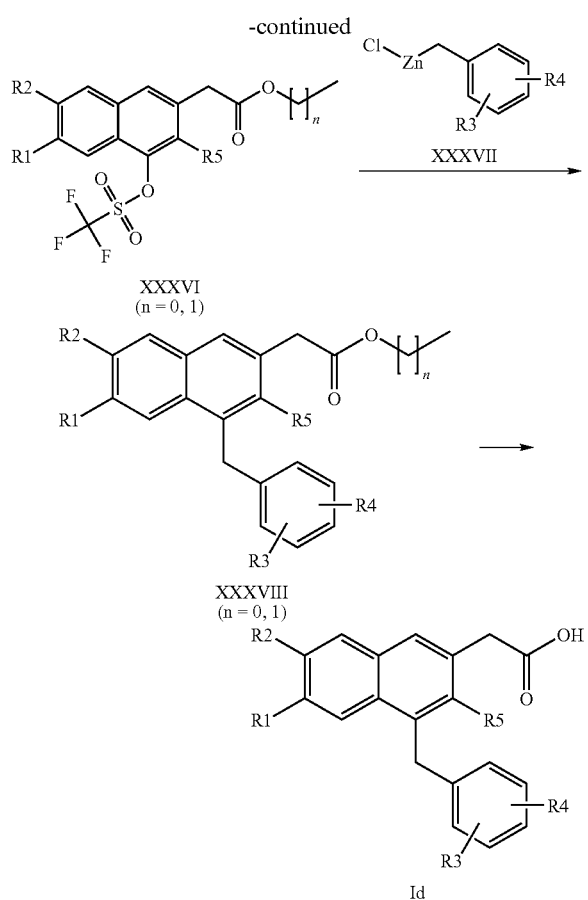

Compounds of interest Id (where R1-R5 are defined in the same manner as defined previously for the genus of formula I and R6=H) can generally be prepared according to Scheme 9. Starting with benzaldehydes XXVI and succinate esters XXVII, a Stobbe condensation reaction affords 3-carboalkoxy-4-phenyl-3-butenoic acids XXVIII. Benzannulation of compounds XXVIII gives 4-acetoxy-naphthalene carboxylic acid esters XXIXa or, alternatively, 4-trifluoroacetoxy-naphthalene carboxylic acid esters XXIXb. Hydrolysis of the acetate ester in compounds XXIXa or removal of the trifluoroacetate ester in XXIXb generates the 4-hydroxy-naphthalene carboxylic acid esters XXX. Protection of the hydroxyl group in XXX as a benzyl ether gives 4-benzyloxy-naphthalene carboxylic acid esters XXXI. Reduction of the ester group in XXXI affords naphthalen-2-yl methanol compounds XXXII, which can be transformed to chloromethyl substituted naphthalenes XXXIII. A carbonylation reaction of XXXIII in the presence of methanol or ethanol gives 4-benzyloxy-naphthylacetic acid esters XXXIV. Deprotection of the benzyl ether in XXXIV affords 4-hydroxy-naphthylacetic acid esters XXXV which can undergo sulfonylation to afford trifluoromethanesulfonates XXXVI. A Negishi coupling reaction between trifluoromethanesulfonates XXXVI and the generated benzylic zinc chlorides XXXVII yields the naphthylacetic acid esters XXXVIII. Hydrolysis of XXXVIII produces the compounds of interest Id.

Stobbe condensation reactions of XXVI with succinate esters XXVII to give intermediates XXVIII can be carried out using a base such as sodium methoxide, sodium ethoxide, potassium tert-butoxide, or sodium hydride in a suitable solvent such as methanol, ethanol, tert-butanol, toluene, benzene, or mixtures thereof, at temperatures between room temperature and 80° C. for one hour to several hours (Bloomer, J. L.; Stagliano, K. W.; Gazzillo, J. A. *J. Org. Chem.* 58 (1993) 7906).

Cyclization of compounds XXVIII to produce 4-acetoxy-naphthalene carboxylic acid esters XXIXa can be achieved in neat acetic anhydride using a base such as sodium acetate or potassium acetate at temperatures between 120° C. and 160° C. (or the reflux temperature) for several hours (El-Abbady, A. M.; El-Assal, L. S. *J. Chem. Soc.* (1959) 1024). For the case where R2 is not hydrogen, it is possible to obtain a mixture of naphthalene regioisomers in the cyclization reactions involving XXVIII. These regioisomers can be separated by conventional chromatography methods, affording the desired intermediates of structure XXIXa (Castellano, S.; Milite, C.; Campiglia, P.; Sbardella, G. *Tetrahedron Lett.* 48 (2007) 4653).

Selective hydrolysis of the acetate group in XXIXa to give the 4-hydroxy-naphthalene carboxylic acid esters XXX can be accomplished in the presence of a base such as potassium carbonate, sodium carbonate, sodium bicarbonate, sodium methoxide or potassium tert-butoxide in a suitable solvent such as methanol, acetone, water, or mixtures thereof, at a temperature between 0° C. and 80° C. for several hours.

Alternatively, compounds XXX can be accessed through cyclization of compounds XXVIII in the presence of trifluoroacetic anhydride and triethylamine in an inert organic solvent such as tetrahydrofuran or dichloromethane at room temperature. The resulting 4-trifluoroacetoxy-naphthalene carboxylic acid esters XXIXb can transformed into compounds XXX by a reduction reaction with sodium borohydride in an alcoholic solvent such as methanol at a temperature between 0° C. and room temperature (Fuganti, C.; Serra, S. *J. Chem. Research* (S) (1998) 638).

Preparation of intermediates XXXI can be accomplished by treating XXX with benzyl chloride or benzyl bromide in the presence of a base such as potassium carbonate, sodium carbonate, or cesium carbonate. This reaction may occur in an inert organic solvent such as acetone, acetonitrile, or N,N-dimethylformamide at a temperature between room temperature and 80° C. for several hours.

Reduction of the ester group in XXXI with lithium aluminum hydride gives the naphthalen-2-yl methanol compounds XXXII. This reaction can be carried out in an inert organic solvent such as tetrahydrofuran, diethyl ether, toluene, or mixtures thereof, at a temperature between 0° C. and 80° C. for several hours.

The chloromethyl naphthalene intermediates XXXIII can be prepared by the reaction of compounds XXXII with carbon tetrachloride and triphenylphosphine in an inert organic solvent such as toluene, acetonitrile, dichloromethane, N,N-dimethylformamide, or tetrahydrofuran at a temperature between 0° C. and 120° C. (or the reflux temperature) for several hours. Alternatively, the chlorination reaction may be accomplished using thionyl chloride either neat or in a suitable solvent such as dichloromethane, chloroform, N,N-dimethylformamide, benzene, or toluene at temperatures between 0° C. and 80° C. (or the reflux temperature) for several hours.

Conversion of chlorides XXXIII to the naphthylacetic acid esters XXXIV can be accomplished by a palladium catalyzed carbonylation reaction under one atmosphere of carbon monoxide in the presence of a base such as potassium carbonate, triethylamine, or diisopropylethylamine in methanol or ethanol and in the presence or absence of a co-solvent such as tetrahydrofuran. This transformation can be carried out using a palladium catalyst such as bis(triphenylphosphine)dichloropalladium(II), palladium(II) acetate, tetrakis(triphenylphosphine)palladium(0), or tris(dibenzylideneacetone)-dipalladium(0) in the presence or absence of a ligand such as tricyclohexylphosphine, triphenylphosphite, or triphenylphosphine at a temperature between room temperature and 90° C. for 10 minutes to several hours (Schoenberg, A.; Bartoletti, I.; Heck, R. F. *J. Org. Chem.* 39 (1974) 3318).

Removal of the benzyl protecting group in XXXIV through catalytic hydrogenolysis affords the 4-hydroxy-naphthylacetic acid esters XXXV. This reaction can be carried out under one atmosphere of hydrogen in the presence of a catalyst such as 10% palladium on carbon or 20% palladium hydroxide on carbon in a solvent such as methanol or ethanol at room temperature for several hours. Alternatively, the benzyl ether can be removed in the presence of boron trifluoride diethyl etherate. This reaction can be performed in acetonitrile using sodium iodide as an additive at temperatures between 0° C. to room temperature for reaction times between one hour to several hours (Vankar, Y. D.; Rao, T. *J. Chem. Research* (S) (1985) 232).

Compounds XXXV can be converted to the trifluoromethanesulfonate esters XXXVI through a reaction with trifluoromethanesulfonic anhydride in the presence of an amine base such as pyridine, triethylamine, or diisopropylethylamine and in the presence or absence of an inert solvent such as dichloromethane for several hours at temperatures between 0° C. and room temperature. Alternatively, the trifluoromethanesulfonate esters XXXVI can be obtained by reacting compounds XXXV with N-phenylbis(trifluoromethane-sulfonimide) in the presence of a base such as triethylamine, diisopropylethylamine, potassium carbonate, or cesium carbonate in an inert solvent such as dichloromethane, tetrahydrofuran, or N,N-dimethylformamide at 0° C. to room temperature for several hours.

The benzyl-substituted naphthylacetic acid esters XXXVIII can be synthesized by Negishi coupling reactions between the trifluoromethanesulfonate esters XXXVI and benzylic zinc chlorides XXXVII. These reactions are carried out in the presence of a palladium catalyst such as palladium (II) acetate and a phosphine ligand such as 2-dicyclohexylphosphino-2',6'-dimethoxybiphenyl (S-Phos) in tetrahydrofuran at temperatures between 60° C. and 70° C. for several hours (Metzger, A.; Schade, M. A.; Knochel, P. *Org. Lett.* 10 (2008) 1107).

Hydrolysis of esters XXXVIII to give the compounds of interest Id can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

The benzylic zinc chlorides XXXVII employed in the Negishi coupling reactions involving intermediate XXXVI can be readily prepared according to Scheme 10. Reaction of benzyl chlorides XXXIX with activated zinc metal in the presence of 1,2-dibromoethane, chlorotrimethylsilane, and lithium chloride in anhydrous tetrahydrofuran at temperatures between 0° C. and 40° C. for several hours gives the intermediate benzylic zinc chlorides XXXVII (Krasovskiy, A.; Malakhov, V.; Gavryushin, A.; Knochel, P. *Angew. Chem. Int. Ed.* 45 (2006) 6040).

Scheme 10

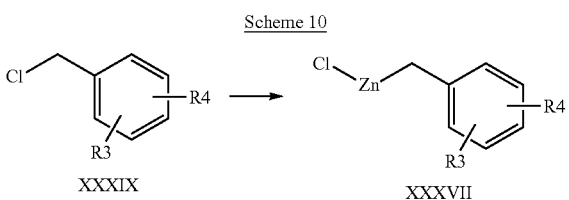

For the specific case where R4 is SO$_2$R7 and R7 is limited to lower alkyl, trifluoromethyl, benzyl, phenyl or phenyl substituted by halogen, the Negishi coupling reactions with trifluoromethanesulfonate intermediates XXXVI may be carried out using sulfanyl-substituted benzylic zinc chlorides XL according to Scheme 11. The resulting sulfanyl-benzyl substituted naphthylacetic acid esters XLI can be oxidized to sulfonyl-benzyl substituted naphthylacetic acid esters XXXVIII where R4 is SO$_2$R7 and R7 is limited to lower alkyl, trifluoromethyl, benzyl, phenyl or phenyl substituted by halogen. Hydrolysis of XXXVIII produces the compounds of interest Id.

Scheme 11

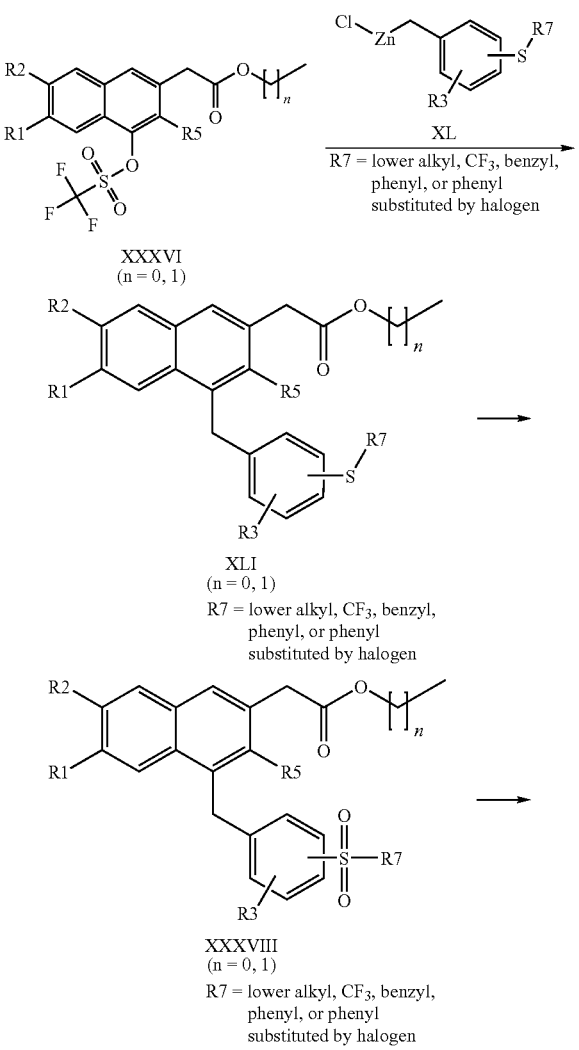

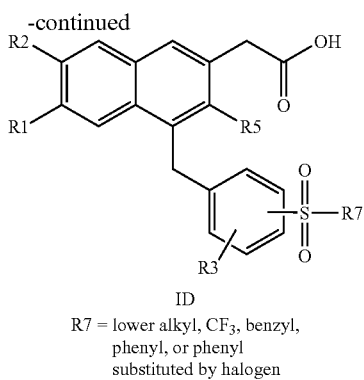

Id

R7 = lower alkyl, CF₃, benzyl, phenyl, or phenyl substituted by halogen

The Negishi coupling reactions between the trifluoromethanesulfonate esters XXXVI and benzylic zinc chlorides XL to provide XLI are performed in the presence of a palladium catalyst such as palladium(II) acetate and a phosphine ligand such as 2-dicyclohexylphosphino-2',6'-dimethoxybiphenyl (S-Phos) in tetrahydrofuran at temperatures between 60° C. and 70° C. for several hours (Metzger, A.; Schade, M. A.; Knochel, P. *Org. Lett.* 10 (2008) 1107).

Oxidation of intermediates XLI to the naphthylacetic acid methyl esters XXXVIII can be accomplished using an oxidation agent such as m-chloroperoxybenzoic acid (m-CPBA) or hydrogen peroxide in a suitable solvent such as dichloromethane or dichloroethane (or an aqueous solution if hydrogen peroxide is used), at a temperature between 0° C. and room temperature for several hours. Alternatively, potassium peroxymonosulfate (OXONE ®) may be employed as an oxidant in mixtures of water with an organic solvent such as tetrahydrofuran at temperatures between 0° C. and room temperature for several hours.

Hydrolysis of esters XXXVIII to give the compounds of interest Id can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

The benzylic zinc chlorides XL employed in the Negishi coupling reactions giving the sulfanyl intermediates XLI can be readily prepared according to Scheme 12. Reaction of benzyl chlorides XLII with activated zinc metal in the presence of 1,2-dibromoethane, chlorotrimethylsilane, and lithium chloride in anhydrous tetrahydrofuran at temperatures between 0° C. and 40° C. for several hours gives the intermediate benzylic zinc chlorides XL (Krasovskiy, A.; Malakhov, V.; Gavryushin, A.; Knochel, P. *Angew. Chem. Int. Ed.* 45 (2006) 6040).

Scheme 12

XLII

R7 = lower alkyl, CF₃, benzyl, phenyl, halogen-substituted phenyl

XL

R7 = lower alkyl, CF₃, benzyl, phenyl, halogen-substituted phenyl

For the specific case where R3 is limited to hydrogen and R4 is limited to either heteroaryl, optionally substituted by lower alkyl, or phenyl, optionally substituted by methanesulfonyl, compounds of interest of type Id may be prepared from the trifluoromethanesulfonate esters XXXVI according to Scheme 13. In this sequence, Negishi coupling reactions between XXXVI and benzyloxy-substituted benzylic zinc chlorides XLIII provide the naphthylacetic acid ester intermediates XLIV. Removal of the benzyl ether group in XLIV generates the phenol compounds XLV which can undergo a sulfonylation reaction to give intermediates XLVI. Suzuki coupling reactions between XLVI and boronic acids XLVII yield the naphthylacetic acid ester compounds XXXVIII where R4 is limited to either heteroaryl, optionally substituted by lower alkyl, or phenyl, optionally substituted by methanesulfonyl. Ester hydrolysis furnishes the compounds of interest Id.

Scheme 13

XXXVI
(n = 0, 1)

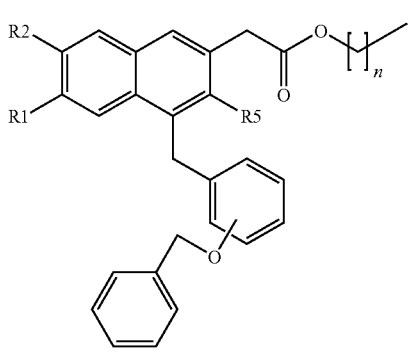

XLIV
(n = 0, 1)

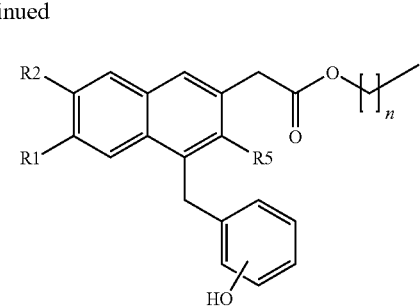

XLV
(n = 0, 1)

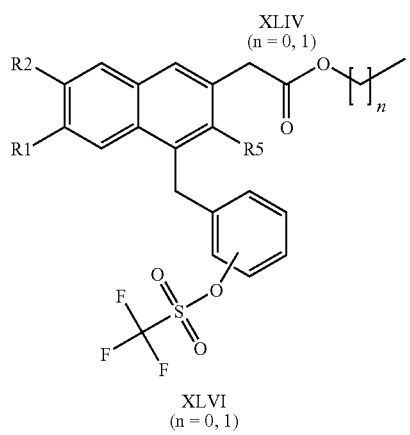

XLVI
(n = 0, 1)

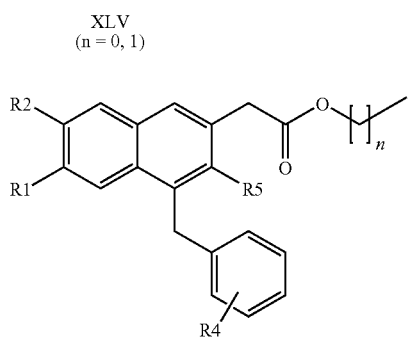

XXXVIII
(n = 0, 1)
R4 = heteroaryl,
optionally substituted
by lower alkyl, or phenyl,
optionally substituted
by SO₂Me

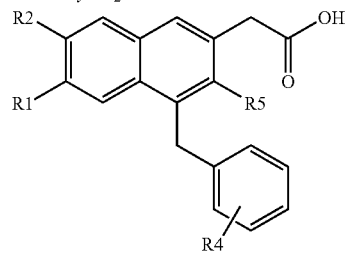

Id
R4 = heteroaryl,
optionally substituted
by lower alkyl, or phenyl,
optionally substituted
by SO₂Me The Negishi coupling reactions between the trifluoromethanesulfonate esters XXXVI and benzyloxy-substituted benzylic zinc chlorides XLIII to provide XLIV are performed in the presence of a palladium catalyst such as palladium(II) acetate and a phosphine ligand such as 2-dicyclohexylphosphino-2',6'-dimethoxybiphenyl (S-Phos) in tetrahydrofuran at temperatures between 60° C. and 70° C. for several hours (Metzger, A.; Schade, M. A.; Knochel, P. Org. Lett. 10 (2008) 1107).

Removal of the benzyl protecting group in XLIV through catalytic hydrogenolysis affords phenols XLV. This reaction can be carried out under one atmosphere of hydrogen in the presence of a catalyst such as 10% palladium on carbon or 20% palladium hydroxide on carbon in a solvent such as methanol or ethanol at room temperature for several hours.

Phenol compounds XLV can be converted to the trifluoromethanesulfonate esters XLVI through a reaction with trifluoromethanesulfonic anhydride in the presence of an amine base such as pyridine, triethylamine, or diisopropylethylamine and in the presence or absence of an inert solvent such as dichloromethane for several hours. Alternatively, the trifluoromethanesulfonate esters XLVI can be obtained by reacting compounds XLV with N-phenylbis(trifluoromethanesulfonimide) in the presence of a base such as triethylamine, diisopropylethylamine, potassium carbonate, or cesium carbonate in an inert solvent such as dichloromethane, tetrahydrofuran, or N,N-dimethylformamide at 0° C. to room temperature for several hours.

The naphthylacetic acid esters XXXVIII, where R3 is limited to hydrogen and R4 is limited to either heteroaryl, optionally substituted by lower alkyl, or phenyl, optionally substituted by methanesulfonyl, can be synthesized by Suzuki coupling reactions between the trifluoromethanesulfonate esters XLVI and boronic acids XLVII. These reactions can be carried out in the presence of a palladium catalyst such as tetrakis(triphenylphosphine)palladium(0), bis(triphenylphosphine)palladium(II) chloride, palladium(II) acetate, or [1,1'-bis(diphenylphosphino)ferrocene]-dichloropalladium(II) and a base such as cesium carbonate, sodium carbonate, potassium carbonate, or triethylamine. The coupling reactions may be performed in a solvent such as toluene, dioxane, 1,2-dimethoxyethane, or N,N-dimethylformamide at the reflux temperature for several hours.

Hydrolysis of esters XXXVIII to give the compounds of interest Id can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and the reflux temperature for several hours.

The benzyloxy-substituted benzylic zinc chlorides XLIII employed in the Negishi coupling reactions giving intermediates XLIV can be readily prepared according to Scheme 14. Reaction of benzyloxy-substituted benzyl chlorides XLVIII with activated zinc metal in the presence of 1,2-dibromoethane, chlorotrimethylsilane, and lithium chloride in anhydrous tetrahydrofuran at temperatures between 0° C. and 40° C. for several hours gives the intermediate benzylic zinc chlorides XLIII (Krasovskiy, A.; Malakhov, V.; Gavryushin, A.; Knochel, P. *Angew. Chem. Int. Ed.* 45 (2006) 6040).

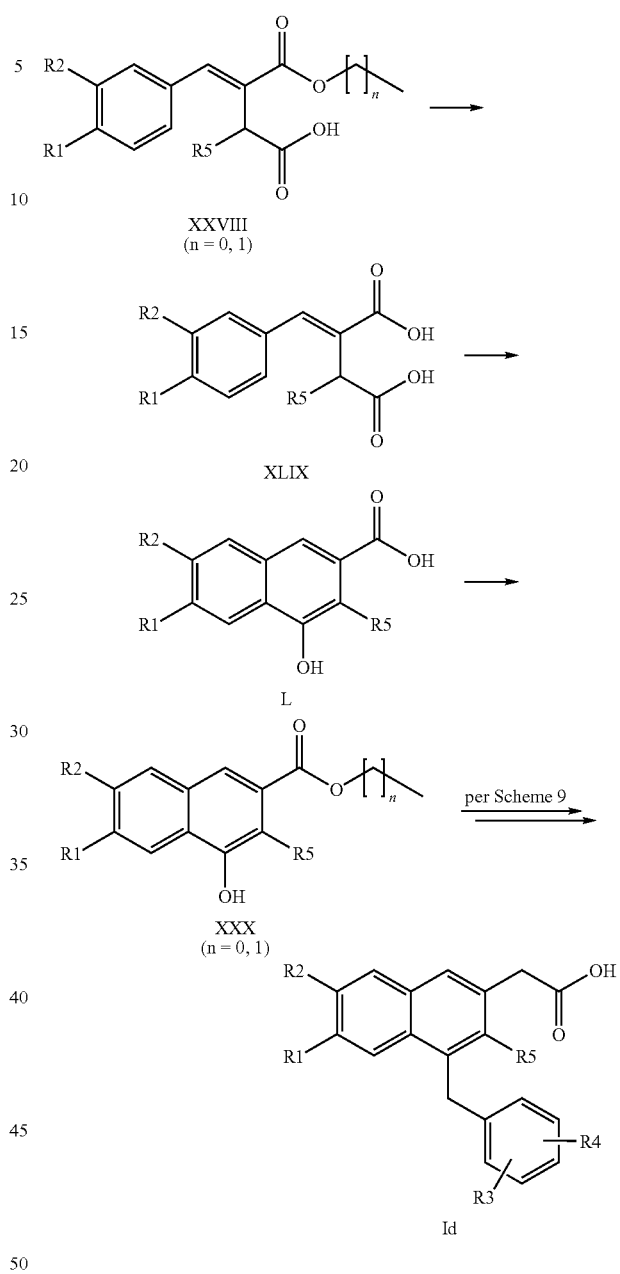

The 4-hydroxy-naphthalene carboxylic acid ester intermediates XXX shown in Scheme 9 can alternatively be prepared according to Scheme 15 starting from the 3-carboalkoxy-4-phenyl-3-butenoic acid compounds XXVIII. Hydrolysis of intermediates XXVIII generates the dicarboxylic acids XLIX which can be cyclized to 4-hydroxynaphthalene carboxylic acids L. An esterification reaction of L affords the 4-hydroxy-naphthalene carboxylic acid ester intermediates XXX. Intermediates XXX thus prepared can be transformed into the compounds of interest Id using the methods outlined in Scheme 9.

Intermediates XXVIII, which can be synthesized as described above in Scheme 9, can readily undergo hydrolysis to afford the dicarboxylic acid intermediates XLIX. This reaction can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and the reflux temperature for several hours.

Cyclization of the dicarboxylic acids XLIX to form 4-hydroxy-naphthalene carboxylic acids L can be accomplished in neat trifluoromethanesulfonic acid at room temperature over several hours (Hong, W. P.; Lim, H. N.; Park, H. W.; Lee, K.-J. *Bull. Korean Chem. Soc.* 26 (2005) 655).

Intermediates L can be readily converted to the 4-hydroxy-naphthalene carboxylic acid ester intermediates XXX in the presence of a catalytic amount of concentrated sulfuric acid and an alcohol solvent such as methanol or ethanol at temperatures between room temperature and 80° C. (or the reflux temperature) for several hours. Alternatively, the esterification reaction can be carried out in the presence of thionyl chloride and a suitable alcohol solvent such as methanol or ethanol at temperatures between 65° C. and 80° C. (or the reflux temperature) for several hours.

The trifluoromethanesulfonate ester intermediates XXXVI described in Scheme 9 can alternatively be synthesized according to Scheme 16 starting with the 4-acetoxy naphthalene carboxylic acid ester intermediates XXIXa. Reduction of compounds XXIXa provides intermediates LI which can subsequently undergo a chlorination reaction to give the chloromethyl naphthalene compounds LII. Compounds LII can be transformed into trifluoromethanesulfonate esters LIII. A carbonylation reaction of LIII in the presence of methanol or ethanol gives intermediates XXXVI which can be transformed into compounds of interest Id as described above in Scheme 9.

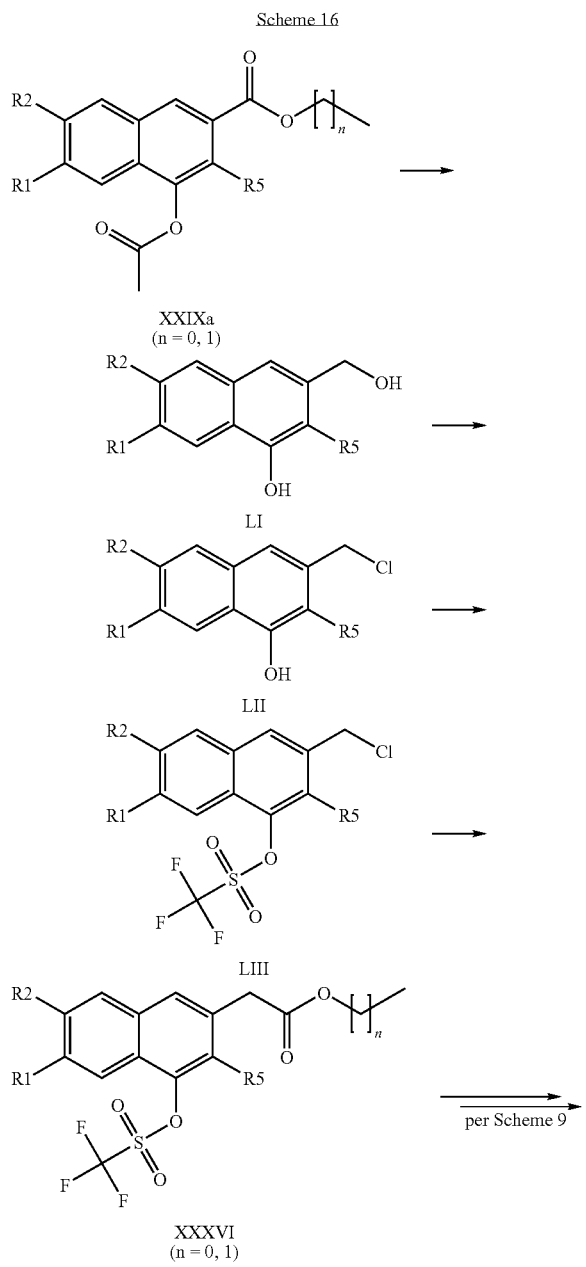

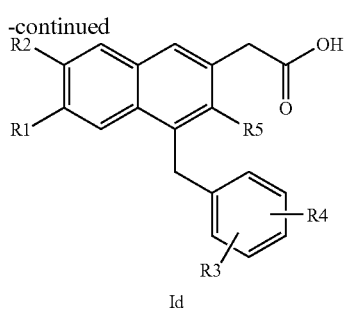

The 4-acetoxy-naphthalene carboxylic acid ester intermediates XXIXa, which can be prepared as described above in Scheme 9, can undergo a reduction reaction to form alcohols LI in the presence of a suitable reducing agent such as diisobutylaluminum hydride or lithium aluminum hydride in an inert organic solvent such as methylene chloride, hexane, toluene, diethyl ether, tetrahydrofuran, or mixtures thereof. The reactions can occur at temperatures ranging from −78° C. to room temperature for several hours.

Chlorination of alcohols LI to form intermediates LII can be accomplished using carbon tetrachloride and triphenylphosphine in an inert organic solvent such as toluene, acetonitrile, dichloromethane, N,N-dimethylformamide, or tetrahydrofuran at a temperature between 0° C. and 120° C. for several hours.

Compounds LII can be converted to the trifluoromethanesulfonate esters LIII through a reaction with trifluoromethanesulfonic anhydride in the presence of an amine base such as pyridine, triethylamine, or diisopropylethylamine and in the presence or absence of an inert solvent such as methylene chloride for several hours at temperatures between 0° C. and room temperature.

Conversion of compounds LIII to the trifluoromethanesulfonate ester intermediates XXXVI can be accomplished by a palladium catalyzed carbonylation reaction under one atmosphere of carbon monoxide in the presence of a base such as potassium carbonate, triethylamine, diisopropylethylamine, or sodium methoxide in methanol and in the presence or absence of a co-solvent such as tetrahydrofuran. This transformation can be carried out using a palladium catalyst such as bis(triphenylphosphine)dichloropalladium(II), palladium (II) acetate, tetrakis(triphenylphosphine)palladium(0), or tris (dibenzylideneacetone)-dipalladium(0), in the presence or absence of a ligand such as tricyclohexylphosphine, triphenylphosphite, or triphenylphosphine at a temperature between room temperature and 90° C. for 10 minutes to several hours (Schoenberg, A.; Bartoletti, I.; Heck, R. F. *J. Org. Chem.* 39 (1974) 3318).

The 4-hydroxy-naphthylacetic acid ester intermediates XXXV described above in Scheme 9 can alternatively be prepared according to Scheme 17. Starting with the naphthalene carboxylic acid compounds L described in Scheme 15, a reduction reaction affords alcohol intermediates LI which then undergo a chlorination reaction to provide compounds LII. A carbonylation reaction in the presence of methanol or ethanol gives intermediates XXXV which can be converted to compounds of interest Id using the methods outlined in Scheme 9.

Scheme 17

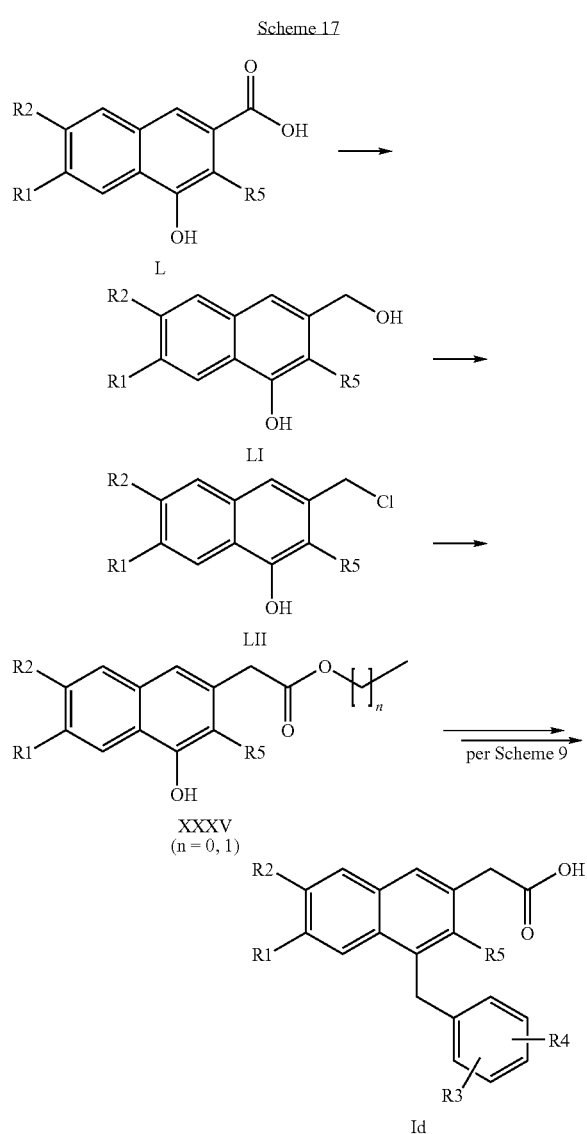

Reduction of the carboxyl group in intermediates L, which can be synthesized according to Scheme 15, can be accomplished in the presence of lithium aluminum hydride to afford the alcohols LI. This reaction can be carried out in an inert organic solvent such as tetrahydrofuran, diethyl ether, toluene or mixtures thereof, at a temperature between room temperature and 80° C. for several hours.

Transformation of alcohols LI into chlorides LII can proceed using carbon tetrachloride in the presence of triphenylphosphine. This reaction can occur in an inert organic solvent such as tetrahydrofuran, acetonitrile, toluene, N,N-dimethylformamide, or dichloromethane, at a temperature between 0° C. and 120° C. for several hours.

Conversion of the chlorides LII to the intermediates XXXV can be accomplished by a palladium catalyzed carbonylation reaction under one atmosphere of carbon monoxide in the presence of a base such as potassium carbonate, triethylamine, or diisopropylethylamine in methanol or ethanol and in the presence or absence of a co-solvent such as tetrahydrofuran. This transformation can be carried out using a palladium catalyst such as bis(triphenylphosphine)dichloropalladium(II), palladium(II) acetate, tetrakis(triphenylphosphine)palladium(0), or tris(dibenzylideneacetone)-dipalladium(0), in the presence or absence of a ligand such as tricyclohexylphosphine, triphenylphosphite, or triphenylphosphine at a temperature between room temperature and 90° C. for 10 minutes to several hours (Schoenberg, A.; Bartoletti, I.; Heck, R. F. *J. Org. Chem.* 39 (1974) 3318).

Alternatively, compounds of interest Id can be prepared according to Scheme 18 starting from the 4-hydroxy-naphthalene carboxylic acid ester intermediates XXX which were described above in Scheme 9. Sulfonylation of XXX provides the perfluoroalkylsulfonate esters LIV. A Negishi coupling reaction between intermediates LIV and benzylic zinc chlorides XXXVII gives the naphthalene carboxylic acid esters LV. Reduction of the ester group in LV affords naphthalen-2-yl methanol compounds LVI, which can be transformed to chloromethyl substituted naphthalenes LVII. A carbonylation reaction in the presence of methanol or ethanol gives the 4-benzyl substituted naphthylacetic acid esters XXXVIII. Ester hydrolysis furnishes the compounds of interest Id.

Scheme 18

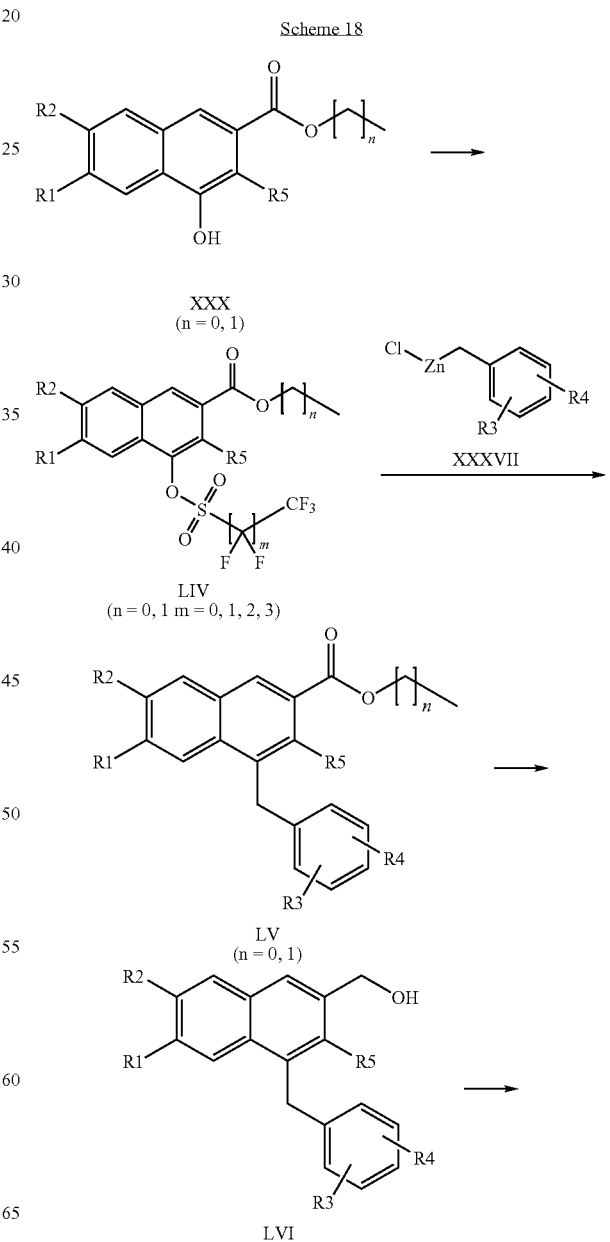

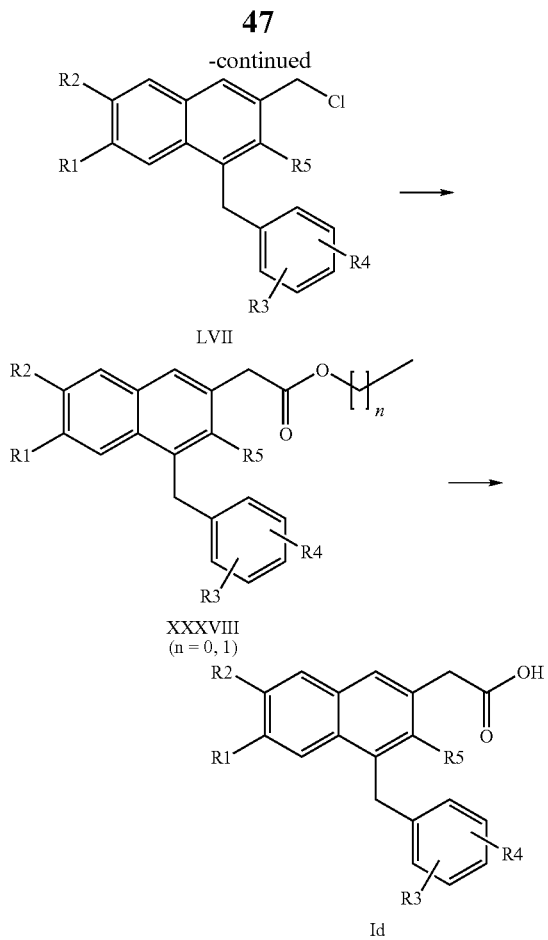

LVII

XXXVIII
(n = 0, 1)

Id

The perfluoroalkylsulfonate esters LIV can be prepared by a reaction between intermediate XXX and a sulfonylation reagent such as trifluoromethanesulfonic anhydride, N-phenylbis(trifluoromethanesulfonimide), or perfluorobutanesulfonyl fluoride in the presence of a base such as triethylamine, diisopropylethylamine or sodium hydride in an inert solvent such as dichloromethane, tetrahydrofuran, or N,N-dimethylformamide at 0° C. to room temperature for several hours.

The naphthalene carboxylic acid esters LV can be synthesized by Negishi coupling reactions between the perfluoroalkylsulfonate esters LIV and the benzylic zinc chlorides XXXVII. These reactions are carried out in the presence of a palladium catalyst such as palladium(II) acetate or tetrakis(triphenylphosphine)palladium(0) and a phosphine ligand such as 2-dicyclohexylphosphino-2',6'-dimethoxybiphenyl (S-Phos) in tetrahydrofuran at temperatures between 60° C. and 70° C. for several hours (Metzger, A.; Schade, M. A.; Knochel, P., *Org. Lett.* 10 (2008) 1107). The benzylic zinc chlorides XXXVII employed in the Negishi coupling reactions can be readily prepared according to Scheme 10 as described above.

Reduction of the ester group in LV with lithium aluminum hydride gives the naphthalen-2-yl methanol compounds LVI. This reaction can be carried out in an inert organic solvent such as tetrahydrofuran, diethyl ether, toluene, or mixtures thereof, at a temperature between 0° C. and 80° C. for several hours.

The chloromethyl naphthalene intermediates LVII can be prepared by the treatment of compounds LVI with carbon tetrachloride and triphenylphosphine in an inert organic solvent such as toluene, acetonitrile, dichloromethane, N,N-dimethylformamide, or tetrahydrofuran, at a temperature between 0° C. and 120° C. (or the reflux temperature) for several hours. Alternatively, the chlorination reaction can be accomplished using thionyl chloride either neat or in a suitable solvent such as dichloromethane, chloroform, N,N-dimethylformamide, benzene, or toluene at temperatures between 0° C. and 80° C. (or the reflux temperature) for several hours.

Conversion of chlorides LVII to the naphthylacetic acid esters XXXVIII can be accomplished by a palladium catalyzed carbonylation reaction under one atmosphere of carbon monoxide in the presence of a base such as potassium carbonate or triethylamine in methanol or ethanol and in the presence or absence of a co-solvent such as tetrahydrofuran. This transformation can be carried out in the presence of a palladium catalyst such as bis(triphenylphosphine)dichloropalladium(II), palladium(II) acetate, tetrakis(triphenylphosphine)palladium(0), or tris(dibenzylideneacetone)dipalladium(0) in the presence or absence of a ligand such as tricyclohexylphosphine, triphenylphosphite, or triphenylphosphine at a temperature between room temperature and 90° C. for 10 minutes to several hours (Schoenberg, A.; Bartoletti, I.; Heck, R. F. *J. Org. Chem.* 39 (1974) 3318).

As described above, hydrolysis of esters XXXVIII to give the compounds of interest Id can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

The compounds of interest Id can also be prepared according to Scheme 19. Starting with the perfluoroalkylsulfonate intermediates LIV described in Scheme 18, a palladium catalyzed borylation reaction furnishes the boronate ester compounds LIX. A Suzuki coupling reaction between LIX and benzyl bromides LX or benzyl chlorides XXXIX gives the intermediate naphthalene carboxylic acid esters LV described above in Scheme 18. Transformation of intermediates LV into the compounds of interest Id subsequently proceeds as described in Scheme 18.

Scheme 19

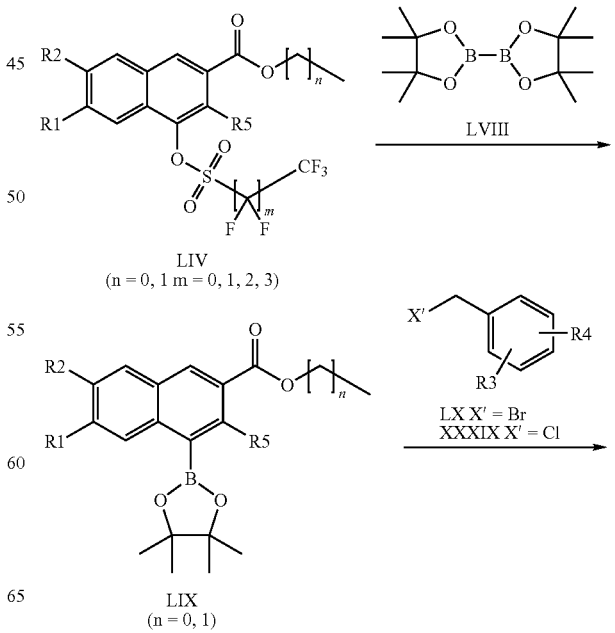

LIV
(n = 0, 1 m = 0, 1, 2, 3)

LVIII

LIX
(n = 0, 1)

LX X' = Br
XXXIX X' = Cl

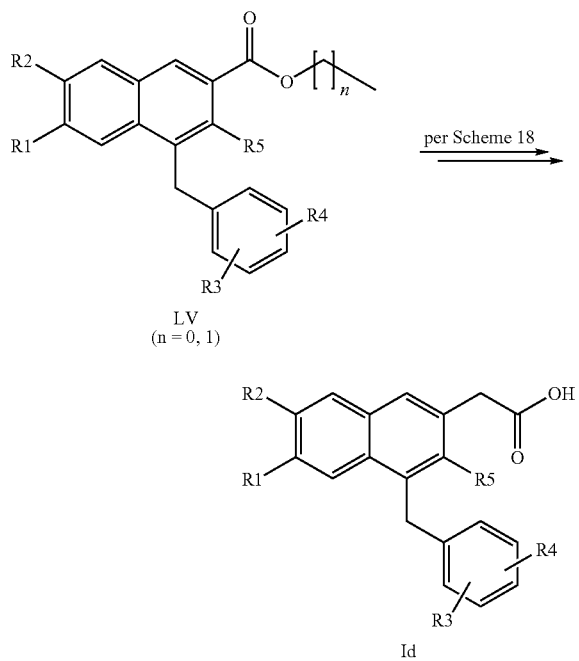

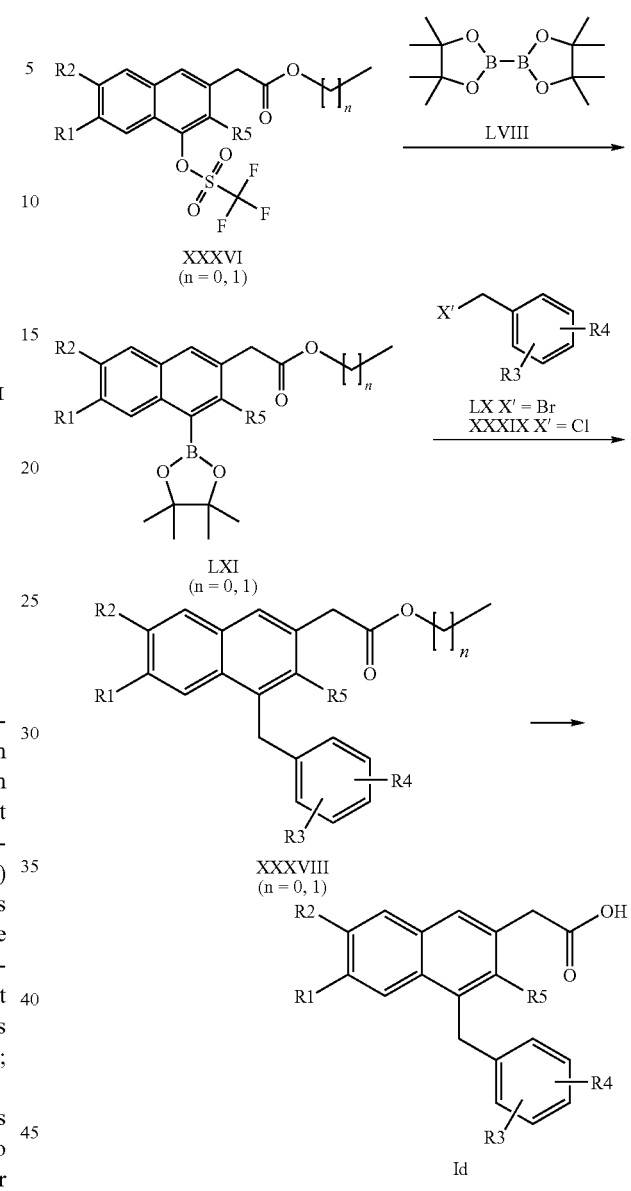

Scheme 20

The palladium catalyzed borylation of perfluoroalkylsulfonates LIV to give the boronate ester intermediates LIX can be performed in the presence of bis(pinacolato)diboron LVIII, a base such as potassium acetate, a palladium catalyst such as dichloro 1,1'-bis(diphenylphosphino)ferrocene palladium(II) or bis(triphenylphosphine)-dichloropalladium(II) and in the presence or absence of a phosphine ligand such as 1,1'-bis(diphenylphosphino)ferrocene. The reactions can be carried out in an anhydrous organic solvent such as 1,4-dioxane, N,N-dimethylformamide, or dimethyl sulfoxide at temperatures between 90° C. and 150° C. for reaction times between three hours and 24 hours (Ishiyama, T.; Murata, M.; Miyaura, N. *J. Org. Chem.* 60 (1995) 7508).

The Suzuki coupling reactions between boronate esters LIX and benzyl bromides LX or benzyl chlorides XXXIX to form the benzyl substituted naphthalene carboxylic acid ester intermediates LV can be accomplished in the presence of a palladium catalyst such as palladium(II) acetate, tetrakis(triphenylphosphine)palladium(0) or palladium(II) chloride, a base such as sodium carbonate, potassium carbonate, or potassium phosphate, and in the presence or absence of a phosphine ligand such as triphenylphosphine. The reactions occur readily in mixtures of solvents such as tetrahydrofuran, 1,2-dimethoxyethane, ethanol, toluene, or acetone with water at temperatures between room temperature and 110° C. (or the reflux temperature) for 30 minutes to 20 hours (Chowdhury, S.; Georghiou, P. E., *Tetrahedron Lett.* 40 (1999) 7599).

The naphthalene carboxylic acid ester intermediates LV prepared by the benzyl halide Suzuki coupling reaction according to Scheme 19 can be used in the preparation of compounds of interest Id using the methods described above for the preparation of compounds Id from LV according to Scheme 18.

Alternatively, compounds of interest Id can be synthesized according to Scheme 20. Starting with the trifluoromethanesulfonate intermediates XXXVI described in Scheme 9, a palladium catalyzed borylation reaction furnishes the boronate ester compounds LXI. A Suzuki coupling reaction between LXI and benzyl bromides LX or benzyl chlorides XXXIX gives the intermediate naphthyl acetic acid esters XXXVIII Hydrolysis of the ester group in intermediates XXXVIII provides the compounds of interest Id.

The palladium catalyzed borylation of trifluoromethanesulfonates XXXVI to give the boronate ester intermediates LXI can be performed in the presence of bis(pinacolato) diboron LVIII, a base such as potassium acetate, a palladium catalyst such as dichloro 1,1'-bis(diphenylphosphino)ferrocene palladium(II) (dichloromethane adduct) or bis(triphenylphosphine)dichloropalladium(II) and in the presence of a phosphine ligand such as 1,1'-bis(diphenylphosphino)ferrocene. The reactions can be carried out in an anhydrous organic solvent such as 1,4-dioxane, N,N-dimethylformamide, or dimethyl sulfoxide at temperatures between 90° C. and 150° C. for reaction times between three hours and 24 hours (Ishiyama, T.; Murata, M.; Miyaura, N. *J. Org. Chem.* 60 (1995) 7508).

The Suzuki coupling reactions between boronate esters LXI and benzyl bromides LX or benzyl chlorides XXXIX to form the benzyl substituted naphthylacetic acid ester intermediates XXXVIII can be accomplished in the presence of a palladium catalyst such as palladium(II) acetate, tetrakis(triphenyl-phosphine)palladium(0) or palladium(II) chloride, a base such as sodium carbonate, potassium carbonate, or potassium phosphate, and in the presence or absence of a phosphine ligand such as triphenylphosphine. The reactions occur readily in mixtures of solvents such as tetrahydrofuran, 1,2-dimethoxyethane, ethanol, toluene, or acetone with water at temperatures between room temperature and 110° C. (or the reflux temperature) for 30 minutes to 20 hours (Chowdhury, S.; Georghiou, P. E., *Tetrahedron Lett.* 40 (1999) 7599).

As described above, hydrolysis of esters XXXVIII to give the compounds of interest Id can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

Alternatively, compounds of interest Id can be prepared according to Scheme 21 starting from the trifluoromethanesulfonate intermediate XXXVI described above. Suzuki coupling reactions between XXXVI and the 4,4,5,5-tetramethyl-2-(benzyl)-1,3,2-dioxaborolanes LXII provide naphthylacetic acid methyl ester intermediates XXXVIII. Hydrolysis of the ester groups in XXXVIII affords the naphthylacetic acid compounds of interest 1d.

The Suzuki coupling reactions between XXXVI and the 4,4,5,5-tetramethyl-2-(benzyl)-1,3,2-dioxaborolanes LXII can be performed in the presence of a palladium catalyst such as palladium(II) acetate and in the presence of a phosphine ligand such as 2-dicyclohexyl-phosphino-2',6'-dimethoxybiphenyl (S-Phos). The reactions can be carried out in the presence of an aqueous solution of a base such as potassium phosphate in a suitable solvent such as toluene at reflux temperature for several hours. The 4,4,5,5-tetramethyl-2-(benzyl)-1,3,2-dioxaborolane reagents LXII employed in the Suzuki coupling reactions are commercially available, or they are prepared according to the procedures described in a) Giroux, A. *Tetrahedron Lett.* 44 (2003) 233 and b) Ishiyama, T.; Oohashi, Z.; Ahiko, T.; Miyaura, N. *Chem. Lett.* (2002) 780.

As described above, hydrolysis of esters XXXVIII to give the compounds of interest Id can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

Compounds of interest IC can be prepared by a hydride reduction or partial hydrogenation of the corresponding ketones IA, as illustrated in Scheme 22. Alternatively, IC can be obtained by hydride reduction or partial hydrogenation of keto esters IG, followed by ester hydrolysis of compounds LXIII.

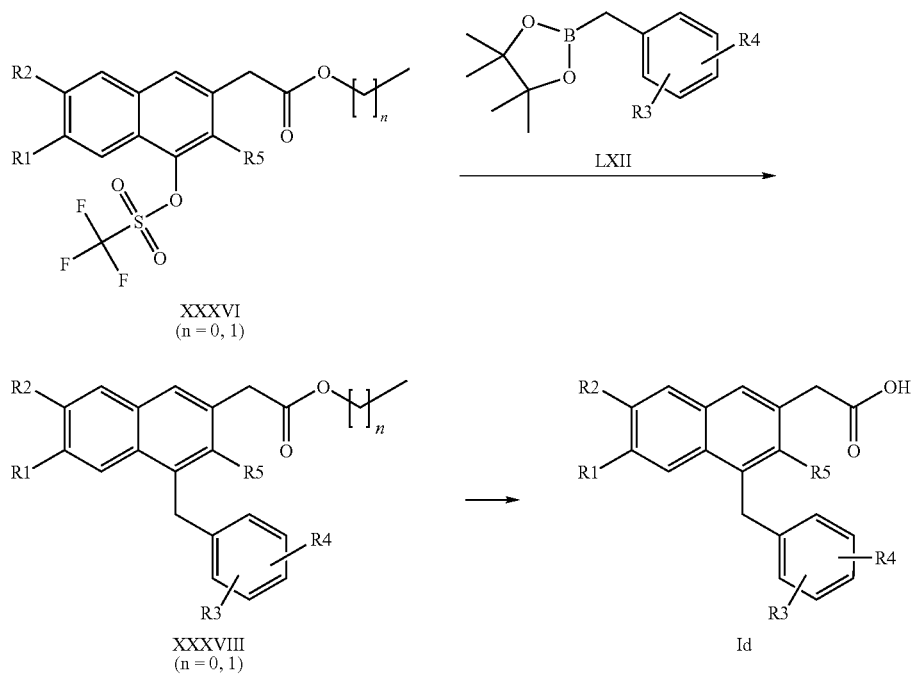

Scheme 21

Scheme 22

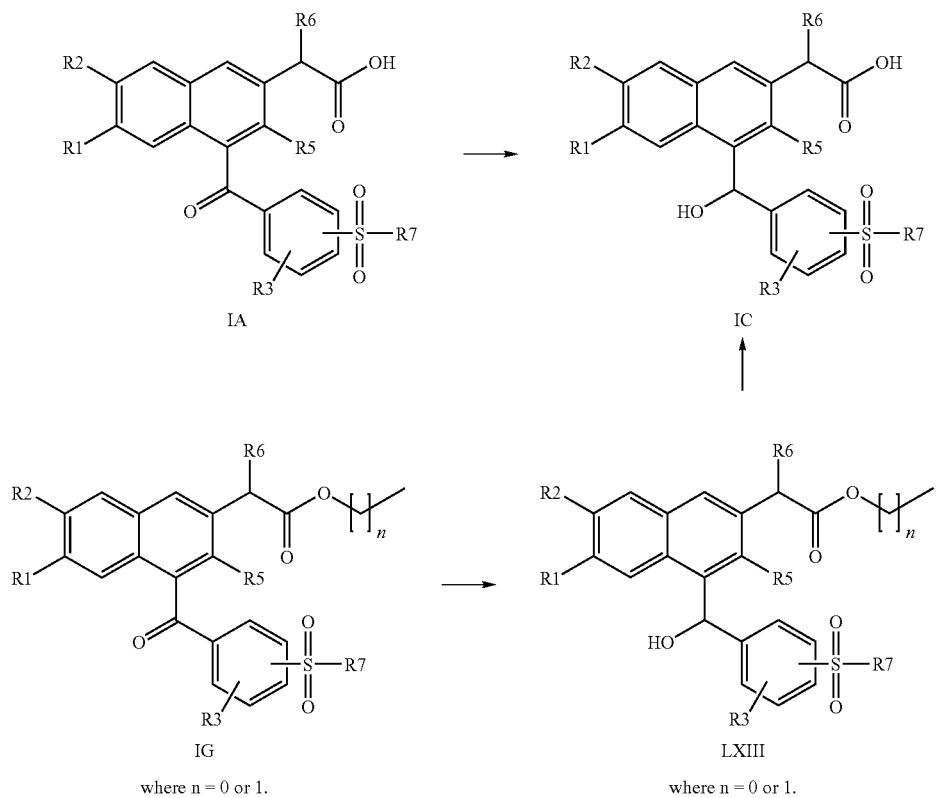

Selective reduction of the ketones IA to the corresponding hydroxyl derivatives IC or keto esters IG to the intermediates LXIII can be achieved using methods which are well known to someone skilled in the art. For example, a mild hydride donor reagent such as sodium borohydride can be used. The reactions can be carried out in a suitable solvent such as tetrahydrofuran, dichloromethane or methanol, at a temperature between 0° C. and room temperature for several hours.

Hydrolysis of ester compounds LXIII to give the compounds of interest IC can be easily accomplished using methods that are well known to someone skilled in the art. For example, the reactions can be carried out in the presence of an aqueous solution of base such as sodium hydroxide or lithium hydroxide, in an inert solvent such as tetrahydrofuran, 1,4-dioxane, water, or mixtures thereof, at a temperature between room temperature and reflux temperature for several hours.

In addition, partial hydrogenation of ketones IA to the compounds of interest IC or keto esters IG to the intermediates LXIII can occur under controlled conditions. The reactions can be carried out in the presence of 10% palladium on carbon under an atmospheric pressure or higher pressure of hydrogen in an alcohol solvent such as ethanol or methanol at about room temperature or mild elevated temperature for several hours. The reaction can be carried out in an atmospheric pressure hydrogenation apparatus, under a balloon of hydrogen gas, in a Parr hydrogenator, or in a continuous-flow hydrogenation reactor (e.g. H-Cube).

Resolution of the racemic alcohols IC into their optically pure enantiomers can be achieved by chiral chromatography.

Scheme 23

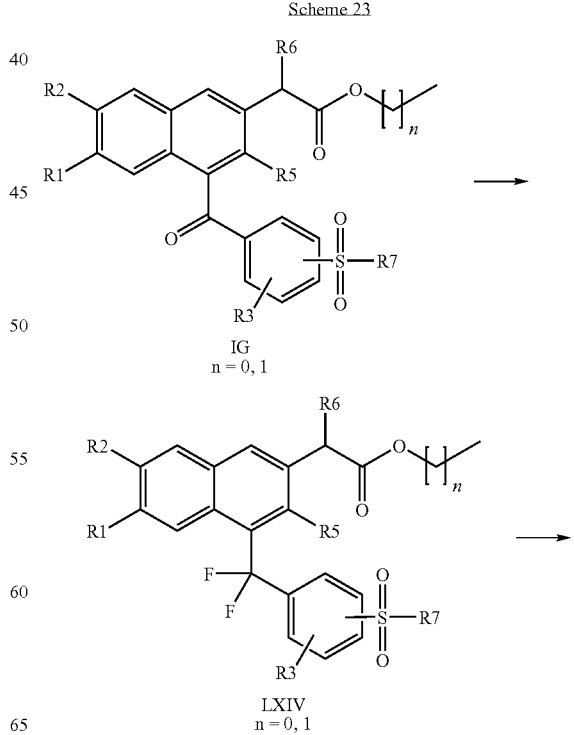

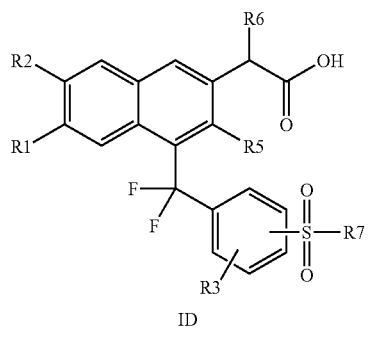

ID

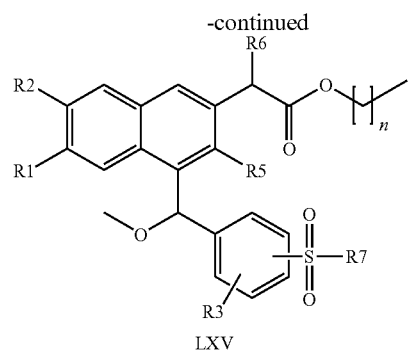

LXV where n = 0 or 1.

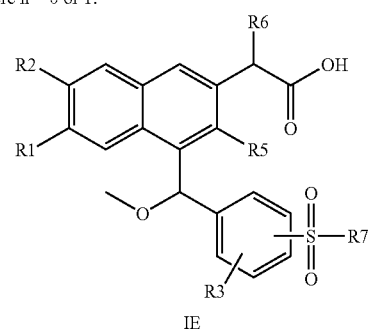

IE

Introduction of the gem-difluoromethyl group to generate compounds ID is shown in Scheme 23. Conversion of the ketones IG to the corresponding gem-difluorides LXIV can be accomplished with nucleophilic fluorinating sources. Hydrolysis of the esters LXIV affords compounds of interest ID.

Transformation of the ketones IG to the gem-difluorides LXIV can be accomplished using nucleophilic fluorinating sources such as diethylaminosulfur trifluoride (DAST), bis(2-methoxyethyl)aminosulfur trifluoride $(CH_3OCH_2CH_2)_2NSF_3$ (Deoxo-Fluor reagent), α,α-difluoroamines or N,N-diethyl-α,α-difluoro-(m-methylbenzyl)amine (DFMBA), either without or with a solvent such as tetrahydrofuran, dichloromethane, or mixtures thereof, at a temperature between room temperature and 180° C. for several hours (reference: Lal, G. S.; Pez, G. P.; Pesaresi, R. J.; Prozonic, F. M.; Cheng, H. *J. Org. Chem.* 64 (1999) 7048).

Hydrolysis of esters LXIV to give the compounds of interest ID can be easily achieved using methods that are well known to someone skilled in the art. For example, the reactions can be carried out in the presence of an aqueous solution of a base such as sodium hydroxide or lithium hydroxide, in an inert solvent such as tetrahydrofuran, 1,4-dioxane, water, or mixtures thereof, at a temperature between room temperature and reflux temperature for several hours.

Compounds of interest IE can be prepared according to Scheme 24. The reaction of alcohols LXIII with methanol under acidic conditions affords the methoxy derivatives LXV. Ester hydrolysis produces compounds IE.

Transformation of the hydroxyl intermediates LXIII to the corresponding methoxy compounds LXV can be accomplished using methods that are well known to one skilled in the art. For instance, the reactions can be readily carried out in the presence of concentrated sulfuric acid as a catalyst in methanol at reflux temperature for several hours.

Hydrolysis of esters LXV to give the compounds of interest IE can be carried out in the presence of an aqueous solution of base such as sodium hydroxide or lithium hydroxide, in an inert solvent such as tetrahydrofuran, 1,4-dioxane, water or mixtures thereof, at a temperature between room temperature and reflux temperature for several hours.

Scheme 24

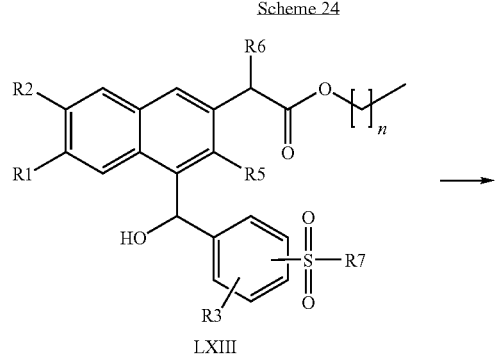

LXIII where n = 0 or 1.

Scheme 25

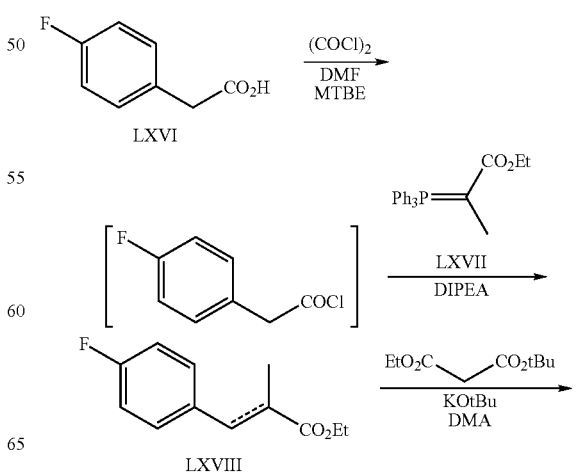

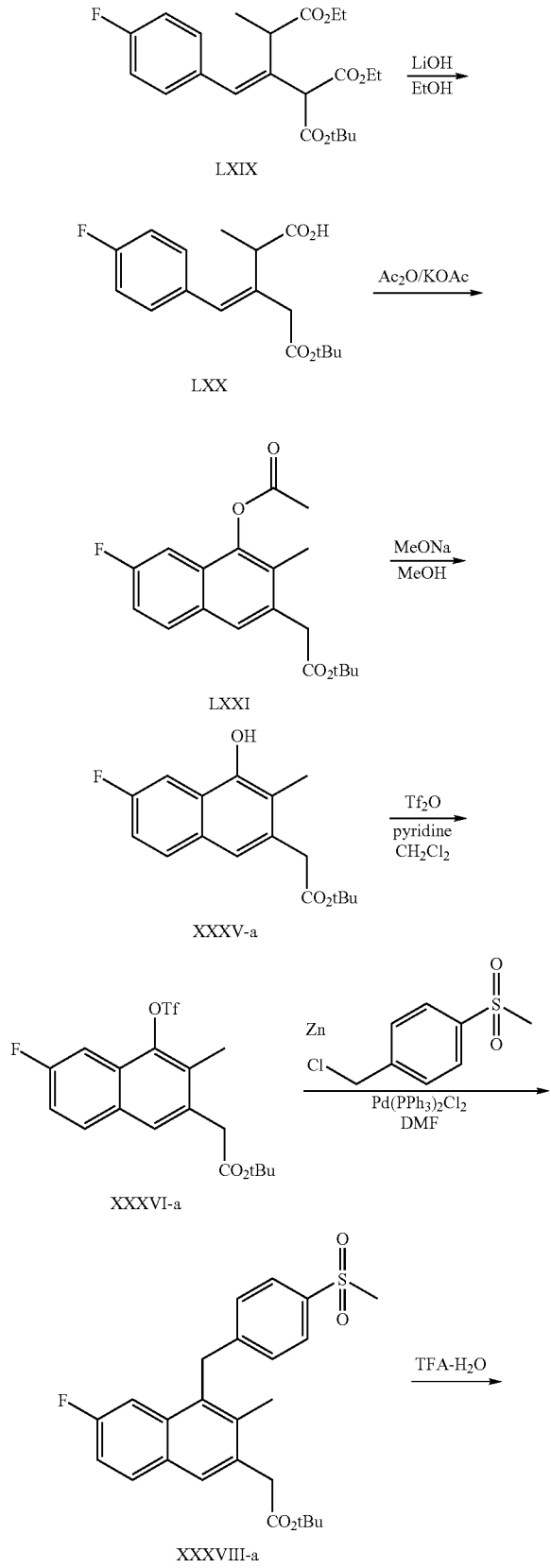

The key intermediate XXXVI-a (which can be used as a replacement for intermediate XXXVI in schemes 9, 11, 13, 20, and 21 to make the compounds of formula Id) can also be prepared as described in Scheme 25. Treatment of (4-fluorophenyl)-acetic acid (LXVI) with oxalyl chloride generates the corresponding acid chloride in situ, which is not isolated, but treated with the Wittig-type reagent LXVII in the presence of a base to produce the allene derivative LXVIII. A conjugate addition reaction of the allene with malonic acid tert-butyl ester ethyl ester produces the tri-ester derivative LXIX, which upon hydrolysis and subsequent decarboxylation generates the acid derivative LXX. Acetic anhydride-promoted cyclization of LXX furnishes the naphthalene derivative Dal, which upon hydrolysis of the acetyl group produces the key intermediate XXXV-a. Treatment of XXXV-a with trifluoromethansulfonic anhydride produces the key intermediate triflate XXXVI-a. A Pd-catalyzed coupling between XXXVI-a and a benzylic zinc reagent (generated in situ) can produce the ester XXXVIII-a, which upon acid-catalyzed hydrolysis furnishes the desired compound Id-a.

The conversion of (4-fluorophenyl)-acetic acid to its corresponding acid chloride derivatives can be performed by methods known in the art. For example, the reaction can be carried out with oxalyl chloride and a catalytic amount of N,N-dimethylformamide (DMF), in an ether solvent, at room temperature. Subsequent treatment of the in situ generated acid chloride with a base such as N,N-diisopropylethylamine will lead to the generation of the corresponding ketene, which upon treatment with a Wittig type reagent such as LXVII in an ether solvent at a temperature between 0-10° C. produces the allene derivative LXVIII.

The conjugate addition reaction between the allene derivative LXVIII and malonic acid tert-butyl ester ethyl ester to produce the tri-ester derivative LXIX is conducted in the presence of a base such as potassium tert-butoxide, in a solvent such as N,N-dimethyl acetamide at room temperature.

The ester hydrolysis of the two ethyl esters in LXIX can be accomplished using methods known in the art. For example, the reaction can be conducted using an aqueous base such as lithium hydroxide, in the presence of a solvent such as ethanol, at room temperature overnight. The subsequent decarboxylation reaction can then be carried out by heating the solution of the resulting diacid at reflux for several hours, to produce LXX.

The cyclization of the unsaturated acid derivative LXX to the naphthalene LXXI can be accomplished as previously described (similar to Scheme 9), in the presence of acetic anhydride and potassium acetate or sodium acetate, at a temperature of about 85° C., for several hours.

The acetate derivative LXXI then undergoes a hydrolysis, upon treatment with a base such as sodium methoxide, in a solvent such as methanol, at room temperature, to produce the phenol intermediate XXXV-a.

The conversion of the phenol XXXV-a to the corresponding triflate XXXVI-a can be accomplished by methods known in the art. For example, the reaction can be carried out using trifluoromethanesulfonic anhydride, in the presence of a base such as pyridine or DMAP, in a solvent such as dichloromethane, at a temperature around 0-25° C.

The Negishi-type Pd-catalyzed coupling reaction of XXXVI-a and the in situ generated zinc reagent prepared from a benzyl chloride such as 1-chloromethyl-4-methanesulfonyl-benzene can be carried out using a Pd catalyst such as dichlorobis(triphenylphosphine)palladium(II), in a solvent such as DMF, at a temperature around 65° C. to produce XXXVIII-a.

The ester hydrolysis of XXXVIII-a to produce the corresponding acid Id-a can be accomplished by methods known in the art. For example, the reaction can be carried out under acid catalysis, using trifluoroacetic acid (TFA) and water, at about 30-35° C.

EXAMPLES

Although certain exemplary embodiments are depicted and described herein, the compounds of the present invention can be prepared using appropriate starting materials according to the methods described generally herein and/or by methods available to one of ordinary skill in the art.

Materials and Instrumentation in General

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 μm, 20×150 mm) from Varian, Inc., an Xbridge™ Prep $C_{18}$ column (5 μm, OBD™ 20×100 mm) from Waters Corporation, or a SunFire™ Prep $C_{18}$ column (5 μm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex® II FTICR with a 4.7 Tesla magnet (from Bruker Corporation), a Waters® Alliance® 2795-ZQ™ 2000 (from Waters Corporation), or an MDS Sciex™ API-2000™ n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz) and a Varian® Inova400 NMR spectrometer (for the $^1$H NMR spectra acquired at 400 MHz) both from Varian Inc. NMR data is provided for a particular intermediate or compound where indicated.

The microwave assisted reactions were carried out in a Biotage Initiator™ Sixty (or early models) (from Biotage AB) or by a CEM Discover® model (with gas addition accessory) (from CEM Corporation).

Continuous flow hydrogenation reactions were performed using an H-Cube® hydrogenation reactor (from Thales Nanotechnology, Inc.).

Ozonolysis reactions were carried out using a Welsbach Ozonator (from Welsbach, a division of Ozone Engineering).

All reactions involving air-sensitive reagents were performed under an inert atmosphere. Reagents were used as received from commercial suppliers unless otherwise noted.

Part I: Preparation of Starting Materials and Intermediates

Preparation of 4-oxo-butyric acid methyl ester

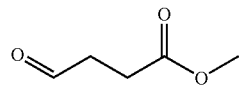

Trifluoroacetic acid (6.0 mL, 81 mmol) was added slowly drop-wise to a stirred solution of methyl 4,4-dimethoxybutyrate (5.0 g, 31 mmol) in dichloromethane (125 mL) and water (13 mL). The reaction mixture was stirred for 16 hours at room temperature. The reaction mixture was then washed with saturated aqueous sodium bicarbonate. The organic layer was dried over sodium sulfate, filtered, and concentrated in vacuo to afford 4-oxo-butyric acid methyl ester (3.03 g, 85%) as a light yellow oil. The crude product was used in subsequent reactions without further purification. $^1$H NMR (300 MHz, CDCl$_3$) δ 9.81 (s, 1 H), 3.69 (s, 3 H), 2.80 (t, 2 H, J=6.64 Hz), 2.63 (t, 2 H, J=6.64 Hz).

Preparation of 4-oxo-butyric acid ethyl ester

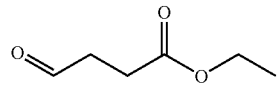

A solution of ethyl 4-octenoate (34 mL, 173 mmol) in methanol (240 mL) was placed in a 3-neck round bottomed flask and cooled at −60° C., and then $O_3/O_2$ was bubbled through the reaction mixture. After 4 hours at ca. −60° C., the reaction mixture had a slight blue tint, and TLC (1:9 ethyl acetate:hexane, stained in phosphomolybdic acid (PMA)) showed no starting material remaining. The reaction mixture was then flushed with $O_2$ for 10 minutes. To the above reaction mixture was added slowly dimethyl sulfide (26 mL, 345 mmol) while maintaining the reaction temperature below −55° C. After the addition was complete, the reaction mixture was allowed to warm to room temperature and stirred overnight. Argon was then bubbled through for 2 hours. The reaction mixture was then concentrated in vacuo. Low pressure fractional distillation afforded 4-oxo-butyric acid ethyl ester (14.3 g, 63%, contained a small amount of dimethyl sulfoxide) as a clear, colorless oil. Alternatively, purification can be accomplished using silica gel chromatography (100% hexanes-20% ethyl acetate in hexane). $^1$H NMR (300 MHz, CDCl$_3$) δ ppm 9.81 (s, 1 H), 4.14 (q, J=7.2 Hz, 2 H), 2.79 (t, J=6.6 Hz, 2 H), 2.62 (t, J=6.6 Hz, 2 H), 1.26 (t, J=7.2 Hz, 3 H).

Preparation of pent-3-ynoic acid methyl ester

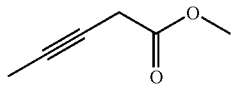

Pent-3-ynoic acid

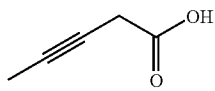

Jones reagent (CrO$_3$—H$_2$SO$_4$) (105 mL of freshly made solution, prepared by combining ice cold H$_2$SO$_4$ (35 mL) with chromium (VI) oxide (35.0 g, 350 mmol) and 100 mL of ice cold water) was added slowly drop-wise to 3-pentyn-1-ol (10 g, 118 mmol) in acetone (800 mL) in a 3-neck round bottomed flask at 0° C. The reaction mixture was allowed to warm to room temperature and stirred for 2 hours. After completion of the reaction, the mixture was cooled at 0° C., and methanol (45 mL) was added in portions. After mechanical stirring for 30 minutes, the reaction mixture was filtered through a pad of celite. The filtrate was concentrated to approximately 20 mL, and then partitioned between water (50 mL) and ethyl acetate (150 mL). The combined organic layers were dried over sodium sulfate, filtered, and concentrated to give the crude product pent-3-ynoic acid (~11.66 g) as a clear oil, which solidified at temperatures below 0° C. The crude product was used in the next step without further purification.

Pent-3-ynoic acid methyl ester

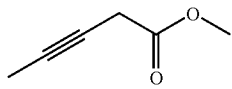

To a solution of pent-3-ynoic acid (11.66 g, 118.8 mmol) in methanol (60 mL), was added 2,2-dimethoxypropane (8 mL, 6.51 mmol), followed by 3 drops of concentrated hydrochloric acid. The reaction mixture was stirred at room temperature for 16 hours. The solvent was removed under reduced pressure. The residue was dissolved in ethyl acetate, and washed with 10% sodium bicarbonate solution, dried over sodium sulfate, filtered, and concentrated in vacuo to give a light yellow oil. Distillation under reduced pressure gave pent-3-ynoic acid methyl ester (5.68 g, 43% over two steps) as a clear, colorless oil. $^1$H NMR (300 MHz, CDCl$_3$) δ ppm 3.73 (s, 3 H), 3.24 (d, J=2.4 Hz, 2 H), 1.83 (t, J=2.4 Hz, 3 H). MS (EI+) cald. for C$_6$H$_8$O$_2$ [M$^+$] 112, obsd. 112.

Preparation of 2-bromo-4,5-difluoro-benzaldehyde

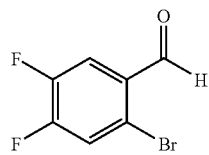

2-Bromo-4,5-difluoro-benzoic acid methyl ester

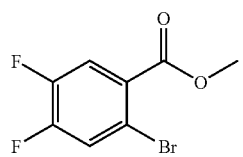

To a solution of 2-bromo-4,5-difluoro-benzoic acid (5 g, 21.10 mmol) in methanol (100 mL) was added concentrated sulfuric acid (0.21 mL, 2.11 mmol) at 0° C. The reaction mixture was then heated at 80° C. for 4 hours. After cooling to room temperature, the mixture was poured into ice water, and extracted with ethyl acetate. The organic layer was washed with saturated sodium bicarbonate, then brine, dried over sodium sulfate, filtered, and concentrated to afford the crude product 2-bromo-4,5-difluoro-benzoic acid methyl ester (1.48 g, 28%) as a clear oil, which was used in the next step without further purification.

(2-Bromo-4,5-difluoro-phenyl)-methanol

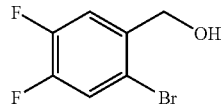

A solution of 2-bromo-4,5-difluoro-benzoic acid methyl ester (1.45 g, 5.78 mmol) in toluene (42 mL) was cooled at −78° C. under nitrogen. Diisobutylaluminum hydride (1 M in toluene) (7.51 mL, 7.51 mmol) was added drop-wise over 20 minutes. The reaction mixture was stirred at −78° C. for another hour, and then allowed to warm to room temperature overnight. The reaction mixture was then cooled to 0° C. and quenched with ethyl acetate, followed by addition of saturated Rochelle's salt solution. The biphasic slurry was then allowed to warm to room temperature and stirred for 2 hours. The organic layer was collected, dried over sodium sulfate, filtered, and concentrated to afford crude (2-bromo-4,5-difluoro-phenyl)-methanol (1.55 g, 90%), which was used in the next step without further purification.

2-Bromo-4,5-difluoro-benzaldehyde

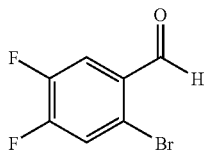

A solution of (2-bromo-4,5-difluoro-phenyl)-methanol (1.23 g, 5.50 mmol), triethylamine (1.39 g, 13.75 mmol) and dimethyl sulfoxide (1.72 g, 22.00 mmol) in dichloromethane (25 mL) was cooled to 0° C. Then, sulfur trioxide-pyridine (1.32 g, 8.25 mmol) was added portionwise. After one hour stirring at 0° C., a second batch of triethylamine (1.39 g, 13.75 mmol), dimethyl sulfoxide (1.72 g, 22.00 mmol) and sulfur trioxide-pyridine (1.32 g, 8.25 mmol) were added to the above reaction mixture. After another 30 minutes at 0° C., the reaction solution was diluted with dichloromethane (50 mL), and then washed with saturated sodium bicarbonate and saturated sodium thiosulfate. The organic phase was dried over sodium sulfate, filtered, and concentrated in vacuo. Flash chromatography (RediSep® Flash column, 230-400 mesh, 10-30% ethyl acetate in hexane) afforded 2-bromo-4,5-difluoro-benzaldehyde (0.47 g, 39%). $^1$H NMR (300 MHz, CDCl$_3$) δ 10.23 (s, 1 H), 7.77 (m, 1 H), 7.52 (m, 1 H).

Preparation of 2-bromo-4-chloro-benzaldehyde

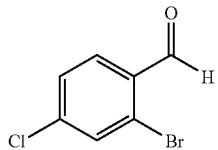

2-Bromo-4-chloro-benzoic acid methyl ester

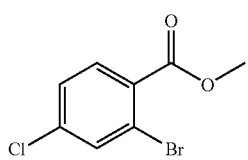

Concentrated sulfuric acid (5 mL) was added drop-wise to an ice-cold mixture of 2-bromo-4-chloro-benzoic acid (10.14 g, 0.0431 mol) and methanol (40 mL). The resulting mixture was heated at reflux for 17 hours. After this time, the reaction mixture was cooled to room temperature, and then poured into ice-cold water (150 mL), creating a white suspension. The suspension was extracted with ethyl acetate (150 mL). The organic phase was washed with saturated aqueous NaHCO$_3$ (100 mL), followed by saturated aqueous NaCl (100 mL). The organic layer was dried over Na$_2$SO$_4$, filtered, and concentrated to afford 2-bromo-4-chloro-benzoic acid methyl ester (10.57 g, 98% yield) as a clear oil.

(2-Bromo-4-chloro-phenyl)-methanol

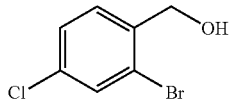

A 1.0 M solution of diisobutylaluminum hydride in toluene (43 mL, 0.043 mol) was added slowly drop-wise to a −78° C. solution of 2-bromo-4-chloro-benzoic acid methyl ester (10.57 g, 0.042 mol) in toluene (50 mL) and hexanes (425 mL). The reaction mixture was stirred at −78° C. for 1.5 hours. After this time, a white solid had precipitated out of solution. The reaction mixture was quenched at −78° C. with ethyl acetate (100 mL). Saturated aqueous sodium potassium tartrate was added, and the reaction mixture was warmed to room temperature. The organic phase was separated, dried over Na$_2$SO$_4$, filtered, and concentrated to a clear oil. TLC (30% ethyl acetate/hexanes) and $^1$H NMR revealed a mixture with unreacted 2-bromo-4-chloro-benzoic acid methyl ester as the major component. The crude material was dissolved in toluene (300 mL), and the resulting solution was cooled to −78° C. A 1.0 M solution of diisobutylaluminum hydride in toluene (55 mL, 0.055 mol) was added slowly drop-wise to the reaction mixture. The reaction mixture was warmed to −45° C. and stirred at this temperature for 35 minutes. At this time, TLC (10% ethyl acetate/hexanes) indicated nearly complete consumption of the starting material. The reaction mixture was quenched at −45° C. with ethyl acetate. Saturated aqueous sodium potassium tartrate was added, and the reaction mixture was warmed to room temperature and stirred at room temperature for 1 hour. The organic phase was separated, dried over Na$_2$SO$_4$, and concentrated to a yellow oil. A solution of this crude product and dichloromethane (200 mL) was evaporated onto silica gel, and the dry silica gel-supported product was loaded onto a 120 g silica gel column. Flash chromatography was carried out using an ISCO purification system (95:5 hexanes-ethyl acetate ramped to 4:1 hexanes-ethyl acetate). (2-Bromo-4-chloro-phenyl)-methanol was isolated as 5.57 g (60% yield) of a white solid.

2-Bromo-4-chloro-benzaldehyde

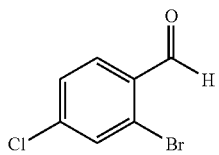

To a 0° C. solution of (2-bromo-4-chloro-phenyl)-methanol (5.57 g, 0.025 mol), dichloromethane (250 mL), diisopropylethylamine (22 mL, 0.126 mol), and dimethyl sulfoxide (15 mL, 0.211 mol) was added sulfur trioxide-pyridine (12.0 g, 0.075 mol), in portions, over 15 minutes. The resulting solution was stirred at 0° C. for 45 minutes. The reaction mixture was diluted with 250 mL dichloromethane, then washed with saturated aqueous NaHCO$_3$ (500 mL). The organic phase was washed with saturated aqueous sodium thiosulfate (500 mL) to reduce excess oxidant. The organic phase was dried over Na$_2$SO$_4$, filtered and concentrated to afford a yellow oily solid. A solution of this crude product and CH$_2$Cl$_2$ (200 mL) was evaporated onto silica gel, and the dry silica gel-supported product was loaded onto a 120 g silica gel column. Flash chromatography was carried out using an ISCO purification system (95:5 hexanes-ethyl acetate). 2-Bromo-4-chloro-benzaldehyde was isolated as 4.43 g (81% yield) of a white solid. $^1$H NMR (300 MHz, CDCl$_3$) δ ppm 10.31 (s, 1 H), 7.88 (d, J=8.2 Hz, 1 H), 7.69 (d, J=1.6 Hz, 1 H), 7.44 (dd, J=8.2, 1.6 Hz, 1 H).

Preparation of trifluoromethanesulfonic acid 2-formyl-5-methoxy-phenyl ester

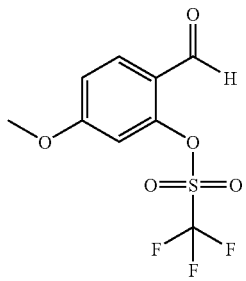

A mixture of 2-hydroxy-4-methoxybenzaldehyde (30.0 g, 154 mmol) and N-phenylbis(trifluoromethanesulfonimide) (78.1 g, 214 mmol) in dichloromethane (200 mL) was cooled to 0° C. in an ice bath. Triethylamine (31 mL) was added slowly via an addition funnel while maintaining the reaction temperature below 3° C. The reaction mixture was stirred at 0° C. for 20 minutes, and then allowed to warm to room temperature and stirred overnight. The solvent was removed under reduced pressure. To the residue, diethyl ether (600 mL) was added, and the resulting mixture was subsequently washed with water, 1.0 N aqueous sodium hydroxide, water, and brine, then dried over magnesium sulfate, filtered, and concentrated to give the crude product (62.59 g) as an oil. Flash chromatography (RediSep® Flash column, 230-400 mesh, 10%-60% dichloromethane in hexane) afforded 52.8 g (95% yield) of trifluoromethanesulfonic acid 2-formyl-5-methoxy-phenyl ester as a light yellow oil. $^1$H NMR (300 MHz, CDCl$_3$) δ ppm 10.13 (s, 1 H), 7.96 (d, J=8.8 Hz, 1 H), 7.04 (d, J=8.8 Hz, 1 H), 6.88 (s, 1 H), 3.93 (s, 3 H).

Preparation of 2-iodo-4-trifluoromethyl-benzaldehyde

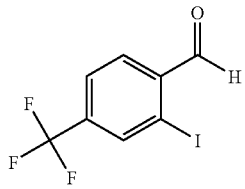

2-Amino-4-trifluoromethyl-benzonitrile

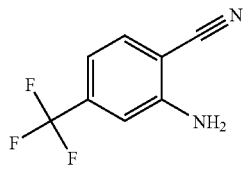

Zinc dust (30 g) was added in portions to a 5° C. solution of 2-nitro-4-trifluoromethyl-benzonitrile (3.0 g, 14 mmol) in glacial acetic acid (260 mL). The reaction mixture was allowed to warm to room temperature, then stirred at room temperature for 1 hour. The reaction mixture was filtered through a celite plug, and the celite layer was washed with glacial acetic acid. The combined filtrate and washings were concentrated to afford 2-amino-4-trifluoromethyl-benzonitrile as an oily, orange solid which was used in subsequent reactions without additional purification.

2-Iodo-4-trifluoromethyl-benzonitrile

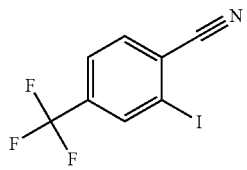

Potassium iodide (5.6 g, 34 mmol) and sodium nitrite (2.4 g, 35 mmol) were added to a solution of 2-amino-4-trifluoromethyl-benzonitrile (2.58 g, 14 mmol) in acetonitrile (60 mL). The resultant mixture was cooled to 0° C. in an ice-water bath with magnetic stirring. Ice-cold concentrated HCl (14 mL) was added slowly drop-wise to the reaction mixture, causing the reaction mixture to become cloudy and deep red in color. The reaction mixture was stirred at 0° C. for 30 minutes, then warmed to room temperature. Stirring at room temperature proceeded for 3 hours. The reaction mixture was poured into water, and the resulting suspension was extracted with ethyl acetate. The organic layer was dried (Na$_2$SO$_4$), filtered, and concentrated to give a purple liquid. A solution of this crude product and dichloromethane (200 mL) was evaporated onto silica gel, and the dry silica gel-supported product was loaded onto a silica gel column. Manual flash chromatography using 5% ethyl acetate in hexanes afforded 2-iodo-4-trifluoromethyl-benzonitrile as 3.58 g (87%) of a purple, crystalline solid.

2-Iodo-4-trifluoromethyl-benzaldehyde

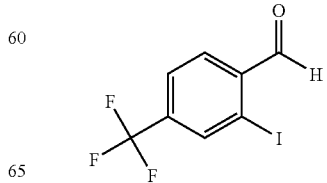

A 1.0 M solution of diisobutylaluminum hydride in toluene (13 mL, 13 mmol) was added slowly drop-wise to a 0° C. solution of 2-iodo-4-trifluoromethyl-benzonitrile (3.58 g, 12 mmol) in toluene (11 mL). The reaction mixture was stirred at 0° C. for 30 minutes. The reaction mixture was warmed to room temperature, then stirred at room temperature for 24 hours. The reaction mixture was cooled to 0° C., then ethyl acetate (5 mL), and ethanol (5 mL) were added dropwise to the cold reaction mixture. After stirring at 0° C. for 10 minutes, the reaction mixture was concentrated to give a yellow, oily liquid. The residue was cooled to 0° C. Methylene chloride (10 mL) was added. Water (10 mL) was added slowly drop-wise, then 1.0 N aqueous HCl was added slowly drop-wise. After stirring at 0° C. for 10 minutes, concentrated HCl (1 mL) was added followed by additional methylene chloride (60 mL). The mixture was stirred at 0° C. for 10 minutes, then warmed to room temperature. Stirring at room temperature continued for 105 minutes. The mixture was poured into a separatory funnel, and the organic phase was separated, dried over $Na_2SO_4$, filtered, and concentrated to an oily, yellow solid. The crude product was purified using flash chromatography (RediSep® Flash column, 230-400 mesh, 0-3% ethyl acetate in hexanes) to give 1.44 g (40%) of 2-iodo-4-trifluoromethyl-benzaldehyde as a slightly yellow solid. $^1$H NMR (300 MHz, $CDCl_3$) δ ppm 10.11 (s, 1 H), 8.20 (s, 1 H), 7.97 (d, J=8.2 Hz, 1 H), 7.73 (d, J=8.2 Hz, 1 H).

Preparation of
2-chloro-1-iodo-4-methanesulfonyl-benzene

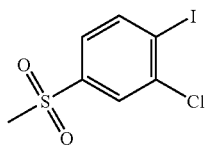

A solution of 2-chloro-4-(methanesulfonyl)aniline (25 g, 122 mmol) in acetonitrile (500 mL) was cooled to 0° C., then sodium nitrite (20.97 g, 303.9 mmol) and potassium iodide (50.45 g, 303.9 mmol) were added. After the reaction mixture was stirred for 30 minutes at 0° C., concentrated hydrochloric acid (50 mL) was added drop-wise via an addition funnel. The reaction was stirred at 0° C. for an additional 45 minutes. The reaction mixture was warmed to room temperature, then stirred for 2.5 hours. The reaction mixture was poured into ice water (800 mL), and extracted with dichloromethane. The organic layer was washed with water, dried over sodium sulfate, filtered, and concentrated. Flash chromatography (RediSep® Flash column, 230-400 mesh, 10%-35% ethyl acetate in hexane) gave 2-chloro-1-iodo-4-methanesulfonyl-benzene (13.88 g, 36%). $^1$H NMR (300 MHz, $CDCl_3$) δ ppm 8.11 (d, J=8.4 Hz, 1 H), 8.00 (d, J=1.9 Hz, 1 H), 7.51 (dd, J=8.4, 1.9 Hz, 1 H), 3.07 (s, 3 H).

Preparation of 1-bromo-4-methanesulfonyl-2-methyl benzene

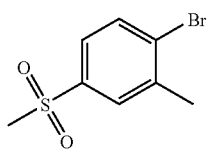

1-Bromo-4-methanesulfanyl-2-methyl benzene

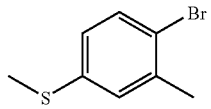

To a solution of 1-methyl-3-methanesulfanyl benzene (20 g, 145 mmol) in glacial acetic acid (68 mL) was added bromine (12.5 mL, 243.98 mmol) drop-wise at 0° C. The reaction mixture was then allowed to warm up to room temperature and stirred for 4 hours. The solvent was evaporated under reduced pressure. Flash chromatography (J. T. Baker silica gel, 60-200 mesh, 100% hexane) gave 1-bromo-4-methanesulfanyl-2-methyl benzene (30.5 g, 97%) as a clear, colorless oil.

1-Bromo-4-methanesulfonyl-2-methyl benzene

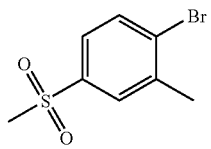

To a solution of 1-bromo-4-methanesulfanyl-2-methyl benzene (30.5 g, 140 mmol) in dichloromethane (450 mL) was added 3-chloroperoxybenzoic acid (m-CPBA) (72 g, 420 mmol) in portions over 40 minutes at 0° C. The reaction mixture was then warmed to room temperature and stirred for 2 hours. To the reaction mixture, was added 10% sodium sulfite solution. The organic layer was separated, dried over sodium sulfate, filtered, and concentrated to give a white solid. Flash chromatography (J. T. Baker silica gel, 60-200 mesh, 15-20% ethyl acetate in hexane) furnished 1-bromo-4-methanesulfonyl-2-methyl benzene (20.34 g, 58%) as a white crystalline solid. $^1$H NMR (400 MHz, $CDCl_3$) δ ppm 7.80 (d, J=1.9 Hz, 1 H), 7.74 (d, J=8.3 Hz, 1 H), 7.61 (dd, J=8.3, 1.9 Hz, 1 H), 3.04 (s, 3 H), 2.50 (s, 3 H). HRMS (EI+) cald. for $C_8H_9BrO_2S$ [M$^+$] 247.9507, obsd. 247.9508.

Preparation of
1-bromo-2-fluoro-4-methanesulfonyl-benzene

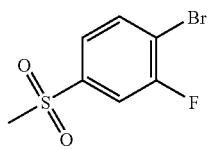

To a solution of 1-bromo-2-fluoro-4-methanesulfanyl-benzene (1 g, 4.52 mmol) in dichloromethane (15 mL) was added 3-chloroperoxybenzoic acid (m-CPBA) (2 g, 11.30 mmol). The reaction mixture was stirred at room temperature overnight. To the reaction mixture was added a 10% aqueous solution of sodium sulfite. The organic layer was separated, dried over sodium sulfate, filtered, and concentrated in vacuo. Flash chromatography (RediSep® Flash column, 230-400 mesh, 5-40% ethyl acetate in hexane) gave 1-bromo-2-fluoro-4-methanesulfonyl-benzene (1 g, 88%) as a white solid. ¹H NMR (300 MHz, CDCl₃) δ ppm 7.76-7.87 (m, 1 H), 7.68-7.75 (m, 1 H), 7.64 (d, J=8.2 Hz, 1 H), 3.08 (s, 3 H).

Preparation of
1-bromo-2-chloro-4-ethanesulfonyl-benzene

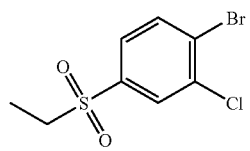

1-Chloro-3-ethanesulfanyl-benzene

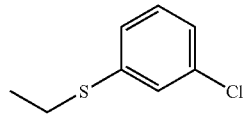

A mixture of 3-chlorobenzenethiol (1.5 g, 10.37 mmol), iodoethane (0.837 mL, 10.37 mmol) and potassium carbonate (4.1 g, 31.11 mmol) in N,N-dimethylformamide (20 mL) was stirred at room temperature overnight. Ice water was added, and the resulting mixture was extracted with diethyl ether (3×). The organic layers were combined, washed with water and brine, dried over sodium sulfate, filtered, and concentrated to give 1-chloro-3-ethanesulfanyl-benzene (1.14 g, 64%), which was used in the next step without further purification.

1-Bromo-2-chloro-4-ethanesulfanyl-benzene

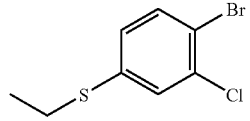

To a solution of 1-chloro-3-ethanesulfanyl-benzene (1.14 g, 6.63 mmol) in acetic acid (10 mL) was added bromine (338 μL, 6.63 mmol) at 0° C. The mixture was then allowed to warm to room temperature and stirred overnight. To the reaction mixture was added ethyl acetate, and the resulting solution was subsequently washed twice with water, then saturated sodium bicarbonate, dried over sodium sulfate, filtered, and concentrated in vacuo. Flash chromatography (RediSep® Flash column, 230-400 mesh, 0-12.5% ethyl acetate in hexane) gave 1-bromo-2-chloro-4-ethanesulfanyl-benzene (1.4 g, 85%).

1-Bromo-2-chloro-4-ethanesulfonyl-benzene

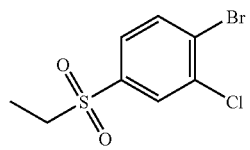

To a solution of 1-bromo-2-chloro-4-ethanesulfanyl-benzene (1.4 g, 5.60 mmol) in dichloromethane (10 mL) was added 3-chloroperoxybenzoic acid (m-CPBA) (2.4 g, 14 mmol). The reaction mixture was stirred at room temperature overnight. The solid was filtered off, and the filtrate was concentrated to afford 1-bromo-2-chloro-4-ethanesulfonyl-benzene (1.4 g, 89%) as a white solid, which was used without further purification. ¹H NMR (300 MHz, CDCl₃) δ ppm 7.98 (d, J=2.1 Hz, 1 H), 7.84 (d, J=8.5 Hz, 1 H), 7.64 (dd, J=8.5, 2.1 Hz, 1 H), 3.13 (q, J=7.5 Hz, 2 H), 1.30 (t, J=7.5 Hz, 3 H).

Preparation of
4-bromo-2-ethyl-1-methanesulfonyl-benzene

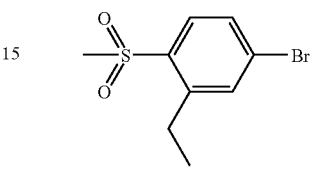

To a mixture of sodium sulfite (4.44 g, 35.3 mmol) and sodium bicarbonate (2.96 g, 35.3 mmol) in water (100 mL) at 70° C. was added 4-bromo-2-ethyl-benzenesulfonyl chloride (5 g, 17.6 mmol) in dioxane (20 mL) drop-wise via an addition funnel. After an hour, the mixture was heated at 100° C. and bromoacetic acid (4.90 mL, 35.3 mmol) was added. After an hour, the reaction mixture was cooled to 90° C., and sodium hydroxide (2.82 g, 70.5 mmol) was added. The resulting mixture was stirred at 90° C. overnight. After cooling to room temperature, water was added to the resulting suspension. The aqueous layer was extracted with dichloromethane (250 mL×3). The collected organic layers were washed with brine, dried over sodium sulfate, filtered, and concentrated to give 4-bromo-2-ethyl-1-methanesulfonyl-benzene (4.62 g, 100%), which was used in the next step without further purification. ¹H NMR (300 MHz, CDCl₃) δ ppm 7.89 (d, J=8.5 Hz, 1 H), 7.56 (d, J=1.5 Hz, 1 H), 7.51 (dd, J=8.5, 1.5 Hz, 1 H), 3.07 (s, 3 H), 3.05 (q, J=7.4 Hz, 2 H), 1.33 (t, J=7.4 Hz, 3 H).

Preparation of 4-bromo-1-methanesulfonyl-2-trifluoromethyl-benzene

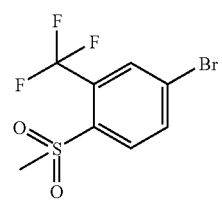

4-Bromo-1-methanesulfanyl-2-trifluoromethyl-benzene

To a solution of 4-bromo-1-fluoro-2-(trifluoromethyl)benzene (5 g, 20.58 mmol) in N,N-dimethylformamide (20 mL)

was added sodium thiomethoxide (1.58 g, 22.54 mmol) at room temperature. The resulting solution was heated at 50° C. for 1 hour, then stirred at room temperature for 16 hours. The reaction mixture was poured into cold water. The resulting suspension was extracted with ethyl acetate. The organic layer was dried over sodium sulfate, filtered, and concentrated to afford the crude 4-bromo-1-methanesulfanyl-2-trifluoromethyl-benzene (5.5 g) which was used in the next step without further purification.

4-Bromo-1-methanesulfonyl-2-trifluoromethyl-benzene

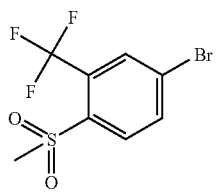

To a solution of 4-bromo-1-methanesulfanyl-2-trifluoromethyl-benzene (5.5 g, 20.29 mmol) in dichloromethane (62 mL) was added 3-chloroperoxybenzoic acid (m-CPBA) (10.5 g, 60.9 mmol) in portions at 0° C. over 30 minutes. The reaction mixture was then allowed to warm to room temperature, and stirred at this temperature for 16 hours. The reaction was poured into 10% aqueous sodium sulfite solution. The organic layer was separated, dried over sodium sulfate, filtered, and concentrate in vacuo. Column chromatography (Biotage, 230-400 mesh, 20% ethyl acetate in hexane) gave 4-bromo-1-methanesulfonyl-2-trifluoromethyl-benzene (4.79 g, 78% over two steps). $^1$H NMR (300 MHz, CDCl$_3$) δ ppm 8.18 (d, J=8.5 Hz, 1 H), 8.04 (s, 1 H), 7.92 (d, J=8.5 Hz, 1 H), 3.18 (s, 3 H). HRMS (EI+) cald. for C$_8$H$_6$BrF$_3$O$_2$S [M$^+$] 301.9225, obsd. 301.9223.

Preparation of 1-bromo-4-ethanesulfonyl-2-methyl benzene

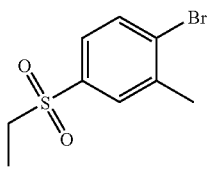

1-Methyl-3-ethanesulfanyl-benzene

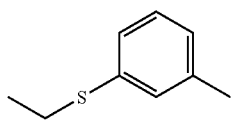

A mixture of 3-methyl-benzenethiol (25 g, 0.20 mol), iodoethane (16.1 mL, 0.20 mmol) and potassium carbonate (27.7 g, 0.201 mmol) in N,N-dimethylformamide (200 mL) was stirred at 0° C. over 30 minutes. The reaction mixture was allowed to slowly warm to room temperature, and then stirred at room temperature overnight. The reaction mixture was poured into water, and the resulting suspension was extracted with ethyl acetate The organic phase was dried over sodium sulfate, filtered, and concentrated to give 1-methyl-3-ethanesulfanyl-benzene, which was used in the next step without further purification.

1-Bromo-4-ethanesulfanyl-2-methyl benzene

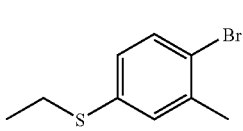

A solution of 1-methyl-3-ethanesulfanyl benzene (32.97 g, 0.217 mol) in glacial acetic acid (100 mL) was cooled in an ice-water bath. Bromine (14 mL, 0.238 mol) was added dropwise to the ice-cold reaction mixture over the course of 1 hour. The reaction mixture was then allowed to warm to room temperature and stirred at room temperature for 6 hours. The solvent was evaporated under reduced pressure. Flash chromatography (J. T. Baker silica gel, 60-120 mesh, 100% heptane) gave 1-bromo-4-ethanesulfanyl-2-methyl benzene (33.41 g, 67%) as a light tan oil.

1-Bromo-4-ethanesulfonyl-2-methyl benzene

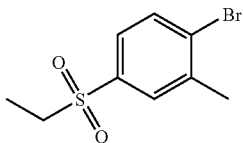

To a solution of 1-bromo-4-ethanesulfanyl-2-methyl benzene (17.01 g, 73.6 mmol) in dichloromethane (373 mL) was added 3-chloroperoxybenzoic acid (m-CPBA) (59 g, 342 mmol) in portions over 60 minutes at 0° C. The reaction mixture was then slowly warmed to room temperature and stirred overnight. The reaction mixture was washed with saturated aqueous NaHCO$_3$, followed by an aqueous 10% sodium sulfite solution. The organic layer was dried over sodium sulfate, filtered, and concentrated to give an oily, yellow solid. Flash chromatography (RediSep® Flash column, 230-400 mesh, 15% ethyl acetate in hexane) furnished 1-bromo-4-ethanesulfonyl-2-methyl benzene (9.5 g, 49%) as a white crystalline solid. MS (EI+) cald. for C$_9$H$_{11}$BrO$_2$S [M$^+$] 263, obsd. 263.

Preparation of 1-bromo-4-N,N-diethylbenzenesulfonamide

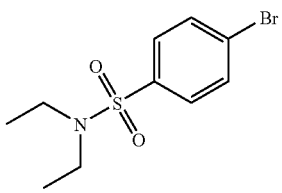

Diisopropylethylamine (10.47 mL, 58.79 mmol) was added at 0° C. to a stirred solution of diethyl amine (1.7 g, 23.5 mmol) in tetrahydrofuran (50 mL) and the reaction mixture was stirred at room temperature for 15 minutes. A 0.1 M solution of 4-bromo-benzenesulfonyl chloride (6.01 g, 23.5 mmol) in tetrahydrofuran was added at room temperature and the reaction mixture was stirred at room temperature for 2 hours. The solvent was evaporated off under reduced pressure. The residue was diluted with ethyl acetate, and the inorganic salts were filtered through a celite bed. The filtrate was washed with 2 N aqueous HCl, dried over anhydrous sodium sulfate, filtered, and concentrated in vacuo to afford 1-bromo-4-N,N,-diethylbenzenesulfonamide, which was used in subsequent reactions without further purification. MS cald. for $C_{10}H_{14}BrNO_2S$ [M+] 292, obsd 293.

Preparation of 1-(4-bromobenzenesulfonyl)-piperidine

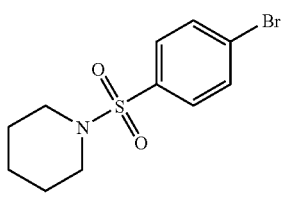

Diisopropylethylamine (2.09 mL, 11.7 mmol) was added at 0° C. to a stirred solution of piperidine (0.40 g, 4.7 mmol) in tetrahydrofuran (10 mL) and the reaction mixture was stirred at room temperature for 15 minutes. A 0.1 M solution of 4-bromo-benzenesulfonyl chloride (1.20 g, 4.7 mmol) in tetrahydrofuran was added at room temperature and the reaction mixture was stirred at room temperature for 2 hours. The solvent was evaporated off under reduced pressure. The residue was diluted with ethyl acetate, and the inorganic salts were filtered through a celite bed. The filtrate was washed with 2 N aqueous HCl, dried over anhydrous sodium sulfate, filtered, and concentrated in vacuo to afford 1-(4-bromobenzenesulfonyl)-piperidine, which was used in subsequent reactions without further purification. MS cald. for $C_{11}H_{14}BrNO_2S$ [M+] 304, obsd. 304.

Preparation of 1-(4-bromobenzenesulfonyl)-4-(2-fluoro-phenyl)-piperazine

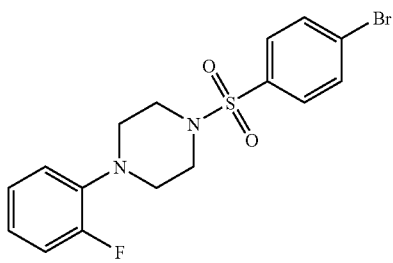

Triethylamine (1.37 mL, 9.78 mmol) was added at 0° C. to a stirred solution of 1-(2-fluorophenyl)piperazine (0.705 g, 3.91 mmol) in tetrahydrofuran (12 mL) and the reaction mixture was stirred at room temperature for 15 minutes. 4-Bromo-benzenesulfonyl chloride (1.00 g, 3.91 mmol) was added to the reaction mixture at room temperature and the reaction mixture was stirred at room temperature for 5 hours. Tetrahydrofuran was evaporated off under reduced pressure. The residue was diluted with ethyl acetate (20 mL), and the inorganic salts were filtered through a celite bed. The filtrate was washed with 2.0 N aqueous HCl (8 mL), dried over anhydrous sodium sulfate and concentrated in vacuo to provide 1.40 g (89%) of 1-(4-bromobenzenesulfonyl)-4-(2-fluoro-phenyl)piperazine as white solid. MS cald. for $C_{16}H_{16}BrFN_2O_2S$ [M+] 399, obsd. 399.

Preparation of 4-(4-bromo-3-methyl-benzenesulfonyl)-morpholine

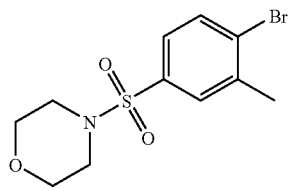

Diisopropylethylamine (8.25 mL, 46.4 mmol) was added at 0° C. to a stirred solution of morpholine (1.62 g, 18.5 mmol) in tetrahydrofuran (40 mL) and the reaction mixture was stirred at room temperature for 15 minutes. A 0.1 M solution of 4-bromo-3-methyl-benzenesulfonyl chloride (5.0 g, 19 mmol) in tetrahydrofuran was added at room temperature and the reaction mixture was stirred at room temperature for 2 hours. The solvent was evaporated off under reduced pressure. The residue was diluted with ethyl acetate, and the inorganic salts were filtered through a celite bed. The filtrate was washed with 2 N aqueous HCl, dried over anhydrous sodium sulfate, filtered, and concentrated in vacuo to afford 4-(4-bromo-3-methyl-benzenesulfonyl)-morpholine, which was used in subsequent reactions without further purification. MS cald. for $C_{11}H_{14}BrNO_3S$ [M+] 320.2, obsd. 321.9.

Preparation of 4-bromo-3-methyl-N,N-dimethyl-benzenesulfonamide

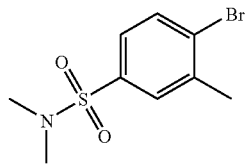

Diisopropylethylamine (4.95 mL, 27.8 mmol) was added at 0° C. to a stirred solution of dimethylamine (3.70 mL, 55.6 mmol) in tetrahydrofuran (25 mL) and the reaction mixture was stirred at room temperature for 15 minutes. A 0.1 M solution of 4-bromo-3-methyl-benzenesulfonyl chloride (3.0 g, 11 mmol) in tetrahydrofuran was added at room temperature and the reaction mixture was stirred at room temperature for 2 hours. The solvent was evaporated off under reduced pressure. The residue was diluted with ethyl acetate, and the inorganic salts were filtered through a celite bed. The filtrate was washed with 2 N aqueous HCl, dried over anhydrous sodium sulfate, filtered, and concentrated in vacuo to afford 2.90 g (94%) of 4-bromo-3-methyl-N,N-dimethyl-benzenesulfonamide, which was used in subsequent reactions without further purification. MS calcd. for $C_9H_{12}BrNO_2S$ [M⁺] 278.2, obsd. 280.0.

Preparation of 4-bromo-3-methyl-N-methyl-benzenesulfonamide

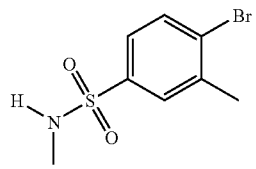

Methylamine (2.0 M in tetrahydrofuran, 46.37 mL, 92.75 mmol) was added to a stirred solution of 4-bromo-3-methyl-benzenesulfonyl chloride (5.0 g, 19 mmol) in tetrahydrofuran at 0° C., and the reaction mixture was stirred at room temperature for 3 h. The reaction mixture was concentrated under reduced pressure, diluted with ethyl acetate (50 mL), washed with 2.0 N aqueous HCl (20 mL), dried over anhydrous sodium sulfate and concentrated under reduced pressure to provide 4-bromo-3-methyl-N-methyl-benzenesulfonamide (4.2 g, 85.7%) as a white solid. MS calcd. for $C_8H_{10}BrNO_2S$ [M⁺] 264.1, obsd. 263.9.

Preparation of 3-(methanesulfonyl)benzyl chloride

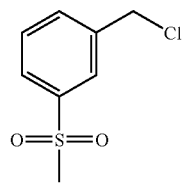

3-Methanesulfanyl benzoic acid methyl ester

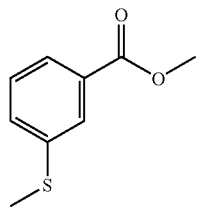

Concentrated sulfuric acid (3.4 mL) was added drop-wise to an ice cold mixture of 3-methanesulfanyl benzoic acid (5.0 g, 30 mmol) and methanol (30 mL). After the addition was complete, the reaction mixture was warmed to room temperature, then stirred overnight. The reaction mixture was concentrated in vacuo. The resulting oil was diluted with ethyl acetate, and then washed with water followed by saturated sodium bicarbonate. The organic phase was dried over $MgSO_4$, filtered, and concentrated to give 5.4 g of 3-methanesulfanyl benzoic acid methyl ester as a clear oil. This crude product was used in subsequent steps without further purification.

(3-Methanesulfanyl-phenyl)-methanol

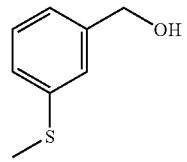

A 1.0 M solution of diisobutylaluminum hydride in toluene (90 mL, 90 mmol) was added rapidly drop-wise to a −78° C. solution of 3-methanesulfanyl benzoic acid methyl ester (5.4 g, 30 mmol) in toluene (150 mL). The reaction mixture was stirred at −78° C. for 1 hour, then warmed to room temperature. After stirring at room temperature for 18 hours, the reaction mixture was cooled to 0° C. Ethyl acetate (100 mL) was added carefully to quench the excess diisobutylaluminum hydride. The mixture was combined with a saturated aqueous solution of sodium potassium tartrate (300 mL), then stirred at room temperature for 1.5 hours. The organic phase was separated, dried over $MgSO_4$, filtered, and evaporated to afford 4.57 g of (3-methanesulfanyl-phenyl)-methanol as a clear oil. This crude product was used in subsequent steps without further purification.

(3-Methanesulfonyl-phenyl)-methanol

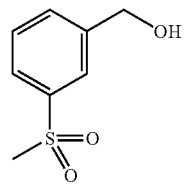

To a 0° C. solution of (3-methanesulfanyl-phenyl)-methanol (4.57 g, 30 mmol) in dichloromethane (100 mL) was added m-chloroperoxybenzoic acid (16 g, 93 mmol), in portions over the course of 1 hour. The reaction mixture was allowed to warm to room temperature, then stirred for 24 hours. The reaction mixture was washed with a saturated aqueous solution of sodium sulfite followed by a saturated aqueous solution of sodium bicarbonate. The organic phase was dried over $Na_2SO_4$, filtered, and evaporated. Flash chromatography (Analogix SuperFlash™ column, 35%-50% ethyl acetate in hexanes) gave 2.68 g (49% over three steps) of (3-methanesulfonyl-phenyl)-methanol as a white solid.

3-(Methanesulfonyl)benzyl chloride

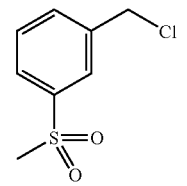

Triphenylphosphine (7.5 g, 29 mmol), carbon tetrachloride (11.0 mL, 114 mmol) and tetrahydrofuran (18 mL) were combined and stirred at room temperature for 10 minutes. A suspension of (3-methanesulfonyl-phenyl)-methanol (2.68 g, 14.3 mmol) in 18 mL tetrahydrofuran was added, then the reaction mixture was heated at 75° C. for 3 hours. The reaction mixture was cooled to room temperature, then partitioned between ethyl acetate and water. The organic phase was dried over MgSO$_4$, filtered, and concentrated to give the crude product as an oily solid. A solution of this crude product and dichloromethane was evaporated over silica gel, and the resulting silica gel supported crude product was loaded onto an Analogix SuperFlash™ column. Flash chromatography (15%-35% ethyl acetate in hexanes) afforded 2.26 g (77%) of 3-(methanesulfonyl)benzyl chloride as a white solid. $^1$H NMR (300 MHz, DMSO-d$_6$) δ ppm 8.01 (s, 1 H), 7.91 (d, J=7.8 Hz, 1 H), 7.81 (d, J=7.8 Hz, 1 H), 7.68 (t, J=7.8 Hz, 1 H), 4.90 (s, 2 H), 3.24 (s, 3 H). HRMS (EI+) cald. for C$_8$H$_9$ClO$_2$S [M$^+$] 204.0012, obsd. 204.0012.

Preparation of 4-(ethanesulfonyl)benzyl chloride

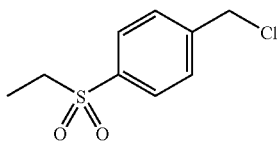

(4-Ethanesulfanyl-phenyl)-methanol

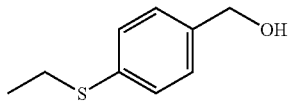

Sodium borohydride (3.2 g, 84 mmol) was added slowly in portions to an ice cold mixture of 4-ethanesulfanyl benzaldehyde (7.0 g, 42 mmol) and methanol (400 mL). After the addition was complete, the reaction mixture was warmed to room temperature, then stirred for 1 hour. The reaction mixture was concentrated in vacuo. The resulting oily solid was diluted with ethyl acetate, and then washed with water. The organic phase was dried over MgSO$_4$, filtered, and concentrated to give 7 g of (4-ethanesulfanyl-phenyl)-methanol as a clear oil. This crude product was used in subsequent steps without further purification.

(4-Ethanesulfonyl-phenyl)-methanol

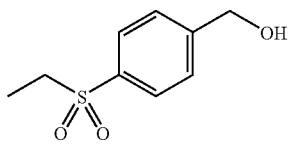

To a 0° C. solution of (4-ethanesulfanyl-phenyl)-methanol (7 g, 42 mmol) in dichloromethane (140 mL) was added m-chloroperoxybenzoic acid (20 g, 99 mmol), in portions over the course of 1.5 hours. The reaction mixture was allowed to warm to room temperature, then stirred for 18 hours. The reaction mixture was washed with a 10% aqueous solution of sodium sulfite followed by a saturated aqueous solution of sodium bicarbonate. The organic phase was dried over MgSO$_4$, filtered, and concentrated. A solution of the crude product and dichloromethane was evaporated over silica gel, and the resulting silica gel supported crude product was loaded onto an Analogix SuperFlash™ column. Flash chromatography (30%-60% ethyl acetate in hexanes) gave 4.87 g (58% over two steps) of (4-ethanesulfonyl-phenyl)-methanol as a white solid.

4-(Ethanesulfonyl)benzyl chloride

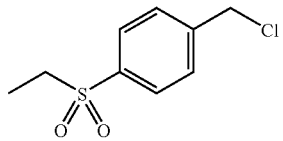

Triphenylphosphine (12.77 g, 481 mmol), carbon tetrachloride (19.0 mL, 197 mmol) and tetrahydrofuran (40 mL) were combined and stirred at room temperature for 15 minutes. A solution of (4-ethanesulfonyl-phenyl)-methanol (4.87 g, 24.4 mmol) in 45 mL tetrahydrofuran was added, then the reaction mixture was heated at 75° C. for 3 hours. The reaction mixture was cooled to room temperature, then partitioned between ethyl acetate (100 mL) and water (100 mL). The organic phase was dried over MgSO$_4$, filtered, and concentrated to give the crude product as an oily solid. A solution of this crude product and dichloromethane was evaporated over silica gel, and the resulting silica gel supported crude product was loaded onto an Analogix SuperFlash™ column. Flash chromatography (15%-35% ethyl acetate in hexanes) afforded 5.16 g (97%) of 4-(ethanesulfonyl)benzyl chloride as a white, crystalline solid. $^1$H NMR (300 MHz, DMSO-d$_6$) δ ppm 7.88 (d, J=8.2 Hz, 2 H), 7.70 (d, J=8.2 Hz, 2 H), 4.86 (s, 2 H), 3.29 (q, J=7.4 Hz, 2 H), 1.07 (t, J=7.4 Hz, 3 H).

Preparation of 4-(benzylsulfanyl)benzyl chloride

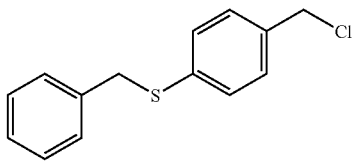

4-(Benzylsulfanyl)-benzaldehyde

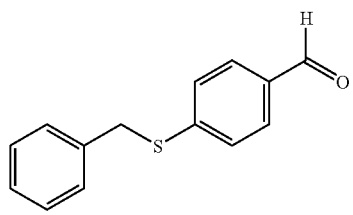

To a stirred mixture of cesium carbonate (12.81 g, 39.33 mmol), benzyl mercaptan (4.7 mL, 39 mmol), and N,N,-dimethylformamide (80 mL) was added 4-fluorobenzaldehyde, slowly over several minutes. The reaction mixture was stirred at 40° C. overnight. The reaction mixture was cooled to room temperature, then diluted with water (500 mL). The resulting mixture was acidified to pH 4 using 1 N aqueous HCl, then extracted with ethyl acetate (3×150 mL). The combined organic layers were washed with water and brine, dried over MgSO$_4$, filtered, and concentrated. A solution of the crude product and dichloromethane was concentrated over silica gel, and the resulting silica gel supported crude product was loaded onto an Analogix SuperFlash™ column. Flash chromatography (100% hexanes -15% ethyl acetate in hexanes) afforded 7.70 g (90%) of 4-(benzylsulfanyl)-benzaldehyde as a slightly pink solid.

4-(Benzylsulfanyl-phenyl)-methanol

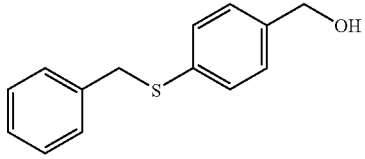

Sodium borohydride (2.7 g, 67 mmol) was added slowly in three portions to an ice cold mixture of 4-(benzylsulfanyl)-benzaldehyde (7.70 g, 33.7 mmol) and methanol (150 mL). After the addition was complete, the reaction mixture was warmed to room temperature, then stirred for 1 hour. The reaction mixture was cooled again in an ice bath, then 1 N aqueous HCl (80 mL) was added. The resulting mixture was diluted with water (600 mL), then extracted with ethyl acetate (3×250 mL). The combined organic layers were washed with brine, dried over MgSO$_4$, filtered, and concentrated. Flash chromatography (Analogix SuperFlash™ column, 5%-50% ethyl acetate in hexanes) gave 6.33 g (81%) of (4-benzylsulfanyl-phenyl)-methanol as a white solid.

4-(Benzylsulfanyl)benzyl chloride

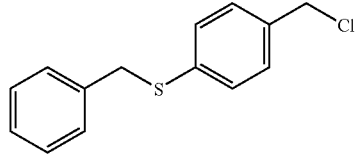

Triphenylphosphine (14.9 g, 56.8 mmol), carbon tetrachloride (35 mL, 360 mmol), (4-benzylsulfanyl-phenyl)-methanol (6.33 g, 27.5 mmol), and tetrahydrofuran (120 mL) were combined and stirred at reflux temperature overnight. The reaction mixture was cooled to room temperature, then partitioned between ethyl acetate and water (750 mL). The organic phase was dried over MgSO$_4$, filtered, and concentrated to give the crude product. Flash chromatography (Analogix SuperFlash™ column, 100% hexanes -25% ethyl acetate in hexanes) afforded 4.57 g (67%) of 4-(benzylsulfanyl)benzyl chloride as an off-white solid. $^1$H NMR (300 MHz, DMSO-d$_6$) δ ppm 7.16-7.44 (m, 9 H), 4.72 (s, 2 H), 4.26 (s, 2 H).

Preparation of 4-(benzenesulfonyl)benzyl chloride

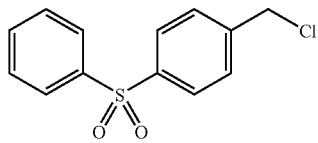

4-(Benzenesulfonyl)-benzaldehyde

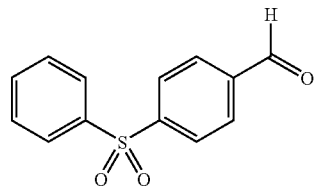

A mixture of 4-fluorobenzaldehyde (6 g, 48 mmol), sodium benzenesulfinate (7.5 g, 4.6 mmol), and dimethylsulfoxide (30 mL) was heated at 100° C. for 20 hours. The reaction mixture was cooled to room temperature, then partitioned between ethyl acetate and water. The organic phase was dried over MgSO$_4$, filtered, and concentrated to give a white solid. A solution of this crude product and dichloromethane was evaporated over silica gel, and the resulting silica gel supported crude product was purified using flash chromatography (Analogix SuperFlash™ column, 15%-40% ethyl acetate in hexanes) to give 4.29 g (41%) of 4-(benzenesulfonyl)-benzaldehyde as a white solid.

(4-Benzenesulfonyl-phenyl)-methanol

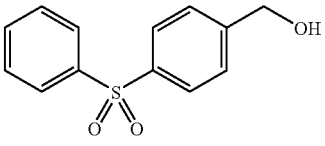

Sodium borohydride (777 mg, 20.5 mmol) was added slowly in portions to a 0° C. solution of 4-(benzenesulfonyl)-benzaldehyde (4.29 g, 18.6 mmol) and tetrahydrofuran (60 mL). The reaction mixture was allowed to warm to room temperature, then stirred at room temperature for 4 hours. The reaction mixture was then cooled over an ice-water bath, diluted with ethyl acetate (80 mL), then carefully quenched with a saturated aqueous solution of ammonium chloride (10 mL). The mixture was washed with water (80 mL), then the organic phase was dried over MgSO$_4$, filtered, and concentrated to afford 2.83 g (61%) of (4-benzenesulfonyl-phenyl)-methanol as a white solid. This product was used in subsequent steps without further purification.

4-(Benzenesulfonyl)benzyl chloride

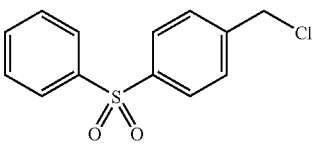

Triphenylphosphine (5.98 g, 22.8 mmol), carbon tetrachloride (9 mL, 93 mmol), (4-benzenesulfonyl-phenyl)-methanol (2.83 g, 11.4 mmol) and tetrahydrofuran (42 mL) were combined and heated at 100° C. for 4 hours. The reaction mixture was cooled to room temperature, then partitioned between ethyl acetate (100 mL) and water (100 mL). The organic phase was dried over MgSO$_4$, filtered, and concentrated to give the crude product as an oily solid. A solution of this crude product and dichloromethane was evaporated over silica gel, and the resulting silica gel supported crude product was loaded onto an Analogix SuperFlash™ column. Flash chromatography (15%-35% ethyl acetate in hexanes) afforded 3.09 g (100%) of 4-(benzenesulfonyl)benzyl chloride as a white, crystalline solid. $^1$H NMR (300 MHz, DMSO-d$_6$) δ ppm 7.89-8.04 (m, 4 H), 7.53-7.75 (m, 5 H), 4.81 (s, 2 H).

Preparation of 2-(benzenesulfonyl)benzyl chloride

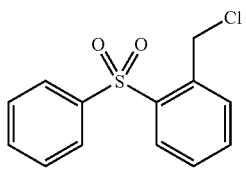

2-(Benzenesulfonyl)-benzaldehyde

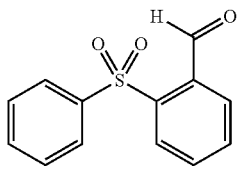

A mixture of 2-fluorobenzaldehyde (4.67 g, 37.6 mmol), sodium benzenesulfinate (6.79 g, 41.3 mmol), and dimethylsulfoxide (30 mL) was heated at 95° C. for 18 hours. The reaction mixture was cooled to room temperature, then partitioned between ethyl acetate and water. The organic phase was dried over MgSO$_4$, filtered, and concentrated to give a white solid. NMR analysis of this crude mixture indicated unreacted 2-fluorobenzaldehyde to be the major component. The crude mixture was redissolved in dimethylsulfoxide (30 mL), then sodium benzenesulfinate (5.0 g, 30 mmol) was added. The resulting mixture was heated at 95° C. for another 16 hours. The reaction mixture was cooled to room temperature, then partitioned between ethyl acetate and water. The organic phase was dried over MgSO$_4$, filtered, and concentrated. A solution of this crude product and dichloromethane was evaporated over silica gel, and the resulting silica gel supported crude product was loaded onto an Analogix SuperFlash™ column. Flash chromatography (5%-35% ethyl acetate in hexanes) provided 1.96 g (23%) of 2-(benzenesulfonyl)-benzaldehyde as a clear, colorless oil which partially solidified over time.

(2-Benzenesulfonyl-phenyl)-methanol

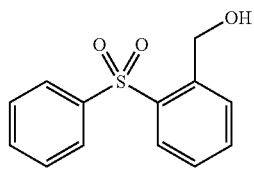

Sodium borohydride (690 mg, 18.2 mmol) was added to a solution of 2-(benzenesulfonyl)-benzaldehyde (1.98 g, 8.04 mmol) and methanol (50 mL). The reaction mixture was stirred at room temperature. When vigorous bubbling subsided, the reaction mixture was cooled in an ice-water bath, then carefully quenched with a 1.0 N aqueous solution of HCl (20 mL). The mixture was concentrated to remove methanol, then the residue was diluted with water and extracted three times with ethyl acetate. The combined organic phases were dried over MgSO$_4$, filtered, and concentrated to afford 1.94 g (97%) of (2-benzenesulfonyl-phenyl)-methanol as an oil. This product was used in subsequent steps without further purification.

2-(Benzenesulfonyl)benzyl chloride

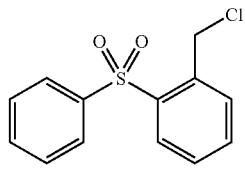

Triphenylphosphine (4.08 g, 15.5 mmol), carbon tetrachloride (7.0 mL, 73 mmol), (2-benzenesulfonyl-phenyl)-methanol (1.90 g, 7.65 mmol) and tetrahydrofuran (40 mL) were combined and heated at reflux for 2 hours. The reaction mixture was cooled to room temperature, then stirred at room temperature for 60 hours. The reaction mixture was diluted with water, then extracted three times with ethyl acetate. The combined organic phases were washed with brine, dried over MgSO$_4$, filtered, and concentrated to give the crude product as an oily solid. A solution of this crude product and dichloromethane was evaporated over silica gel, and the resulting silica gel supported crude product was loaded onto an Analogix SuperFlash™ column. Flash chromatography (0%-15% ethyl acetate in hexanes) afforded 1.73 g (85%) of 2-(benzenesulfonyl)benzyl chloride as an off-white, crystalline solid. $^1$H NMR (300 MHz, DMSO-d$_6$) δ ppm 8.14 (d, J=7.8 Hz, 1 H), 7.93 (d, J=7.2 Hz, 2 H), 7.56-7.82 (m, 6 H), 5.07 (s, 2 H). HRMS (EI+) cald. for C$_{13}$H$_{11}$ClO$_2$S [M$^+$] 266.0168, obsd. 266.0168.

Preparation of 3-(1-methyltetrazol-5-yl)benzyl chloride

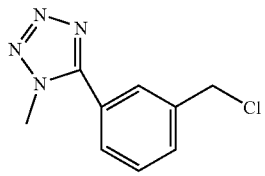

3-(Chloromethyl)-N-methyl-benzamide

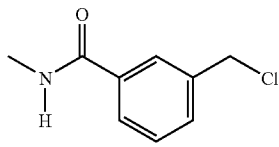

To a solution of 3-(chloromethyl)-benzoic acid (34.1 g, 200 mmol) in toluene (125 mL) was added thionyl chloride (21.9 mL, 300 mmol) at room temperature. The resulting solution was heated at reflux for 15 hours. The reaction mixture was cooled to room temperature and concentrated under vacuum. The resulting oily residue was azeotroped with toluene and dried under high vacuum to obtain the crude acid chloride. To a suspension of the above crude acid chloride (200 mmol) in dichloromethane (400 mL) was added methylamine hydrochloride (14.9 g, 220 mmol) at −5° C. to 0° C. Diisopropylethylamine (69.6 mL, 400 mmol) was added drop-wise over 15-20 minutes at 0° C. After completion of the addition, the mixture was stirred for 45 minutes at 0° C., then warmed to room temperature. After stirring at room temperature for 15 minutes, the reaction mixture was diluted with water (300 mL) and the aqueous layer was extracted with dichloromethane (100 mL). The combined organic layers were washed with brine and dried over anhydrous magnesium sulfate. Filtration and concentration gave the crude solid which was dissolved in toluene at ~60-70° C. The resulting solution was stored in the refrigerator overnight and the precipitated solids were collected by filtration and then washed with hexanes. After drying in air, 3-(chloromethyl)-N-methyl-benzamide (80%) was isolated as a light yellow solid.

3-(1-Methyltetrazol-5-yl)benzyl chloride

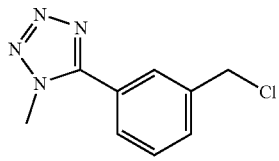

To a suspension of 3-(chloromethyl)-N-methyl-benzamide (27.2 g, 148 mmol) in toluene (100 mL) was added thionyl chloride (16.2 mL, 222 mmol) at room temperature. The resulting suspension was heated at reflux for 15 hours. The reaction mixture was cooled to room temperature and then concentrated under vacuum. The residue was azeotroped with toluene and dried under high vacuum. To a suspension of sodium azide (11.6 g, 178 mmol) in acetonitrile (140 mL) was added chlorotrimethylsilane (23.7 mL, 187 mmol) at room temperature and the suspension was stirred for 1.5 hours. The reaction mixture was cooled to −10° C. and the above crude imidoyl chloride (148 mmol) in acetonitrile (40 mL) was added over 5 minutes. The mixture was stirred for 2 hours at 0° C. and then stirred at room temperature for 15 hours. The reaction mixture was diluted with water (200 mL) and extracted with ethyl acetate (2×100 mL). The combined organic extracts were washed with brine and dried over anhydrous magnesium sulfate. Filtration and concentration gave a light yellow solid which was dissolved in hexanes-ethyl acetate (220 mL, 11:9 ratio) at 60-70° C. The resulting solution was stored in the refrigerator and the precipitated solids were collected by filtration and washed with hexanes. After drying in air, 3-(1-methyltetrazol-5-yl)benzyl chloride was isolated as 24.5 g (79.5%) of a white amorphous solid, mp 63-65° C.; HRMS (ES+) cald. for $C_9H_9ClN_4$ $[(M+H)^+]$ 209.0589, obsd. 209.0588.

Preparation of 4-(1-methyltetrazol-5-yl)benzyl chloride

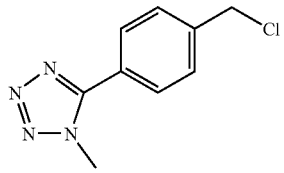

4-(Chloromethyl)-N-methyl-benzamide

To a solution of 4-(chloromethyl)-benzoic acid (8.53 g, 50 mmol) in toluene (100 mL) was added thionyl chloride (14.5 mL, 200 mmol) at room temperature. The resulting solution was heated at reflux for 15 hours. The reaction mixture was cooled to room temperature and concentrated under vacuum. The resulting oily residue was azeotroped with toluene and dried under high vacuum to obtain the crude acid chloride. To a suspension of the above crude acid chloride (50 mmol) in dichloromethane (110 mL) was added methylamine hydrochloride (3.72 g, 55 mmol) at −5° C. to 0° C. Diisopropylethylamine (19.3 mL, 110 mmol) was added drop-wise over 15-20 minutes at 0° C. After completion of the addition, the mixture was stirred for 45 minutes at 0° C., then warmed to room temperature. After stirring at room temperature for 15 minutes, the reaction mixture was diluted with water and the aqueous layer was extracted with dichloromethane. The combined organic layers were washed with brine and dried over anhydrous magnesium sulfate. Filtration and concentration gave the crude solid which was dissolved in toluene at ~60-70° C. The resulting solution was stored in the refrigerator overnight and the precipitated solids were collected by filtration and then washed with hexanes. After drying in air, 4-(chloromethyl)-N-methyl-benzamide was isolated as a light yellow solid.

4-(1-Methyltetrazol-5-yl)benzyl chloride

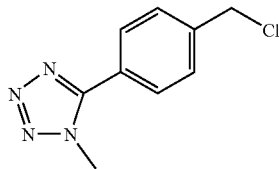

To a suspension of 4-(chloromethyl)-N-methyl-benzamide (50 mmol) in toluene (200 mL) was added thionyl chloride (29.1 mL, 400 mmol) at room temperature. The resulting suspension was heated at reflux for 15 hours. The reaction mixture was cooled to room temperature and then concentrated under vacuum. The residue was azeotroped with toluene and dried under high vacuum. To a suspension of sodium azide (4.55 g, 70 mmol) in acetonitrile (100 mL) was added chlorotrimethylsilane (9.15 mL, 73.4 mmol) at room temperature and the suspension was stirred for 1.5 hours. The reaction mixture was cooled to −10° C. and the above crude imidoyl chloride (50 mmol) in acetonitrile (65 mL) was added over 5 minutes. The mixture was stirred for 2 hours at 0° C. and then stirred at room temperature for 15 hours. The reaction mixture was diluted with water and extracted with ethyl acetate (2×100 mL). The combined organic extracts were washed with brine and dried over anhydrous magnesium sulfate. Filtration and concentration gave a light yellow solid which was dissolved in hexanes-ethyl acetate (220 mL, 11:9 ratio) at 60-70° C. The resulting solution was stored in the refrigerator overnight and the precipitated solids were collected by filtration and washed with hexanes. After drying in air, 4-(1-methyltetrazol-5-yl)benzyl chloride was isolated as 6.26 g (60%) of a white solid. $^1$H NMR (300 MHz, CDCl$_3$) δ ppm 7.76 (d, J=8.2 Hz, 2 H), 7.61 (d, J=8.2 Hz, 2 H), 4.67 (s, 2 H), 4.20 (s, 3 H). HRMS (ES+) cald. for C$_9$H$_9$ClN$_4$ [(M+H)$^+$] 209.0589, obsd. 209.0588.

Preparation of
1-chloromethyl-4-methanesulfonylmethyl benzene

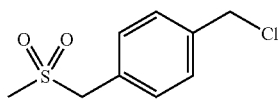

(4-Methanesulfonylmethyl-phenyl)-methanol

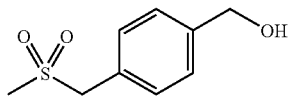

A 1.0 M solution of diisobutylaluminum hydride in toluene (44 mL, 44 mmol) was added slowly drop-wise to a 0° C. solution of methyl 4-(methanesulfonylmethyl)benzoate (4.00 g, 17.5 mmol) and toluene (220 mL). After the addition was complete, the reaction mixture was warmed to room temperature, then stirred at room temperature for 16 hours. After this time, thin-layer chromatography indicated some starting material to remain. The reaction mixture was cooled to 0° C., then additional 1.0 M diisobutylaluminum hydride in toluene (44 mL, 44 mmol) was added slowly drop-wise to the cold reaction mixture. The reaction mixture was warmed to room temperature, and then stirred for 20 minutes. The reaction mixture was again cooled to 0° C. Ethyl acetate (50 mL) was added followed by methanol (1 mL). The reaction mixture was allowed to stand for 6 minutes at 0° C., during which time the mixture became cloudy and thick. A saturated aqueous solution of sodium potassium tartrate was added, and the heterogeneous mixture was warmed to room temperature. Water and additional ethyl acetate (50 mL) were added. The organic phase was separated, dried over MgSO$_4$, filtered, and concentrated to give 2.18 g (62%) of (4-methane-sulfonylmethyl-phenyl)-methanol as a white solid.

1-Chloromethyl-4-methanesulfonylmethyl benzene

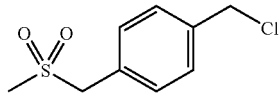

Triphenylphosphine (5.71 g, 21.8 mmol), carbon tetrachloride (8.4 mL, 87 mmol), and tetrahydrofuran (12 mL) were combined in a round bottom flask under argon and stirred at room temperature for 10 minutes. A heterogeneous mixture of (4-methanesulfonylmethyl-phenyl)-methanol (2.18 g, 10.9 mmol) and tetrahydrofuran (37 mL) were added to the reaction mixture, and then the mixture was heated at 75° C. for 3 hours. The reaction mixture was cooled to room temperature, and then partitioned between ethyl acetate and water. The organic phase was dried over MgSO$_4$, filtered, and concentrated to give the crude product as an oily solid. A solution of this crude product and dichloromethane was concentrated over silica gel, and the resulting silica gel supported crude product was loaded onto a RediSep® Flash column. Flash chromatography (25%-40% ethyl acetate in hexanes) afforded 1.59 g (67%) of 1-chloromethyl-4-methanesulfonylmethyl benzene as a white solid. $^1$H NMR (300 MHz, DMSO-d$_6$) δ ppm 7.47 (d, J=8.2 Hz, 2 H), 7.41 (d, J=8.2 Hz, 2 H), 4.78 (s, 2 H), 4.50 (s, 2 H), 2.91 (s, 3 H).

Preparation of (6-fluoro-3-methyl-4-trifluoromethanesulfonyloxy-naphthalen-2-yl)-acetic acid tert-butyl ester

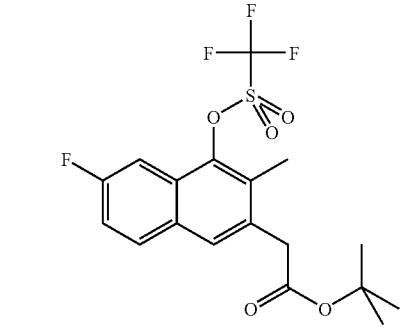

4-(4-Fluoro-phenyl)-2-methyl-buta-2,3-dienoic acid ethyl ester

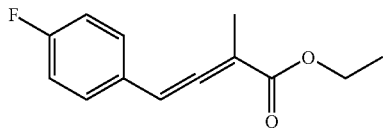

To a solution of (4-fluoro-phenyl)-acetic acid (22.33 g, 144.9 mmol) in 100 mL of methyl tert-butyl ether and 250 μL of DMF was added 13.02 mL (146.3 mmol) of oxalyl chloride at room temperature dropwise over 30 minutes. The resulting mixture was stirred at room temperature for an additional 20 minutes (HPLC indicated completed reaction), and then the entire solution was added dropwise over 1 hour to a solution of N,N-diisopropylethylamine (50.48 mL, 289.8 mmol) and ethyl 2-(triphenylphosphoranylidene)propionate (50.0 g, 138.0 mmol) in 100 mL of methyl tert-butyl ether, while maintaining the internal temperature between 0-15° C. After the addition was complete, the reaction mixture was stirred for an additional 10 minutes at 0-10° C., when HPLC indicated a completed reaction. The reaction mixture was then diluted with 100 mL of heptane, and stirred for 30 minutes at 0-10° C. The resulting solid was filtered and washed with 2×100 mL of 1:1 methyl tert-butyl ether:heptane. The filtrate and the washings were combined and washed with 100 mL of water, 100 mL of 1M citric acid, 2×100 mL of water, then concentrated azeotropically at 25° C./60 mmHg to a total volume of ~40 mL. The residue was diluted with 60 mL of methyl tert-butyl ether. This solution was then directly used for the next step.

2-Ethoxycarbonyl-3-[1-(4-fluoro-phenyl)-meth-(E)-ylidene]-4-methyl-pentanedioic acid 1-tert-butyl ester 5-ethyl ester

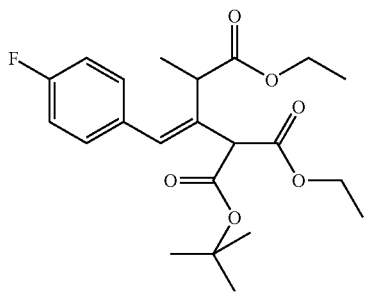

Malonic acid tert-butyl ester ethyl ester (30.08 g, 151.8 mmol) was added to a solution of potassium tert-butoxide (16.30 g, 138.0 mmol) in 200 mL of N,N-dimethyl acetamide, while the reaction temperature was maintained at ~25° C. To the resulting mixture was then added the solution of 4-(4-fluoro-phenyl)-2-methyl-buta-2,3-dienoic acid ethyl ester prepared above, at such a rate that the reaction temperature was maintained between 20-28° C. After the addition was complete, the reaction mixture was stirred at room temperature for 20 minutes, when HPLC indicated completed reaction. The mixture was then treated with 100 mL of 1M citric acid and 150 mL of ice-water, and then extracted with 400 mL of methyl tert-butyl ether. The organic extract was separated and washed with 2×200 mL of water, and then concentrated to produce 56.36 g of a yellow oil, which was used in the next step without further purification.

3-[1-(4-Fluoro-phenyl)-meth-(Z)-ylidene]-2-methyl-pentanedioic acid 5-tert-butyl ester

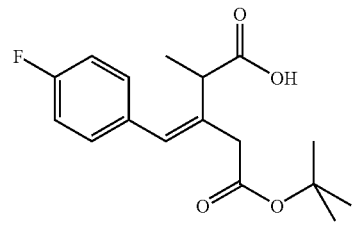

The malonate ester derivative prepared above (56.36 g, 138 mmol) was dissolved in 280 mL of absolute ethanol. Lithium hydroxide (1M solution, 414.0 mL, 414.0 mmol) was added slowly over 15 minutes, and the resulting reaction mixture was stirred at room temperature overnight. The solution was then heated at reflux for 3 hours (HPLC analysis indicated completed decarboxylation). At this time, the solution was concentrated at 30° C./30 mmHg to remove ~350 mL of solvent. The residue was cooled to 10° C., and treated with concentrated hydrochloric acid (32.0 mL, 389.7 mmol) dropwise, in order to adjust the pH to 2.75. The reaction mixture was then extracted with methyl tert-butyl ether (400 mL). The organic phase was separated and washed with 200 mL of water, then treated with 17.00 mL of 1M sodium carbonate in 150 mL of water, washed with an additional 200 mL of water, and then concentrated azeotropically at 30° C./80 mmHg to produce an oil. Methyl tert-butyl ether (200 mL) was added, and the residue was concentrated azeotropically at 30° C./80 mmHg to produce 38.3 g of a yellow oil, which was used in the next step without further purification.

(4-Acetoxy-6-fluoro-3-methyl-naphthalen-2-yl)-acetic acid tert-butyl ester

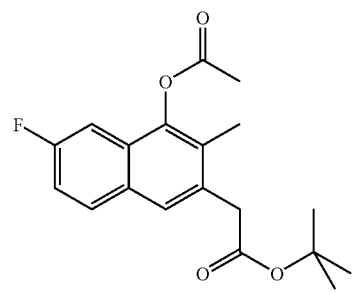

The above prepared 3-[1-(4-fluoro-phenyl)-meth-(Z)-ylidene]-2-methyl-pentanedioic acid 5-tert-butyl ester (38.3 g, 124.2 mmol) was dissolved in acetic anhydride (96.00 mL, 995.3 mmol). To this solution was added potassium acetate (18.66 g, 186.3 mmol), and the reaction mixture was stirred at 85±2° C. for 10 hours, when HPLC analysis showed completed reaction. The reaction mixture was then cooled to room temperature and diluted with 96 mL of heptane. To this solution, 270 mL of water was added over 1 hour, while maintaining the internal temperature at ~23° C. The mixture was then cooled to 0-5° C., and stirred for 2 hours. The solid formed was filtered, and then washed with water (2×40 mL), heptane (2×40 mL), and then dried under vacuum to furnish 28.5 g of a yellow solid, which was used in the next step without further purification.

(6-Fluoro-4-hydroxy-3-methyl-naphthalen-2-yl)-acetic acid tert-butyl ester

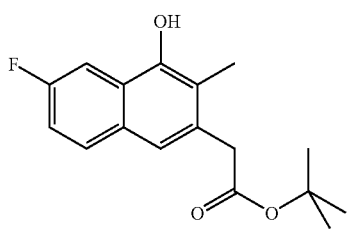

To a mixture of the above prepared (4-acetoxy-6-fluoro-3-methyl-naphthalen-2-yl)-acetic acid tert-butyl ester (28.4 g, 85.44 mmol) in 140 mL of methanol was added sodium methoxide (25% solution in methanol, 23.44 mL, 102.5 mmol) rapidly dropwise. The resulting reaction mixture was stirred at room temperature for 20 minutes, when HPLC analysis indicated a completed reaction. The mixture was cooled to 0° C., and then acidified to pH 2 with 1N hydrochloric acid solution (111.1 mL, 111.1 mmol). The mixture was then stirred at 0-5° C. for an additional 30 minutes. The resulting solid was filtered, and washed with water (2×40 mL), then dried under vacuum overnight (40° C.), to produce 23.7 g of (6-fluoro-4-hydroxy-3-methyl-naphthalen-2-yl)-acetic acid tert-butyl ester as a light yellow solid. $^1$H NMR (300 MHz, DMSO-$d_6$) δ ppm 9.09 (s, 1 H), 7.76-7.86 (m, 2 H), 7.26-7.35 (m, 2 H), 3.71 (s, 2 H), 2.23 (s, 3 H), 1.41 (s, 9 H).

(6-Fluoro-3-methyl-4-trifluoromethanesulfonyloxy-naphthalen-2-yl)-acetic acid tert-butyl ester

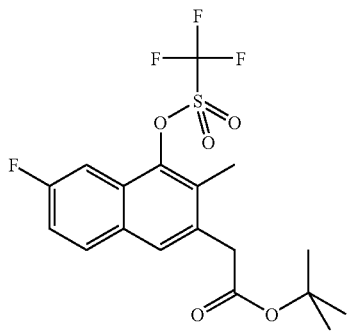

A solution of (6-fluoro-4-hydroxy-3-methyl-naphthalen-2-yl)-acetic acid tert-butyl ester (8.00 g, 27.52 mmol), in 48.0 mL of dichloromethane was cooled to 0-5° C. To this solution was added pyridine (4.451 mL, 55.04 mmol) in one portion. Then, trifluoromethanesulfonic anhydride (5.556 mL, 33.04 mmol) was added dropwise over 5 minutes, in order to maintain the internal temperature between 5-15° C. The resulting reaction mixture was stirred at 10° C. for an additional 10 minutes, then warmed up to room temperature, and stirred for an additional 5 minutes. HPLC analysis indicated complete disappearance of the starting phenol. The reaction mixture was then quenched with 40.0 mL of water. The organic layer was separated and washed with 1M citric acid (33.33 mL, 33.33 mmol), followed by 40.0 mL of water. The resulting organic layer was then concentrated to a viscous oil, dissolved in 20 mL of 1:1 dichloromethane:heptane, and filtered through a thin silica gel plug (elution with 1:1 dichloromethane:heptane), to furnish 11.5 g of (6-fluoro-3-methyl-4-trifluoromethanesulfonyloxy-naphthalen-2-yl)-acetic acid tert-butyl ester as an off-white solid. $^1$H NMR (300 MHz, DMSO-$d_6$) δ ppm 8.13 (dd, J=8.9, 5.7 Hz, 1 H), 8.00 (s, 1 H), 7.60 (dd, J=8.9, 2.1 Hz, 1 H), 7.49-7.56 (m, 1 H), 3.91 (s, 2 H), 2.41 (s, 3 H), 1.39 (s, 9 H).

Part II: Preparation of Compounds of Interest

Example 1-1

[4-(4-Dimethylsulfamoyl-benzoyl)-naphthalen-2-yl]-acetic acid

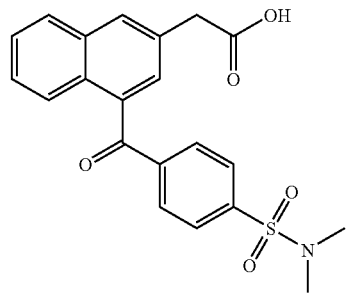

2-Trimethylsilanylethynyl-benzaldehyde

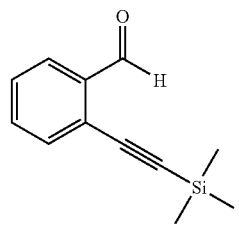

A solution of 2-bromo-benzaldehyde (20.0 g, 108.1 mmol) in anhydrous tetrahydrofuran (200 mL) was degassed with argon for 30 minutes at room temperature. To the above solution was added bis(triphenylphosphine)palladium(II) chloride (Pd(PPh$_3$)$_2$Cl$_2$) (3.79 g, 5.4 mmol) and the mixture was degassed again for an additional 15 minutes. To the reaction mixture were added trimethylsilanyl acetylene (33.97 mL, 216.2 mmol), copper(I) iodide (1.0 g, 5.4 mmol) and triethylamine (29.5 mL, 216.2 mmol), and the mixture was stirred for 16 hours at room temperature. Tetrahydrofuran was removed in vacuo. To the residue was added water (100 mL), and the resulting mixture was extracted with ethyl acetate (3×100 mL). The combined organic layers were dried over anhydrous sodium sulfate, filtered, and concentrated in vacuo to give a black colored crude product. Flash chromatography (silica gel, 100-200 mesh, 2-5% ethyl acetate in hexane) afforded 2-trimethylsilanylethynyl-benzaldehyde (18.0 g, 82%) as a brown colored solid. MS (ESI+) cald. for C$_{12}$H$_{14}$OSi [(M+H)$^+$] 202, obsd. 203.

2-Ethynyl-benzaldehyde

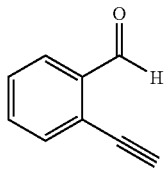

To a solution of 2-trimethylsilanylethynyl-benzaldehyde (6 g, 29.70 mmol) in N,N-dimethylformamide (10 mL) was added potassium fluoride (1 g, 17.2 mmol). The reaction mixture was stirred at room temperature for 30 minutes. The resulting solution was poured into water, and then extracted with dichloromethane. The collected organic layers were dried over magnesium sulfate, filtered, and concentrated in vacuo. Flash chromatography (RediSep® Flash column, 230-400 mesh, 0-25% ethyl acetate in hexane) gave 2-ethynyl-benzaldehyde (2.8 g, 73%) as a white solid. MS (ESI+) cald for $C_9H_6O$ [(M+H)$^+$] 130, obsd. 131.

4-(2-Formyl-phenylethynyl)-N,N-dimethyl-benzenesulfonamide

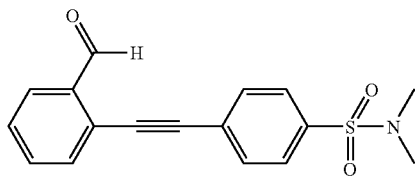

A mixture of 4-bromo-N,N-dimethylbenzenesulfonamide (610 mg, 2.31 mmol) bis(triphenylphosphine)palladium(II) chloride (Pd(PPh$_3$)$_2$Cl$_2$) (33 mg, 0.05 mmol), copper (I) iodide (5 mg, 0.03 mmol) and triethylamine (3 mL) was degassed with argon. To the above mixture was added a degassed solution of 2-ethynyl-benzaldehyde (300 mg, 2.31 mmol) in acetonitrile (3 mL). The resulting mixture was heated at 80° C. for 3 hours under argon, and then cooled to room temperature, treated with ethyl acetate, and then washed with water. The organic layer was dried over anhydrous sodium sulfate, filtered, and concentrated in vacuo. Flash chromatography (RediSep® Flash column, 230-400 mesh, 5-40% ethyl acetate in hexane) gave 4-(2-formyl-phenylethynyl)-N,N-dimethyl-benzenesulfonamide (454 mg, 63%) as a brown oil. MS (ESI+) cald. for $C_{17}H_{15}NO_3S$ [(M+H)$^+$] 313, obsd. 314.

[4-(4-Dimethylsulfamoyl-benzoyl)-naphthalen-2-yl] acetic acid ethyl ester

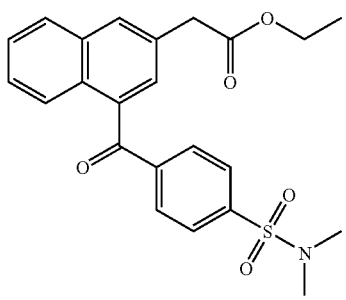

A suspension of gold(III) bromide (38 mg, 0.087 mmol), 4-oxo-butyric acid ethyl ester (377 mg, 2.9 mmol) and 4-(2-formyl-phenylethynyl)-N,N-dimethyl-benzenesulfonamide (454 mg, 1.45 mmol) in anhydrous dioxane (10 mL) was heated at 100° C. for 4 hours. After being cooled to room temperature, the mixture was treated with ethyl acetate, and then washed with water. The collected organic layer was dried over anhydrous sodium sulfate, filtered, and concentrated in vacuo. Flash chromatography (RediSep® Flash column, 230-400 mesh, 25-60% ethyl acetate in hexane) gave [4-(4-dimethylsulfamoyl-benzoyl)-naphthalen-2-yl]-acetic acid ethyl ester (180 mg, 29%). MS (ESI+) cald. for $C_{23}H_{23}NO_5S$ [(M+H)$^+$] 425, obsd. 426.

[4-(4-Dimethylsulfamoyl-benzoyl)-naphthalen-2-yl]-acetic acid

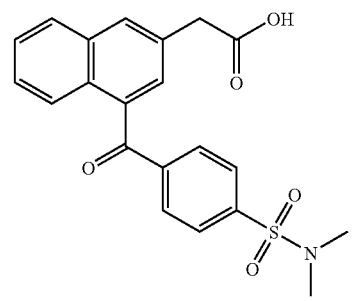

To a stirred solution of [4-(4-dimethylsulfamoyl-benzoyl)-naphthalen-2-yl]-acetic acid ethyl ester (180 g, 0.42 mmol) in tetrahydrofuran:water (1:1; 4 mL) was added lithium hydroxide (40 mg, 0.97 mmol) at room temperature, and the resulting mixture was heated at reflux for 6 hours. The solvents were removed under reduced pressure, and the residue was washed with diethyl ether (5×5 mL), and then acidified with 50% aqueous hydrochloric acid solution (10 mL) and extracted with ethyl acetate (3×25 mL). The collected organic layers were dried over anhydrous sodium sulfate, filtered and concentrated in vacuo to give a crude solid, which was further washed with a hexane/ethyl acetate/ether mixture and freeze dried to give pure [4-(4-dimethylsulfamoyl-benzoyl)-naphthalen-2-yl]-acetic acid (130 g, 77%) as a brown solid. $^1$H NMR (300 MHz, DMSO-d$_6$) δ ppm 12.35 (br. s, 1 H), 7.96-8.11 (m, 5 H), 7.91 (d, J=8.2 Hz, 2 H), 7.52-7.68 (m, 3 H), 3.83 (s, 2 H), 2.66 (s, 6 H); HRMS cald. for $C_{21}H_{19}NO_5S$ (ESI$^+$) [(M+H)$^+$] 398.1057, obsd. 398.1056.

Examples 1-2 to 1-5

The following examples 1-2 to 1-5 were prepared in an analogous manner to example 1-1, starting with the appropriate commercially available or prepared aldehydes, aryl halides, and 4-oxo-butyric acid methyl ester (or ethyl ester).

| Example No. | Aldehyde | Aryl halide | Systematic Name | $^1$H NMR (300 MHz, DMSO-$d_6$) δ ppm | MS (M + H)$^+$ | Structure |
|---|---|---|---|---|---|---|
| 1-2 | 2-Bromo-4-fluoro-benzaldehyde | 4-Iodo-benzene-sulfon-amide | [6-Fluoro-4-(4-sulfamoyl-benzoyl)-naphthalen-2-yl]-acetic acid | (400 MHz, DMSO-$d_6$) 12.51 (br. s, 1 H), 8.11-8.19 (m, 1 H), 7.90-8.01 (m, 4 H), 7.85 (dd, J = 11.1, 2.4 Hz, 1 H), 7.68 (d, J = 1.2 Hz, 1 H), 7.61 (s, 2 H), 7.57 (td, J = 8.6, 2.4 Hz, 2 H), 3.82 (s, 2 H) | 388 | 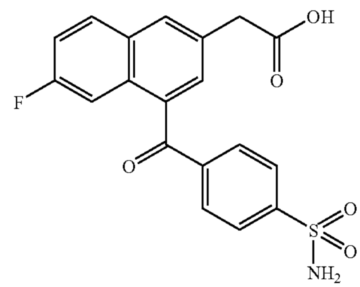 |
| 1-3 | 2-Bromo benzaldehyde | 4-Iodo-benzene-sulfon-amide | [4-(4-Sulfamoyl-benzoyl)-naphthalen-2-yl]-acetic acid | (400 MHz, DMSO-$d_6$) 12.50 (br. s, 1 H), 7.86-8.17 (m, 7 H), 7.51-7.68 (m, 5 H), 3.83 (s, 2 H) | 370 | 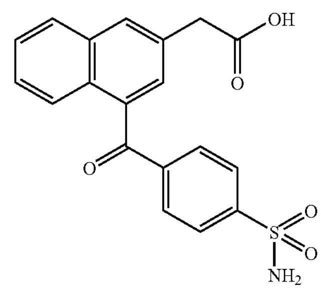 |
| 1-4 | 2-Bromo-4-fluoro-benzaldehyde | 1-Bromo-2-chloro-4-ethane sulfonyl-benzene | [4-(2-Chloro-4-ethane-sulfonyl-benzoyl)-6-fluoro-naphthalen-2-yl]-acetic acid | 12.27 (br. s, 1 H), 8.66 (dd, J = 12.1, 2.6 Hz, 1 H), 8.21 (s, 1 H), 8.17 (dd, J = 9.0, 6.3 Hz, 1 H), 8.10 (d, J = 1.6 Hz, 1 H), 8.01 (dd, J = 8.0, 1.6 Hz, 1 H), 7.90 (d, J = 8.0 Hz, 1 H), 7.69 (br. s, 1 H), 7.63 (td, J = 9.0, 2.6 Hz, 1 H), 3.75 (s, 2 H), 3.48 (q, J = 7.4 Hz, 2 H), 1.17 (t, J = 7.4 Hz, 3 H) | 457.0279$^b$ | 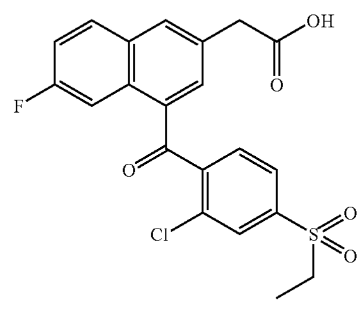 |
| 1-5 | 2-Bromo-4-fluoro-benzaldehyde | 1-bromo-4-[(3-chloro phenyl)sulfonyl]benzene | {4-[4-(3-Chloro-benzene-sulfonyl)-benzoyl]-6-fluoro-naphthalen-2-yl}-acetic acid | 12.42 (br. s, 1 H), 8.19 (d, J = 8.5 Hz, 2 H), 8.11-8.16 (m, 2 H), 8.09 (t, J = 1.8 Hz, 1 H), 7.97 (d, J = 8.5 Hz, 2 H), 7.93-8.03 (m, 1 H), 7.88 (dd, J = 11.5, 2.4 Hz, 1 H), 7.81-7.86 (m, 1 H), 7.69 (s, 1 H), 7.70 (t, J = 7.8 Hz, 1 H), 7.56 (td, J = 8.8, 2.7 Hz, 1 H), 3.80 (s, 2 H) | 505.0283$^b$ | | a: HRMS (ESI+, [(M + H)$^+$]);
$^b$HRMS (ESI+, [(M + Na)$^+$])

Example 2-1

[6-Fluoro-4-(4-methanesulfonyl-benzoyl)-naphthalen-2-yl]-acetic acid

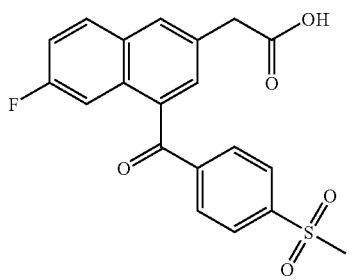

(4-Methanesulfonyl-phenylethynyl)-trimethyl-silane

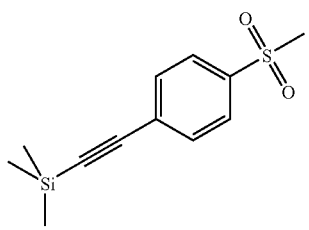

Bromo-4-methanesulfonyl benzene (50.78 g, 213 mmol) was placed in a 3-necked round bottomed flask and purged with argon. Copper(I) iodide (2.05 g, 10.6 mmol) and bis(triphenylphosphine)palladium(II) chloride (PdCl$_2$(PPh$_3$)$_2$) (7.55 g, 10.6 mmol) were added while purging with argon, followed by the addition of triethylamine (200 mL) and anhydrous dichloromethane (200 mL). (Trimethylsilyl)acetylene (61 mL, 425 mmol) was added and the reaction mixture was stirred at room temperature over 72 hours. The mixture was concentrated, then partitioned between ethyl acetate and water. The combined organic layers were washed with 1 N hydrochloric acid, water, and brine, dried over magnesium sulfate, filtered, and concentrated to afford crude (4-methanesulfonyl-phenylethynyl)-trimethyl-silane (54 g, 213 mmol), which was used in the next step without further purification. MS (ESI$^+$) cald. for C$_{12}$H$_{16}$O$_2$SSi [(M+H)$^+$] 252, obsd. 253.

1-Ethynyl-4-methanesulfonyl-benzene

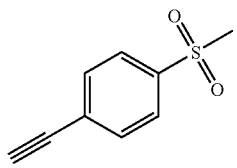

To a solution of (4-methanesulfonyl-phenylethynyl)-trimethyl-silane (20.7 g, 82.0 mmol) in tetrahydrofuran (450 mL) was added tetrabutylammonium fluoride hydrate (8.80 g, 27.3 mmol). An immediate color change from yellow to red was observed. After 5 minutes, the reaction was complete, and the solvent was removed in vacuo. Water was added, and the resulting mixture was then extracted three times with ethyl acetate. The combined organic layers were washed with water and brine, dried over magnesium sulfate, filtered, and concentrated. The residue was suspended in dichloromethane, and the insoluble material was filtered off. The filtrate was concentrated to give the crude product. Flash chromatography (RediSep® Flash column, 230-400 mesh, 0-25% ethyl acetate in hexane) afforded 1-ethynyl-4-methanesulfonyl-benzene (10.7 g, 72% yield) as a yellow solid.

4-Fluoro-2-(4-methanesulfonyl-phenylethynyl)-benzaldehyde

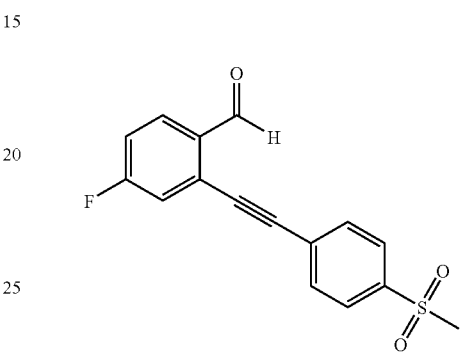

A degassed mixture of 1-ethynyl-4-methanesulfonyl-benzene (2.5 g, 13.87 mmol), bis(triphenylphosphine)palladium(II) chloride (0.49 g, 0.69 mmol), copper(I) iodide (0.13 g, 0.69 mmol), triethylamine (28 mL), and 2-bromo-4-fluorobenzaldehyde (3.38 g, 16 mmol) in dichloromethane (10 mL) was stirred at 80° C. for 3.5 hours, then at room temperature overnight. The reaction mixture was partitioned between dichloromethane and water. The organic layer was dried over sodium sulfate, filtered, and concentrated in vacuo. Flash chromatography (RediSep® Flash column, 230-400 mesh, 15-35% ethyl acetate in hexane) gave 4-fluoro-2-(4-methanesulfonyl-phenylethynyl)-benzaldehyde (3.32 g, 79%). MS (ESI+) cald. for C$_{16}$H$_{11}$FO$_3$S [(M+H)$^+$] 302, obsd. 302.

[6-Fluoro-4-(4-methanesulfonyl-benzoyl)-naphthalen-2-yl]acetic acid ethyl ester

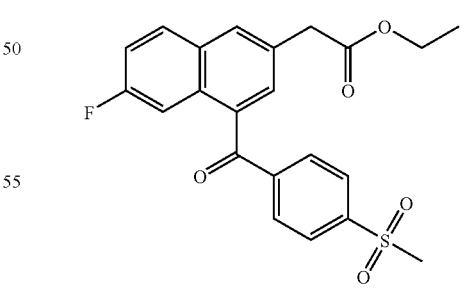

To a mixture of 4-fluoro-2-(4-methanesulfonyl-phenylethynyl)-benzaldehyde (1.74 g, 5.77 mmol) and gold(III) bromide (0.15 g, 0.35 mmol) in dioxane (8 mL) was added 4-oxo-butyric acid ethyl ester (1.50 g, 11.53 mmol). The reaction mixture was heated at 100° C. under nitrogen for 4 hours. The solvent was removed in vacuo to afford a deep red viscous oil. Flash chromatography (RediSep® Flash column, 230-400 mesh, 25-65% ethyl acetate in hexane) gave [6-fluoro-4-(4-methanesulfonyl-benzoyl)-naphthalen-2-yl]-acetic acid ethyl ester (0.63 g, 26%). MS (ESI+) cald. for $C_{22}H_{19}FO_5S$ [(M+H)$^+$] 414, obsd. 415. It is noted that in some instances, this reaction also produced some amount of [6-fluoro-4-(4-methanesulfonyl-benzoyl)-naphthalen-2-yl]-acetic acid.

[6-Fluoro-4-(4-methanesulfonyl-benzoyl)-naphthalen-2-yl]acetic acid

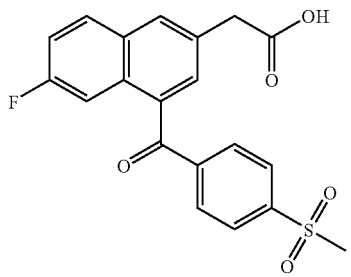

To a solution of [6-fluoro-4-(4-methanesulfonyl-benzoyl)-naphthalen-2-yl]-acetic acid ethyl ester (0.63 g, 1.52 mmol) in tetrahydrofuran (6 mL) and water (6 mL) was added lithium hydroxide monohydrate (0.83 g, 1.98 mmol). The reaction mixture was heated at reflux for 3 hours. After cooling to room temperature, more water was added, and tetrahydrofuran was removed under reduced pressure. The pH was adjusted to 2 with ca. 2 mL of 4 N hydrochloric acid. The resulting light tan solid was collected by filtration to give pure [6-fluoro-4-(4-methanesulfonyl-benzoyl)-naphthalen-2-yl]-acetic acid (0.53 g, 90%).

$^1$H NMR (300 MHz, DMSO-d$_6$) δ ppm 12.48 (br. s, 1 H), 8.15 (s, 1 H), 8.12-8.20 (m, 1 H), 8.11 (d, J=8.3 Hz, 2 H), 8.00 (d, J=8.3 Hz, 2 H), 7.90 (dd, J=11.5, 2.4 Hz, 1 H), 7.70 (s, 1 H), 7.57 (td, J=8.8, 2.4 Hz, 1 H), 3.82 (s, 2H), 3.32 (br. s, 3 H); HRMS cald. for $C_{20}H_{16}FO_6S$ (ES+) [(M+Na)]. 409.0516, obsd. 409.0515.

Examples 2-2 to 2-32

The following examples 2-2 to 2-32 were prepared in an analogous manner to example 2-1, starting with the appropriate commercially available or prepared aldehydes and aryl halides and 4-oxo-butyric acid ethyl ester (or methyl ester).

| Example No. | Aldehyde | Aryl halide | Systematic Name | $^1$H NMR (300 MHz, DMSO-d$_6$) δ ppm | MS (M + H)$^+$ | Structure |
|---|---|---|---|---|---|---|
| 2-2 | Trifluoromethanesulfonic acid 2-formyl-5-methoxyphenyl ester | 1-Bromo-4-methanesulfonyl benzene | [4-(4-Methanesulfonyl-benzoyl)-6-methoxy-naphthalen-2-yl]-acetic acid | 12.43 (br. s, 1 H), 8.10 (d, J = 8.5 Hz, 2 H), 7.94-8.03 (m, 4 H), 7.58 (d, J = 1.5 Hz, 1 H), 7.55 (d, J = 2.5 Hz, 1 H), 7.29 (dd, J = 8.9, 2.5 Hz, 1 H), 3.77 (s, 3 H), 3.76 (s, 2 H), 3.33 (br. s, 3 H) | 389.0897$^a$ | 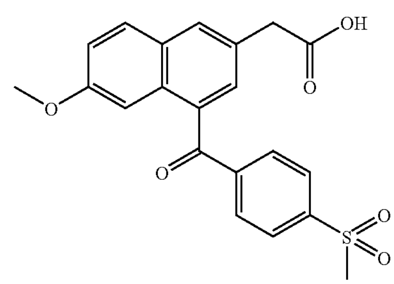 |
| 2-3 | 2-Bromobenzaldehyde | 1-Bromo-4-methanesulfonyl benzene | [4-(4-Methanesulfonyl-benzoyl)-naphthalen-2-yl]-acetic acid | 12.49 (br. s, 1 H), 8.08-8.13 (m, J = 8.4 Hz, 2 H), 8.08 (s, 1 H), 8.00-8.07 (m, 2 H), 8.00 (d, J = 8.4 Hz, 2 H), 7.53-7.66 (m, 3 H), 3.83 (s, 2 H), 3.31 (s, 3H) | 369 | 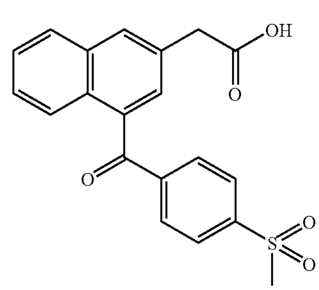 |

-continued

| Example No. | Aldehyde | Aryl halide | Systematic Name | $^1$H NMR (300 MHz, DMSO-$d_6$) δ ppm | MS (M + H)$^+$ | Structure |
| --- | --- | --- | --- | --- | --- | --- |
| 2-4 | 2-Bromo-5-fluoro-benzaldehyde | 1-Bromo-4-methane-sulfonyl benzene | [7-Fluoro-4-(4-methane-sulfonyl-benzoyl)-naphthalen-2-yl]-acetic acid | 12.49 (br. s, 1 H), 8.12 (m, 1 H), 8.10 (d, J = 8.5 Hz, 2 H), 8.06 (br. s, 1 H), 8.00 (d, J = 8.5 Hz, 2 H), 7.86 (dd, J = 10.0, 2.8 Hz, 1 H), 7.58 (d, J = 1.5 Hz, 1 H), 7.49 (td, J = 9.1, 2.8 Hz, 1 H), 3.82 (s, 2 H), 3.29 (s, 3 H) | 387.0697$^a$ | 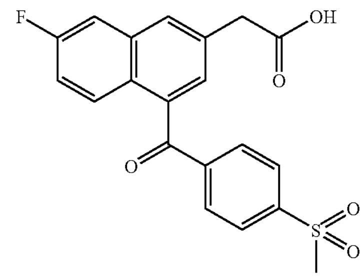 |
| 2-5 | 2-Bromo-4-fluoro-benzaldehyde | 1-Bromo-4-methane-sulfonyl 2-methyl-benzene | [6-Fluoro-4-(4-methane-sulfonyl-2-methyl-benzoyl)-naphthalen-2-yl]-acetic acid | (CDCl$_3$) 8.58 (dd, J = 11.8, 2.5 Hz, 1 H), 7.98 (s, 1 H), 7.90 (s, 1 H), 7.89-7.96 (m, 1 H), 7.80-7.88 (m, 1 H), 7.54 (d, J = 7.8 Hz, 1 H), 7.49 (s, 1 H), 7.41 (td, J = 8.5, 2.5 Hz, 1 H), 3.78 (s, 2 H), 3.13 (s, 3 H), 2.45 (s, 3H) | 401.0852$^a$ | 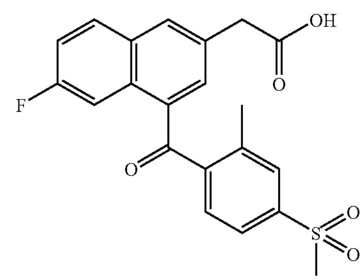 |
| 2-6 | 2-Bromo-4,5-difluoro-benzaldehyde | 1-Bromo-4-methane-sulfonyl benzene | [6,7-Difluoro-4-(4-methane-sulfonyl-benzoyl)-naphthalen-2-yl]-acetic acid | (CDCl$_3$) 8.16 (dd, J = 12.1, 8.2 Hz, 1 H), 8.08 (d, J = 8.2 Hz, 2 H), 8.02 (d, J = 8.2 Hz, 2 H), 7.90 (s, 1 H), 7.66 (dd, J = 10.4, 8.0 Hz, 1 H), 7.55 (s, 1 H), 3.84 (s, 2 H), 3.13 (s, 3 H) | 405.0603$^a$ | 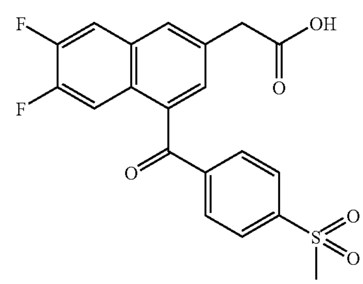 |
| 2-7 | 6-Bromo-benzo[1,3]dioxole-5-carbaldehyde | 1-Bromo-4-methane-sulfonyl benzene | [8-(4-Methane-sulfonyl-benzoyl)-naphtho[2,3-d][1,3]dioxol-6-yl]-acetic acid | (400 MHz) 12.44 (br. s, 1 H), 8.09 (d, J = 8.6 Hz, 2 H), 7.97 (d, J = 8.6 Hz, 2 H), 7.89 (br. s, 2 H), 7.45 (s, 2 H), 7.40 (d, J = 1.7 Hz, 1 H), 6.17 (s, 2 H), 3.73 (s, 2 H), 3.32 (s, 3 H) | 413 | 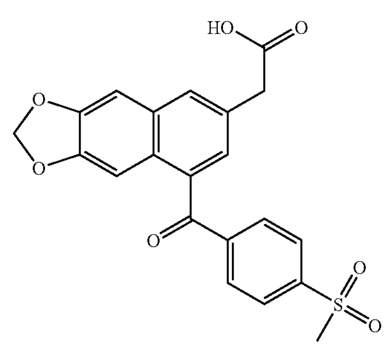 |

-continued

| Example No. | Aldehyde | Aryl halide | Systematic Name | $^1$H NMR (300 MHz, DMSO-$d_6$) δ ppm | MS (M + H)$^+$ | Structure |
| --- | --- | --- | --- | --- | --- | --- |
| 2-8 | 2-Bromo-4-fluoro-benzaldehyde | 2-chloro-1-iodo-4-methane-sulfonyl benzene | [4-(2-Chloro-4-methane-sulfonyl-benzoyl)-6-fluoro-naphthalen-2-yl]-acetic acid | 12.43 (br. s, 1 H), 8.65 (dd, J = 11.9, 2.5 Hz, 1 H), 8.21 (br. s, 1 H) 8.16-8.22 (m, 1 H), 8.14 (d, J = 1.4 Hz, 1 H), 8.03 (dd, J = 7.9, 1.4 Hz, 1 H), 7.87 (d, J = 7.9 Hz, 1 H), 7.67 (d, J = 1.2 Hz, 1 H), 7.61 (td, J = 8.9, 2.5 Hz, 1 H), 3.75 (s, 2 H), 3.37 (s, 3 H) | 443.0125$^b$ | 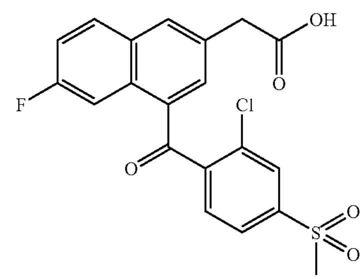 |
| 2-9 | 2-bromo-5-methoxy-benzaldehyde | 1-Bromo-4-methane-sulfonyl benzene | [4-(4-Methane-sulfonyl-benzoyl)-7-methoxy-naphthalen-2-yl]-acetic acid | (400 MHz) 12.46 (s, 1 H), 8.10 (d, J = 8.6 Hz, 2 H), 7.98 (d, J = 8.6 Hz, 2 H) 7.95-7.98 (m, 1 H), 7.95 (d, J = 9.4 Hz, 1 H), 7.45 (d, J = 2.7 Hz, 1 H), 7.42 (d, J = 1.5 Hz, 1 H), 7.22 (dd, J = 9.4, 2.7 Hz, 1 H), 3.90 (s, 3 H), 3.78 (s, 2 H), 3.31 (s, 3 H) | 399 | 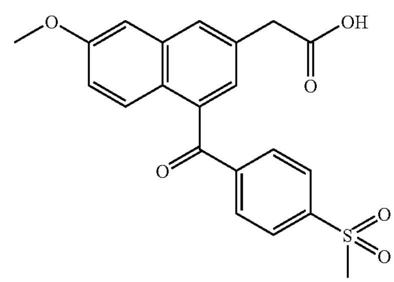 |
| 2-10 | 2-bromo-4-fluoro-benzaldehyde | 1-Bromo-3-methane-sulfonyl benzene | [6-Fluoro-4-(3-methane-sulfonyl-benzoyl)-naphthalen-2-yl]-acetic acid | 12.52 (br. s, 1 H), 8.27-8.29 (m, 1 H), 8.23-8.27 (m, 1 H), 8.13-8.19 (m, 2 H), 8.08 (dt, J = 7.8, 1.4 Hz, 1 H), 7.87-7.91 (m, 1 H), 7.82-7.87 (m, 1 H), 7.71 (d, J = 1.0 Hz, 1 H), 7.57 (td, J = 8.7, 2.5 Hz, 1 H), 3.82 (s, 2 H), 3.30 (s, 3 H) | 387 | 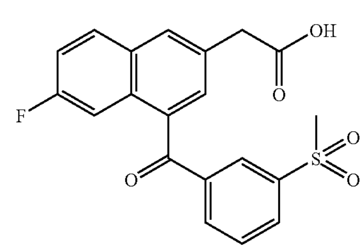 |

-continued

| Example No. | Aldehyde | Aryl halide | Systematic Name | ¹H NMR (300 MHz, DMSO-d₆) δ ppm | MS (M + H)⁺ | Structure |
|---|---|---|---|---|---|---|
| 2-11 | 2-Bromo-benzaldehyde | 1-Bromo-3-methane-sulfonyl benzene | [4-(3-Methane-sulfonyl-benzoyl)-naphthalen-2-yl]-acetic acid | (400 MHz) 12.49 (br. s, 1 H), 8.29 (s, 1 H), 8.26 (d, J = 8.3 Hz, 1 H), 7.99-8.12 (m, 4 H), 7.84 (t, J = 7.8 Hz, 1 H), 7.62 (d, J = 1.2 Hz, 1 H), 7.52-7.67 (m, 2 H), 3.83 (s, 2 H), 3.30 (s, 3 H) | 369 | 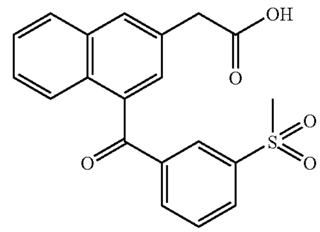 |
| 2-12 | 6-Bromo-benzo[1,3]dioxole-5-carbaldehyde | 1-Bromo-3-methane-sulfonyl benzene | [8-(3-Methane-sulfonyl-benzoyl)-naphtho[2,3-d][1,3]dioxol-6-yl]-acetic acid | (400 MHz) 12.43 (br. s, 1 H), 8.21-8.27 (m, 2 H), 8.01-8.07 (m, 1H), 7.89 (s, 1 H), 7.83 (t, J = 7.8 Hz, 1 H), 7.43-7.48 (m, 2H), 7.42 (d, J = 2.0 Hz, 1 H), 6.17 (s, 2 H), 3.73 (s, 2 H), 3.30 (s, 3 H) | 413 | 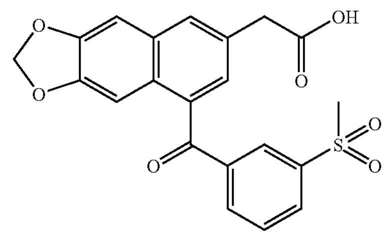 |
| 2-13 | 2-Bromo-4-fluoro-benzaldehyde | 1-Bromo-4-ethane-sulfonyl benzene | [4-(4-Ethane-sulfonyl-benzoyl)-6-fluoro-naphthalen-2-yl]-acetic acid | (400 MHz) 12.51 (br. s, 1 H), 8.13-8.19 (m, 2 H), 8.04-8.09 (m, 2 H), 7.99-8.03 (m, 2 H), 7.90 (dd, J = 11.5, 2.4 Hz, 1 H), 7.71 (d, J = 1.2 Hz, 1 H), 7.57 (td, J = 8.7, 2.4 Hz, 1 H), 3.82 (s, 2 H), 3.40 (q, J = 7.2 Hz, 2 H), 1.14 (t, J = 7.2 Hz, 3 H) | 401 | 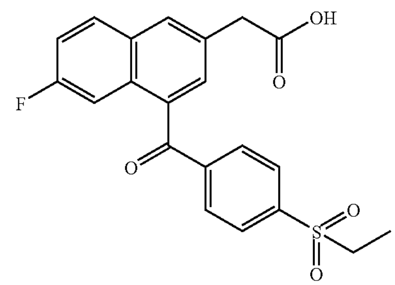 |
| 2-14 | 2-Bromo-4-fluoro-benzaldehyde | 4-Bromo-N,N-dimethyl-benzene-sulfonamide | [4-(4-Dimethyl-sulfamoyl-benzoyl)-6-fluoro-naphthalen-2-yl]-acetic acid | (400 MHz) 12.50 (br. s, 1 H), 8.12-8.20 (m, 2 H), 8.00 (d, J = 8.3 Hz, 2 H), 7.92 (d, J = 8.3 Hz, 2 H), 7.87 (dd, J = 11.7, 2.4 Hz, 1 H), 7.71 (s, 1 H), 7.57 (td, J = 8.8, 2.4 Hz, 1 H), 3.82 (s, 2 H), 2.68 (s, 6 H) | 416 | 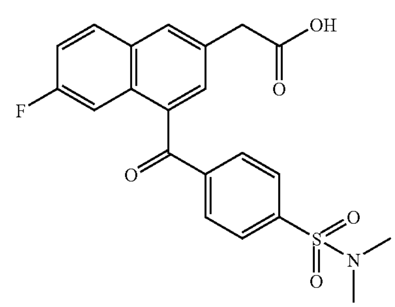 |

-continued

| Example No. | Aldehyde | Aryl halide | Systematic Name | $^1$H NMR (300 MHz, DMSO-$d_6$) δ ppm | MS (M + H)$^+$ | Structure |
| --- | --- | --- | --- | --- | --- | --- |
| 2-15 | 2-Bromo-4-fluoro-benzaldehyde | 4-Bromo-N-methyl-benzene-sulfonamide | [6-Fluoro-4-(4-methyl-sulfamoyl-benzoyl)-naphthalen-2-yl]-acetic acid | (400 MHz) 12.52 (br. s, 1 H), 8.11-8.20 (m, 2 H), 7.98 (d, J = 8.7 Hz, 2 H), 7.93 (d, J = 8.7 Hz, 2 H), 7.86 (dd, J = 11.5, 2.5 Hz, 1 H), 7.71-7.76 (m, 1 H), 7.70 (s, 1 H), 7.57 (td, J = 8.9, 2.5 Hz, 1 H), 3.82 (s, 2 H), 2.47 (d, 3 H) | 402 | 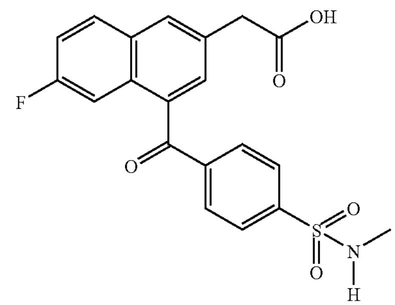 |
| 2-16 | 2-Bromo-4-fluoro-benzaldehyde | 4-(4-bromo-benzene-sulfonyl)-morpholine | {6-Fluoro-4-[4-(morpholine-4-sulfonyl)-benzoyl]-naphthalen-2-yl}-acetic acid | (400 MHz) 12.51 (br. s, 1 H), 8.12-8.20 (m, 2 H), 8.02 (d, J = 8.4 Hz, 2 H), 7.91 (d, J = 8.4 Hz, 2 H), 7.85-7.93 (m, 1 H), 7.73 (s, 1 H), 7.57 (td, J = 8.8, 2.4 Hz, 1 H), 3.83 (s, 2 H), 3.61-3.70 (m, 4 H), 2.94 (m, 4 H) | 458 | 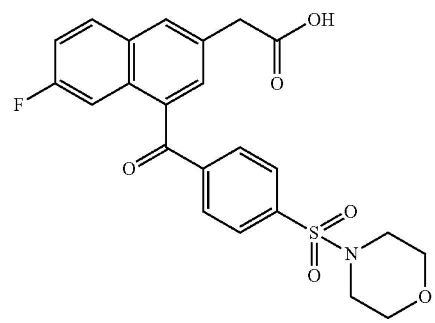 |
| 2-17 | 2-Bromo-4-fluoro-benzaldehyde | 1-Bromo-2-fluoro-4-methane-sulfonyl benzene | [6-Fluoro 4-(2-fluoro-4-methane-sulfonyl-benzoyl)-naphthalen-2-yl]-acetic acid | 12.46 (br. s, 1 H), 8.54 (dd, J = 12.1, 2.7 Hz, 1 H), 8.10-8.18 (m, 2 H), 7.71 (d, J = 8.5 Hz, 1 H), 7.63-7.68 (m, 3H), 7.59 (td, J = 8.7, 2.7 Hz, 1 H), 3.75 (s, 2 H), 3.72 (s, 3 H) | 405 | 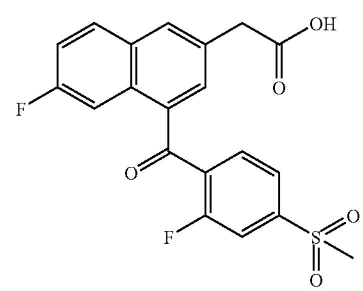 |
| 2-18 | 2-Bromo-4-fluoro-benzaldehyde | 4-Bromo-1-methane-sulfonyl-2-trifluoro methyl-benzene | [6-Fluoro-4-(4-methane-sulfonyl-3-trifluoro-methyl-benzoyl)-naphthalen-2-yl]-acetic acid | (CDCl$_3$) 8.45 (d, J = 8.2 Hz, 1 H), 8.42 (d, J = 1.6 Hz, 1 H), 8.17 (dd, J = 8.2, 1.6 Hz, 1 H), 8.02-8.11 (m, 1 H), 8.01 (s, 1 H), 7.95 (dd, J = 8.9, 5.6 Hz, 1 H), 7.61 (s, 1 H), 7.36-7.48 (m, 1 H), 3.85 (s, 2 H), 3.26 (s, 3 H) | 477.0386$^b$ | 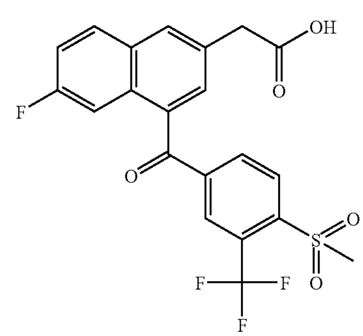 |

-continued

| Example No. | Aldehyde | Aryl halide | Systematic Name | $^1$H NMR (300 MHz, DMSO-$d_6$) δ ppm | MS (M + H)$^+$ | Structure |
|---|---|---|---|---|---|---|
| 2-19 | 2-Bromo-4-fluoro-benzaldehyde | 4-Bromo-2-ethyl-1-methane-sulfonyl benzene | [4-(3-Ethyl-4-methane-sulfonyl-benzoyl)-6-fluoro-naphthalen-2-yl]-acetic acid | 12.58 (br. s, 1 H), 8.15 (s, 1 H), 8.11-8.21 (m, 1 H), 8.07 (d, J = 8.4 Hz, 1 H), 7.94 (dd, J = 11.6, 2.6 Hz, 1 H), 7.88 (d, J = 1.8 Hz, 1 H), 7.81 (dd, J = 8.4, 1.8 Hz, 1 H), 7.70 (s, 1 H), 7.57 (td, J = 8.8, 2.6 Hz, 1 H), 3.82 (s, 2 H), 3.32 (s, 3 H), 3.08 (q, J = 7.5 Hz, 2 H), 1.24 (t, J = 7.5 Hz, 3 H) | 437.0827$^b$ | 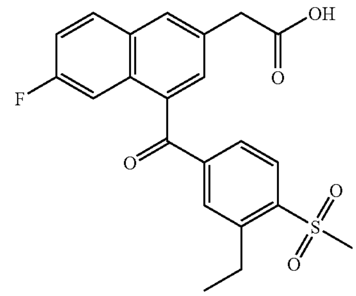 |
| 2-20 | 2-Bromo-4-fluoro-benzaldehyde | 1-Bromo-4-ethane-sulfonyl-2-methyl-benzene | [4-(4-Ethane-sulfonyl-2-methyl-benzoyl)-6-fluoro-naphthalen-2-yl]-acetic acid | 12.44 (br. s, 1 H) 8.45 (dd, J = 11.9, 2.3 Hz, 1 H) 8.10-8.22 (m, 2 H), 7.91 (s, 1 H), 7.82 (d, J = 9.1 Hz, 1 H), 7.55-7.68 (m, 3 H) 3.76 (s, 2 H) 3.34-3.42 (m, 2 H) 2.35 (s, 3 H) 1.05-1.23 (m, 3 H) | 415.1011$^a$ | 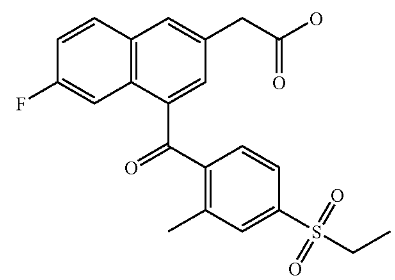 |
| 2-21 | 2-Bromo-4-fluoro-benzaldehyde | 1-(4-Bromo-benzene-sulfonyl)-piperidine | {6-Fluoro-4-[4-(piperidine-1-sulfonyl)-benzoyl]-naphthalen-2-yl}-acetic acid | 8.15 (d, J = 6.3 Hz, 2 H), 8.11 (br. s, 1 H), 7.97 (d, J = 8.2 Hz, 2 H), 7.87 (d, J = 8.5 Hz, 2 H), 7.84 (m, 1 H), 7.69 (s, 1 H), 7.55 (td, J = 5.7, 2.4 Hz, 1 H), 3.78 (s, 2 H), 2.93 (m, 4 H), 1.53 (m, 4 H), 1.36 (m, 3 H) | 456.1 | 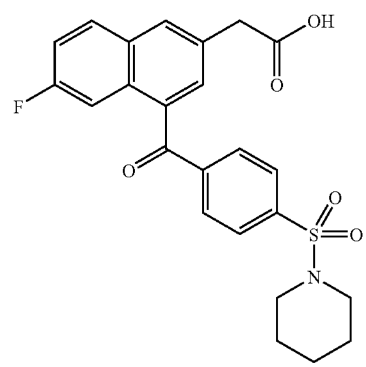 |
| 2-22 | 2-Bromo-4-fluoro-benzaldehyde | 4-Bromo-N,N-diethyl-benzene-sulfonamide | [4-(4-Diethyl-sulfamoyl-benzoyl)-6-fluoro-naphthalen-2-yl]-acetic acid | (400 MHz) 12.48 (br. s, 1 H), 8.10-8.19 (m, 2 H), 7.96 (s, 4 H), 7.84 (d, J = 11.2 Hz, 1 H), 7.69 (br. s, 1 H), 7.56 (t, J = 8.1 Hz, 1 H), 3.82 (br. s, 2 H), 3.22 (q, J = 6.7 Hz, 4 H), 1.07 (t, J = 6.7 Hz, 6 H) | 444.2 | 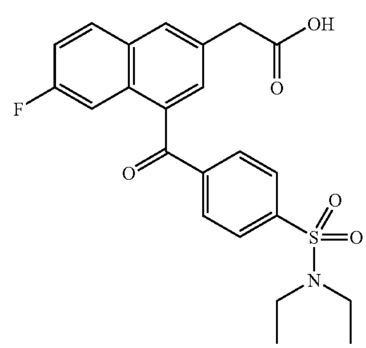 |

| Example No. | Aldehyde | Aryl halide | Systematic Name | $^1$H NMR (300 MHz, DMSO-$d_6$) δ ppm | MS (M + H)$^+$ | Structure |
|---|---|---|---|---|---|---|
| 2-23 | 2-Bromo-4-fluoro-benzaldehyde | 4-(4-Bromo-3-methyl-benzene-sulfonyl)-morpholine | {6-Fluoro-4-[2-methyl-4-(morpholine-4-sulfonyl)-benzoyl]-naphthalen-2-yl}-acetic acid | (400 MHz) 12.29 (br. s, 1 H), 8.41 (d, J = 11.7 Hz, 1 H), 8.13-8.20 (m, 2 H), 7.75 (s, 1 H), 7.56-7.70 (m, 4 H), 3.77 (s, 2 H), 3.66 (br. s, 4 H), 2.95 (br. s, 4 H), 2.36 (s, 3 H) | 472.3 | 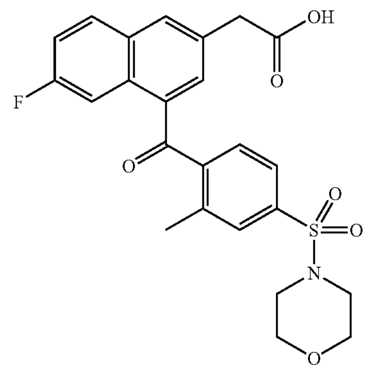 |
| 2-24 | 2-Bromo-4-fluoro-benzaldehyde | 4-Bromo-3-methyl-N,N-dimethyl-benzene-sulfonamide | [4-(4-Dimethyl-sulfamoyl-2-methyl-benzoyl)-6-fluoro-naphthalen-2-yl]-acetic acid | (400 MHz) 12.44 (br. s, 1 H), 8.41 (dd, J = 12.0, 2.2 Hz, 1 H), 8.13-8.20 (m, 2 H), 7.76 (s, 1 H), 7.68 (d, J = 8.1 Hz, 1 H), 7.56-7.64 (m, 3 H), 3.76 (br. s, 2 H), 2.67 (s, 6 H), 2.36 (s, 3 H) | 430.0 | 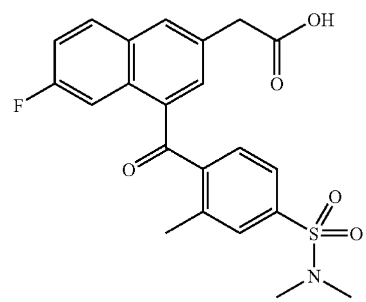 |
| 2-25 | 2-Bromo-4-fluoro-benzaldehyde | 4-Bromo-3-methyl-N-methyl-benzene-sulfonamide | [6-Fluoro-4-(2-methyl-4-methyl-sulfamoyl-benzoyl)-naphthalen-2-yl]-acetic acid | (400 MHz) 12.48 (br. s, 1 H), 8.39 (dd, J = 12.0, 2.2 Hz, 1 H), 8.13-8.21 (m, 2 H), 7.77 (s, 1 H), 7.70 (d, J = 7.8 Hz, 1 H), 7.55-7.67 (m, 4 H), 3.77 (s, 2 H), 2.48 (d, J = 5.1 Hz, 3 H), 2.35 (s, 3 H) | 416.2 | 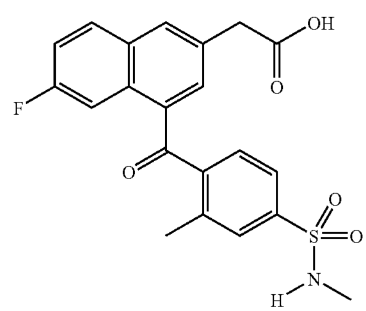 |
| 2-26 | 2-Bromo-4-fluoro-benzaldehyde | 1-(4-Bromo-benzenesulfonyl)-4-(2-fluoro-phenyl)-piperazine | (6-Fluoro-4-{4-[4-(2-fluoro-phenyl)-piperazine-1-sulfonyl]-benzoyl}-naphthalen-2-yl)-acetic acid | (400 MHz) 12.25 (br. s, 1 H), 8.10-8.18 (m, 2 H), 8.04 (d, J = 7.8 Hz, 2 H), 7.95 (d, J = 7.8 Hz, 2 H), 7.88 (d, J = 11.2 Hz, 1 H), 7.74 (s, 1 H), 7.56 (t, J = 8.6 Hz, 1 H), 6.94-7.16 (m, 4 H), 3.79 (s, 2 H), 3.11 (m, 8 H) | 551.1 | 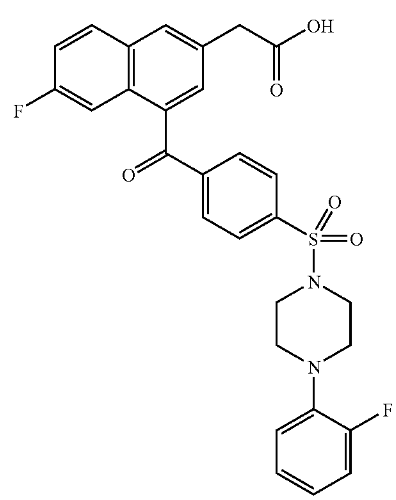 |

| Example No. | Aldehyde | Aryl halide | Systematic Name | $^1$H NMR (300 MHz, DMSO-$d_6$) δ ppm | MS (M + H)$^+$ | Structure |
| --- | --- | --- | --- | --- | --- | --- |
| 2-27 | 2-Bromo-4-chloro-benzaldehyde | 1-Bromo-4-methane-sulfonyl benzene | [6-Chloro-4-(4-methane-sulfonyl-benzoyl)-naphthalen-2-yl]-acetic acid | 12.50 (br. s, 1 H), 8.21 (s, 1 H), 8.07-8.16 (m, 4 H), 8.01 (d, J = 8.5 Hz, 2 H), 7.69 (d, J = 1.5 Hz, 1 H), 7.67 (dd, J = 9.1, 1.5 Hz, 1 H), 3.83 (s, 2 H), 3.31 (br. s, 3 H) | 403.0401$^a$ | 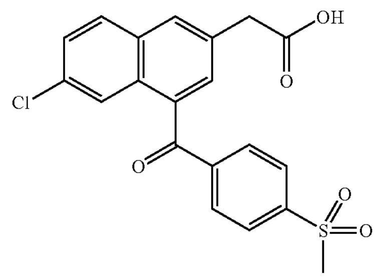 |
| 2-28 | 2-Bromo-4-methyl-benzaldehyde | 1-Bromo-4-methane-sulfonyl benzene | [4-(4-Methane-sulfonyl-benzoyl)-6-methyl-naphthalen-2-yl]-acetic acid | 12.41 (br. s, 1 H), 8.08 (d, J = 8.2 Hz, 2 H), 7.95-8.01 (m, 3 H), 7.92 (d, J = 8.4 Hz, 1 H), 7.82 (s, 1 H), 7.52 (d, J = 1.2 Hz, 1 H), 7.45 (d, J = 8.4 Hz, 1 H), 3.77 (s, 2 H), 3.28 (br. s, 3 H), H), 2.42 (s, 3 H) | 383.0947$^a$ | 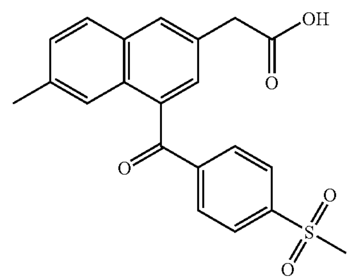 |
| 2-29 | 2-Iodo-4-trifluoro-methyl-benzaldehyde | 1-Bromo-4-methane-sulfonyl benzene | [4-(4-Methane-sulfonyl-benzoyl)-6-trifluoro-methyl-naphthalen-2-yl]-acetic acid | 12.55 (br. s, 1 H), 8.57 (s, 1 H), 8.30 (d, J = 8.8 Hz, 1 H), 8.25 (s, 1 H), 8.12 (d, J = 8.5 Hz, 2 H), 8.04 (d, J = 8.5 Hz, 2 H), 7.89 (d, J = 8.8 Hz, 1 H), 7.80 (s, 1 H), 3.89 (s, 2 H), 3.30 (br. s, 3 H) | 437.0663$^a$ | 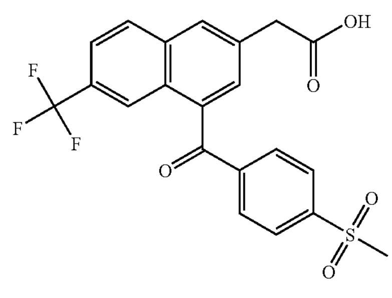 |
| 2-30 | 2-Bromo-4-chloro-benzaldehyde | 1-Bromo-3-methane-sulfonyl benzene | [6-Chloro-4-(3-methane-sulfonyl-benzoyl)-naphthalen-2-yl]-acetic acid | (400 MHz) 12.54 (br. s, 1 H), 8.29 (s, 1 H), 8.26 (d, J = 7.8 Hz, 1 H), 8.19 (d, J = 1.8 Hz, 1 H), 8.07-8.15 (m, 3 H), 7.85 (t, J = 7.8 Hz, 1 H), 7.71 (d, J = 1.2 Hz, 1 H), 7.67 (dd, J = 8.8, 1.8 Hz, 1 H), 3.83 (s, 2 H), 3.30 (s, 3 H) | 403.0 | 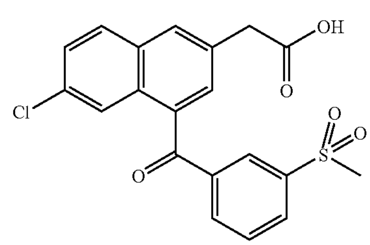 |

-continued

| Example No. | Aldehyde | Aryl halide | Systematic Name | $^1$H NMR (300 MHz, DMSO-$d_6$) δ ppm | MS $(M + H)^+$ | Structure |
| --- | --- | --- | --- | --- | --- | --- |
| 2-31 | 2-Bromo-4-fluoro-benzaldehyde | 2-Fluoro-5-bromo-phenyl-methyl-sulfone | [6-Fluoro-4-(4-fluoro-3-methane-sulfonyl-benzoyl)-naphthalen-2-yl]-acetic acid | (400 MHz) 12.50 (br. s, 1 H), 8.25 (dd, J = 6.8, 2.1 Hz, 1 H), 8.11-8.19 (m, 3 H), 7.83 (dd, J = 11.5, 2.1 Hz, 1 H), 7.67-7.75 (m, 2 H), 7.51-7.61 (m, 1 H), 3.82 (s, 2 H), 3.40 (s, 2 H) | 405.3 | 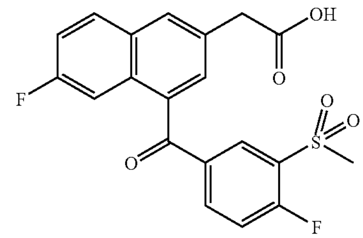 |
| 2-32 | 2-Bromo-5-trifluoro-methyl-benzaldehyde | 1-Bromo-4-methane-sulfonyl-benzene | [4-(4-Methane-sulfonyl-benzoyl)-7-trifluoro-methyl-naphthalen-2-yl]-acetic acid | (CDCl$_3$) 8.30 (d, J = 9.4 Hz, 1 H), 8.23 (s, 1 H), 8.07 (s, 1 H), 8.06 (m, 4 H), 7.72 (d, J = 8.2 Hz, 1 H), 7.66 (s, 1 H), 3.90 (s, 2 H), 3.12 (s, 3 H) | 437.0666$^a$ | 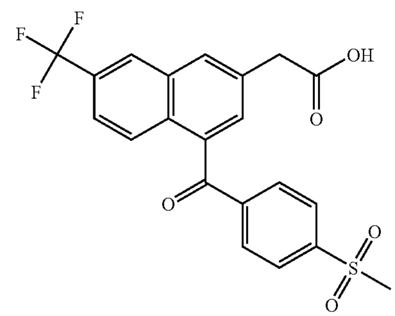 |

$^a$HRMS (ES+, [(M + H)$^+$]);
$^b$HRMS (ES+, [(M + Na)$^+$]).

Example 3-1

{6-Fluoro-4-[4-(piperazine-1-sulfonyl)-benzoyl]-naphthalen-2-yl}-acetic acid

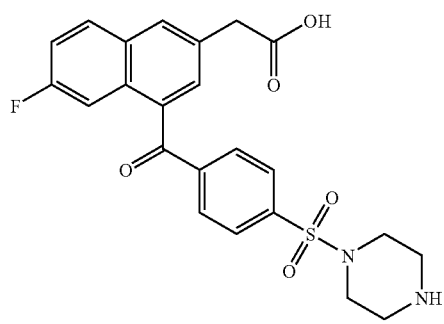

4-(4-Bromo-benzenesulfonyl)-piperazine-1-carboxylic acid tert-butyl ester

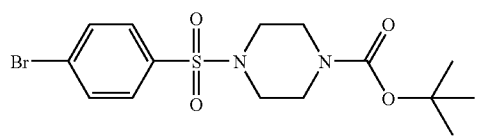

Triethylamine (0.94 mL, 6.71 mmol) was added to a stirred reaction mixture of N-tert-butoxycarbonyl piperazine (0.50 g, 2.68 mmol) in tetrahydrofuran (6 mL) at 0° C., then the reaction mixture was stirred at room temperature for 15 minutes. A solution of 4-bromo-benzenesulfonyl chloride (0.686 g, 2.68 mmol) in tetrahydrofuran (4 mL) was added to the reaction mixture and stirring continued for another 2 hours. Tetrahydrofuran was evaporated off under reduced pressure, then the reaction mixture was diluted with ethyl acetate (20 mL). The inorganic materials were filtered off through a celite bed. The filtrate was washed with 2 N aqueous HCl (5 mL), dried over anhydrous sodium sulfate and concentrated in vacuo to yield 1.00 g (92%) of 4-(4-bromo-benzenesulfonyl)-piperazine-1-carboxylic acid tert-butyl ester as a white solid, which was used in the next step without further purification. MS cald. for C$_{15}$H$_{21}$BrN$_2$O$_4$S [(M+NH$_4$)$^+$] 422, obsd. 422.1.

4-(4-Trimethylsilanylethynyl-benzenesulfonyl)-piperazine-1-carboxylic acid tert-butyl ester

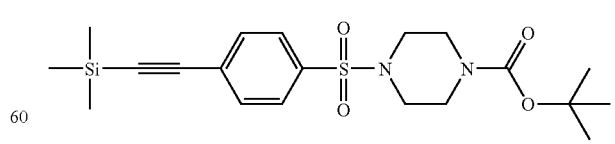

Trimethylsilylacetylene (0.70 mL, 4.94 mmol) and triethylamine (2.80 mL, 19.74 mmol) were added to a stirred solution of 4-(4-bromo-benzenesulfonyl)-piperazine-1-carboxylic acid tert-butyl ester (1.00 g, 2.468 mmol) in dry dichloromethane (12 mL), then the reaction mixture was degassed with argon for 30 minutes at room temperature. To the reaction mixture were added Pd(PPh$_3$)$_2$Cl$_2$ (0.173 g, 0.25 mmol) and CuI (0.047 g, 0.25 mmol), then the reaction mixture was heated at 50° C. for 14 hours under an argon atmosphere. The reaction mixture was cooled to room temperature and then concentrated in vacuo to yield a crude residue, which was dissolved in dichloromethane (20 mL) and washed with water (2×5 mL) and brine (5 mL). The organic phase was dried over anhydrous sodium sulfate and concentrated in vacuo to afford a black colored crude product, which was finally purified using silica gel (100-200 mesh) column chromatography (2:23 ethyl acetate-hexanes to 2:18 ethyl acetate in hexanes) to furnish 1.20 g (80%) of 4-(4-trimethylsilanyl-ethynyl-benzenesulfonyl)-piperazine-1-carboxylic acid tert-butyl ester as a brown solid. MS cald. for C$_{20}$H$_{30}$N$_2$O$_4$SSi [(M+NH$_4$)$^+$] 440, obsd. 440.0.

4-[4-(5-Fluoro-2-formyl-phenylethynyl)-benzene-sulfonyl]-piperazine-1-carboxylic acid tert-butyl ester

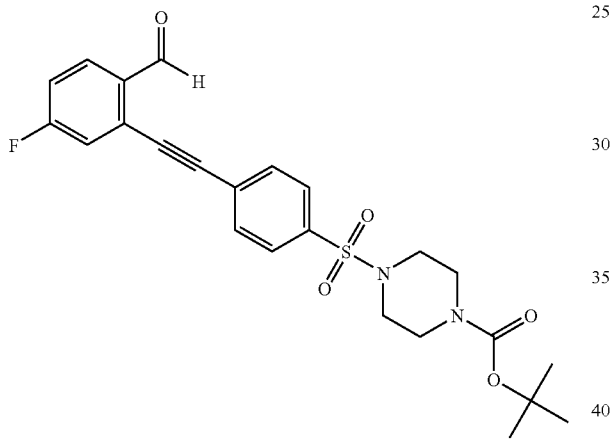

A solution of 4-(4-trimethylsilanylethynyl-benzenesulfonyl)-piperazine-1-carboxylic acid tert-butyl ester (4.100 g, 9.70 mmol) in dry N,N-dimethylformamide (30 mL) was degassed with argon for 30 minutes at room temperature. Potassium fluoride (1.690 g, 29.10 mmol) was added, then the reaction mixture was purged with argon once again for another 30 minutes. The intermediate deprotected acetylene thus formed was not isolated. Pd(PPh$_3$)$_2$Cl$_2$ (0.681 g, 0.97 mmol), CuI (4.100 g, 0.97 mmol), 2-bromo-4-fluoro benzaldehyde (1.780 g, 8.73 mmol) and triethylamine (2.00 mL, 14.55 mmol) were added simultaneously to the above reaction mixture and stirring was continued for an additional 2 hours. Water (60 mL) was added, then the reaction mixture was extracted with ethyl acetate (3×30 mL). The combined organic layers were washed with brine (2×20 mL), dried over anhydrous sodium sulfate and concentrated in vacuo to get a black colored crude product, which was purified using silica gel (100-200 mesh) column chromatography (10% ethyl acetate in hexanes) to furnish 2.00 g (43.9%) of 4-[4-(5-fluoro-2-formyl-phenylethynyl)-benzenesulfonyl]-piperazine-1-carboxylic acid tert-butyl ester as a yellow solid. MS cald. for C$_{24}$H$_{25}$FN$_2$O$_5$S [(M+NH$_4$)$^+$] 490, obsd. 490.4.

4-Fluoro-2-[4-(piperazine-1-sulfonyl)-phenylethynyl]-benzaldehyde

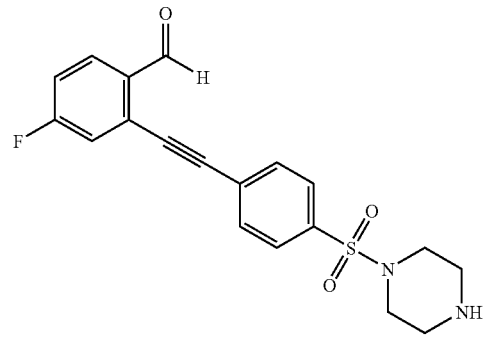

Trifluoroacetic acid (1.18 mL, 15.87 mmol) was added to a stirred solution of 4-[4-(5-fluoro-2-formyl-phenylethynyl)-benzenesulfonyl]-piperazine-1-carboxylic acid tert-butyl ester (0.500 g, 1.06 mmol) in dichloromethane (10 mL) at 0° C. The reaction mixture was stirred at room temperature for 4 hours, then concentrated under reduced pressure. The viscous liquid was washed with ether (3×5 mL) to obtain 0.310 g (60.2%) of 4-fluoro-2-[4-(piperazine-1-sulfonyl)-phenylethynyl]-benzaldehyde as a yellow solid. MS cald. for C$_{19}$H$_{17}$FN$_2$O$_3$S [(M+H)$^+$] 373, obsd. 373.3.

{6-Fluoro-4-[4-(piperazine-1-sulfonyl)-benzoyl]-naphthalen-2-yl}-acetic acid ethyl ester

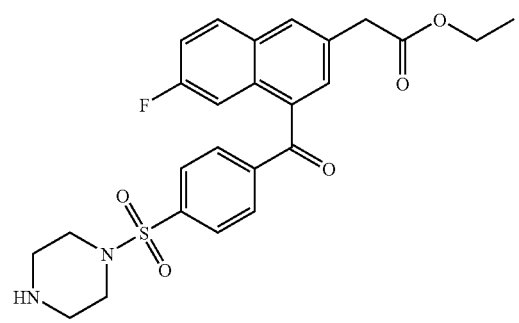

To a stirred solution of 4-fluoro-2-[4-(piperazine-1-sulfonyl)-phenylethynyl]-benzaldehyde (0.500 g, 1.03 mmol) in anhydrous 1,4 dioxane (10 mL) was added 4-oxobutyric acid ethyl ester (0.200 g, 1.54 mmol) at room temperature under an argon atmosphere. Gold (III) bromide (0.135 g, 0.31 mmol) was added, and the reaction mixture was stirred at 110° C. for 5 hours. After cooling to room temperature, the reaction mixture was concentrated under reduced pressure and then diluted with ethyl acetate (20 mL). The organic phase was washed with water (2×5 mL), dried over anhydrous sodium sulfate and concentrated under reduced pressure to obtain 0.466 g, (65%) of crude {6-fluoro-4-[4-(piperazine-1-sulfonyl)-benzoyl]-naphthalen-2-yl}-acetic acid ethyl ester as a light brown oil. Triethyl amine (0.35 mL, 2.51 mmol) was added to a stirred mixture of the crude product from above in dichloromethane (10 mL) at 0° C. The reaction mixture was stirred for 15 minutes at 0° C. Di-tert-butyl-dicarbonate (0.23 mL, 1.09 mmol) was added drop-wise to the reaction mixture at 0° C., then the reaction mixture was stirred at room temperature for 14 hours. The mixture was diluted with dichloromethane (15 mL), washed with a saturated solution of sodium bicarbonate (5 mL) followed by water (5 mL). The organic phase was dried over anhydrous sodium sulfate and concentrated under reduced pressure to obtain the crude product, which was purified by silica gel (100-200 mesh) column chromatography (ethyl acetate-hexane=1:19). The resulting purified tert-butyl carbamate (0.110 g) was dissolved in dichloromethane, then the mixture was cooled to 0° C. with stirring. Excess trifluoroacetic acid was added to the cold reaction mixture under nitrogen, then the reaction mixture was stirred for 4 hours. The reaction mixture was concentrated under reduced pressure to obtain a viscous oil, which on triturating with diethyl ether gave pure {6-fluoro-4-[4-(piperazine-1-sulfonyl)-benzoyl]-naphthalen-2-yl}-acetic acid ethyl ester as a yellow solid. MS calcd. for $C_{25}H_{25}FN_2O_5S$ [(M+H)$^+$] 485, obsd. 485.2.

{6-Fluoro-4-[4-(piperazine-1-sulfonyl)-benzoyl]-naphthalen-2-yl}-acetic acid

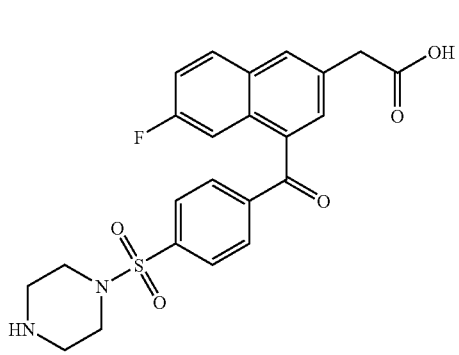

To a stirred solution of {6-fluoro-4-[4-(piperazine-1-sulfonyl)-benzoyl]-naphthalen-2-yl}-acetic acid ethyl ester (0.100 g, 0.17 mmol) in tetrahydrofuran (6 mL) was added a solution of lithium hydroxide monohydrate (0.035 g, 0.83 mmol) in water (1.5 mL) and the reaction mixture was stirred for 48 hours at room temperature. The reaction mixture was concentrated under reduced pressure, diluted with water (8 mL) and washed with ethyl acetate (2×5 mL). The aqueous layer was acidified with an aqueous solution of hydrochloric acid (1 N), then extracted with ethyl acetate (3×10 mL). The combined organic extracts were dried over anhydrous sodium sulfate and concentrated under reduced pressure to give 0.050 g (52%) of {6-fluoro-4-[4-(piperazine-1-sulfonyl)-benzoyl]-naphthalen-2-yl}-acetic acid as an off-white solid. $^1$H NMR (400 MHz, DMSO-d$_6$) δ ppm 8.13-8.17 (m, 1 H), 8.12 (s, 1 H), 7.99 (d, J=8.0 Hz, 2 H), 7.93-7.98 (m, 1 H), 7.89 (d, J=8.0 Hz, 2 H), 7.67 (s, 1 H), 7.57 (td, J=8.6, 2.0 Hz, 1 H), 3.76 (s, 2 H), 2.89 (br. s, 4 H), 2.76 (br. s, 4 H). MS calcd. for $C_{23}H_{21}FN_2O_5S$ [M$^+$] 456, obsd. 456.9.

Example 4-1

4-[4-(3-Carboxymethyl-7-fluoro-naphthalene-1-carbonyl)-benzenesulfonyl]-piperazine-1-carboxylic acid ethyl ester

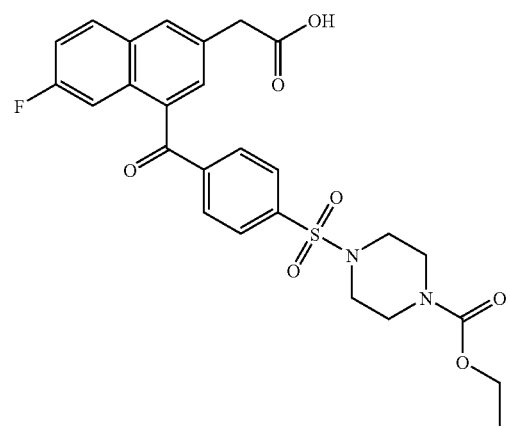

4-[4-(3-Ethoxycarbonylmethyl-7-fluoro-naphthalene-1-carbonyl)-benzenesulfonyl]-piperazine-1-carboxylic acid ethyl ester Triethylamine (0.19 mL, 1.34 mmol) was added slowly at 0° C. to a stirred reaction mixture of {6-fluoro-4-[4-(piperazine-1-sulfonyl)-benzoyl]-naphthalen-2-yl}-acetic acid ethyl ester (0.200 g, 0.33 mmol, prepared as described above) in dichloromethane (7 mL). The reaction mixture was stirred at room temperature for 15 minutes. Ethyl chloroformate (0.07 mL, 0.73 mmol) was added slowly to the reaction mixture and stirring was continued for an additional 3 hours at room temperature. The mixture was diluted with dichloromethane (10 mL), then washed with a saturated solution of sodium bicarbonate (5 mL) and water (5 mL). The organic layer was collected, dried over anhydrous sodium sulfate and concentrated under reduced pressure. The crude product was purified by silica gel (100-200 mesh) column chromatography (1:3 ethyl acetate -hexane) to give 0.077 g (41.4%) of 4-[4-(3-ethoxycarbonylmethyl-7-fluoro-naphthalene-1-carbonyl)-benzenesulfonyl]-piperazine-1-carboxylic acid ethyl ester as a viscous yellow solid. MS cald. for $C_{28}H_{29}FN_2O_7S$ ($[M+H]^+$) 556, obsd. 557.2.

4-[4-(3-Carboxymethyl-7-fluoro-naphthalene-1-carbonyl)-benzenesulfonyl]-piperazine-1-carboxylic acid ethyl ester

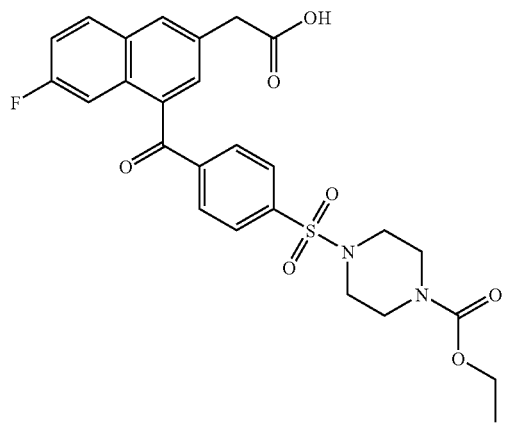

To a stirred solution of 4-[4-(3-ethoxycarbonylmethyl-7-fluoro-naphthalene-1-carbonyl)-benzenesulfonyl]-piperazine-1-carboxylic acid ethyl ester (0.110 g, 0.20 mmol) in tetrahydrofuran (12 mL) was added a solution of lithium hydroxide monohydrate (0.042 g, 0.99 mmol) in water (3 mL) and the reaction mixture was stirred for 14 hours at room temperature. The reaction mixture was concentrated under reduced pressure, diluted with water (6 mL) and washed with ethyl acetate (2×5 mL). The aqueous layer was acidified with an aqueous solution of hydrochloric acid (1 N), then extracted with ethyl acetate (3×10 mL). The combined organic layers were dried over anhydrous sodium sulfate and concentrated under reduced pressure to afford 0.058 (56%) of 4-[4-(3-carboxymethyl-7-fluoro-naphthalene-1-carbonyl)-benzenesulfonyl]-piperazine-1-carboxylic acid ethyl ester as yellow solid. $^1$H NMR (400 MHz, DMSO-$d_6$) δ ppm 12.51 (br. s, 1 H), 8.10-8.20 (m, 2H), 8.00 (d, J=8.3 Hz, 2 H), 7.90 (d, J=8.3 Hz, 2 H), 7.82-7.88 (m, 1 H), 7.72 (s, 1 H), 7.57 (td, J=8.7, 2.2 Hz, 1 H), 3.99 (q, J=6.9 Hz, 2 H), 3.82 (s, 2 H), 3.46 (br. s, 4 H), 2.96 (br. s, 4 H), 1.13 (t, J=6.9 Hz, 3 H). MS cald. for $C_{26}H_{25}FN_2O_7S$ ($[M+H]^+$) 529, obsd. 529.3.

Example 4-2

The following example 4-2 was prepared in an analogous manner to example 4-1, starting with {6-fluoro-4-[4-(piperazine-1-sulfonyl)-benzoyl]-naphthalen-2-yl}-acetic acid ethyl ester and di-tert-butyl dicarbonate.

| Example No. | Systematic Name | $^1$H NMR (400 MHz, DMSO-$d_6$) δ ppm | MS (M − H)⁻ | Structure |
|---|---|---|---|---|
| 4-2 | 4-[4-(3-Carboxymethyl-7-fluoro-naphthalene-1-carbonyl)-benzenesulfonyl]-piperazine-1-carboxylic acid tert-butyl ester | 12.51(br. s, 1 H), 8.11-8.19 (m, 2 H), 8.00 (d, J = 7.8 Hz, 2 H), 7.82-7.93 (m, 3 H), 7.72 (br. s, 1 H), 7.57 (t, J = 7.8 Hz, 1 H), 3.82(br. s, 2 H), 3.40(br. s, 4 H), 2.94(br. s, 4 H), 1.35(s, 9 H) | 555.2 | 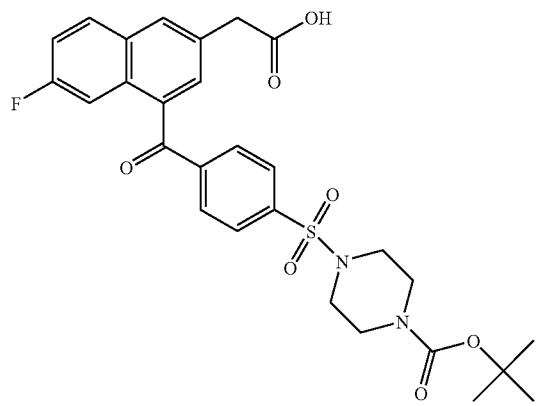 |

Example 5-1

{6-Fluoro-4-[4-(4-methyl-piperazine-1-sulfonyl)-benzoyl]-naphthalen-2-yl}-acetic acid

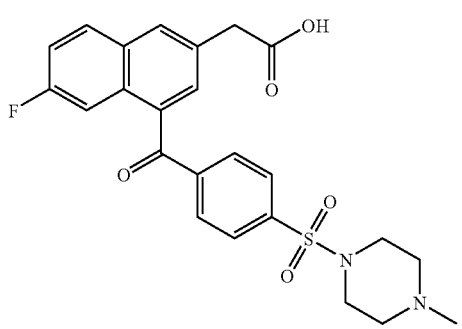

{6-Fluoro-4-[4-(4-methyl-piperazine-1-sulfonyl)-benzoyl]-naphthalen-2-yl}-acetic acid ethyl ester

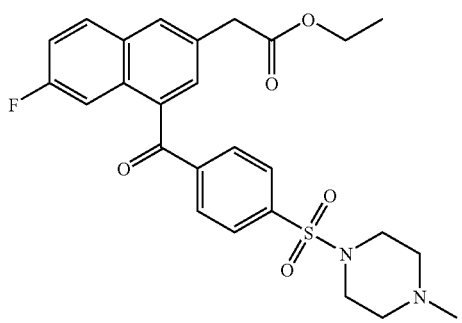

Triethylamine (0.04 mL, 0.27 mmol) was added to a stirred mixture of {6-fluoro-4-[4-(piperazine-1-sulfonyl)-benzoyl]-naphthalen-2-yl}-acetic acid ethyl ester (0.10 g, 0.17 mmol) in acetonitrile (4 mL) at 0° C. and the reaction mixture was stirred for 15 minutes. Formaldehyde (0.02 mL, 0.83 mmol) and sodium cyanoborohydride (0.017 g, 0.27 mmol) were added to the reaction mixture at 0° C., then the mixture was stirred for another 15 minutes. The reaction mixture was neutralized to pH ~7 by gradual addition of acetic acid. The reaction mixture was concentrated, and the residue was made alkaline by the addition of a 2.0 N aqueous solution of KOH. The resulting mixture was extracted with diethyl ether (2×15 mL). The combined organic layers were dried over anhydrous sodium sulfate and concentrated under reduced pressure to obtain the crude product. Silica gel (100-200 mesh) column chromatography (4:1 ethyl acetate-hexanes) afforded 0.05 g (60%) of {6-fluoro-4-[4-(4-methyl-piperazine-1-sulfonyl)-benzoyl]-naphthalen-2-yl}-acetic acid ethyl ester as an off-white sticky solid. MS calcd. for $C_{26}H_{27}FN_2O_5S$ ([M+H]$^+$) 499, obsd. 499.3.

{6-Fluoro-4-[4-(4-methyl-piperazine-1-sulfonyl)-benzoyl]-naphthalen-2-yl}-acetic acid

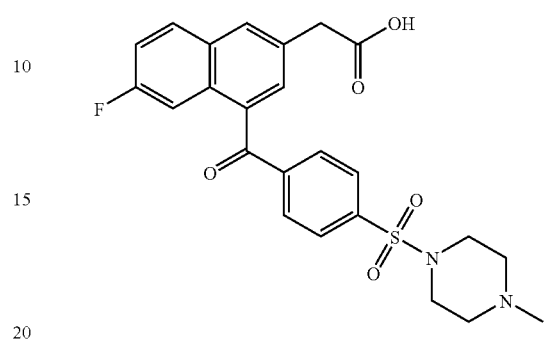

To a stirred solution of {6-fluoro-4-[4-(4-methyl-piperazine-1-sulfonyl)-benzoyl]-naphthalen-2-yl}-acetic acid ethyl ester (0.05 g, 0.10 mmol) in tetrahydrofuran (6 mL) was added a solution of lithium hydroxide monohydrate (0.021 g, 0.50 mmol) in water (1.5 mL) and the reaction mixture was stirred for 48 hours at room temperature. The solvents were distilled off under reduced pressure, then the residue was diluted with water (4 mL) and washed with ethyl acetate (2×3 mL) to remove unwanted organic products. The aqueous layer was separated and acidified to pH ~3-4 with a 1.0 N aqueous solution of hydrochloric acid. The resulting mixture was extracted with ethyl acetate (2×10 mL). The combined organic phases were dried over anhydrous sodium sulfate and concentrated under reduced pressure to yield 0.020 g (42%) of {6-fluoro-4-[4-(4-methyl-piperazine-1-sulfonyl)-benzoyl]-naphthalen-2-yl}-acetic acid as white solid. $^1$H NMR (400 MHz, DMSO-d$_6$) δ ppm 8.09-8.19 (m, 2 H), 7.84-8.05 (m, 5 H), 7.71 (s, 1 H), 7.48-7.61 (m, 1 H), 3.81 (s, 2 H), 2.97 (br. s, 4 H), 2.38 (br. s, 4 H), 2.15 (s, 3 H). MS calcd. for $C_{24}H_{23}FN_2O_5S$ ([M+H]$^+$) 471, obsd. 471.3.

Example 6-1

[6-Fluoro-4-(4-methanesulfonyl-benzoyl)-3-methyl-naphthalen-2-yl]-acetic acid

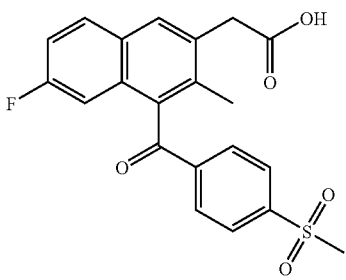

123
[6-Fluoro-4-(4-methanesulfonyl-benzoyl)-3-methyl-naphthalen-2-yl]-acetic acid methyl ester

124
[6-Fluoro-4-(4-methanesulfonyl-benzoyl)-3-methyl-naphthalen-2-yl]-acetic acid

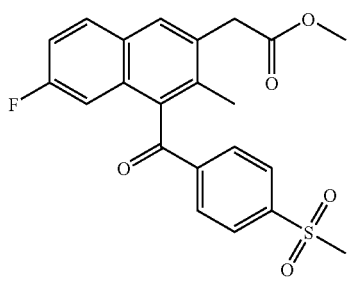

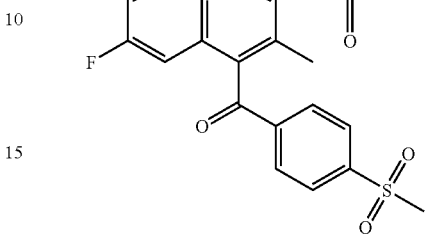

To a mixture of 4-fluoro-2-(4-methanesulfonyl-phenylethynyl)-benzaldehyde (example 2-1, 3$^{rd}$ step) (2.02 g, 6.68 mmol) and pent-3-ynoic acid methyl ester (3.03 g, 26.8 mmol) in 1,2-dichloroethane (40 mL), was added gold(III) bromide (0.264 g, 1.18 mmol). The resulting mixture was heated at 80° C. for 2 hours before additional gold(III) bromide (0.125 g, 0.59 mmol) was added. Another portion of gold(III) bromide (0.125 g, 0.59 mmol) was added after 2 more hours. After a total of 6 hours of heating, the reaction mixture was cooled to room temperature, and the solvent was removed to afford a brown oil. Flash chromatography (Aspire FlashReady™, 50 μm, 30% ethyl acetate in hexane) gave [6-fluoro-4-(4-methanesulfonyl-benzoyl)-3-methyl-naphthalen-2-yl]-acetic acid methyl ester (87 mg, 3.1%). HRMS (ESI+) cald. for $C_{22}H_{19}FO_5S$ [(M+Na)$^+$] 437.0829, obsd. 437.0827.

Starting with [6-fluoro-4-(4-methanesulfonyl-benzoyl)-3-methyl-naphthalen-2-yl]-acetic acid methyl ester (182 mg, 0.44 mmol), and using a method analogous to the one described for example 2-1, final step, [6-fluoro-4-(4-methanesulfonyl-benzoyl)-3-methyl-naphthalen-2-yl]-acetic acid (131 mg, 75%) was obtained as a solid. $^1$H NMR (300 MHz, DMSO-$d_6$) δ ppm: 12.55 (br. s, 1 H), 7.98-8.14 (m, 4 H), 7.93 (d, J=8.5 Hz, 2 H), 7.38-7.51 (m, 1 H), 6.99 (dd, J=10.7, 2.3 Hz, 1 H), 3.88 (s, 2 H), 3.29 (s, 3 H), 2.14 (s, 3 H); HRMS (ESI+) cald. for $C_{20}H_{17}FO_5S$ [(M+Na)$^+$] 423.0672, obsd. 423.0673.

Examples 6-2 to 6-3

The following examples 6-2 to 6-3 were prepared in an analogous manner to example 6-1, starting with the appropriate commercially available or prepared aldehydes and aryl halides and pent-3-ynoic acid methyl ester.

| Example No. | Aldehyde | Aryl halide | Systematic Name | $^1$H NMR (300 MHz) δ ppm | HRMS (M + H)$^+$ | Structure |
|---|---|---|---|---|---|---|
| 6-2 | 2-Bromo-4-chloro-benzaldehyde | 1-Bromo-4-methanesulfonylbenzene | [6-Chloro-4-(4-methanesulfonyl-benzoyl)-3-methyl-naphthalen-2-yl]-acetic acid | (DMSO-$d_6$) 12.56(br. s, 1 H), 8.11(d, J = 8.4 Hz, 2 H), 8.04(d, J = 9.0 Hz, 1 H), 8.02(s, 1 H), 7.94(d, J = 8.4 Hz, 2 H), 7.55(dd, J = 9.0, 1.4 Hz, 1 H), 7.29(br. s, 1 H), 3.89(s, 2 H), 3.30(br. s, 3 H), 2.14 (s, 3 H) | 417.0556 | 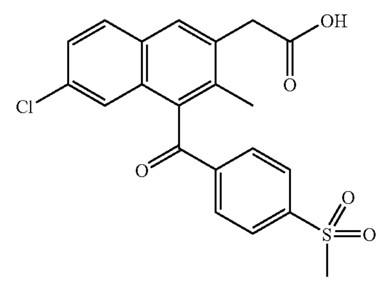 |

| Example No. | Aldehyde | Aryl halide | Systematic Name | $^1$H NMR (300 MHz) δ ppm | HRMS (M + H)$^+$ | Structure |
|---|---|---|---|---|---|---|
| 6-3 | 2-Bromo-4-fluorobenz aldehyde | 1-Bromo-4-ethane sulfonyl benzene | [4-(4-Ethanesulf onyl-benzoyl)-6-fluoro-3-methyl-naphthalen-2-yl]-acetic acid | (CDCl$_3$) 7.99 (s, 4 H), 7.80-7.91(m, 2 H), 7.20-7.29(m, 1 H), 7.00(dd, J = 10.3, 2.1 Hz, 1 H), 3.89(s, 2 H), 3.15(q, J = 7.4 Hz, 2 H), 2.24(s, 3 H), 1.31(t, J = 7.4 Hz, 3 H) | 4415.1007 | 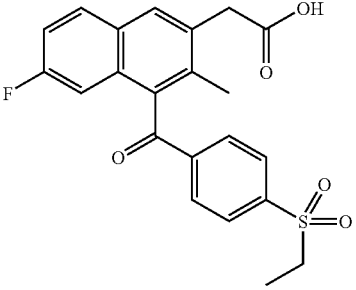 |

Example 7-1

2-[6-Fluoro-4-(4-methanesulfonyl-benzoyl)-naphthalen-2-yl]-propionic acid

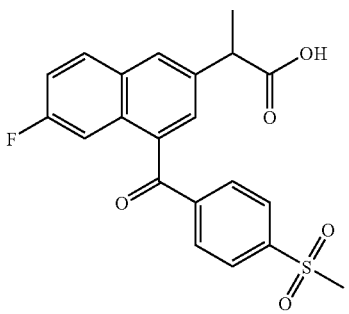

2-[6-Fluoro-4-(4-methanesulfonyl-benzoyl)-naphthalen-2-yl]-propionic acid methyl ester

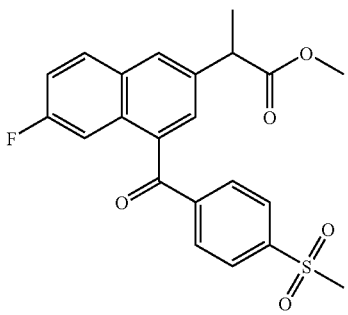

To in situ generated lithium diisopropylamide (LDA) (0.33 mmol) [from diisopropylamine (0.33 mmol) and n-butyllithium (0.36 mmol)] in tetrahydrofuran (1.5 mL) at −78° C. under nitrogen was added a solution of [6-fluoro-4-(4-methanesulfonyl-benzoyl)-naphthalen-2-yl]-acetic acid methyl ester (0.120 g, 0.30 mmol, prepared in an analogous manner to the precursor of example 2-1 according to Scheme 2) in tetrahydrofuran (1.0 mL) drop-wise. The reaction mixture was stirred for 30 minutes at −78° C. Methyl iodide (0.051 g, 0.36 mmol) in hexamethylphosphoramide (HMPA) (2.4 mL) was then added drop-wise. The resulting mixture was stirred at −78° C. for 20 minutes, then warmed to −30° C. and stirred for an additional 2 hours. The reaction was quenched with an aqueous solution of saturated ammonium chloride (2 mL), and the resulting mixture was extracted with ethyl acetate (3×5 mL). The combined organic layers were dried over anhydrous sodium sulfate, filtered, and concentrated under reduced pressure. Flash chromatography (silica gel, 100-200 mesh, 20% ethyl acetate in hexane) gave 2-[6-fluoro-4-(4-methanesulfonyl-benzoyl)-naphthalen-2-yl]-propionic acid methyl ester (0.070 g, 56.4%) as an off-white solid. MS cald. for C$_{22}$H$_{19}$FO$_5$S [(M+H)$^+$] 415, obsd. 415.

2-[6-Fluoro-4-(4-methanesulfonyl-benzoyl)-naphthalen-2-yl]-propionic acid

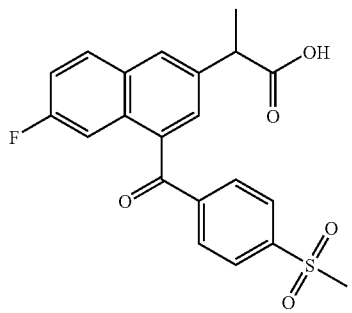

Starting with 2-[6-fluoro-4-(4-methanesulfonyl-benzoyl)-naphthalen-2-yl]-propionic acid methyl ester (0.070 g, 0.17 mmol), and using a method analogous to the one described for example 1-1, final step, 2-[6-fluoro-4-(4-methanesulfonyl-benzoyl)-naphthalen-2-yl]-propionic acid (0.040 g, 59.7%) was obtained as a semi-solid. $^1$H NMR (400 MHz, DMSO-d$_6$) δ ppm 12.58 (s, 1 H), 8.17-8.23 (m, 2 H), 8.11 (d, J=8.7 Hz, 2 H), 8.00 (d, J=8.7 Hz, 2 H), 7.87 (dd, J=11.4, 2.3 Hz, 1 H), 7.70 (d, J=1.7 Hz, 1 H), 7.58 (td, J=8.9, 2.6 Hz, 1 H), 3.88-3.98 (m, 1 H), 3.57 (s, 3 H), 1.46 (d, J=7.1 Hz, 3 H); MS cald. for C$_{21}$H$_{17}$FO$_5$S [(M+H)$^+$] 401, obsd. 401.

Example 8-1

[4-(4-Methanesulfonyl-benzyl)-6-methyl-naphthalen-2-yl]-acetic acid

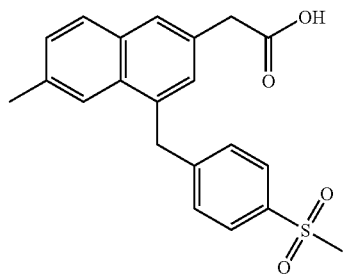

A solution of [6-methyl-4-(4-methanesulfonyl-benzoyl)-naphthalen-2-yl]-acetic acid (example 2-28) (70 mg, 0.183 mmol) in methanol (8 mL) was hydrogenated using a H-cube hydrogenation reactor with a flow rate of 1 mL/min and a 10% palladium on carbon catalyst cartridge at 30° C. under 10 bar hydrogen pressure. After the reaction was complete (monitored by TLC, 4% methanol in dichloromethane), the solvent was evaporated in vacuo. Reverse-phase preparative HPLC (using a Waters® Delta-Prep™ 3000 with a Varian Pursuit® C-18 column [10 μm, 20×150 mm]) gave [4-(4-methanesulfonyl-benzyl)-6-methyl-naphthalen-2-yl]-acetic acid (14.4 mg, 21%) as a white solid. $^1$H NMR (300 MHz, CDCl$_3$) δ ppm: 7.83 (d, J=8.4 Hz, 2 H), 7.74 (d, J=8.7 Hz, 1 H), 7.66 (s, 1H), 7.60 (s, 1 H), 7.38 (d, J=8.4 Hz, 2 H), 7.32 (d, J=8.7 Hz, 1 H), 7.22 (s, 1 H), 4.48 (s, 2 H), 3.78 (s, 2 H), 3.02 (s, 3 H), 2.46 (s, 3 H); HRMS cald. for O$_{21}$H$_{20}$O$_4$S (ESI$^+$) [(M+Na)$^+$] 391.0974, obsd. 391.0976.

Examples 8-2 to 8-9

The following examples 8-2 to 8-9 were prepared in an analogous manner to example 8-1, starting with the corresponding ketone derivatives.

| Example No | Systematic Name | $^1$H NMR (300 MHz, CDCl$_3$) δ ppm | HRMS (ESI+, (M + Na)$^+$) | Structure |
|---|---|---|---|---|
| 8-2 | [4-(4-Methanesulfonyl-benzyl)-6-trifluoromethyl-naphthalen-2-yl]-acetic acid | 8.19(s, 1 H), 7.97 (d, J = 8.5 Hz, 1 H), 7.87(d, J = 8.2 Hz, 2 H), 7.78 (s, 1 H), 7.66(dd, J = 8.5, 1.5 Hz, 1 H), 7.39(d, J = 8.2 Hz, 2 H), 7.35 (s, 1 H), 4.56(s, 2 H), 3.85(s, 2 H), 3.04(s, 3 H) | 377.0829$^a$ | 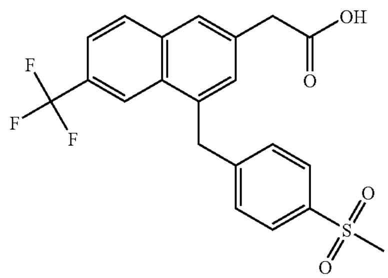 |
| 8-3 | [4-(4-Methanesulfonyl-benzyl)-7-trifluoromethyl-naphthalen-2-yl]-acetic acid | (CD$_3$OD) 8.22(s, 1 H), 8.11(d, J = 8.8 Hz, 1 H), 7.87 (s, 1 H), 7.83(d, J = 8.2 Hz, 2 H), 7.54-7.63(m, 2 H), 7.47(d, J = 8.2 Hz, 2 H), 4.61 (s, 2 H), 3.81(s, 2 H), 3.06(s, 3 H) | 445.0691 | 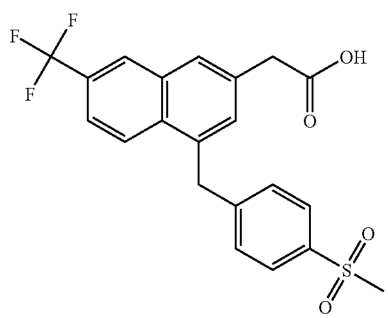 |
| 8-4 | [6-Fluoro-4-(4-methanesulfonyl-benzyl)-naphthalen-2-yl]-acetic acid | 7.78-7.88(m, 3 H), 7.71(br. s, 1 H), 7.39-7.46(m, 1 H), 7.37(d, J = 7.8 Hz, 2 H), 7.28-7.34(m, 2 H), 4.49(s, 2 H), 3.79 (s, 2 H), 3.04(s, 3 H) | 395.0724 | 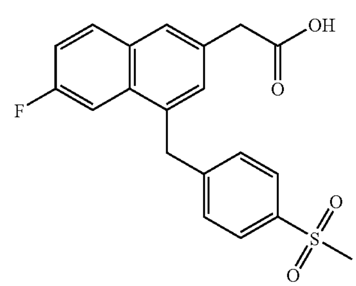 |
| 8-5 | [6-Fluoro-4-(4-methanesulfonyl-2-methyl-benzyl)-naphthalen-2-yl]-acetic acid | 7.87(dd, J = 8.6, 6.2 Hz, 1 H), 7.82 (s, 1 H), 7.71(s, 1 H), 7.59-7.67(m, 1 H), 7.37-7.46 (m, 1 H), 7.31(dd, J = 10.6, 2.1 Hz, 1 H), 7.05(s, 1 H), 7.01(d, J = 8.2 Hz, 1 H), 4.37(s, 2 H), 3.77(s, 2 H), 3.06(s, 3 H), 2.45(s, 3 H) | 409.0881 | 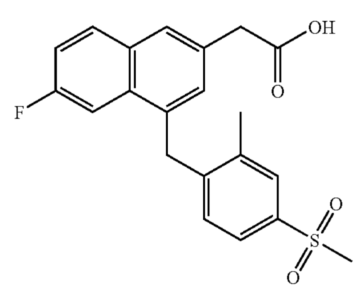 |

| Example No | Systematic Name | $^1$H NMR (300 MHz, CDCl$_3$) δ ppm | HRMS (ESI+, (M + Na)$^+$) | Structure |
|---|---|---|---|---|
| 8-6 | [6-Fluoro-4-(4-methanesulfonyl-3-trifluoromethyl-benzyl)-naphthalen-2-yl]-acetic acid | 8.19(d, J = 7.8 Hz, 1 H), 7.82-7.92(m, 1 H), 7.75(br. s, 2 H), 7.49(d, J = 7.5 Hz, 1 H), 7.39(d, J = 10.3 Hz, 1 H), 7.28-7.34(m, 2 H), 4.51(s, 2 H), 3.84(s, 2 H), 3.17 (s, 3 H) | 463.0597 | 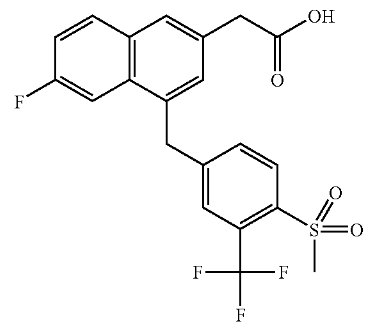 |
| 8-7 | [4-(4-Ethanesulfonyl-2-methyl-benzyl)-6-fluoro-naphthalen-2-yl]-acetic acid | (DMSO-d$_6$) 12.35 (br. s, 1 H), 8.01 (dd, J = 9.1, 6.0 Hz, 1 H), 7.75(d, J = 3.3 Hz, 2 H) 7.63(dd, J = 11.5, 2.1 Hz, 1 H), 7.54 (dd, J = 8.1, 1.4 Hz, 1 H), 7.42(td, = 8.8, 2.1 Hz, 1 H) 7.09(s, 1 H) 6.96(d, J = 8.1 Hz, 1 H), 4.44(s, 2 H) 3.65(s, 2 H) 3.23(q, J = 7.4 Hz, 2 H) 2.41(s, 3 H) 1.06(t, J = 7.4 Hz, 3 H) | 401.1215$^d$ | 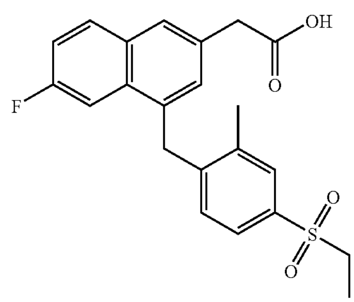 |
| 8-8 | [4-(4-Dimethylsulfamoyl-benzyl)-6-fluoro-naphthalen-2-yl]-acetic acid | (DMSO-d$_6$) 7.99 (dd, J = 9.1, 6.0 Hz, 1 H) 7.76(s, 1 H) 7.72(dd, J = 11.5, 2.1 Hz, 1 H) 7.66(d, J = 8.3 Hz, 2 H) 7.49(d, J = 8.3 Hz, 2 H) 7.36-7.45(m, 2 H) 4.51(s, 2 H) 3.72(s, 2 H) 2.56 (s, 6 H) | 402.1169$^b$ | 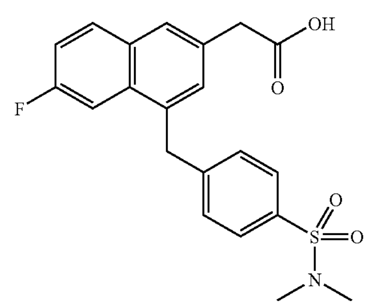 |
| 8-9 | [4-(4-Ethanesulfonyl-benzyl)-6-fluoro-naphthalen-2-yl]-acetic acid | (DMSO-d$_6$) 12.41 (br. s, 1 H) 7.98 (dd, J = 9.0, 6.2 Hz, 1 H) 7.74-7.81 (m, 3 H) 7.71(dd, J = 11.6, 2.4 Hz, 1 H) 7.49(d, J = 8.2 Hz, 2 H) 7.42 (s, 1 H) 7.37(dd, J = 9.0, 2.4 Hz, 1 H) 4.50(s, 2 H) 3.71(s, 2 H) 3.21 (q, J = 7.3 Hz, 2 H) 1.03(t, J = 7.3 Hz, 3 H) | 409.0880 | 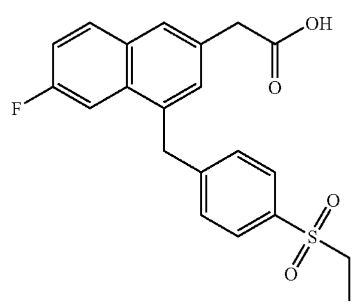 |

$^a$HRMS reported as [M − COOH]$^−$;
$^b$HRMS (ES+), [(M + H)$^+$].

Example 9-1

[6-Fluoro-4-(4-methylsulfamoyl-benzyl)-naphthalen-2-yl]-acetic acid

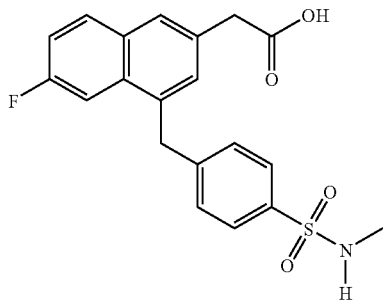

[6-Fluoro-4-(4-methylsulfamoyl-benzyl)-naphthalen-2-yl]acetic acid methyl ester

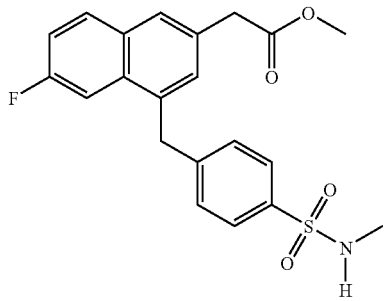

A solution of [6-fluoro-4-(4-methylsulfamoyl-benzoyl)-naphthalen-2-yl]-acetic acid methyl ester (prepared in an analogous manner to the ethyl ester precursor to example 2-1) in methanol (20 mL) was hydrogenated using a H-cube hydrogenation reactor with a flow rate of 1 mL/min and a 10% palladium on carbon catalyst cartridge at 30° C. under 10 bar hydrogen pressure. The reaction gave a mixture of [6-fluoro-4-(4-methylsulfamoyl-benzyl)-naphthalen-2-yl]acetic acid methyl ester, and the corresponding alcohol {6-fluoro-4-[hydroxy-(4-methylsulfamoyl-phenyl)-methyl]-naphthalen-2-yl}-acetic acid methyl ester, a precursor to example 20-1. Reverse-phase preparative HPLC (using a Waters® Delta-Prep™ 3000 with a Varian Pursuit® C-18 column [10 µm, 20×150 mm]) was used to separate these products, giving [6-fluoro-4-(4-methylsulfamoyl-benzyl)-naphthalen-2-yl]-acetic acid methyl ester (3.0 mg) as a white solid. MS cald. for $C_{21}H_{20}FNO_4S$ [(M+H$^+$)] 401, obsd. 402.

[6-Fluoro-4-(4-methylsulfamoyl-benzyl)-naphthalen-2-yl]acetic acid

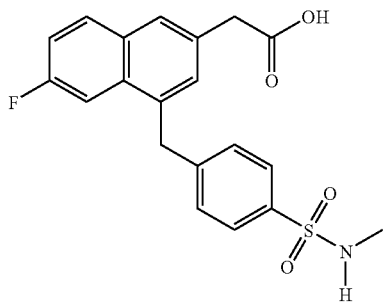

Starting with [6-fluoro-4-(4-methylsulfamoyl-benzyl)-naphthalen-2-yl]-acetic acid methyl ester, using a method analogous to the one described for example 2-1, final step, [6-fluoro-4-(4-methylsulfamoyl-benzyl)-naphthalen-2-yl]-acetic acid (2.8 mg, 96%) was obtained as a yellow oil. $^1$H NMR (300 MHz, CDCl$_3$) δ ppm 7.84 (dd, J=9.1, 5.7 Hz, 1 H), 7.76 (d, J=7.9 Hz, 2 H), 7.70 (s, 1 H), 7.44 (d, J=10.6 Hz, 1 H), 7.32 (d, J=8.5 Hz, 2 H), 7.28 (s, 1 H), 4.43 (s, 3 H), 3.81 (s, 2 H), 2.65 (d, J=5.4 Hz, 3 H); HRMS cald. for $C_{21}H_{20}O_4S$ [(M+Na)$^+$] 410.0833, obsd. 410.0833.

Example 10-1

[6-Fluoro-4-(4-methanesulfonyl-benzyl)-3-methyl-naphthalen-2-yl]-acetic acid

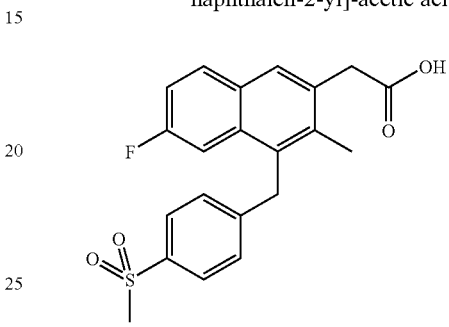

First Method of Preparing Example 10-1

2-(4-Fluoro-benzylidene)-3-methyl-succinic acid 1-methyl ester

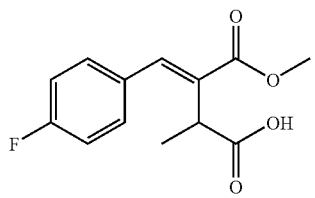

A 2 L three-neck flask fitted with a drop-wise addition funnel and a mechanical stirrer was charged with 18.63 g (0.466 mol) of sodium hydride (60% suspension in mineral oil) under a stream of argon gas. The sodium hydride was washed twice with 100 mL portions of hexane and once with a 100 mL portion of toluene in order to remove the mineral oil. The reaction flask was then charged with toluene (220 mL) followed by a catalytic amount of methanol (0.5 mL, 12.3 mmol). A mixture of 4-fluorobenzaldehyde (21 mL, 0.196 mol) and dimethyl methylsuccinate (87.61 g, 0.547 mol) was added drop-wise to the mechanically stirred solution. Drop-wise addition occurred slowly over 1.5 hours such that the reaction temperature did not exceed 35° C. and evolution of hydrogen gas occurred at a steady, moderate rate. After the drop-wise addition was complete, the reaction mixture was stirred for 3 hours. The reaction mixture was cooled in an ice-water bath. Concentrated HCl (100 mL) was added slowly drop-wise at a rate such that the reaction temperature did not exceed 20° C. Water (100 mL) was added, and the biphasic mixture was poured into a separatory funnel. The organic layer was separated, then extracted twice with 1 M aqueous potassium carbonate. The combined aqueous extracts were carefully acidified to pH 2 with concentrated HCl. The resultant cloudy suspension was extracted three times with 500 mL portions of diethyl ether. The combined organic extracts were dried over $Na_2SO_4$, filtered, and evaporated to yield 2-(4-fluoro-benzylidene)-3-methyl-succinic acid 1-methyl ester as an orange oil which contained excess dimethyl methylsuccinate as a major impurity and minor amounts of other impurities. This crude product was used in the next reaction without further purification.

4-Acetoxy-6-fluoro-3-methyl-naphthalene-2-carboxylic acid methyl ester

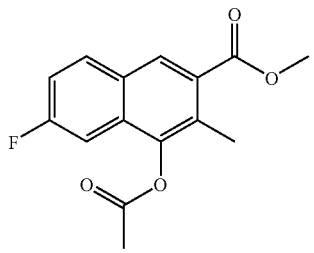

To a solution of crude 2-(4-fluoro-benzylidene)-3-methyl-succinic acid 1-methyl ester (approximately 49 g, 0.196 mol) in acetic anhydride (490 mL) was added sodium acetate (32.15 g, 0.392 mol) in one portion. The reaction mixture was stirred at 150° C. for 3 hours. After this time, the reaction mixture was cooled to room temperature, then stirred overnight. Acetic anhydride was removed in vacuo, providing a viscous brown oil. This crude product was dissolved in ethyl acetate. The resulting solution was washed with a saturated, aqueous ammonium chloride solution. The organic phase was dried over $Na_2SO_4$, filtered, and concentrated. Flash chromatography (Analogix SuperFlash™ 10% ethyl acetate in hexane) gave 18.4 g (34%) of 4-acetoxy-6-fluoro-3-methyl-naphthalene-2-carboxylic acid methyl ester as a yellow oil.

6-Fluoro-4-hydroxy-3-methyl-naphthalene-2-carboxylic acid methyl ester

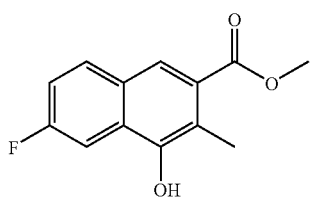

A heterogeneous mixture of potassium carbonate (46 g, 0.33 mol), water (260 mL), and acetone (260 mL) was added in three portions to a 0° C. solution of 4-acetoxy-6-fluoro-3-methyl-naphthalene-2-carboxylic acid methyl ester (18.4 g, 0.066 mol) in methanol (1 L). The resulting mixture was stirred at 0° C. for 15 minutes, then warmed to room temperature and stirred at room temperature for 1 hour. The reaction mixture was concentrated in vacuo. The remaining oily suspension was diluted with ethyl acetate and washed with 1 N aqueous HCl. The organic phase was dried ($MgSO_4$), filtered, and concentrated to yield 9.64 g (62%) of 6-fluoro-4-hydroxy-3-methyl-naphthalene-2-carboxylic acid methyl ester as a yellowish tan solid. HRMS (ES−) cald. for $C_{13}H_{11}FO_3$ [(M−H)−] 233.0619, obsd. 233.0619.

4-Benzyloxy-6-fluoro-3-methyl-naphthalene-2-carboxylic acid methyl ester

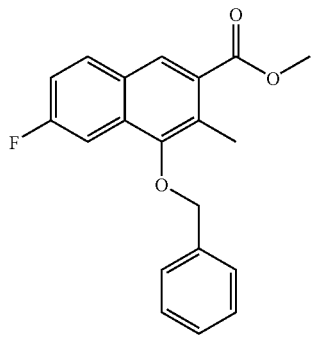

Benzyl bromide (10 mL, 82.51 mmol) was added to a mixture of 6-fluoro-4-hydroxy-3-methyl-naphthalene-2-carboxylic acid methyl ester (15.56 g, 66.43 mmol) and potassium carbonate (19.26 g, 136.6 mmol) in acetone (300 mL). The reaction mixture was heated at reflux for 3 hours. The acetone was removed in vacuo. The residue was diluted with water, and the resulting mixture was extracted three times with ethyl acetate. The combined organic phases were washed with brine, dried over $MgSO_4$, filtered, and concentrated. A concentrated solution of the crude product in 25% ethyl acetate in hexanes was loaded onto a Analogix Super-Flash™ column. Flash chromatography (25-50% ethyl acetate in hexanes) provided 14.27 g (66% yield) of 4-benzyloxy-6-fluoro-3-methyl-naphthalene-2-carboxylic acid methyl ester as a slightly yellow solid. $^1$H NMR (300 MHz, DMSO-$d_6$) δ ppm 8.34 (s, 1 H), 8.19 (dd, J=8.9, 5.9 Hz, 1 H), 7.64 (dd, J=10.7, 2.3 Hz, 1 H), 7.57 (d, J=6.6 Hz, 2 H), 7.36-7.54 (m, 4 H), 4.98 (s, 2 H), 3.89 (s, 3 H), 2.56 (s, 3 H).

(4-Benzyloxy-6-fluoro-3-methyl-naphthalen-2-yl)-methanol

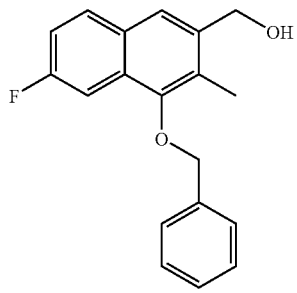

A round-bottom flask was charged with lithium aluminum hydride (3.5 g, 88 mmol), and the flask was placed in an brine/ice bath. Tetrahydrofuran (100 mL) was added slowly. The resulting solution was maintained at −4° C. with stirring. A solution of 4-benzyloxy-6-fluoro-3-methyl-naphthalene-2-carboxylic acid methyl ester (14.27 g, 44.00 mmol) in tetrahydrofuran (30 mL) was slowly added to the cold lithium aluminum hydride suspension drop-wise via an addition funnel. The rate of drop-wise addition was monitored so that the reaction temperature did not exceed 6° C. After the drop-wise addition was complete, the reaction was warmed to room temperature. The reaction mixture was stirred at room temperature for 1 hour. After this time, the reaction mixture was cooled to 4° C. in an ice bath. Water (3.5 mL) was added slowly, keeping the reaction temperature below 4° C. A 15% aqueous NaOH solution (3.5 mL) was next added, followed by an additional portion of water (10.5 mL). The precipitated solids were filtered, and then rinsed with ethyl acetate. The combined filtrates were concentrated to obtain 13.09 g (quantitative yield) of (4-benzyloxy-6-fluoro-3-methyl-naphthalen-2-yl)-methanol as a white solid. This product was used in the next step without additional purification. $^1$H NMR (300 MHz, DMSO-$d_6$) δ ppm 8.00 (dd, J=8.9, 5.9 Hz, 1 H), 7.77 (s, 1 H), 7.54-7.63 (m, 3 H), 7.31-7.51 (m, 4 H), 5.26-5.35 (m, 1 H), 4.94 (s, 2 H), 4.64 (d, J=5.1 Hz, 2 H), 2.34 (s, 3 H).

1-Benzyloxy-3-chloromethyl-7-fluoro-2-methyl-naphthalene

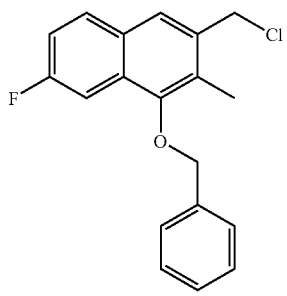

A three-neck round-bottom flask was charged with triphenylphosphine (23.33 g, 88.34 mmol), tetrahydrofuran (70 mL), and carbon tetrachloride (35 mL, 0.36 mol) under an argon atmosphere. The resulting mixture was stirred at room temperature for 20 minutes. A solution of (4-benzyloxy-6-fluoro-3-methyl-naphthalen-2-yl)-methanol (13.09 g, 44.17 mmol) in tetrahydrofuran (50 mL) was added rapidly to the reaction mixture via an addition funnel. The reaction mixture was heated at reflux for 1 hour. The reaction mixture was cooled to room temperature, and the solvents were removed in vacuo. The residue was diluted with water, and the resulting mixture was extracted twice with ethyl acetate. The organic phases were washed twice with water, and the resulting aqueous layers were extracted with ethyl acetate. The combined organic extracts were washed with brine, dried over MgSO$_4$, filtered, and concentrated. The crude product was purified using flash chromatography (Analogix SuperFlash™ column, 10-25% dichloromethane in hexane), affording 10.8 g (77%) 1-benzyloxy-3-chloromethyl-7-fluoro-2-methyl-naphthalene as a white solid. $^1$H NMR (300 MHz, DMSO-$d_6$) δ ppm 8.02 (dd, J=8.9, 5.9 Hz, 1 H), 7.89 (s, 1 H), 7.53-7.65 (m, 3 H), 7.35-7.50 (m, 4 H), 4.97 (s, 4 H), 2.47 (s, 3 H).

(4-Benzyloxy-6-fluoro-3-methyl-naphthalen-2-yl)-acetic acid methyl ester

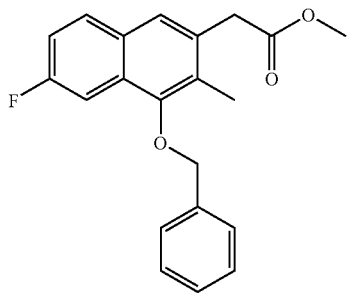

A 2 L round bottom flask containing 1-benzyloxy-3-chloromethyl-7-fluoro-2-methyl-naphthalene (10.84 g, 34.44 mmol), PdCl$_2$(PPh$_3$)$_2$ (1.22 g 1.72 mmol, 0.05 eq), and potassium carbonate (5.04 g, 36.50 mmol, 1.06 eq) was evacuated and then backfilled with carbon monoxide gas. A balloon of carbon monoxide was connected into the reaction flask to provide an extra reservoir of CO gas. Tetrahydrofuran (120 mL) was added to the reaction mixture, followed by methanol (58 mL). The reaction mixture was stirred at room temperature for 3 hours, and then diluted with water (600 mL). The resulting mixture was extracted twice with 300 mL portions of ethyl acetate. The combined organic layers were washed with water and brine, dried over MgSO$_4$, filtered, and concentrated to obtain 12.6 g of the crude product. Flash chromatography (Analogix SuperFlash™, 0-15% ethyl acetate in hexane) was used to isolate 11.7 g (quantitative yield) of (4-benzyloxy-6-fluoro-3-methyl-naphthalen-2-yl)-acetic acid methyl ester as a clear, colorless oil that crystallized upon standing at room temperature. $^1$H NMR (300 MHz, DMSO-$d_6$) δ ppm 7.96 (dd, J=9.1, 5.7 Hz, 1 H), 7.65 (s, 1 H), 7.52-7.62 (m, 3 H), 7.32-7.50 (m, 4 H), 4.94 (s, 2 H), 3.89 (s, 2 H), 3.64 (s, 3 H), 2.31 (s, 3 H).

(6-Fluoro-4-hydroxy-3-methyl-naphthalen-2-yl)-acetic acid methyl ester

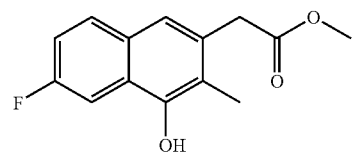

A round-bottom flask was charged with (4-benzyloxy-6-fluoro-3-methyl-naphthalen-2-yl)-acetic acid methyl ester (11.7 g, 34.58 mmol) in ethanol (350 mL). Some heating was required in order to dissolve all of the starting material in ethanol. A full spatula scoop of 10% palladium on carbon was added into the reaction flask. The reaction mixture was stirred under hydrogen gas at atmospheric pressure overnight at room temperature. After this time, it appeared that approximately 750 mL hydrogen gas had been consumed, and TLC (1:3 ethyl acetate, hexanes) indicated that the starting material had been consumed. The reaction mixture was filtered through a bed of celite. The filtrate was concentrated to afford 7.91 g (92%) of (6-fluoro-4-hydroxy-3-methyl-naphthalen-2-yl)-acetic acid methyl ester, which was used in the next step without further purification. MS (ES−) cald. for C$_{14}$H$_{13}$FO$_3$ [(M−H)$^-$] 247, obsd. 247.1.

(6-Fluoro-3-methyl-4-trifluoromethanesulfonyloxy-naphthalen-2-yl)-acetic acid methyl ester

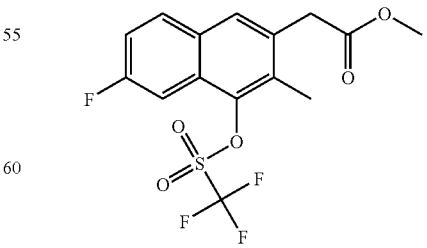

Trifluoromethanesulfonic anhydride (0.35 mL, 2.1 mmol) was added drop-wise to a 0° C. solution of (6-fluoro-4-hydroxy-3-methyl-naphthalen-2-yl)-acetic acid methyl ester (400 mg, 1.61 mmol) and pyridine (0.195 mL, 2.42 mmol) in dichloromethane (12.0 mL). The reaction mixture was stirred at 0° C. for 30 minutes. The reaction mixture was warmed to room temperature, and stirred for 4 hours. The reaction mixture was then cooled to 0° C. Water (150 mL) was added, and the mixture was extracted three times with 50 mL portions of dichloromethane. The combined organic layers were dried over $Na_2SO_4$, filtered, and evaporated to yield a yellow oil. A solution of this crude product in dichloromethane was evaporated over silica gel, and the resulting silica gel-supported product was subjected to flash chromatography (RediSep® Flash column, 230-400 mesh, 28% ethyl acetate in hexane) to give 514 mg (84%) of (6-fluoro-3-methyl-4-trifluoromethanesulfonyloxy-naphthalen-2-yl)-acetic acid methyl ester as a white, crystalline solid. $^1$H NMR (300 MHz, $CDCl_3$) δ ppm 7.82 (dd, J=8.9, 5.6 Hz, 1 H), 7.73 (s, 1 H), 7.64 (d, J=10.0 Hz, 1 H), 7.27-7.35 (m, 1 H), 3.84 (s, 2 H), 3.73 (s, 3 H), 2.49 (s, 3 H). HRMS (ES+) cald. for $C_{15}H_{12}F_4O_5S$ [(M+Na)$^+$] 403.0234, obsd. 403.0233.

[6-Fluoro-4-(4-methanesulfonyl-benzyl)-3-methyl-naphthalen-2-yl]-acetic acid methyl ester

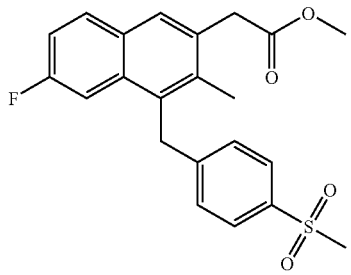

Step 1. Preparation of the Benzylic Zinc Chloride: An oven dried 3-neck 250 mL round-bottom flask was charged with zinc dust (13.08 g, 200 mmol) and previously dried lithium chloride (8.47 g, 200 mmol) under nitrogen. The mixture was heated to 171° C. and stirred for 1.5 hours under high vacuum. The mixture was cooled to room temperature. The reaction flask was backfilled with nitrogen and equipped with a thermometer. To the gray zinc/lithium chloride mixture was added freshly distilled tetrahydrofuran (8 mL) under nitrogen. Then, 1,2-dibromoethane (0.52 mL, 6.0 mmol) was added. The zinc suspension was then heated gently with a heat gun to ebullition. After being allowed to cool (50° C.), the mixture was heated again. This process was repeated three times to make sure the zinc dust was activated completely. The activated zinc dust was then treated with trimethylsilyl chloride (0.761 mL, 6.0 mmol), and the suspension was stirred for 15 min at room temperature. The reaction mixture was then treated drop-wise with a solution of 4-methanesulfonylbenzyl chloride (10.24 g, 50.0 mmol) in dry tetrahydrofuran (25 mL) at 5-10° C. (ice bath with water). After the addition, the reaction mixture was allowed to warm to room temperature in an ambient temperature water bath. After 2 hours, the zinc insertion reaction was complete (as indicated by TLC analysis of a small aliquot from the reaction mixture which was quenched with a saturated solution of $NH_4Cl$ and then diluted with ethyl acetate). The reaction mixture was diluted with freshly distilled tetrahydrofuran (25 mL), and the stirring was stopped to allow the excess zinc dust to settle over 15 hours.

Step 2. Negishi Coupling Reaction: In a separate reaction flask, palladium (II) acetate (643 mg, 2.86 mmol) and S-Phos (2-dicyclohexylphosphino-2',6'-dimethoxybiphenyl) (2.35 g, 5.73 mmol) were combined with freshly distilled tetrahydrofuran (80 mL) at room temperature under nitrogen. The resulting mixture was stirred at room temperature for 10 minutes. A solution of (6-fluoro-3-methyl-4-trifluoromethanesulfonyloxy-naphthalen-2-yl)-acetic acid methyl ester (10.92 g, 28.66 mmol) in freshly distilled tetrahydrofuran (80 mL) was added to the light brown reaction mixture. After 2-3 minutes, the benzyl zinc reagent in tetrahydrofuran (prepared above) was added at room temperature. The resulting dark brown solution was heated at 60° C. for 1 hour. During this time, the initial dark brown solution turned to a cloudy light brown and then slowly to a dark brown solution. The reaction mixture was cooled to room temperature and then diluted with saturated ammonium chloride solution (200 mL). The organic compound was extracted into ethyl acetate (2×150 mL) and the combined organic extracts were washed with brine (200 mL). The organic layers were dried over anhydrous magnesium sulfate, filtered, and concentrated to give the crude product which was first purified on a 1 kg silica gel plug [eluting with hexanes (500 mL), 20% ethyl acetate in hexanes (1.0 L) and 40%-60% ethyl acetate in hexanes (each 2.0 L)]. The pure fractions gave 9.33 g of the desired pure material from this purification and ±4.0 g of impure compound. The impure product was again purified by flash chromatography (ISCO RediSep® Flash column, 230-400 mesh, eluting with 0-40% ethyl acetate in hexanes) to obtain another 2 g of the desired product. The combined yield of [6-fluoro-4-(4-methanesulfonyl-benzyl)-3-methyl-naphthalen-2-yl]-acetic acid methyl ester was 11.33 g (98%), isolated as a light yellow solid. HRMS (EI+) cald. for $C_{22}H_{21}FO_4S$ [M$^+$] 400.1145, obsd. 400.1144.

[6-Fluoro-4-(4-methanesulfonyl-benzyl)-3-methyl-naphthalen-2-yl]-acetic acid

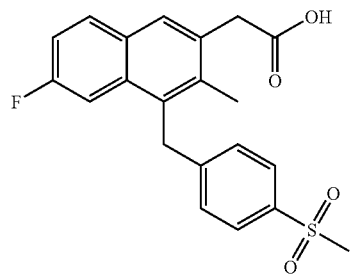

Starting with [6-fluoro-4-(4-methanesulfonyl-benzyl)-3-methyl-naphthalen-2-yl]-acetic acid methyl ester (11.33 g, 28.3 mmol), using a method analogous to the one described for example 2-1, final step, [6-fluoro-4-(4-methanesulfonyl-benzyl)-3-methyl-naphthalen-2-yl]-acetic acid was obtained. Further purification was accomplished by recrystallization from acetonitrile to give the final product in two crops as 10.07 g (92%) of a white solid. $^1$H NMR (300 MHz, $CDCl_3$) δ ppm 7.77-7.85 (m, 3 H), 7.72 (s, 1 H), 7.39 (d, J=11.8 Hz, 1 H), 7.16-7.26 (m, 3 H), 4.54 (s, 2 H), 3.91 (s, 2 H), 3.03 (s, 3 H), 2.38 (s, 3 H); HRMS (ESI+) cald. for $C_{21}H_{19}O_4SF$ [(M+Na)$^+$] 409.0880, obsd. 409.0880.

Second Method of Preparing Example 10-1

[6-Fluoro-4-(4-methanesulfonyl-benzyl)-3-methyl-naphthalen-2-yl]-acetic acid tert-butyl ester

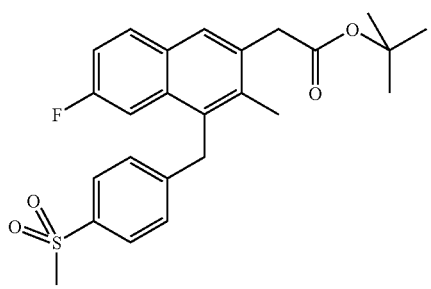

To a mixture of Zn dust (14.21 g, 213.1 mmol) in DMF (45.00 mL) was added trimethylchlorosilane (910.5 μL, 7.102 mmol) via syringe, and the reaction mixture was stirred at room temperature for 30 minutes. A solution of 1-chloromethyl-4-methanesulfonyl-benzene (19.28 g, 92.33 mmol) in 35.00 mL of DMF was then added over 5 minutes via syringe (the syringe was rinsed with an additional 5 mL of DMF). When the reaction temperature elevated to 45° C., a cold water bath was used to maintain the reaction temperature between 35-45° C., and the reaction mixture was stirred at that temperature range for an additional 20 minutes. The triflate XXXVI-a (prepared as described above in scheme 25, 30.00 g, 71.02 mmol) and dichlorobis(triphenylphosphine)palladium(II) (254.3 mg, 0.355 mmol) were then added, and the resulting reaction mixture was heated at 64° C. over 10 minutes, to initiate the reaction. The external heating source was then removed, and the internal temperature raised to 67° C. and slowly dropped to 64° C. The reaction mixture was stirred at 64±3° C. for 3 hours, when HPLC analysis indicated 99.7% conversion. The reaction mixture was then cooled to 15° C., and diluted with 150 mL of ethyl acetate and 15 mL of water. The resulting mixture was stirred at room temperature for 20-30 minutes, and then filtered through a thin cake of celite. The celite cake was washed with ethyl acetate (3×30 mL), and the combined organic phases were washed with water (2×150 mL), and then concentrated (25 C/60 mmHg) to furnish 35.1 g of crude [6-fluoro-4-(4-methanesulfonyl-benzyl)-3-methyl-naphthalen-2-yl]-acetic acid tert-butyl ester, which was directly used in the next step without further purification.

[6-Fluoro-4-(4-methanesulfonyl-benzyl)-3-methyl-naphthalen-2-yl]-acetic acid

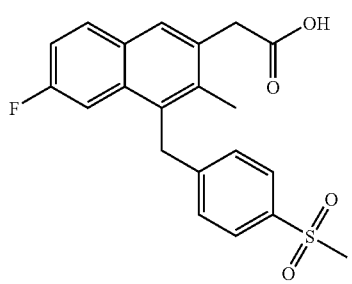

The tert-butyl ester above (43.00 g, 97.16 mmol) was dissolved in freshly prepared warm (35° C.) 4:1 trifluoroacetic acid:water solution (240 mL). The resulting mixture was stirred at 30-35° C. for 30 minutes, and then diluted with water (336 mL). The warm mixture (~30° C.) was then filtered and washed with water (3×200 mL), then dried under vacuum overnight to provide 36.28 g of a white solid, which contained 1.1% trifluoroacetic acid (TFA). The solid was further dried at 50° C. under vacuum overnight, to furnish 35.7 g of [6-fluoro-4-(4-methanesulfonyl-benzyl)-3-methyl-naphthalen-2-yl]-acetic acid as a white solid. $^1$H NMR (300 MHz, DMSO-$d_6$) δ ppm 12.44 (br. s, 1 H), 7.95 (dd, J=8.8, 6.3 Hz, 1H), 7.77-7.83 (m, 3 H), 7.68 (d, J=12.0 Hz, 1 H), 7.36 (td, J=8.8, 2.3 Hz, 1 H), 7.29 (d, J=8.1 Hz, 2 H), 4.60 (s, 2 H), 3.84 (s, 2 H), 3.15 (s, 3 H), 2.32 (s, 3 H).

Examples 10-2 to 10-13

The following examples 10-2 to 10-13 were prepared in an analogous manner to the first method of preparing example 10-1, starting with the indicated substituted benzaldehyde and dimethyl methylsuccinate and using the indicated benzyl chloride as a precursor to the benzylic zinc reagent in the Negishi coupling step.

| Example No | Systematic Name | Benzaldehyde | Benzyl Chloride | $^1$H NMR (300 MHz, DMSO-$d_6$) δ ppm | HRMS (ES$^+$, (M + Na)$^+$) | Structure |
|---|---|---|---|---|---|---|
| 10-2 | [6-Fluoro-4-(3-methanesulfonyl-benzyl)-3-methyl-naphthalen-2-yl]-acetic acid | 4-Fluorobenzaldehyde | 3-(Methanesulfonyl)benzyl chloride | 12.42(br. s, 1 H), 7.85-7.98(m, 1 H), 7.77(s, 1 H), 7.64-7.75 (m, 3 H), 7.48 (t, J = 8.0 Hz, 1 H), 7.34(t, J = 8.6 Hz, 1 H), 7.23(d, J = 7.5 Hz, 1 H), 4.59(s, 2 H), 3.82(s, 2 H), 3.15(s, 3 H), 2.30(s, 3 H) | 409.0882 | 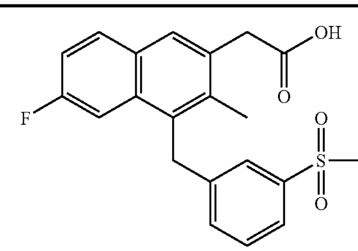 |

-continued

| Example No | Systematic Name | Benzaldehyde | Benzyl Chloride | $^1$H NMR (300 MHz, DMSO-$d_6$) δ ppm | HRMS (ES$^+$, (M + Na)$^+$) | Structure |
| --- | --- | --- | --- | --- | --- | --- |
| 10-3 | [4-(4-Benzenesulfonyl-benzyl)-6-fluoro-3-methyl-naphthalen-2-yl]-acetic acid | 4-Fluorobenz-aldehyde | 4-(Benzene sulfonyl) benzyl chloride | 12.44(br. s, 1 H), 7.88-7.97(m, 3 H), 7.84(d, J = 8.4 Hz, 2 H), 7.77(s, 1 H), 7.54-7.71 (m, 4 H), 7.34 (td, J = 8.8, 2.1 Hz, 1 H), 7.25(d, J = 8.4 Hz, 2 H), 4.55(s, 2 H), 3.81(s, 2 H), 2.26(s, 3 H) | 471.1038 | 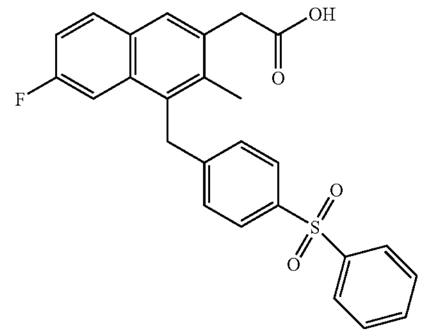 |
| 10-4 | [4-(4-Bromo-benzyl)-6-fluoro-3-methyl-naphthalen-2-yl]-acetic acid | 4-Fluorobenz-aldehyde | 4-bromoben-zyl chloride | 12.44(s, 1 H), 7.93(dd, J = 8.8, 6.3 Hz, 1 H), 7.76(s, 1 H), 7.65(dd, J = 12.1, 2.2 Hz, 1 H), 7.43(d, J = 8.4 Hz, 2 H), 7.34(td, J = 8.8, 2.2 Hz, 1 H), 6.99(d, J = 8.4 Hz, 2 H), 4.44(s, 2 H), 3.82(s, 2 H), 2.31(s, 3 H) | 385.0244$^b$ | 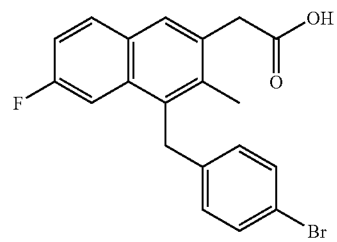 |
| 10-5 | [4-(4-Cyano-benzyl)-6-fluoro-3-methyl-naphthalen-2-yl]-acetic acid | 4-Fluorobenz-aldehyde | 4-cyanoben-zyl chloride | 12.44(s, 1 H), 7.92(dd, J = 8.9, 6.3 Hz, 1 H), 7.76(s, 1 H), 7.70(d, J = 8.2 Hz, 2 H), 7.65(dd, J = 12.1, 2.2 Hz, 1 H), 7.34(td, J = 8.8, 2.2 Hz, 1 H), 7.21(d, J = 8.2 Hz, 2 H), 4.56(s, 2 H), 3.81(s, 2 H), 2.29(s, 3 H) | 356.1057 | 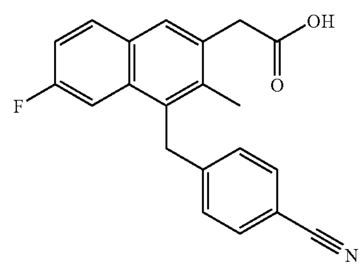 |
| 10-6 | [6-Fluoro-3-methyl-4-(4-pyrazol-1-yl-benzyl)-naphthalen-2-yl]-acetic acid | 4-Fluorobenz-aldehyde | 1-(4-Chloromethyl-phenyl)-1H-pyrazole | 12.15(br, s, 1 H), 8.38(s, 1 H), 7.94(t, J = 7.2 Hz, 1 H), 7.77(s, 1 H), 7.59-7.73 (m, 4 H), 7.35 (t, J = 8.8 Hz, 1 H), 7.15(d, J = 7.5 Hz, 2 H), 6.49(d, J = 1.5 Hz, 1 H), 4.50(s, 2 H), 3.84(s, 2 H), 2.35(s, 3 H) | 375.1503$^a$ | 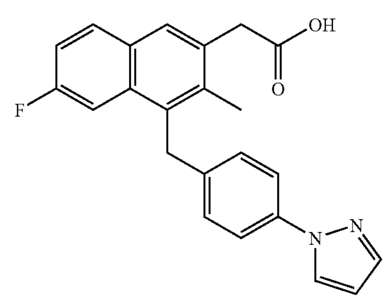 |

-continued

| Example No | Systematic Name | Benzaldehyde | Benzyl Chloride | ¹H NMR (300 MHz, DMSO-$d_6$) δ ppm | HRMS (ES⁺, (M + Na)⁺) | Structure |
|---|---|---|---|---|---|---|
| 10-7 | (6-Fluoro-3-methyl-4-[3-(1-methyl-1H-tetrazol-5-yl)-benzyl]-naphthalen-2-yl]-acetic acid | 4-Fluorobenz-aldehyde | 3-(1-methyl-tetrazol-5-yl)benzyl chloride | 12.44(s, 1 H), 7.92(dd, J = 8.8, 6.3 Hz, 1 H), 7.76(s, 1 H), 7.64(m, 2 H), 7.56(s, 1 H), 7.43-7.53 (m, 1 H), 7.33 (td, J = 8.8, 2.4 Hz, 1 H), 7.27(d, J = 7.5 Hz, 1 H), 4.58(s, 2 H), 4.06(s, 3 H), 3.83(s, 2 H), 2.36(s, 3 H) | 391.1564[a] | 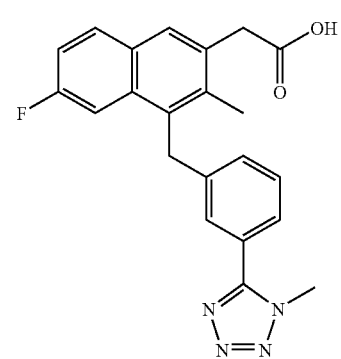 |
| 10-8 | [4-(4-Benzyloxy-benzyl)-6-fluoro-3-methyl-naphthalen-2-yl]-acetic acid | 4-Fluorobenz-aldehyde | 4-(Benzyloxy) benzyl chloride | 12.38(br. s, 1 H), 7.91 (dd, J = 9.1, 6.3 Hz, 1 H), 7.74(s, 1 H), 7.64(d, J = 12.1 Hz, 1 H), 7.27-7.44(m, 6 H), 6.96(d, J = 8.8 Hz, 2 H), 6.88(d, J = 8.8 Hz, 2 H), 5.01(s, 2 H), 4.38(s, 2 H), 3.82(s, 2 H), 2.33(s, 3 H) | 437.1521 | 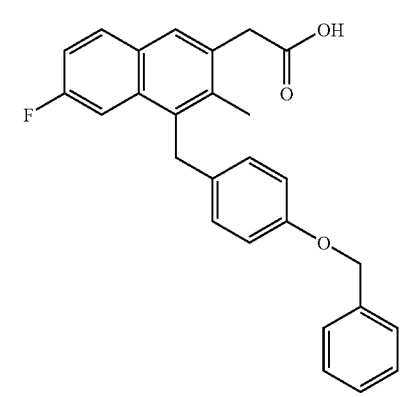 |
| 10-9 | [4-(3-Cyano-benzyl)-6-fluoro-3-methyl-naphthalen-2-yl]-acetic acid | 4-Fluorobenz-aldehyde | 3-cyanobenzyl chloride | 12.45(br. s, 1 H), 7.93 (dd, J = 8.9, 6.2 Hz, 1 H), 7.77(s, 1 H), 7.59-7.71(m, 2 H), 7.49(s, 1 H), 7.43(t, J = 7.7 Hz, 1 H), 7.27-7.38 (m, 2 H), 4.53 (s, 2 H), 3.82 (s, 2 H), 2.30 (s, 3 H) | 332.1090[b] | 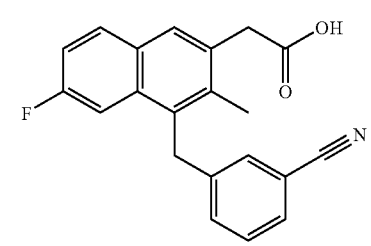 |
| 10-10 | {6-Fluoro-3-methyl-4-[4-(1-methyl-1H-tetrazol-5-yl)-benzyl]-naphthalen-2-yl}-acetic acid | 4-Fluorobenz-aldehyde | 4-(1-methyl-tetrazol-5-yl)benzyl chloride | 12.26(br. s, 1 H), 7.95 (dd, J = 8.8, 6.2 Hz, 1 H), 7.68-7.81 (m, 4 H), 7.36 (td, J = 8.8, 2.3 Hz, 1 H), 7.28(d, J = 8.2 Hz, 2 H), 4.59(s, 2 H), 4.12(s, 3 H), 3.84(s, 2 H), 2.36(s, 3 H) | 389.1417[b] | 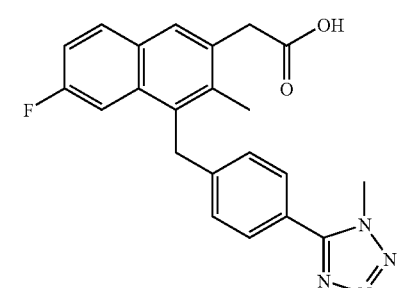 |

-continued

| Example No | Systematic Name | Benzaldehyde | Benzyl Chloride | $^1$H NMR (300 MHz, DMSO-$d_6$) δ ppm | HRMS (ES$^+$, (M + Na)$^+$) | Structure |
|---|---|---|---|---|---|---|
| 10-11 | [4-(4-Benzylsulfanyl-benzyl)-6-fluoro-3-methyl-naphthalen-2-yl]-acetic acid | 4-Fluorobenz-aldehyde | (4-benzyl-sulfanyl)ben-zyl chloride | 7.89(dd, J = 8.6, 6.5 Hz, 1 H), 7.70(s, 1 H), 7.61(d, J = 11.8 Hz, 1 H), 7.21-7.38(m, 6 H), 7.19(d, J = 8.2 Hz, 2 H), 6.96(d, J = 8.2 Hz, 2 H), 4.39(s, 2 H), 4.14(s, 2 H), 3.74(s, 2 H), 2.31(s, 3 H) | 431.1475$^a$ | 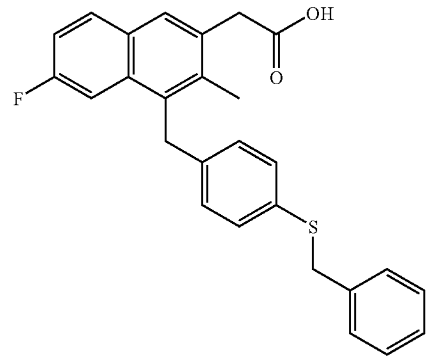 |
| 10-12 | [6-Chloro-4-(4-methanesul-fonyl-benzyl)-3-methyl-naphthalen-2-yl]-acetic acid | 4-Chlorobenz-aldehyde | 4-(Methane-sulfonyl) benzyl chloride | 12.43(br. s, 1 H), 7.98(s, 1 H), 7.91(d, J = 8.8 Hz, 1 H), 7.77-7.84 (m, 3 H), 7.46 (dd, J = 8.6, 1.4 Hz, 1 H), 7.28(d, J = 8.2 Hz, 2 H), 4.63(s, 2 H), 3.84(s, 2 H), 3.16(s, 3 H), 2.31(s, 3 H) | 425.0587 | 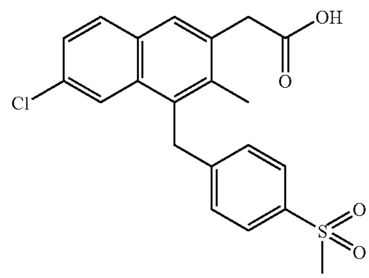 |
| 10-13 | [6-Chloro-4-(4-methanesul-fonylmethyl-benzyl)-3-methyl-naphthalen-2-yl]-acetic acid | 4-Chlorobenz-aldehyde | 1-chloromethyl-4-methane sulfonylmethyl benzene | 12.70(br. s, 1 H), 7.96(s, 1 H), 7.89(d, J = 8.7 Hz, 1 H), 7.76(s, 1 H), 7.44(d, J = 8.7 Hz, 1 H), 7.27(d, J = 8.0 Hz, 2 H), 7.05(d, J = 8.0 Hz, 2 H), 4.50(s, 2 H), 4.39(s, 2 H), 3.83(s, 2 H), 2.87(s, 3 H), 2.33(s, 3 H) | 439.0741 | 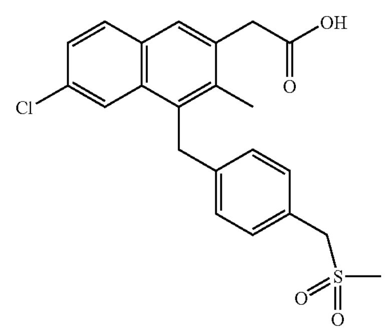 |

$^a$HRMS (ES+), [(M + H)$^+$];
$^b$HRMS (ES−), [(M − H)$^−$].

Example 11-1

[6-Fluoro-3-methyl-4-(4-trifluoromethanesulfonyl-benzyl)-naphthalen-2-yl]-acetic acid

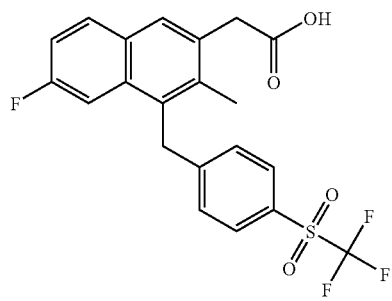

[6-Fluoro-3-methyl-4-(4-trifluoromethanesulfanyl-benzyl)-naphthalen-2-yl]-acetic acid methyl ester

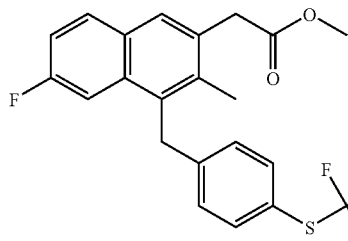

Step 1. Preparation of the Benzylic Zinc Chloride: To an oven-dried 3-neck 50 mL round bottom flask equipped with a rubber septum and an L-shaped adapter was added zinc dust (1.3 g, 20 mmol) and previously dried lithium chloride (850 mg, 20 mmol) under nitrogen. The flask was heated to 171° C.

and stirred for 1.5 hours under high vacuum. The mixture was then cooled to room temperature and backfilled with nitrogen. To this gray mixture was added dry tetrahydrofuran (2 mL) under nitrogen. Then, the reaction mixture was treated with 1,2-dibromoethane (0.170 mL, 2.0 mmol). The suspension was heated gently with a heat gun to ebullition and then allowed to cool (~50° C.), and heated again to reflux. This process was repeated three times to make sure the zinc dust was activated completely. The activated zinc dust was then treated with trimethylsilyl chloride (0.254 mL, 2.0 mmol), and the suspension was stirred for 15 minutes at room temperature. The reaction mixture was then treated drop-wise with a solution of (4-trifluoromethanesulfanyl)benzyl chloride (1.13 g, 5.0 mmol) in dry tetrahydrofuran (5 mL) at 5-10° C. (ice with water bath) for 5-10 minutes. After the addition was complete, the reaction mixture was allowed to warm to room temperature. An ambient temperature water bath was used as necessary to keep the temperature from exceeding 50° C. The reaction mixture was stirred at room temperature for 2 hours, then diluted with dry tetrahydrofuran (5 mL). Stirring was halted to allow the excess zinc dust to settle over about 3 hours.

Step 2. Negishi Coupling Reaction: In a separate reaction flask, palladium(II) acetate (34 mg, 0.15 mmol) and 2-dicyclohexylphosphino-2',6'-dimethoxybiphenyl (S-Phos) (123 mg, 0.3 mmol) were combined with dry tetrahydrofuran (3 mL) under nitrogen, and the mixture was stirred for 5 minutes. A solution of (6-fluoro-3-methyl-4-trifluoromethanesulfonyloxy-naphthalen-2-yl)-acetic acid methyl ester (570 mg, 1.5 mmol) in dry tetrahydrofuran (5 mL) was added to the above light brown solution. After 2-3 minutes, the above freshly prepared and clear organozinc compound in tetrahydrofuran was added at room temperature. The resulting dark brown colored solution was heated to 61° C. (oil bath temperature) for 1 hour. During this 1 hour, the initial dark brown solution turned to a cloudy light brown color and then slowly to a dark brown solution. The reaction mixture was cooled to room temperature and diluted with saturated ammonium chloride solution (50 mL). The organic compound was extracted into ethyl acetate (2×50 mL) and the combined organic extracts were washed with brine solution (100 mL). The organic layers were dried over anhydrous magnesium sulfate, filtered, and concentrated to give the crude product which was purified by flash chromatography using an ISCO RediSep® Flash column, 230-400 mesh, eluting with 0-15% ethyl acetate in hexanes to obtain [6-fluoro-3-methyl-4-(4-trifluoromethanesulfanyl-benzyl)-naphthalen-2-yl]-acetic acid methyl ester (460 mg, 80%) as a light brown solid: HRMS (ESI+) cald. for $C_{22}H_{18}F_4O_2S$ $[(M+H)^+]$ 423.1037, obsd. 423.1038.

[6-Fluoro-3-methyl-4-(4-trifluoromethanesulfonyl-benzyl)-naphthalen-2-yl]-acetic acid methyl ester

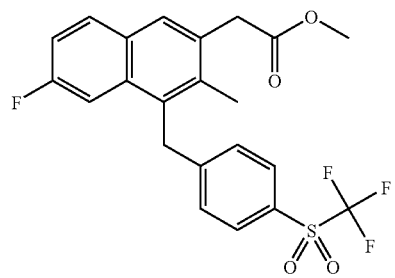

To a solution of [6-fluoro-3-methyl-4-(4-trifluoromethanesulfanyl-benzyl)-naphthalen-2-yl]-acetic acid methyl ester (392 mg, 0.93 mmol) in dichloromethane (10 mL) was added m-chloroperoxybenzoic acid (480 mg, 2.78 mmol) at −10° C. The resulting clear solution was stirred for 30 minutes at a temperature between −10° C. and 0° C. and then it was allowed to warm to room temperature. The resulting clear solution was stirred for 15 hours, by which time a white solid had formed. Then, the reaction mixture was diluted with water (20 mL) and the dichloromethane was removed under vacuum. The organic compound was extracted into ethyl acetate (2×40 mL) and the organic layer was washed with saturated sodium bicarbonate solution (3×50 mL). Then, the ethyl acetate layer was washed with brine solution (100 mL) and dried over anhydrous magnesium sulfate, filtered, and concentrated in vacuo. The crude residue was purified by flash chromatography using an ISCO RediSep® Flash column, 230-400 mesh, eluting with 0-30% ethyl acetate in hexanes to afford [6-fluoro-3-methyl-4-(4-trifluoromethanesulfonyl-benzyl)-naphthalen-2-yl]-acetic acid methyl ester (404 mg, 96%) as a white solid. HRMS (ES−) calcd for $C_{22}H_{18}F_4O_4S$ $[(M−H)^−]$ 453.0789, obsd. 453.0790.

[6-Fluoro-3-methyl-4-(4-trifluoromethanesulfonyl-benzyl)-naphthalen-2-yl]-acetic acid

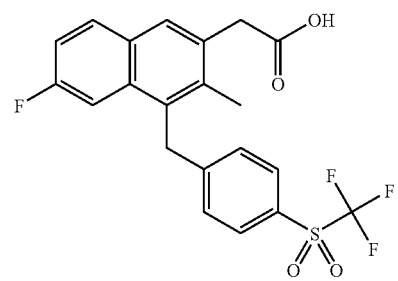

To a solution of [6-fluoro-3-methyl-4-(4-trifluoromethanesulfonyl-benzyl)-naphthalen-2-yl]-acetic acid methyl ester (395 mg, 0.87 mmol) in tetrahydrofuran (15 mL) was added a solution of lithium hydroxide monohydrate (208 mg, 8.7 mmol) in water (3 mL) at room temperature. The resulting clear solution was stirred for 15 hours. Then, the tetrahydrofuran was removed under vacuum and the residue was diluted with water (10 mL). The aqueous solution was acidified with 1.0 N hydrochloric acid and the organic compound was extracted into ethyl acetate (2×20 mL). The combined organic extracts were washed with brine solution (50 mL) and dried over anhydrous magnesium sulfate. Filtration of the drying agent and concentration of the solvent under vacuum provided 343 mg (90%) of [6-fluoro-3-methyl-4-(4-trifluoromethanesulfonyl-benzyl)-naphthalen-2-yl]-acetic acid as a white solid. mp=200-201° C.: $^1$H NMR (300 MHz, DMSO-$d_6$) δ ppm 12.45 (br. s, 1 H), 8.04 (d, J=8.4 Hz, 2 H), 7.96 (dd, J=9.1, 6.0 Hz, 1 H), 7.81 (s, 1 H), 7.69-7.80 (m, 1 H), 7.48 (d, J=8.4 Hz, 2 H), 7.29-7.43 (m, 1 H), 4.71 (s, 2 H), 3.84 (s, 2 H), 2.30 (s, 3 H). ES(+)-HRMS cald. for $C_{21}H_{16}F_4O_4S$ $[(M+Na)^+]$ 463.0597, obsd. 463.0598.

Examples 11-2 to 11-3

The following examples 11-2 to 11-3 were prepared in an analogous manner to example 11-1, starting with (6-fluoro-3-methyl-4-trifluoromethanesulfonyloxy-naphthalen-2-yl)-acetic acid methyl ester and the appropriate benzyl chloride as a precursor to the benzylic zinc reagent.

| Example No | Systematic Name | Benzyl Chloride | 1H NMR (300 MHz, DMSO-d6) δ ppm | MS | Structure |
|---|---|---|---|---|---|
| 11-2 | [6-Fluoro-3-methyl-4-(3-trifluoromethanesulfonyl-benzyl)-naphthalen-2-yl]-acetic acid | (3-trifluoromethanesulfanyl)benzyl chloride | 12.85(br. s, 1 H), 7.85-7.97 (m, 3 H), 7.63-7.79(m, 3 H), 7.51-7.61(m, 1 H), 7.34(td, J = 8.7, 2.0 Hz, 1 H), 4.68(s, 2 H), 3.79(s, 2 H), 2.30(s, 3 H) | 463.0598[a] | 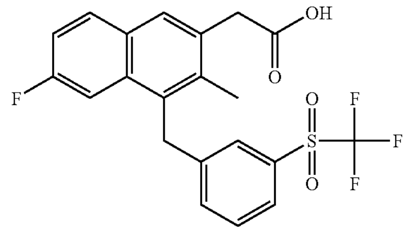 |
| 11-3 | [6-Fluoro-3-methyl-4-(4-phenylmethanesulfonyl-benzyl)-naphthalen-2-yl]-acetic acid | (4-benzylsulfanyl)benzyl chloride | 12.46(br. s, 1 H), 7.95(dd, J = 8.9, 6.3 Hz, 1 H), 7.79(s, 1 H), 7.65(dd, J = 12.1, 1.9 Hz, 1 H), 7.57(d, J = 8.5 Hz, 2 H), 7.37(td, J = 8.9, 1.9 Hz, 1 H), 7.16-7.31(m, 5 H), 7.06(d, J = 7.2 Hz, 2 H), 4.58(s, 4 H), 3.84(s, 2 H), 2.31(s, 3 H) | 461.1226[b] | 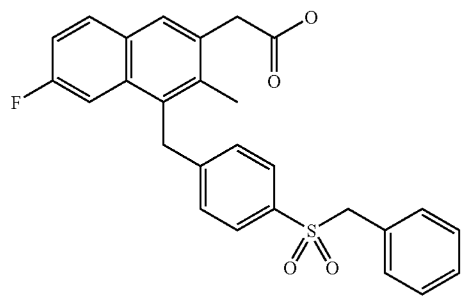 |

[a] HRMS (ES+), [(M + Na)+];
[b] HRMS (ES-), [(M - H)-].

Example 12-1

[6-Fluoro-4-(4'-methanesulfonyl-biphenyl-4-ylmethyl)-3-methyl-naphthalen-2-yl]-acetic acid

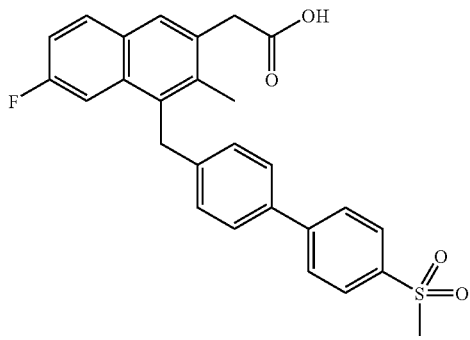

[4-(4-Benzyloxy-benzyl)-6-fluoro-3-methyl-naphthalen-2-yl]-acetic acid methyl ester

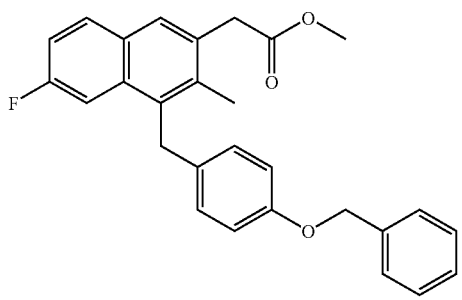

Step 1. Preparation of the Benzylic Zinc Chloride: To an oven-dried 3-neck 100 mL round bottom flask equipped with a rubber septum and an argon inlet was added zinc dust (4.82 g, 73.6 mmol) and previously dried lithium chloride (3.12 g, 73.6 mmol) under nitrogen. The flask was heated at 170° C. for 1.5 hours under high vacuum. The mixture was then cooled to 50° C. and backfilled with argon. To this gray mixture was added dry tetrahydrofuran (5 mL) and 1,2-dibromoethane (0.20 mL, 2.3 mmol). The resulting suspension was heated gently with a heat gun to ebullition and then allowed to cool (~50° C.), and heated again to reflux. This process was repeated three times to make sure the zinc dust was activated completely. The activated zinc dust was then treated with trimethylsilyl chloride (0.29 mL, 2.3 mmol), and the suspension was stirred for 15 min at room temperature. The reaction mixture was cooled to 5° C., and then treated drop-wise with a solution of (4-benzyloxy)benzyl chloride (4.29 g, 18.4 mmol) in dry tetrahydrofuran (14 mL) over 5-10 minutes. After the addition was complete, the reaction mixture was allowed to warm to room temperature, and then stirred at room temperature for 3 hours. An ambient temperature water bath was used as necessary to keep the temperature from exceeding 50° C. After 3 hours, stirring was halted to allow the excess zinc dust to settle over several hours.

Step 2. Negishi Coupling Reaction: In a separate reaction flask, palladium(II) acetate (236 mg, 1.05 mmol) and 2-dicyclohexylphosphino-2',6'-dimethoxybiphenyl (S-Phos) (891 mg, 2.1 mmol) were combined with dry tetrahydrofuran (20 mL) under argon. The mixture was stirred at room temperature for 5 minutes. A solution of (6-fluoro-3-methyl-4-trifluoromethanesulfonyloxy-naphthalen-2-yl)-acetic acid methyl ester (4.0 g, 1.5 mmol) in dry tetrahydrofuran (10 mL) was added to the above light brown solution. After 2-3 minutes, the above freshly prepared and clear organozinc compound in tetrahydrofuran was added at room temperature. The resulting orange colored solution was heated to 61° C. (oil bath temperature) for 30 minutes. The reaction mixture was cooled to room temperature and diluted with saturated ammonium chloride solution (100 mL). The organic compound was extracted into ethyl acetate (2×100 mL) and the combined organic extracts were washed with brine solution. The organic layers were dried over anhydrous magnesium sulfate, filtered, and concentrated to give the crude product. A silica gel plug (eluting with dichloromethane) was used to give 4.23 g (84%) of [4-(4-Benzyloxy-benzyl)-6-fluoro-3-methyl-naphthalen-2-yl]-acetic acid methyl ester (460 mg, 80%) as a solid with 90% purity. This product was used in the subsequent reaction without further purification. $^1$H NMR (300 MHz, DMSO-$d_6$) δ ppm 7.92 (dd, J=8.9, 6.2 Hz, 1 H), 7.75 (s, 1 H), 7.65 (dd, J=12.2, 2.0 Hz, 1 H), 7.25-7.47 (m, 6 H), 6.95 (d, J=8.7 Hz, 2 H), 6.88 (d, J=8.7 Hz, 2 H), 5.01 (s, 2 H), 4.38 (s, 2 H), 3.93 (s, 2 H), 3.64 (s, 3 H), 2.31 (s, 3 H).

[6-Fluoro-4-(4-hydroxy-benzyl)-3-methyl-naphthalen-2-yl]acetic acid methyl ester

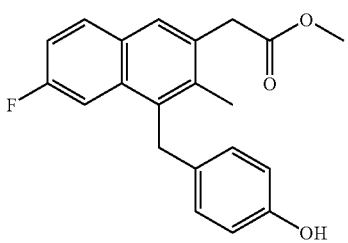

A round-bottom flask was charged with [4-(4-benzyloxy-benzyl)-6-fluoro-3-methyl-naphthalen-2-yl]-acetic acid methyl ester (4.17 g, 9.73 mmol) in ethanol (250 mL). A full spatula scoop of 10% palladium on carbon was added into the reaction flask. The reaction mixture was stirred under hydrogen gas at atmospheric pressure overnight at room temperature. The reaction mixture was then filtered through a bed of celite. The filtrate was concentrated to afford 3.96 g (100%) of [6-fluoro-4-(4-hydroxy-benzyl)-3-methyl-naphthalen-2-yl]-acetic acid methyl ester, which was used in the next step without further purification. $^1$H NMR (300 MHz, DMSO-$d_6$) δ ppm 9.17 (br. s, 1 H), 7.91 (dd, J=8.7, 6.2 Hz, 1 H), 7.74 (s, 1 H), 7.64 (dd, J=12.2, 1.9 Hz, 1 H), 7.33 (td, J=8.7, 1.9 Hz, 1 H), 6.83 (d, J=8.5 Hz, 2 H), 6.62 (d, J=8.5 Hz, 2 H), 4.32 (s, 2 H), 3.93 (s, 2 H), 3.64 (s, 3 H), 2.30 (s, 3 H).

[6-Fluoro-3-methyl-4-(4-trifluoromethanesulfonyloxy-benzyl)-naphthalen-2-yl]-acetic acid methyl ester

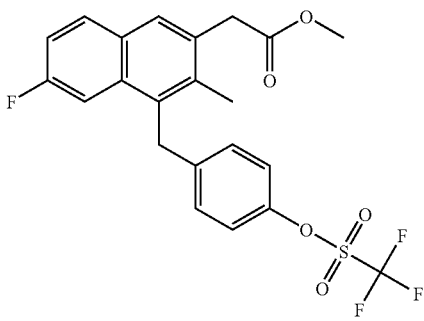

Trifluoromethanesulfonic anhydride (2.6 mL, 15.0 mmol) was added drop-wise to a -6° C. solution of [6-fluoro-4-(4-hydroxy-benzyl)-3-methyl-naphthalen-2-yl]-acetic acid methyl ester (3.9 g, 11.5 mmol) and pyridine (1.4 mL, 17.4 mmol) in dichloromethane (100 mL). The reaction mixture was warmed to room temperature, and stirred for 1 hour. The reaction mixture was then cooled to 4° C. Water (20 mL) was added, and the organic layer was dried over MgSO$_4$, filtered, and concentrated. A solution of this crude product in dichloromethane was concentrated over silica gel, and the resulting silica gel-supported product was subjected to flash chromatography (Analogix SuperFlash™ column, 5%-20% ethyl acetate in hexane) to give 3.8 g (70%) of [6-fluoro-3-methyl-4-(4-trifluoromethanesulfonyloxy-benzyl)-naphthalen-2-yl]-acetic acid methyl ester as a white solid. $^1$H NMR (300 MHz, DMSO-$d_6$) δ ppm 7.94 (dd, J=8.9, 6.2 Hz, 1 H), 7.79 (s, 1 H), 7.70 (dd, J=12.1, 1.8 Hz, 1 H), 7.37 (d, J=8.8 Hz, 2 H), 7.29-7.38 (m, 1 H), 7.20 (d, J=8.8 Hz, 2 H), 4.53 (s, 2 H), 3.94 (s, 2 H), 3.64 (s, 3 H), 2.29 (s, 3 H).

[6-Fluoro-4-(4'-methanesulfonyl-biphenyl-4-ylmethyl)-3-methyl-naphthalen-2-yl]-acetic acid methyl ester

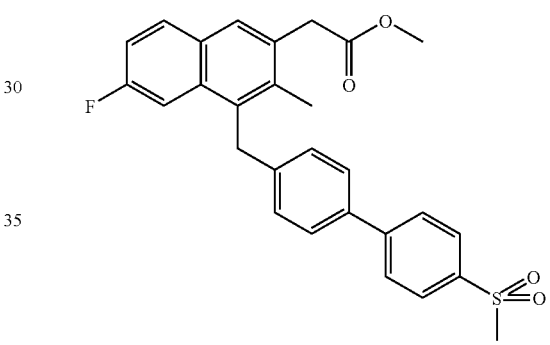

To a mixture of [6-fluoro-3-methyl-4-(4-trifluoromethanesulfonyloxy-benzyl)-naphthalen-2-yl)]-acetic acid methyl ester (117 mg, 0.25 mmol), 4-methanesulfonylphenylboronic acid (150 mg, 0.75 mmol), [1,1'-bis(diphenylphosphino)ferrocene]dichloropalladium(II) (18 mg, 0.025 mmol), and cesium carbonate (244 mg, 0.75 mmol) was added dimethoxyethane (5 mL) at room temperature under a nitrogen atmosphere. The resulting brown reaction mixture was heated to 95° C. and stirred for 15 hours. The reaction mixture was cooled to room temperature and diluted with water (50 mL) and ethyl acetate (50 mL). The two layers were separated and the aqueous layer was extracted with ethyl acetate (25 mL) and the combined organic extracts were washed with brine (100 mL). The organic layer was dried over anhydrous magnesium sulfate, filtered, and concentrated to give a colored residue which was purified by flash chromatography using an ISCO RediSep® Flash column, 230-400 mesh, eluting with 5-30% ethyl acetate in hexanes to afford 49 mg (41%) of [6-fluoro-4-(4'-methanesulfonyl-biphenyl-4-ylmethyl)-3-methyl naphthalen-2-yl]-acetic acid methyl ester as an amorphous white solid. HRMS (ES+) calcd for $C_{28}H_{25}FO_4S$ [(M+Na)$^+$] 499.1350, found 499.1350.

[6-Fluoro-4-(4'-methanesulfonyl-biphenyl-4-ylm-ethyl)-3-methyl-naphthalen-2-yl]-acetic acid

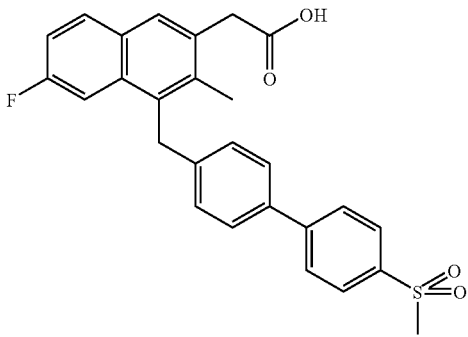

Starting with [6-fluoro-4-(4'-methanesulfonyl-biphenyl-4-ylmethyl)-3-methyl-naphthalen-2-yl]-acetic acid methyl ester, using the method analogous to the one described for example 2-1, final step, [6-fluoro-4-(4'-methanesulfonyl-biphenyl-4-ylmethyl)-3-methyl-naphthalen-2-yl]-acetic acid was obtained as 39 mg (83%) of a white solid. $^1$H NMR (300 MHz, DMSO-$d_6$) δ ppm 12.52 (br. s, 1 H), 7.94 (d, J=8.0 Hz, 2 H), 7.87-7.97 (m, 1 H), 7.86 (d, J=8.0 Hz, 2 H), 7.75 (s, 1 H), 7.69 (d, J=11.8 Hz, 1 H), 7.62 (d, J=8.0 Hz, 2 H), 7.33 (td, J=8.5, 1.8 Hz, 1 H), 7.17 (d, J=8.0 Hz, 2 H), 4.52 (s, 2 H), 3.81 (s, 2 H), 3.22 (s, 3 H), 2.35 (s, 3 H). HRMS (ES−) cald. for $C_{27}H_{23}FO_4S$ [(M−H)$^-$] 461.1228, obsd. 461.1226.

Example 12-2

The following example 12-2 was prepared in an analogous manner to example 12-1, starting with [6-fluoro-3-methyl-4-(4-trifluoromethanesulfonyloxy-benzyl)-naphthalen-2-yl]-acetic acid methyl ester and pyrimidine-5-boronic acid.

Example 13-1

[4-(4-Ethanesulfonyl-benzyl)-6-fluoro-3-methyl-naphthalen-2-yl]-acetic acid

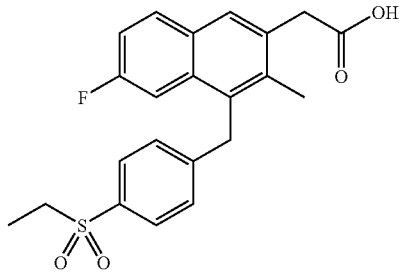

6-Fluoro-3-methyl-4-trifluoromethanesulfonyloxy-naphthalene-2-carboxylic acid methyl ester

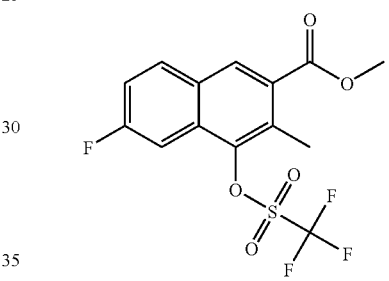

Trifluoromethanesulfonic anhydride (3.52 mL, 20.8 mmol) was added drop-wise over a period of 30 minutes to a 0° C. solution of 6-fluoro-4-hydroxy-3-methyl-naphthalene-2-carboxylic acid methyl ester (3.75 g, 16.0 mmol) in dichloromethane (120 mL) and pyridine (1.95 mL, 24.2 mmol). The resulting mixture was allowed to warm slowly to room temperature with stirring, and the reaction mixture was stirred at

| Example No | Systematic Name | $^1$H NMR (300 MHz, DMSO-$d_6$) δ ppm | HRMS (ES−), (M − H)$^-$ | Structure |
|---|---|---|---|---|
| 12-2 | [6-Fluoro-3-methyl-4-(4-pyrimidin-5-yl-benzyl)-naphthalen-2-yl]-acetic acid | 12.44(br. s, 1 H), 9.15(s, 1 H), 9.08(s, 2 H), 7.94 (dd, J = 8.8, 6.3 Hz, 1 H), 7.78(s, 1 H), 7.68-7.73 (m, 1 H), 7.69 (d, J = 8.2 Hz, 2 H), 7.35(td, J = 8.5, 2.0 Hz, 1 H), 7.20(d, J = 8.2 Hz, 2 H), 4.54(s, 2 H), 3.85(s, 2 H), 2.36(s, 3 H) | 385.1359 | | room temperature for 3.5 hours. After this time, the reaction mixture was cooled to 0° C. Water (150 mL) was added, and the organic phase was separated. The organic phase was dried over Na$_2$SO$_4$, filtered, and concentrated to afford a brown solid. Flash chromatography (Aspire FlashReady™, 50 μm, 10%-18% ethyl acetate in hexane) gave 6-fluoro-3-methyl-4-trifluoromethane-sulfonyloxynaphthalene-2-carboxylic acid methyl ester as 4.52 g (77%) of a yellow, crystalline solid. HRMS (EI+) cald. for C$_{14}$H$_{10}$F$_4$O$_5$S [M$^+$] 366.0185, obsd. 366.0186.

4-(4-Ethanesulfonyl-benzyl)-6-fluoro-3-methyl-naphthalene-2-carboxylic acid methyl ester

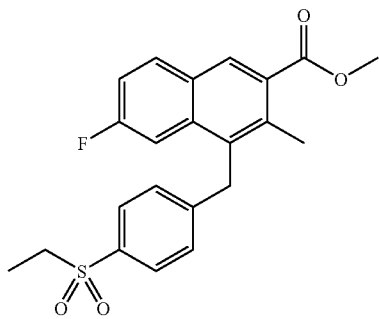

Step 1: Preparation of the Benzylic Zinc Chloride. An oven dried 3-neck 250 mL round-bottom flask was charged with zinc dust (1.80 g, 27.5 mmol) and previously dried lithium chloride (1.17 g, 27.5 mmol) under argon. The mixture was heated at 170° C. (oil bath temperature) for 2 hours under high vacuum. The mixture was cooled to room temperature. The reaction flask was backfilled with argon and equipped with a temperature probe. To the gray zinc/lithium chloride mixture was added freshly distilled tetrahydrofuran (2.5 mL) under argon. Then, 1,2-dibromoethane (0.20 mL, 2.3 mmol) was added. The zinc suspension was then stirred vigorously and heated gently with a heat gun to ebullition. After being allowed to cool to 50° C., the mixture was heated again. This process was repeated two times to ensure that the zinc dust was activated completely. After the third time heating to ebullition, the reaction mixture was cooled to 35° C. with stirring. The activated zinc dust suspension was then treated with chlorotrimethylsilane (0.220 mL, 1.72 mmol), and the mixture was stirred for 10 minutes at room temperature. The reaction mixture was cooled in an ice-water bath and then treated drop-wise with a solution of 4-ethanesulfonylbenzyl chloride (3.00 g, 13.7 mmol) in dry tetrahydrofuran (9 mL). After the addition, the reaction mixture was stirred at 4° C. for 3 minutes, then it was allowed to warm to room temperature in an ambient temperature water bath. After 2.5 hours stirring in the ambient temperature water bath, the reaction mixture was briefly stirred at 40° C. for 2.5 minutes. The reaction mixture was allowed to cool to room temperature, then it was diluted with freshly distilled tetrahydrofuran (7 mL). The stirring was halted, and the reaction mixture was allowed to stand at room temperature for 30 hours under argon so that the zinc dust completely settled. The benzylic zinc chloride thus prepared was subsequently used in the Negishi coupling step.

Step 2: Negishi Coupling Reaction. In a separate reaction flask, palladium (II) acetate (135 mg, 0.601 mmol) and S-Phos (2-dicyclohexylphosphino-2',6'-dimethoxybiphenyl) (493 mg, 1.20 mmol) were combined with freshly distilled tetrahydrofuran (8 mL) at room temperature under argon. A solution of 6-fluoro-3-methyl-4-trifluoromethanesulfonyloxy-naphthalene-2-carboxylic acid methyl ester (2.2 g, 6.0 mmol) in freshly distilled tetrahydrofuran (24 mL) was added to the light brown reaction mixture. The benzylic zinc reagent in tetrahydrofuran (prepared above) was then added at room temperature. The resulting dark brown solution was stirred at 60° C. for 1.25 hours. The reaction mixture was cooled to room temperature and then diluted with a saturated aqueous solution of ammonium chloride. The resulting mixture was extracted with ethyl acetate. The organic phase was dried over MgSO$_4$, filtered, and evaporated. A solution of the crude product in dichloromethane was evaporated over silica gel, and the resulting silica gel supported crude product was loaded onto an Analogix SuperFlash™ column. Flash chromatography (25%-35% ethyl acetate in hexanes) afforded 2.09 g (87%) of 4-(4-ethanesulfonyl-benzyl)-6-fluoro-3-methyl-naphthalene-2-carboxylic acid methyl ester as a light yellow solid. $^1$H NMR (300 MHz, DMSO-d$_6$) δ ppm 8.37 (s, 1 H), 8.16 (dd, J=9.1, 6.3 Hz, 1 H), 7.74-7.81 (m, 1 H), 7.74 (d, J=8.2 Hz, 2 H), 7.45 (td, J=8.6, 2.1 Hz, 1 H), 7.28 (d, J=8.2 Hz, 2 H), 4.63 (s, 2 H), 3.88 (s, 3 H), 3.20 (q, J=7.3 Hz, 2 H), 2.48 (br. s, 3 H), 1.04 (t, J=7.3 Hz, 3 H). HRMS (ES+) cald. for C$_{22}$H$_{21}$FO$_4$S [(M+Na)$^+$] 423.1037, obsd. 423.1036.

[4-(4-Ethanesulfonyl-benzyl)-6-fluoro-3-methyl-naphthalen-2-yl]-methanol

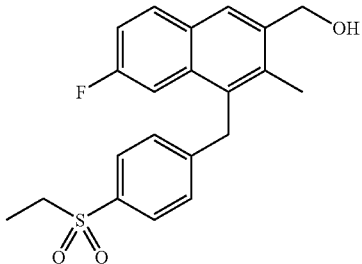

A suspension of lithium aluminum hydride (399 mg, 10.5 mmol) in tetrahydrofuran (25 mL) was cooled to 0° C. under a stream of argon. A solution of 4-(4-ethanesulfonyl-benzyl)-6-fluoro-3-methyl-naphthalene-2-carboxylic acid methyl ester (870 mg, 2.18 mmol) in tetrahydrofuran (30 mL) was added slowly drop-wise to the 0° C. suspension. The reaction mixture was stirred at 0° C. for 15 minutes. The reaction mixture was warmed to room temperature and it was stirred at room temperature for 15 minutes. The reaction mixture was cooled again to 0° C. Ethyl acetate was added drop-wise to quench the unreacted lithium aluminum hydride. A saturated aqueous solution of potassium sodium tartrate was added. The organic phase was separated, dried over MgSO$_4$, filtered, and concentrated to afford 780 mg (96%) of [4-(4-ethane-sulfonyl-benzyl)-6-fluoro-3-methyl-naphthalen-2-yl]-methanol as an oily white solid. This product was used in subsequent reactions without further purification. $^1$H NMR (300 MHz, DMSO-d$_6$) δ ppm 7.98 (dd, J=8.9, 6.2 Hz, 1 H), 7.90 (s, 1 H), 7.73 (d, J=8.2 Hz, 2 H), 7.67 (d, J=12.4 Hz, 1 H), 7.34 (dd, J=8.9, 2.1 Hz, 1 H), 7.29 (d, J=8.2 Hz, 2 H), 5.27 (t, J=5.1 Hz, 1 H), 4.66 (d, J=5.1 Hz, 2 H), 4.58 (s, 2 H), 3.20 (q, J=7.2 Hz, 2 H), 2.31 (s, 3 H), 1.04 (t, J=7.2 Hz, 3 H). HRMS (ES+) cald. for $C_{21}H_{21}FO_3S$ [(M+Na)$^+$] 395.1087, obsd. 395.1088.

1-(4-Ethanesulfonyl-benzyl)-3-chloromethyl-7-fluoro-2-methyl-naphthalene

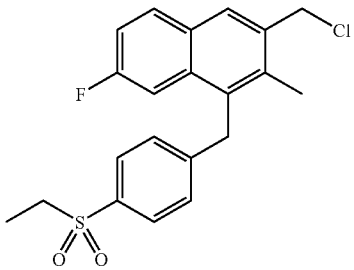

A mixture of triphenylphosphine (1.10 g, 4.19 mmol), carbon tetrachloride (1.62 mL, 16.8 mmol) and tetrahydrofuran (5 mL) was stirred at room temperature for 10 minutes. A mixture of [4-(4-ethanesulfonyl-benzyl)-6-fluoro-3-methyl-naphthalen-2-yl]-methanol (780 mg, 2.09 mmol) in tetrahydrofuran (2.5 mL) was added, and the reaction mixture was stirred at 75° C. for 4 hours. The reaction mixture was cooled to room temperature, and then diluted with ethyl acetate. The resulting mixture was washed with water. The organic phase was dried over MgSO$_4$, filtered, and concentrated. A solution of the crude product in dichloromethane was evaporated over silica gel, and the silica gel supported crude product was loaded onto an Analogix SuperFlash™ column. Flash chromatography (10%-30% ethyl acetate in hexanes) afforded 450 mg (55%) of 1-(4-ethanesulfonyl-benzyl)-3-chloromethyl-7-fluoro-2-methyl-naphthalene as a white solid. $^1$H NMR (300 MHz, DMSO-d$_6$) δ ppm 8.04 (s, 1 H), 7.96-8.04 (m, 1 H), 7.76 (d, J=8.2 Hz, 2 H), 7.68-7.75 (m, 1 H), 7.41 (td, J=8.6, 2.1 Hz, 1 H), 7.30 (d, J=8.2 Hz, 2 H), 5.01 (s, 2 H), 4.63 (s, 2 H), 3.22 (q, J=7.2 Hz, 2 H), 2.47 (s, 3 H), 1.06 (t, J=7.2 Hz, 3 H). MS (ES+) cald. for $C_{21}H_{20}ClFO_2S$ [(M−Cl)$^+$] 355, obsd. 355.

[4-(4-Ethanesulfonyl-benzyl)-6-fluoro-3-methyl-naphthalen-2-yl]-acetic acid methyl ester

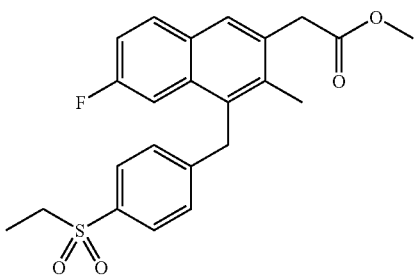

A 500 mL round-bottom flask containing 1-(4-ethanesulfonyl-benzyl)-3-chloromethyl-7-fluoro-2-methyl-naphthalene (450 mg, 1.15 mmol), potassium carbonate (165 mg, 1.20 mmol), and dichlorobis(triphenylphosphine)palladium (II) (40 mg, 0.057 mmol) was evacuated under high vacuum, and then backfilled with carbon monoxide gas via a balloon. Tetrahydrofuran (3.6 mL) and anhydrous methanol (1.8 mL) were added, and the resulting mixture was stirred at room temperature under a balloon of carbon monoxide for 1.5 hours. During this time period, the reaction mixture turned red in color. The carbon monoxide balloon was removed, then the reaction mixture was diluted with water. The resulting mixture was extracted with ethyl acetate, and the organic layer was dried (MgSO$_4$), filtered, and concentrated to a brown-grey oily solid. A solution of this crude product in dichloromethane was evaporated over silica gel. The resulting silica gel supported crude product was loaded onto a RediSep® Flash column. Flash chromatography (20%-35% ethyl acetate in hexanes) afforded 421 mg (88%) of [4-(4-ethanesulfonyl-benzyl)-6-fluoro-3-methyl-naphthalen-2-yl]-acetic acid methyl ester as a light yellow solid. $^1$H NMR (300 MHz, DMSO-d$_6$) δ ppm 7.93 (dd, J=8.8, 6.2 Hz, 1 H), 7.78 (s, 1 H), 7.74 (d, J=8.4 Hz, 2 H), 7.67 (dd, J=12.2, 2.1 Hz, 1 H), 7.34 (td, J=8.8, 2.1 Hz, 1 H), 7.28 (d, J=8.4 Hz, 2 H), 4.59 (s, 2 H), 3.93 (s, 2 H), 3.62 (s, 3 H), 3.20 (q, J=7.2 Hz, 2 H), 2.28 (s, 3 H), 1.04 (t, J=7.2 Hz, 3 H). MS (ES+) cald. for $C_{23}H_{23}FO_4S$ [(M+Na)$^+$] 437, obsd. 437.

[4-(4-Ethanesulfonyl-benzyl)-6-fluoro-3-methyl-naphthalen-2-yl]-acetic acid

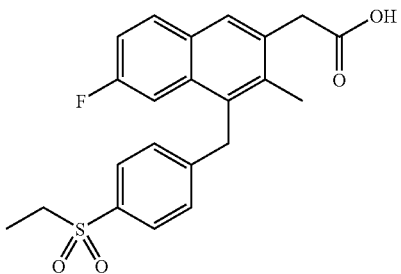

Starting with [4-(4-ethanesulfonyl-benzyl)-6-fluoro-3-methyl-naphthalen-2-yl]-acetic acid methyl ester, using a method analogous to the one described for example 2-1, final step, [4-(4-ethanesulfonyl-benzyl)-6-fluoro-3-methyl-naphthalen-2-yl]-acetic acid (388 mg, 95%) was obtained as a yellow oil. $^1H NMR$ (300 MHz, DMSO-d$_6$) δ ppm 12.45 (br. s, 1 H), 7.92 (dd, J=9.1, 6.3 Hz, 1 H), 7.76 (s, 1 H), 7.73 (d, J=8.2 Hz, 2 H), 7.67 (d, J=11.8 Hz, 1 H), 7.30-7.40 (m, 1 H), 7.28 (d, J=8.2 Hz, 2 H), 4.58 (s, 2 H), 3.81 (s, 2 H), 3.20 (q, J=7.4 Hz, 2 H), 2.29 (s, 3 H), 1.04 (t, J=7.4 Hz, 3 H). MS (ES−) cald. for $C_{22}H_{21}FO_4S$ [(M−H)$^-$] 399, obsd. 399.

Example 14-1

[4-(2-Benzenesulfonyl-benzyl)-6-fluoro-3-methyl-naphthalen-2-yl]-acetic acid

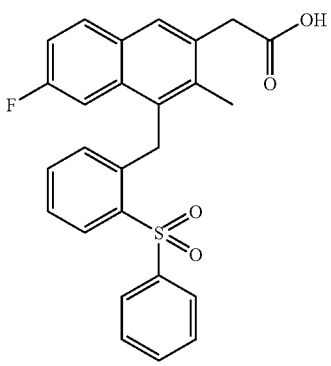

[6-Fluoro-3-methyl-4-(4,4,5,5-tetramethyl-[1,3,2]
dioxaborolan-2-yl)-naphthalen-2-yl]-acetic acid
methyl ester

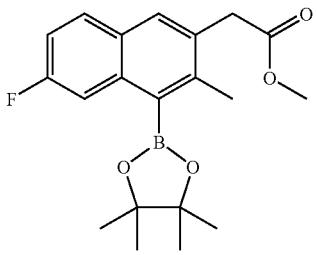

An oven-dried round-bottom flask was charged with (6-fluoro-3-methyl-4-trifluoromethanesulfonyloxy-naphthalen-2-yl)-acetic acid methyl ester (1.00 g, 2.63 mmol), potassium acetate (1.3 g, 13.2 mmol), dichloro 1,1'-bis(diphenylphosphino)ferrocene palladium (II) (288 mg, 0.394 mmol), 1,1'-bis(diphenylphosphino)ferrocene (220 mg, 0.390 mmol), bis(pinacolato)diboron (1.33 g, 5.25 mmol), and 1,4-dioxane (36 mL). The resulting mixture was heated at 120° C. for 10 hours. The reaction mixture was cooled to room temperature, then stirred at room temperature overnight. The reaction mixture was diluted with ethyl acetate, then washed with brine. The organic phase was dried over MgSO$_4$, filtered, and concentrated to afford a dark oil. A solution of the crude product and dichloromethane was evaporated over silica gel, and the resulting silica gel supported crude product was loaded onto an Analogix SF40 Super Flash column. Flash chromatography (0%-10% ethyl acetate in hexane) furnished [6-fluoro-3-methyl-4-(4,4,5,5-tetramethyl-[1,3,2]dioxaborolan-2-yl)-naphthalen-2-yl]-acetic acid methyl ester as 290 mg (31%) of a clear oil. $^1$H NMR (300 MHz, CDCl$_3$) δ ppm 7.64-7.78 (m, 3 H), 7.17 (t, J=8.6 Hz, 1 H), 3.79 (s, 2 H), 3.69 (s, 3 H), 2.56 (s, 3 H), 1.50 (s, 12 H). MS (ES+) cald. for C$_{20}$H$_{24}$BFO$_4$ [(M+H)$^+$] 359, obsd. 359.

4-(2-Benzenesulfonyl-benzyl)-6-fluoro-3-methyl-
naphthalen-2-yl]-acetic acid methyl ester

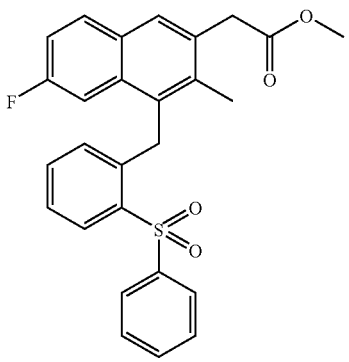

A mixture of [6-fluoro-3-methyl-4-(4,4,5,5-tetramethyl-[1,3,2]dioxaborolan-2-yl)-naphthalen-2-yl]-acetic acid methyl ester (83.5 mg, 0.233 mmol), 2-benzenesulfonyl benzyl chloride (72 mg, 0.270 mmol), tetrakis(triphenylphosphine)palladium(0) (12 mg, 0.010 mmol), a 1.2 M aqueous solution of sodium carbonate (0.5 mL, 0.6 mmol), and tetrahydrofuran (1.5 mL) was stirred at 75° C. for 2 hours. The reaction mixture was cooled to room temperature, then it was diluted with ethyl acetate (30 mL). The resulting mixture was washed with water (30 mL). The organic phase was dried over MgSO$_4$, filtered, and evaporated. A solution of the crude product in dichloromethane was evaporated over silica gel, and the resulting silica gel supported crude product was loaded onto an Analogix SF40 Super Flash column. Flash chromatography (15%-35% ethyl acetate in hexanes) afforded 180 mg (46%) of 4-(2-benzenesulfonyl-benzyl)-6-fluoro-3-methyl-naphthalen-2-yl]-acetic acid methyl ester as a clear oil. $^1$H NMR (300 MHz, CDCl$_3$) δ ppm 8.38 (d, J=7.8 Hz, 1 H), 8.01 (d, J=7.5 Hz, 2 H), 7.55-7.76 (m, 5 H), 7.37-7.48 (m, 1 H), 7.31 (d, J=7.8 Hz, 1 H), 7.09 (td, J=8.5, 2.0 Hz, 1 H), 6.46-6.60 (m, 2 H), 4.51 (s, 2 H), 3.81 (s, 2 H), 3.70 (s, 3 H), 1.98-2.14 (m, 3 H). MS (ES+) cald. for C$_{27}$H$_{23}$FO$_4$S [(M+H)$^+$] 463, obsd. 463.

4-(2-Benzenesulfonyl-benzyl)-6-fluoro-3-methyl-
naphthalen-2-yl]-acetic acid

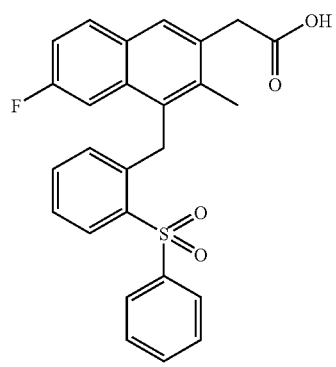

Starting with 4-(2-benzenesulfonyl-benzyl)-6-fluoro-3-methyl-naphthalen-2-yl]-acetic acid methyl ester, using a method analogous to the one described for example 2-1, final step, 4-(2-benzenesulfonyl-benzyl)-6-fluoro-3-methyl-naphthalen-2-yl]-acetic acid (17.6 mg, 31%) was obtained as a yellow oil. $^1$H NMR (300 MHz, DMSO-d$_6$) δ ppm 12.23 (br. s, 1 H), 8.30 (d, J=7.5 Hz, 1 H), 8.05 (d, J=7.5 Hz, 2 H), 7.91 (dd, J=8.7, 6.3 Hz, 1 H), 7.66-7.86 (m, 4 H), 7.56 (t, J=7.4 Hz, 1 H), 7.46 (t, J=7.4 Hz, 1 H), 7.28 (td, J=8.7, 2.0 Hz, 1 H), 6.58 (d, J=11.8 Hz, 1 H), 6.43 (d, J=7.5 Hz, 1 H), 4.42 (br. s, 2 H), 3.80 (br. s, 2 H), 2.07 (s, 3 H). MS (ES+) cald. for C$_{26}$H$_{21}$FO$_4$S [(M+H)$^+$] 449, obsd. 449.0.

Example 15-1

[6-Fluoro-3-methyl-4-(4-methyl-benzyl)-naphthalen-
2-yl]-acetic acid

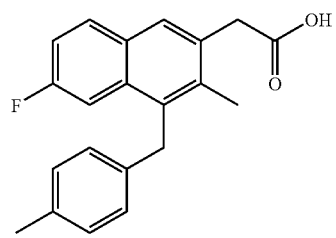

[6-Fluoro-3-methyl-4-(4-methyl-benzyl)-naphthalen-2-yl]acetic acid methyl ester

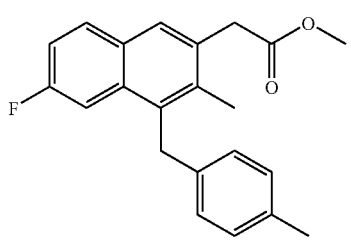

A mixture of (6-fluoro-3-methyl-4-trifluoromethanesulfonyloxy-naphthalen-2-yl)-acetic acid methyl ester (220 mg, 0.578 mmol), 4,4,5,5-tetramethyl-2-(4-methyl-benzyl)-1,3,2-dioxaborolane (402 mg, 1.731 mmol), palladium(II) acetate (17 mg, 0.0757 mmol), 2-dicyclohexylphosphino-2',6'-dimethoxybiphenyl (53 mg, 0.129 mmol), potassium phosphate (246 mg, 1.159 mmol), toluene (5 mL) and water (0.5 mL) was heated at 110° C. for 2 hours. The reaction mixture was cooled to room temperature, diluted with ethyl acetate (100 mL) and washed with brine (25 mL). The organic phase was dried over MgSO$_4$, filtered and concentrated. Silica gel chromatography (93:7 hexanes-ethyl acetate) gave 145.7 mg (74.9%) of [6-fluoro-3-methyl-4-(4-methyl-benzyl)-naphthalen-2-yl]-acetic acid methyl ester as a colorless oil which solidified on standing. $^1$H NMR (300 MHz, DMSO-d$_6$) δ ppm 7.92 (dd, J=8.8, 6.2 Hz, 1 H), 7.75 (s, 1 H), 7.63 (dd, J=12.4, 2.1 Hz, 1 H), 7.33 (td, J=8.8, 2.1 Hz, 1 H), 7.03 (d, J=7.8 Hz, 2 H), 6.92 (d, J=7.8 Hz, 2 H), 4.40 (s, 2 H), 3.93 (s, 2 H), 3.64 (s, 3 H), 2.30 (s, 3 H), 2.21 (s, 3 H).

[6-Fluoro-3-methyl-4-(4-methyl-benzyl)-naphthalen-2-yl]-acetic acid

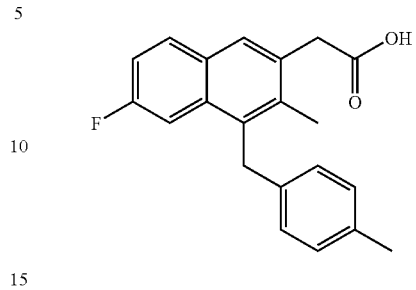

A solution of [6-fluoro-3-methyl-4-(4-methyl-benzyl)-naphthalen-2-yl]-acetic acid methyl ester (140.8 mg, 0.419 mmol) in tetrahydrofuran (14 mL) was treated with a warm solution of lithium hydroxide monohydrate (175.8 mg, 4.19 mmol) in water (3.5 mL). The reaction mixture was stirred at room temperature for 20 hours, diluted with water, acidified with aqueous 3.0 N HCl and extracted with ethyl acetate. The ethyl acetate layers were combined, washed with brine, dried (MgSO$_4$), filtered and concentrated. Purification by reverse phase HPLC gave 81.7 mg (60%) of [6-fluoro-3-methyl-4-(4-methyl-benzyl)-naphthalen-2-yl]-acetic acid as a white solid. $^1$H NMR (300 MHz, DMSO-d$_6$) δ ppm 12.43 (br. s, 1 H), 7.91 (dd, J=8.7, 6.3 Hz, 1 H), 7.74 (s, 1 H), 7.62 (dd, J=12.1, 1.8 Hz, 1 H), 7.33 (td, J=8.8, 1.8 Hz, 1 H), 7.03 (d, J=7.8 Hz, 2 H), 6.92 (d, J=7.8 Hz, 2 H), 4.40 (s, 2H), 3.82 (s, 2 H), 2.32 (s, 3 H), 2.21 (s, 3 H). HRMS (ES−) cald. for C$_{21}$H$_{19}$FO$_2$ [(M−H)$^-$] 321.1296, obsd. 321.1294.

Examples 15-2 to 15-5

The following examples 15-2 to 15-5 were prepared in an analogous manner to example 15-1, starting with (6-fluoro-3-methyl-4-trifluoromethanesulfonyloxy-naphthalen-2-yl)-acetic acid methyl ester and the appropriate 4,4,5,5-tetramethyl-2-(benzyl)-1,3,2-dioxaborolane reagent.

| Example No | Systematic Name | 4,4,5,5-tetra methyl-2-(benzyl)-1,3,2-dioxaborolane | $^1$H NMR (300 MHz, DMSO-d$_6$) δ ppm | HRMS (ES−, (M − H)$^-$) | Structure |
| --- | --- | --- | --- | --- | --- |
| 15-2 | [4-(3-Chloro-benzyl)-6-fluoro-3-methyl-naphthalen-2-yl]-acetic acid | 4,4,5,5,-tetramethyl-2-(3-chloro-benzyl)-1,3,2-dioxaborolane | 12.44(br. s, 1 H), 7.88-8.02 (m, 1 H), 7.77(s, 1 H), 7.68 (d, J = 12.1 Hz, 1 H), 7.19-7.40(m, 3 H), 7.09 (s, 1 H), 6.99(d, J = 6.6 Hz, 1 H), 4.49 (s, 2 H), 3.84(s, 2 H), 2.32 (s, 3 H) | 341.0747 | 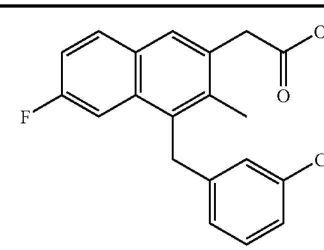 |

-continued

| Example No | Systematic Name | 4,4,5,5-tetra methyl-2-(benzyl)-1,3,2-dioxaborolane | $^1$H NMR (300 MHz, DMSO-d$_6$) δ ppm | HRMS (ES−, (M − H)$^-$) | Structure |
|---|---|---|---|---|---|
| 15-3 | [6-Fluoro-4-(4-fluoro-benzyl)-3-methyl-naphthalen-2-yl]-acetic acid | 4,4,5,5-tetramethyl-2-(4-fluoro-benzyl)-1,3,2-dioxaborolane | 12.46(br. s, 1 H), 7.91(dd, J = 8.6, 6.5 Hz, 1 H), 7.74(s, 1 H), 7.64 (d, J = 11.8 Hz, 1 H), 7.32(t, J = 8.6 Hz, 1 H), 7.05 (d, J = 6.9 Hz, 4 H), 4.43(s, 2 H), 3.80 (s, 2 H), 2.31(s, 3 H) | 325.1045 | 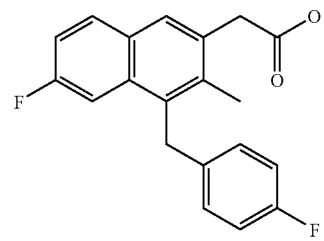 |
| 15-4 | [6-Fluoro-3-methyl-4-(4-trifluoromethoxy-benzyl)-naphthalen-2-yl]-acetic acid | 4,4,5,5-tetramethyl-2-(4-trifluoromethoxy-benzyl)-1,3,2-dioxaborolane | 12.41(br. s, 1 H), 7.92(dd, J = 8.8, 6.3 Hz, 1 H), 7.75(s, 1 H), 7.67 (dd, J = 12.1, 2.0 Hz, 1 H), 7.33(td, J = 8.8, 2.0 Hz, 1 H), 7.23(d, J = 8.4 Hz, 2 H), 7.13 (d, J = 8.4 Hz, 2 H), 4.49(s, 2 H), 3.81 (s, 2 H), 2.30(s, 3 H) | 391.0961 | 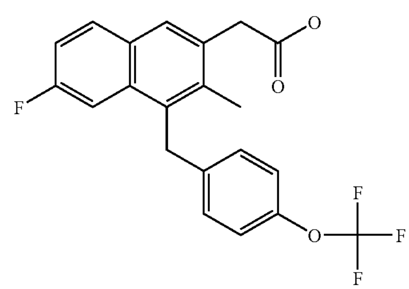 |
| 15-5 | 3-(3-Carboxymethyl-7-fluoro-2-methyl-naphthalen-1-ylmethyl)-benzoic acid methyl ester | 4,4,5,5-tetramethyl-2-(3-carbomethoxy-benzyl)-1,3,2-dioxaborolane | 12.42(br. s, 1 H), 7.94(dd, J = 8.8, 6.3 Hz, 1 H), 7.64-7.83 (m, 4 H), 7.25-7.44 (m, 3 H), 4.55(br. s, 2 H), 3.83 (s, 2 H), 3.78(s, 3 H), 2.32 (s, 3 H) | 389.1160$^a$ | 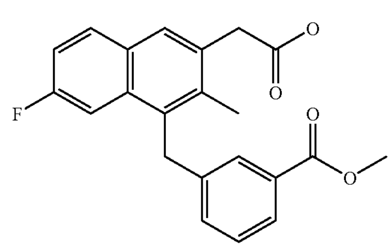 |

$^a$HRMS (ES+), [(M + Na)$^+$].

Example 16-1

{4-[(2-Chloro-4-methanesulfonyl-phenyl)-hydroxy-methyl]-6-fluoro-naphthalen-2-yl}-acetic acid

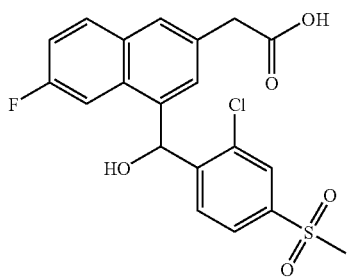

To a solution of [4-(2-chloro-4-methanesulfonyl-benzoyl)-6-fluoro-naphthalen-2-yl]-acetic acid (example 2-8) (920 mg, 2.19 mmol) in methanol (20 mL) was added sodium borohydride (248 mg, 6.56 mmol) at 0° C. The mixture was stirred at 0° C. for 30 minutes before warming to room temperature. After 4 hours, the reaction was once again cooled to 0° C., and additional sodium borohydride (163 mg, 4.31 mmol) was added. The reaction mixture was then warmed to room temperature, and stirred at room temperature overnight. The solvent was removed under reduced pressure. The residue was dissolved in ethyl acetate and washed once with a 0.5 N hydrochloric acid solution. The organic layer was dried over sodium sulfate, filtered, and concentrated in vacuo. Reverse phase preparative HPLC (using a Waters® Delta-Prep™ 3000 with a Varian Pursuit® C-18 column [10 μm, 20×150 mm]) gave {4-[(2-chloro-4-methanesulfonyl-phenyl)-hydroxy-methyl]-6-fluoro-naphthalen-2-yl}-acetic acid (500 mg, 54%) as an off-white powder. $^1$H NMR (300 MHz, 1.8:1 mixture of $CD_3OD$ and $CDCl_3$) δ ppm 7.92 (s, 1 H), 7.75-7.85 (m, 3 H), 7.62-7.71 (m, 2 H), 7.16-7.29 (m, 2 H), 6.70 (s, 1 H), 3.64 (s, 2 H), 3.09 (s, 3 H); HRMS (ESI+) calcd. for $C_{20}H_{16}ClFO_5S$ [(M+Na)$^+$] 445.0283, obsd. 445.0281.

Examples 16-2 to 16-8

The following examples 16-2 to 16-8 were prepared in an analogous manner to example 16-1, starting with the corresponding ketone derivatives.

| Example No | Systematic Name | $^1$H NMR (300 MHz, CDCl$_3$) δ ppm | HRMS (ESI+, (M + Na)$^+$) | Structure |
|---|---|---|---|---|
| 16-2 | {4-[Hydroxy-(4-methanesulfonyl-phenyl)-methyl]-6-methyl-naphthalen-2-yl}-acetic acid | 7.84(d, J = 8.3 Hz, 2 H), 7.76(br. s, 1 H), 7.73(d, J = 8.6 Hz, 1 H), 7.67(br. s, 1 H), 7.60(d, J = 8.3 Hz, 2 H), 7.45(br. s, 1 H), 7.31(d, J = 8.6 Hz, 1 H), 6.54(s, 1 H), 3.78 (br. s, 2 H), 2.98(s, 3 H), 2.46(s, 3 H) | 407.0923 | 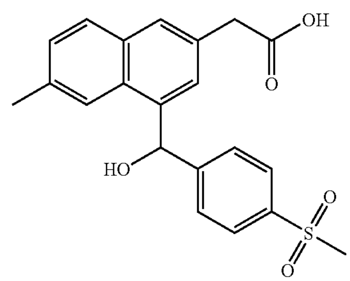 |
| 16-3 | {6-Chloro-4-[hydroxy-(4-methanesulfonyl-phenyl)-methyl]-naphthalen-2-yl}-acetic acid | (CD$_3$OD) 8.08(s, 1 H), 7.90(d, J = 8.4 Hz, 2 H), 7.82(d, J = 8.5 Hz, 1 H), 7.75(br. s, 1H), 7.69(d, J = 8.4 Hz, 2 H), 7.63(br. s, 1 H), 7.33-7.42(m, 1 H), 6.43(s, 1 H), 3.70(s, 2 H), 3.09(s, 3 H) | 427.0376 | 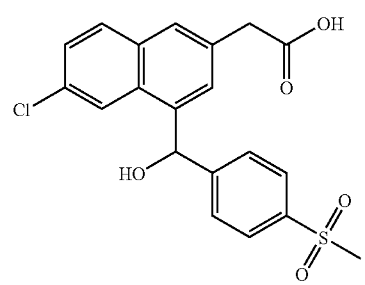 |
| 16-4 | {6-Fluoro-4-[hydroxy-(4-methanesulfonyl-2-methyl-phenyl)-methyl]-naphthalen-2-yl}-acetic acid | 7.74(dd, J = 9.1, 5.7 Hz, 1 H), 7.69(s, 1 H), 7.60(d, J = 7.5 Hz, 1 H), 7.39-7.54(m, 3 H), 7.15-7.25(m, 2 H), 6.46(s, 2 H), 3.47(br. s, 2 H), 3.01(s, 3 H), 2.26(s, 3 H) | 425.0827 | 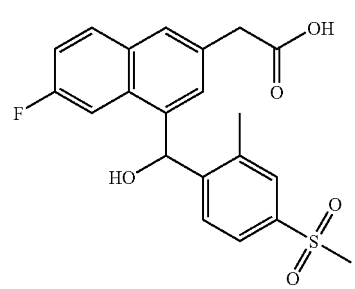 |

-continued

| Example No | Systematic Name | $^1$H NMR (300 MHz, CDCl$_3$) δ ppm | HRMS (ESI+, (M + Na)$^+$) | Structure |
|---|---|---|---|---|
| 16-5 | {6-Fluoro-4-[hydroxy-(4-methanesulfonyl-phenyl)-methyl]-naphthalen-2-yl}-acetic acid | (DMSO-d$_6$) 12.44(br. s, 1 H), 7.98(dd, J = 9.0, 6.0 Hz, 1 H), 7.86-7.90(m, 1 H), 7.85(d, J = 8.4 Hz, 2 H), 7.78(br. s, 1 H), 7.69(br. s, 1 H), 7.66(d, J = 8.4 Hz, 2 H), 7.38(td, J = 9.0, 2.7 Hz, 1 H), 6.45(d, J = 4.0 Hz, 1 H), 6.40(d, J = 4.0 Hz, 1 H), 6.40(d, J = 4.0 Hz, 1 H), 3.76 (s, 2 H), 3.16(s, 3 H) | 411.067 | 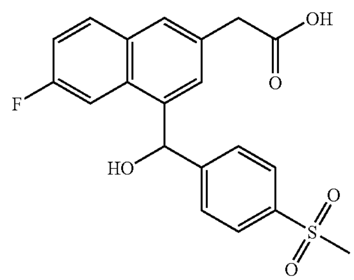 |
| 16-6 | {4-[Hydroxy-(4-methanesulfonyl-phenyl)-methyl]-naphthalen-2-yl}-acetic acid | 7.97(d, J = 8.2 Hz, 1 H), 7.79-7.89(m, 3 H), 7.73(s, 1 H), 7.52-7.66(m, 3 H), 7.36-7.52(m, 2 H), 6.54(s, 1 H), 3.83(s, 2 H), 2.97 (s, 3 H) | 393.0767 | 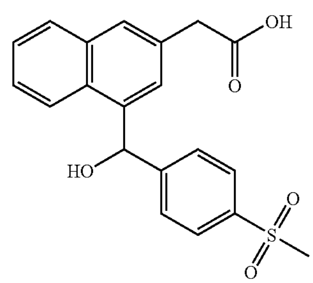 |
| 16-7 | {4-[(4-Ethanesulfonyl-phenyl)-hydroxy-methyl]-6-fluoro-naphthalen-2-yl}-acetic acid | (DMSO-d$_6$) 12.48(br. s, 1 H) 7.96(dd, J = 9.1, 6.3 Hz, 1 H), 7.72-7.88 (m, 4 H) 7.56-7.71(m, 3 H) 7.36(td, J = 8.7, 2.3 Hz, 1 H) 6.34-6.47 (m, 2 H) 3.73(s, 2 H) 3.22(q, J = 7.4 Hz, 2 H) 1.03(t, J = 7.4 Hz, 3 H) | 401$^a$ | 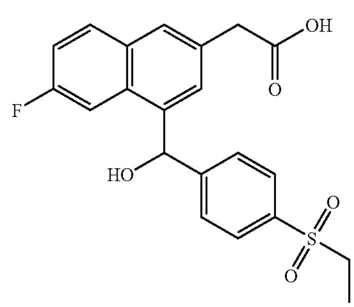 |
| 16-8 | {4-[(4-Ethanesulfonyl-2-methyl-phenyl)-hydroxy-methyl]-6-fluoro-naphthalen-2-yl}-acetic acid | 7.87(dd, J = 8.9, 5.9 Hz, 1 H), 7.67-7.78 (m, 3 H), 7.57-7.66 (m, 2 H), 7.29-7.35 (m, 1 H), 7.24-7.26 (m, 1 H), 6.61(s, 1 H), 3.76(d, J = 16.0 Hz, 1 H), 3.75(d, J = 16.0 Hz, 1 H), 3.12(q, J = 7.3 Hz, 2 H), 2.33(s, 3 H), 1.28(t, J = 7.3 Hz, 3 H) | 439.0983 | 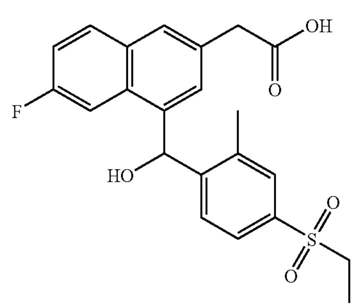 |

$^a$MS reported as [(M − H)$^−$].

Example 17-1

{4-[(2-Chloro-4-methanesulfonyl-phenyl)-difluoro-methyl]-6-fluoro-naphthalen-2-yl}-acetic acid

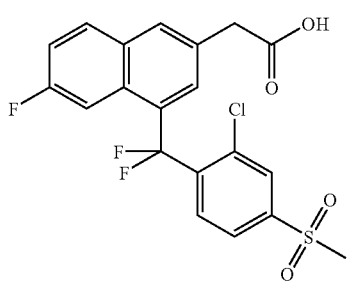

{4-[(2-Chloro-4-methanesulfonyl-phenyl)-difluoro-methyl]-6-fluoro-naphthalen-2-yl}-acetic acid ethyl ester

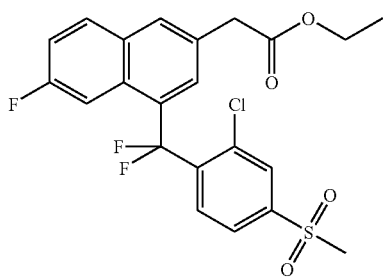

A mixture of [4-(2-chloro-4-methanesulfonyl-benzoyl)-6-fluoro-naphthalen-2-yl]-acetic acid ethyl ester (precursor of example 2-8 prepared according to Scheme 2) (90 mg, 0.20 mmol) and bis(2-methoxyethyl)aminosulfur trifluoride (709 mg, 3.21 mmol) was heated at 85° C. for two days in a high-pressure sealed tube. The crude mixture was directly loaded on to a RediSep® Flash column for purification. Flash chromatography (RediSep® Flash column, 230-400 mesh, 0-50% ethyl acetate in hexane) gave slightly impure {4-[(2-chloro-4-methanesulfonyl-phenyl)-difluoro-methyl]-6-fluoro-naphthalen-2-yl}-acetic acid ethyl ester (22.4 mg, 24%). Additional purification was achieved using reverse phase preparative HPLC (using a Waters® Delta-Prep™ 3000 with a Varian Pursuit® C-18 column [10 μm, 20×150 mm]). MS (ESI+) cald. for $C_{22}H_{18}ClF_3O_4S$ [(M+H)$^+$] 470, obsd. 471.

{4-[(2-Chloro-4-methanesulfonyl-phenyl)-difluoro-methyl]-6-fluoro-naphthalen-2-yl}-acetic acid

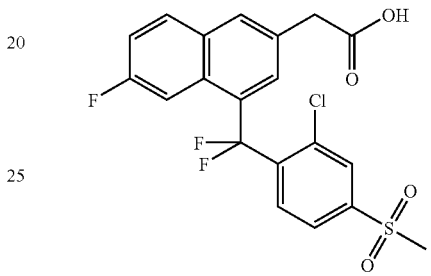

Starting with {4-[(2-chloro-4-methanesulfonyl-phenyl)-difluoro-methyl]-6-fluoro-naphthalen-2-yl}-acetic acid ethyl ester using the method analogous to the one described for example 2-1, final step, {4-[(2-chloro-4-methanesulfonyl-phenyl)-difluoro-methyl]-6-fluoro-naphthalen-2-yl}-acetic acid (17.2 mg, 82%) was obtained as a white crystalline solid. $^1$H NMR (300 MHz, CDCl$_3$) δ ppm: 8.05 (br. s, 1 H), 7.98 (br. s, 2 H), 7.85-7.94 (m, 2 H), 7.72-7.80 (m, 1 H), 7.54 (br. s, 1 H), 7.29-7.38 (m, 1 H), 3.83 (s, 2 H), 3.14 (s, 3 H); HRMS (ESI+) cald. for $C_{20}H_{14}ClF_3O_4S$ [(M+Na)] 465.0145, obsd. 465.0144.

Examples 17-2 to 17-3

The following examples 17-2 to 17-3 were prepared in an analogous manner to example 17-1, starting with the corresponding ketone ester.

| Example No | Systematic Name | $^1$H NMR (300 MHz, CDCl$_3$) δ ppm | HRMS (ESI+, (M + Na)$^+$) | Structure |
|---|---|---|---|---|
| 17-2 | {4-[Difluoro-(4-methanesulfonyl-phenyl)-methyl]-6-fluoro-naphthalen-2-yl}-acetic acid | 8.02(d, J = 8.5 Hz, 2 H), 7.91(s, 1 H), 7.85-7.90(m, 1 H), 7.70-7.80(m, 3 H), 7.51(d, J = 11.2 Hz, 1 H), 7.28-7.35(m, 1 H), 3.88(s, 2 H), 3.09 (s, 3 H) | 431.0535 | 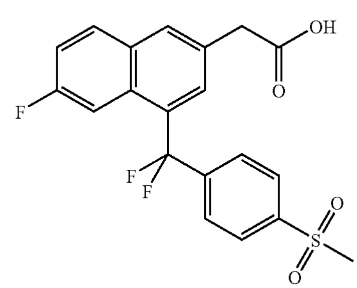 |

-continued

| Example No | Systematic Name | $^1$H NMR (300 MHz, CDCl$_3$) δ ppm | HRMS (ESI+, (M + Na)$^+$) | Structure |
|---|---|---|---|---|
| 17-3 | {4-[(4-Ethanesulfonyl-phenyl)-difluoro-methyl]-6-fluoro-naphthalen-2-yl}-acetic acid | 7.97(d, J = 8.5 Hz, 2 H) 7.90(s, 1 H) 7.83-7.89(m, 1 H) 7.66-7.78(m, 4 H) 7.49(d, J = 10.9 Hz, 1 H) 7.27-7.33(m, 1 H) 3.87 (s, 2 H) 3.14(q, J = 7.4 Hz, 2 H) 1.29 (t, J = 7.4 Hz, 3 H) | 445.0692 | 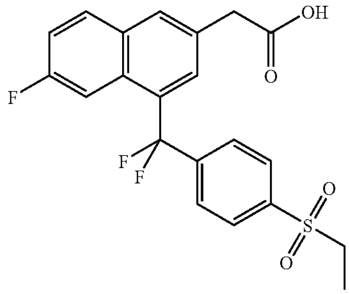 |

Example 18-1

{6-Fluoro-4-[(4-methanesulfonyl-phenyl)-methoxy-methyl]-naphthalen-2-yl}-acetic acid

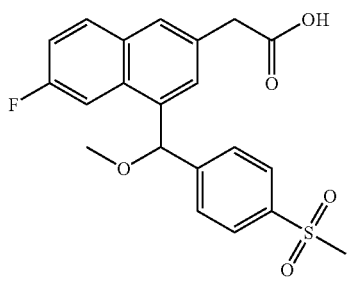

{6-Fluoro-4-[hydroxy-(4-methanesulfonyl-phenyl)-methyl]-naphthalen-2-yl}-acetic acid methyl ester

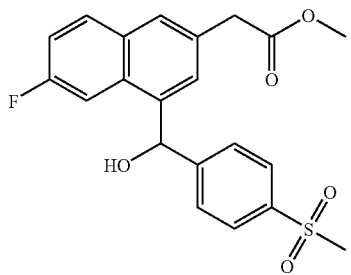

To a solution of [6-fluoro-4-(4-methanesulfonyl-benzoyl)-naphthalen-2-yl]-acetic acid methyl ester (103.5 mg, 0.26 mmol) (example 2-1, 4$^{th}$ step) in methanol (3 mL) was added sodium borohydride (30 mg, 0.78 mmol) at room temperature. The reaction mixture was stirred at room temperature overnight, and then partitioned between ethyl acetate and water. The collected organic layer was dried over magnesium sulfate, filtered, and concentrated in vacuo. Flash chromatography (RediSep® Flash column, 230-400 mesh, 0-40% ethyl acetate in hexane) gave {6-fluoro-4-[hydroxy-(4-methane-sulfonyl-phenyl)-methyl]-naphthalen-2-yl}-acetic acid methyl ester (90 mg, 86%) as a yellow oil. MS (ESI+) cald. for C$_{21}$H$_{19}$FO$_5$S 402 [(M+H)$^+$], obsd. 403.

{6-Fluoro-4-[(4-methanesulfonyl-phenyl)-methoxy-methyl]-naphthalen-2-yl}-acetic acid methyl ester

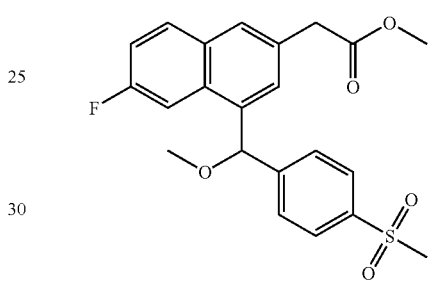

To a solution of {6-fluoro-4-[hydroxy-(4-methanesulfo-nyl-phenyl)-methyl]-naphthalen-2-yl}-acetic acid methyl ester (90 mg, 0.23 mmol) in methanol (5 mL) was added 3 drops of concentrated sulfuric acid. The mixture was heated at reflux overnight. After cooling to room temperature, the reaction mixture was partitioned between ethyl acetate and water. The collected organic layer was dried over sodium sulfate, filtered, and concentrated in vacuo. Flash chromatography (RediSep® Flash column, 230-400 mesh, 0-40% ethyl acetate in hexane) gave {6-fluoro-4-[(4-methanesulfonyl-phenyl)-methoxy-methyl]-naphthalen-2-yl}-acetic acid methyl ester (37.6 mg, 39%) as a clear oil. MS (ESI+) cald. for C$_{22}$H$_{21}$FO$_5$S [(M+H)$^+$] 416, obsd. 417.

{6-Fluoro-4-[(4-methanesulfonyl-phenyl)-methoxy-methyl]-naphthalen-2-yl}-acetic acid

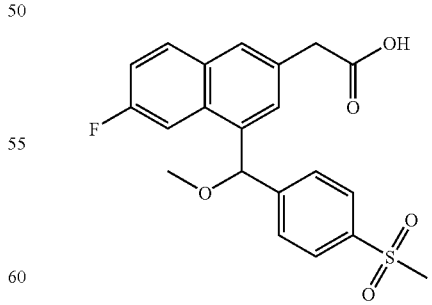

Starting with {6-fluoro-4-[(4-methanesulfonyl-phenyl)-methoxy-methyl]-naphthalen-2-yl}-acetic acid methyl ester, and using the method analogous to the one described for example 2-1, final step, 6-fluoro-4-[(4-methanesulfonyl-phe-nyl)-methoxy-methyl]-naphthalen-2-yl}-acetic acid (36 mg, 99%) was obtained as a white solid. $^1$H NMR (300 MHz, CDCl₃) δ ppm: 7.78-7.93 (m, 3 H), 7.75 (br. s, 1 H), 7.50-7.68 (m, 4 H), 7.16-7.31 (m, 1 H), 5.80 (s, 1 H), 3.84 (s, 2 H), 3.45 (s, 3 H), 3.02 (s, 3 H); HRMS (ESI+) cald. for $C_{21}H_{19}FO_5S$ [(M+Na)⁺] 425.0829, obsd. 425.0827.

Example 19-1

{6-Fluoro-4-[hydroxy-(4-methanesulfonyl-phenyl)-methyl]-3-methyl-naphthalen-2-yl}-acetic acid

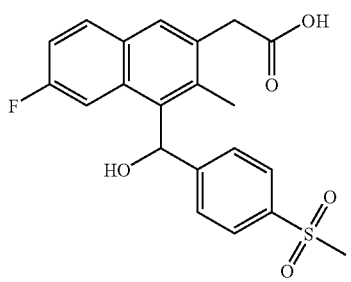

A solution of [6-fluoro-4-(4-methanesulfonyl-benzoyl)-3-methyl-naphthalen-2-yl]-acetic acid (60 mg, 0.15 mmol) (example 6-1) in methanol (12 mL) was hydrogenated using a H-cube hydrogenation reactor with a flow rate of 1.7 mL/min and a 10% palladium on carbon catalyst cartridge at 20° C. under 10 bar hydrogen pressure. The reaction mixture was concentrated in vacuo. The crude product was purified using flash chromatography (RediSep® Flash column, 230-400 mesh, 2%-5% methanol in dichloromethane) to give 11 mg (18%) of {6-fluoro-4-[hydroxy-(4-methanesulfonyl-phenyl)-methyl]-3-methyl-naphthalen-2-yl}-acetic acid as an oil. ¹H NMR (300 MHz, CDCl₃) δ ppm: 7.82 (d, J=8.2 Hz, 2 H), 7.74 (dd, J=9.1, 6.0 Hz, 1 H), 7.61-7.70 (m, 2 H), 7.49 (d, J=8.2 Hz, 2 H), 7.15 (td, J=8.3, 2.1 Hz, 1 H), 6.73 (s, 1 H), 3.86 (br. s, 1 H), 3.48 (s, 2 H), 3.01 (s, 3 H), 2.41 (br. s, 3 H); HRMS (ESI+) cald. for $C_{21}H_{19}FO_5S$ [(M+Na)] 425.0829, obsd. 425.0827.

Example 19-2

The following example 19-2 was prepared in an analogous manner to example 19-1, starting with the corresponding ketone derivative.

Example 20-1

{6-Fluoro-4-[hydroxy-(4-methylsulfamoyl-phenyl)-methyl]-naphthalen-2-yl}-acetic acid

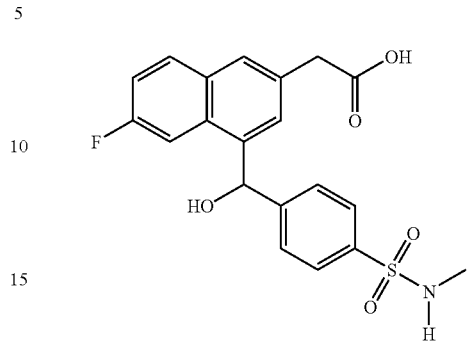

{6-Fluoro-4-[hydroxy-(4-methylsulfamoyl-phenyl)-methyl]-naphthalen-2-yl}-acetic acid methyl ester

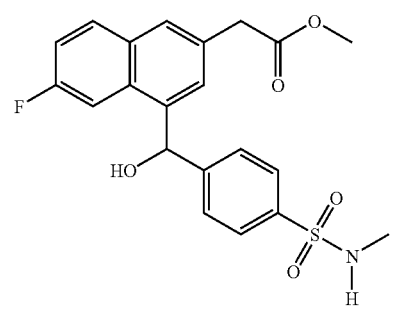

A solution of [6-fluoro-4-(4-methylsulfamoyl-benzoyl)-naphthalen-2-yl]-acetic acid methyl ester (prepared in an analogous manner to example 2-1) in methanol (20 mL) was hydrogenated using a H-cube hydrogenation reactor with a flow rate of 1 mL/min and a 10% palladium on carbon catalyst cartridge at 30° C. under 10 bar hydrogen pressure. The reaction gave a mixture of alcohol {6-fluoro-4-[hydroxy-(4-methylsulfamoyl-phenyl)-methyl]-naphthalen-2-yl}-acetic acid methyl ester and the corresponding fully hydrogenated product [6-fluoro-4-(4-methylsulfamoyl-benzyl)-naphthalen-2-yl]acetic acid methyl ester. Reverse-phase preparative

| Example No | Systematic Name | ¹H NMR (300 MHz, DMSO-d₆) δ ppm | HRMS (ESI+, (M + H)⁺) | Structure |
|---|---|---|---|---|
| 19-2 | (6-Fluoro-4-{hydroxy-[4-(morpholine-4-sulfonyl)-phenyl]-methyl}-naphthalen-2-yl)-acetic acid | 12.40(br. s, 1 H), 7.97 (dd, J = 8.9, 6.3 Hz, 1 H), 7.77(br. s, 1 H), 7.74-7.87(m, 1 H), 7.66(s, 4 H), 7.62(br. s, 1 H), 7.37(td, J = 8.9, 2.3 Hz, 1 H), 6.34-6.49(m, 2 H), 3.73 (s, 2 H), 3.49-3.62 (m ,4 H), 2.78(br. s, 4 H) | 460.1224 | 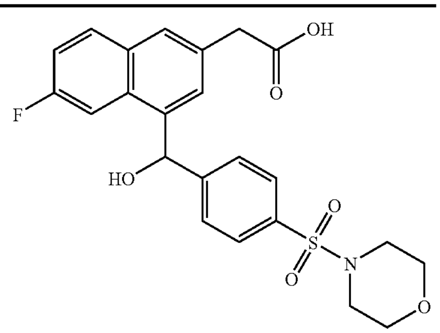 |

HPLC (using a Waters® Delta-Prep™ 3000 with a Varian Pursuit® C-18 column [10 μm, 20×150 mm]) was used to separate these products, giving {6-fluoro-4-[hydroxy-(4-methylsulfamoyl-phenyl)-methyl]-naphthalen-2-yl}-acetic acid methyl ester (4.0 mg) as 3.0 mg of a white solid. MS cald. for $C_{21}H_{20}FNO_5S$ [(M−H)⁻] 417, obsd. 416.

{6-Fluoro-4-[hydroxy-(4-methylsulfamoyl-phenyl)-methyl]-naphthalen-2-yl}-acetic acid

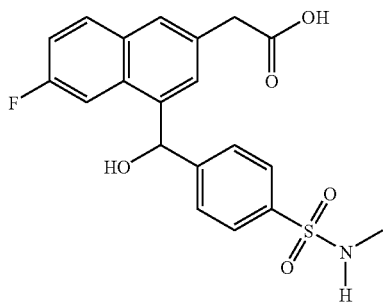

Starting with {6-fluoro-4-[hydroxy-(4-methylsulfamoyl-phenyl)-methyl]-naphthalen-2-yl}-acetic acid methyl ester (3.0 mg, 0.007 mmol), using a method analogous to the one described for example 2-1, final step, {6-fluoro-4-[hydroxy-(4-methylsulfamoyl-phenyl)-methyl]-naphthalen-2-yl}-acetic acid (4.5 mg, 100%) was obtained as a yellow oil. ¹H NMR (300 MHz, CDCl₃) δ ppm 7.72-7.79 (m, 1 H), 7.71 (d, J=8.6 Hz, 2 H), 7.63 (s, 1 H), 7.55 (dd, J=11.5, 2.1 Hz, 1 H), 7.50 (d, J=8.6 Hz, 2 H), 7.48 (br. s, 1 H), 7.16 (td, J=8.6, 2.1 Hz, 1 H), 6.31 (s, 1 H), 3.70 (s, 2 H), 2.51 (s, 3 H); HRMS (ESI+) cald. for $C_{20}H_{18}FNO_5S$ [(M+Na)⁺] 426.0782, obsd. 426.0779.

Activity and Use of the Compounds

The compounds of formula I possess valuable pharmacological properties. It has been found that said compounds are antagonists or partial agonists at the CRTH2 receptor and may be useful in treating diseases and disorders associated with that receptor such as asthma. The activity of the present compounds as CRTH2 receptor antagonists or partial agonists is demonstrated by the following biological assays.

Human CRTH2 Receptor Binding Assay

A whole cell receptor binding assay using [³H]ramatroban as the competing radioactive ligand was employed to evaluate the compound binding activity to human CRTH2. The radioactive ligand [³H]ramatroban was synthesized according to Sugimoto et. al. (*Eur. J. Pharmacol.* 524, 30-37, 2005) to a specific activity of 42 Ci/mmol.

A cell line stably expressing human CRTH2 was established by transfecting CHO-K1 cells with two mammalian expression vectors that harbored human CRTH2 and G-alpha16 cDNAs, respectively, using FuGene® 6 transfection reagent (from Roche). Stable clones expressing CRTH2 were selected by staining each clone with BM16 (BD Pharmingen™ from BD Biosciences, a division of Becton, Dickinson and Company), which is a rat monoclonal antibody to human CRTH2. The cells were maintained as monolayer cultures in Ham's F-12 medium containing 10% fetal bovine serum, 100 units/mL penicillin, 100 μg/mL streptomycin, 2 mM glutamine, 0.5 mg/mL G418 (geneticin) for CRTH2, and 0.2 mg/mL hygromycin-B (for G-alpha 16). For whole cell receptor binding assay, the monolayer cells were rinsed once with PBS (phosphate buffered saline), dissociated using ethylenediaminetetraacetate (Versene™ EDTA from Lonza Inc.), and suspended in PBS containing 10 mM $MgCl_2$ and 0.06% BSA (bovine serum albumin) at $1.5×10^6$ cells/mL.

The binding reactions (0.2 mL) were performed in 96-well plates at room temperature in PBS containing $1.5×10^5$ cells, 10 mM $MgCl_2$, 0.06% BSA, 20 nM [³H]ramatroban, and test compound at various concentrations. After 1 hour of binding reactions, the cells were harvested on GF™/B filter microplates (microtiter plates with embedded glass fiber from Perkin Elmer, Inc.) and washed 5 times with PBS using a Filtermate™ Harvester (a cell harvester that harvests and washes cells from microplates from PerkinElmer, Inc.). The radioactivities bound to the cells were determined using a microplate scintillation counter (TopCount® NXT, from PerkinElmer, Inc.) after adding 50 μL of Microscint™ 20 scintillation fluid (from PerkinElmer, Inc.) to each well of the filter plates. The radioactivity from non-specific binding was determined by replacing compound with 10 μM of 15(R)-15-methyl $PGD_2$ (from Cayman Chemical Company) in the reaction mixtures. The radioactivity bound to the cells in the absence of compound (total binding) was determined by replacing compound with 0.25% of DMSO (dimethyl sulfoxide) in the reaction mixture. Specific binding data were obtained by subtracting the radioactivity of non-specific binding from each binding data.

The $IC_{50}$ value is defined as the concentration of the tested compound that is required for 50% inhibition of total specific binding. In order to calculate the $IC_{50}$ value, the percent inhibition data were determined for 7 concentrations for each compound. The percent inhibition for a compound at each concentration was calculated according to the following formula, [1-(specific binding in the presence of compound)/(total specific binding)]×100. The $IC_{50}$ value was then obtained by fitting the percent inhibition data to a sigmoidal dose-response (4 parameter logistic) model in the XLfit® software Excel add-in program [from ID Business Solutions Ltd., model 205, where $F(x)=(A+(B-A)/(1+((C/x)^D)))$].

The compounds of the foregoing examples (as listed in the following table) were tested using the above Human CRTH2 Receptor Binding Assay. The results of the assay showed that all of these compounds have binding activity exhibiting $IC_{50}$ values ranging from 0.0021 μM to 0.3859 μM as indicated below:

| Example No. | Human CRTH2 Binding $IC_{50}$ (μM) |
|---|---|
| Example 1-1 | 0.0178 |
| Example 1-2 | 0.0402 |
| Example 1-3 | 0.3357 |
| Example 1-4 | 0.0112 |
| Example 1-5 | 0.0062 |
| Example 2-1 | 0.0043 |
| Example 2-2 | 0.0264 |
| Example 2-3 | 0.0170 |
| Example 2-4 | 0.0406 |
| Example 2-5 | 0.0151 |
| Example 2-6 | 0.0155 |
| Example 2-7 | 0.2640 |
| Example 2-8 | 0.0085 |
| Example 2-9 | 0.1994 |
| Example 2-10 | 0.0448 |
| Example 2-11 | 0.1353 |
| Example 2-12 | 0.1525 |
| Example 2-13 | 0.0030 |

-continued

| Example No. | Human CRTH2 Binding IC$_{50}$ (μM) |
|---|---|
| Example 2-14 | 0.0027 |
| Example 2-15 | 0.0033 |
| Example 2-16 | 0.0033 |
| Example 2-17 | 0.0145 |
| Example 2-18 | 0.0042 |
| Example 2-19 | 0.0023 |
| Example 2-20 | 0.0179 |
| Example 2-21 | 0.0038 |
| Example 2-22 | 0.0025 |
| Example 2-23 | 0.0037 |
| Example 2-24 | 0.0069 |
| Example 2-25 | 0.0089 |
| Example 2-26 | 0.007 |
| Example 2-27 | 0.0064 |
| Example 2-28 | 0.0213 |
| Example 2-29 | 0.0075 |
| Example 2-30 | 0.0825 |
| Example 2-31 | 0.1031 |
| Example 2-32 | 0.2719 |
| Example 4-1 | 0.0083 |
| Example 4-2 | 0.0267 |
| Example 6-1 | 0.0021 |
| Example 6-2 | 0.0037 |
| Example 6-3 | 0.0024 |
| Example 7-1 | 0.0533 |
| Example 8-1 | 0.0878 |
| Example 8-2 | 0.0153 |
| Example 8-3 | 0.1625 |
| Example 8-4 | 0.0061 |
| Example 8-5 | 0.0053 |
| Example 8-6 | 0.0054 |
| Example 8-7 | 0.0054 |
| Example 8-8 | 0.0060 |
| Example 8-9 | 0.0043 |
| Example 9-1 | 0.0032 |
| Example 10-1 | 0.0039 |
| Example 10-2 | 0.0540 |
| Example 10-3 | 0.0032 |
| Example 10-4 | 0.024 |
| Example 10-5 | 0.0124 |
| Example 10-6 | 0.0267 |
| Example 10-7 | 0.0067 |
| Example 10-8 | 0.005 |
| Example 10-9 | 0.0599 |
| Example 10-10 | 0.0325 |
| Example 10-11 | 0.0035 |
| Example 10-12 | 0.010 |
| Example 11-1 | 0.0030 |
| Example 11-2 | 0.0680 |
| Example 11-3 | 0.0027 |
| Example 12-1 | 0.0056 |
| Example 12-2 | 0.0102 |
| Example 13-1 | 0.0031 |
| Example 14-1 | 0.0054 |
| Example 15-1 | 0.0601 |
| Example 15-2 | 0.0838 |
| Example 15-3 | 0.0328 |
| Example 15-4 | 0.0793 |
| Example 15-5 | 0.0276 |
| Example 16-1 | 0.0161 |
| Example 16-2 | 0.3859 |
| Example 16-3 | 0.0159 |
| Example 16-4 | 0.0319 |
| Example 16-5 | 0.0080 |
| Example 16-6 | 0.0352 |
| Example 16-7 | 0.0174 |
| Example 16-8 | 0.0189 |
| Example 17-1 | 0.0057 |
| Example 17-2 | 0.0031 |
| Example 17-3 | 0.0039 |
| Example 18-1 | 0.0404 |
| Example 19-1 | 0.0118 |
| Example 19-2 | 0.0095 |
| Example 20-1 | 0.0221 |

Calcium Flux Assay Using FLuorometric Imaging Plate Reader (FLIPR)

Cell Culture Conditions:

CHO-K1 cells previously transfected with G-alpha 16 were subsequently transfected with the human CRTH2 receptor and the neomycin resistance gene. Following selection in 800 μg/mL G418 (geneticin), individual clones were assayed for their receptor expression based on staining with an anti human CRTH2 IgG, followed by assaying for their response to 13,14-dihydro-15-keto Prostaglandin D$_2$ (DK-PDG$_2$) (ligand) in the Ca$^{2+}$Flux assay. Positive clones were then cloned by limiting dilution cloning. The transfected cells were cultured in Ham's F-12 medium supplemented with 10% fetal bovine serum, 2 mM glutamine, 100 U/mL penicillin/100 μg/mL streptomycin, 200 μg/mL hygromycin B, and 800 μg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to 2.5×10$^5$ cells /mL with complete growth media. Aliquots of 50 μL were dispensed into BD Falcon™ 384 well black/clear microplates (from BD Biosciences, a division of Becton, Dickinson and Company) and the microplates were placed in a 37° C. CO$_2$ incubator overnight. The following day, the microplates were used in the assay.

Dye Loading and Assay:

Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 μL of Hank's Balanced Salt Solution (HBSS) containing 20 mM HEPES, 0.05% BSA and 2.5 mM probenecid was added to each well followed by 25 μL of diluted dye using a Multidrop dispenser. The plates were then incubated for 1 hour at 37° C.

During the incubation, test compound plates were prepared by adding 90 μL of HBSS/20 mM HEPES/0.005% BSA buffer to the 2 μL of serial diluted compounds. To prepare serial diluted compounds, 20 mM stocks of compounds were dissolved in 100% DMSO. The compound dilution plate was set up as follows: well #1 received 5 μL of compound plus 10 μL of DMSO. Wells 2-10 received 10 μL of DMSO. 5 μL was mixed and transferred from well #1 into well #2. 1:3 serial dilutions were continued out 10 steps. 2 μL of diluted compound was transferred into duplicate wells of a 384 well "assay plate" and then 90 μL of buffer was added.

After incubation, both the cell and "assay plate" plates were brought to the fluorometric imaging plate reader (FLIPR®) and 20 μL of the diluted compounds were transferred to the cell plates by the FLIPR®. Plates were then incubated for 1 hour at room temperature. After the 1 hour incubation, plates were returned to the FLIPR® and 20 μL of 4.5× concentrated ligand was added to the cell plates. During the assay, fluorescence readings were taken simultaneously from all 384 wells of the cell plate every 1.5 seconds. Five readings were taken to establish a stable baseline, then 20 μL of sample was rapidly (30 μL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^\wedge D)))$].

Specific representative compounds tested in the binding assay were tested using the above FLIPR® assay (examples 1-1 to 1-5, 2-1 to 2-25, 2-27 to 2-30, 6-1 to 6-3, 7-1, 8-1, 8-3 to 8-8, 9-1, 10-1, 10-3 to 10-11, 11-2, 12-1, 13-1, 14-1, 15-1, 16-1, 16-3 to 16-7, 17-1, 7-3, 18-1, 19-1, 19-2, 20-1). The results of the FLIPR assay showed that, with the exception of examples 1-2, 1-3, 2-7, 2-9, 2-11, 2-12, 2-30, and 7-1 (which exhibited $IC_{50}$ values of greater than 3), all of the representative compounds tested in this assay exhibit $IC_{50}$ values ranging from 0.0001 µM to 2.1405 µM.

DK-PGD₂-Induced IL-13 Production Assay in Th2 Cells

Inhibition of 13,14-dihydro-15-keto Prostaglandin $D_2$ ($DK-PGD_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by $CD4^+$ cell purification using a $CD4^+$ T Cell Isolation Kit II (from Miltenyi Biotec Inc.). The $CD4^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to phycoerythrin (PE).

To determine cellular inhibitory potency, compounds at various concentrations were incubated with $2.5 \times 10^4$ Th2 cells and 500 nM $DK-PGD_2$ for 4 hrs at 37° C. in 200 µL of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and $IC_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The $IC_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where $F(x)=(A+(B-A)/(1+((C/x)^\wedge D)))$].

Representative compounds tested in the binding assay were tested using the foregoing $DK-PGD_2$-induced IL-13 production assay (examples 1-1, 1-4, 1-5, 2-1 to 2-3, 2-5, 2-8, 2-13 to 2-29, 6-1 to 6-3, 8-1 to 8-9, 9-1, 10-1, 11-1, 16-1 to 16-6, 17-1 to 17-3, 18-1, 19-1, 19-2). The results of the $DK-PGD_2$-induced IL-13 production assay showed that, with the exception of examples 2-29, 16-2 and 8-3 (which exhibited $IC_{50}$ values of 3.001 µM, 5.7465 µM and greater than 10 µM, respectively), representative compounds tested in this assay exhibited activity in inhibiting IL-13 production, with $IC_{50}$ values ranging from 0.0006 µM to 2.4637 µM.

Thus, the compounds of the present invention are useful since the compounds tested show some activity in at least one of the above three assays (i.e., binding at the CRTH2 receptor), and therefore may be useful as antagonists or partial agonists in treating diseases and disorders associated with this receptor such as asthma.

In one embodiment, the present invention relates to a method for the treatment and/or prevention of diseases and disorders which are associated with the modulation of CRTH2 receptors, which method comprises administering a therapeutically effective amount of a compound of formula I to a human being or animal. A method for the treatment and/or prevention of an inflammatory or allergic disease or disorder is preferred. Such diseases or disorders may include (but are not limited to) asthma, chronic obstructive pulmonary disease (COPD), allergic rhinitis, allergic inflammation, and atopic dermatitis.

The present invention is also directed to the administration of a therapeutically effective amount of a compound of formula I in combination or association with other drugs or active agents for the treatment of inflammatory or allergic diseases and disorders. In one embodiment, the present invention relates to a method for the treatment and/or prevention of such diseases or disorders comprising administering to a human or animal simultaneously, sequentially, or separately, a therapeutically effective amount of a compound of formula I and another drug or active agent (such as another anti-inflammatory or anti-allergic drug or agent). These other drugs or active agents may have the same, similar, or a completely different mode of action. Suitable other drugs or active agents may include, but are not limited to: Beta2-adrenergic agonists such as albuterol or salmeterol; corticosteroids such as dexamethasone or fluticasone; antihistamines such as loratidine; leukotriene antagonists such as montelukast or zafirlukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and pimecrolimus; other antagonists of PGD2 acting at other receptors such as DP antagonists; inhibitors of phosphodiesterase type 4 such as cilomilast; drugs that modulate cytokine production such as inhibitors of TNF-alpha converting enzyme (TACE); drugs that modulate the activity of Th2 cytokines IL-4 and IL-5 such as blocking monoclonal antibodies and soluble receptors; PPAR-gamma agonists such as rosiglitazone; and 5-lipoxygenase inhibitors such as zileuton.

Unless stated to the contrary, all compounds in the examples were prepared and characterized as described. All patents and publications cited herein are hereby incorporated by reference in their entirety.

The invention claimed is:
1. A compound of formula I:

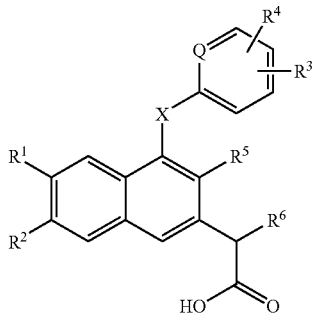

or a pharmaceutically acceptable salt or ester thereof, wherein:
Q is C(H) or N;
X is selected from the group consisting of:
  (1) C(O),
  (2) C(H)(H),
  (3) C(H)(OH),
  (4) C(F)(F),
  (5) C(H)(O—$CH_3$), and
  (6) C(H)($CH_3$);
$R^1$ and $R^2$, independently of each other, are selected from the group consisting of:
  (1) hydrogen,
  (2) halogen,
  (3) lower alkyl, optionally substituted by halogen, and
  (4) lower alkoxy,
or alternatively, $R^1$ and $R^2$ are bonded together to form methylenedioxy;
$R^3$ is selected from the group consisting of:
  (1) hydrogen,
  (2) halogen,
  (3) lower alkyl, optionally substituted by halogen,
  (4) lower alkoxy, and
  (5) cyano;
$R^4$ is
  $S(O)_2$—$R^7$ wherein $R^7$ is selected from the group consisting of:
    (a) lower alkyl optionally substituted by halogen or phenyl,
    (b) amino,
    (c) lower alkylamino,
    (d) lower dialkylamino,
    (e) acetylamino,
    (f) N-acetyl-N-lower alkylamino,
    (g) lower heterocycloalkyl optionally substituted by a substituent selected from the group consisting of:
      (i) lower alkyl,
      (ii) phenyl optionally substituted by halogen, and
      (iii) lower alkoxycarbonyl; and
    (h) phenyl or benzyl, wherein said phenyl or benzyl is optionally substituted by halogen or trifluoromethyl; and
$R^5$ and $R^6$, independently of each other, are hydrogen or methyl.
2. A compound of claim 1 wherein X is C(H)(H).
3. A compound of claim 1 wherein X is C(F)(F).
4. A compound of claim 1 wherein X is C(H)(OH).
5. A compound of claim 1 wherein X is C(O).
6. A compound of claim 1 wherein $R^1$ and $R^2$, independently of each other, are selected from the group consisting of:
  (1) hydrogen,
  (2) fluoro,
  (3) methyl,
  (4) chloro,
  (5) trifluoromethyl, and
  (6) methoxy.
7. A compound of claim 1 wherein $R^1$ or $R^2$ is hydrogen.
8. A compound of formula I:

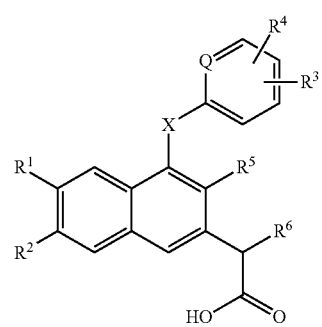

or a pharmaceutically acceptable salt or ester thereof, wherein:
Q is C(H) or N;
X is selected from the group consisting of:
  (1) C(O),
  (2) C(H)(H),
  (3) C(H)(OH),
  (4) C(F)(F),
  (5) C(H)(O—$CH_3$), and
  (6) C(H)($CH_3$);
one of $R^1$ or $R^2$ is fluoro and the other is selected from the group consisting of:
  (1) hydrogen,
  (2) halogen,
  (3) lower alkyl, optionally substituted by halogen, and
  (4) lower alkoxy;
$R^3$ is selected from the group consisting of:
  (1) hydrogen,
  (2) halogen,
  (3) lower alkyl, optionally substituted by halogen,
  (4) lower alkoxy, and
  (5) cyano;
$R^4$ is selected from the group consisting of:
  (1) halogen,
  (2) lower alkyl optionally substituted by halogen,
  (3) lower cycloalkyl,
  (4) lower alkoxy optionally substituted by halogen,
  (5) lower alkoxycarbonyl,
  (6) benzyloxy or benzylsulfanyl,
  (7) heteroaryl optionally substituted by lower alkyl,
  (8) cyano,
  (9) phenyl optionally substituted by methanesulfonyl,
  (10) lower alkanesulfonylmethyl, and
  (11) $S(O)_2$—$R^7$ wherein $R^7$ is selected from the group consisting of:
    (a) lower alkyl optionally substituted by halogen or phenyl,
    (b) amino,
    (c) lower alkylamino, (d) lower dialkylamino,
(e) acetylamino,
(f) N-acetyl-N-lower alkylamino,
(g) lower heterocycloalkyl optionally substituted by a substituent selected from the group consisting of:
  (i) lower alkyl,
  (ii) phenyl optionally substituted by halogen, and
  (iii) lower alkoxycarbonyl; and
(h) phenyl or benzyl, wherein said phenyl or benzyl is optionally substituted by halogen or trifluoromethyl; and $R^5$ and $R^6$, independently of each other, are hydrogen or methyl.

9. A compound of claim 1 wherein $R^3$ is selected from the group consisting of:
(1) hydrogen,
(2) halogen,
(3) lower alkyl, optionally substituted by halogen, and
(4) cyano.

10. A compound of claim 1 wherein $R^3$ is hydrogen, fluoro, or chloro.

11. A compound of claim 1 wherein $R^3$ is methyl or ethyl.

12. A compound of claim 1 $R^7$ is selected from the group consisting of:
(1) lower alkyl,
(2) trifluoromethyl,
(3) benzyl,
(4) amino,
(5) methylamino or ethylamino,
(6) dimethylamino or diethylamino,
(7) morpholin-4-yl,
(8) piperidin-1-yl,
(9) piperazin-1-yl,
(10) 4-methyl-piperazin-1-yl,
(11) 4-tert-butoxycarbonyl-piperazin-1-yl,
(12) 4-methoxycarbonyl-piperazin-1-yl or 4-ethoxycarbonyl-piperazin-1-yl,
(13) 4-(2-fluorophenyl)piperazin-1-yl,
(14) acetylamino or N-acetyl-N-methylamino, and
(15) phenyl substituted by halogen or trifluoromethyl.

13. A compound of claim 1 wherein $R^7$ is methyl or ethyl.

14. A compound of claim 1 wherein $R^5$ or $R^6$ is hydrogen.

15. A compound of claim 1 wherein $R^5$ or $R^6$ is methyl.

16. A compound of claim 1 wherein $R^3$ is bonded to position 2 (or position 6 if Q is C(H)) and $R^4$ is bonded to position 4 on the phenyl ring in formula I as indicated by the following numbered positions for the phenyl ring of formula I:

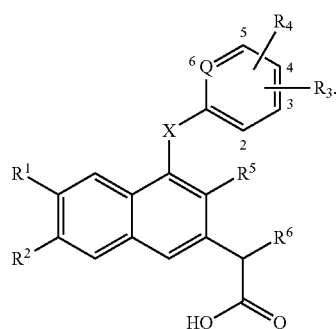

I

17. A compound of claim 1 selected from the group consisting of:

[4-(4-Dimethylsulfamoyl-benzoyl)-naphthalen-2-yl]-acetic acid;
[6-Fluoro-4-(4-sulfamoyl-benzoyl)-naphthalen-2-yl]-acetic acid;
[4-(4-Sulfamoyl-benzoyl)-naphthalen-2-yl]-acetic acid;
[4-(2-Chloro-4-ethanesulfonyl-benzoyl)-6-fluoro-naphthalen-2-yl]-acetic acid;
{4-[4-(3-Chloro-benzenesulfonyl)-benzoyl]-6-fluoro-naphthalen-2-yl}-acetic acid;
[6-Fluoro-4-(4-methanesulfonyl-benzoyl)-naphthalen-2-yl]-acetic acid;
[4-(4-Methanesulfonyl-benzoyl)-6-methoxy-naphthalen-2-yl]-acetic acid;
[7-Fluoro-4-(4-methanesulfonyl-benzoyl)-naphthalen-2-yl]-acetic acid;
[6-Fluoro-4-(4-methanesulfonyl-2-methyl-benzoyl)-naphthalen-2-yl]-acetic acid;
[6,7-Difluoro-4-(4-methanesulfonyl-benzoyl)-naphthalen-2-yl]-acetic acid;
[8-(4-Methanesulfonyl-benzoyl)-naphtho[2,3-d][1,3]dioxol-6-yl]-acetic acid;
[4-(2-Chloro-4-methanesulfonyl-benzoyl)-6-fluoro-naphthalen-2-yl]-acetic acid;
[4-(4-Methanesulfonyl-benzoyl)-7-methoxy-naphthalen-2-yl]-acetic acid;
[6-Fluoro-4-(3-methanesulfonyl-benzoyl)naphthalen-2-yl]-acetic acid;
[4-(3-Methanesulfonyl-benzoyl)naphthalen-2-yl]-acetic acid;
[8-(3-Methanesulfonyl-benzoyl)-naphtho[2,3-d][1,3]dioxol-6-yl]-acetic acid;
[4-(4-Ethanesulfonyl-benzoyl)-6-fluoro-naphthalen-2-yl]-acetic acid;
[4-(4-Dimethylsulfamoyl-benzoyl)-6-fluoro-naphthalen-2-yl]-acetic acid;
[6-Fluoro-4-(4-methylsulfamoyl-benzoyl)naphthalen-2-yl]-acetic acid;
{6-Fluoro-4-[4-(morpholine-4-sulfonyl)-benzoyl]-naphthalen-2-yl}-acetic acid;
[6-Fluoro-4-(2-fluoro-4-methanesulfonyl-benzoyl)-naphthalen-2-yl]-acetic acid;
[6-Fluoro-4-(4-methanesulfonyl-3-trifluoromethyl-benzoyl)-naphthalen-2-yl]-acetic acid;
[4-(3-Ethyl-4-methanesulfonyl-benzoyl)-6-fluoro-naphthalen-2-yl]-acetic acid;
[4-(4-Ethanesulfonyl-2-methyl-benzoyl)-6-fluoro-naphthalen-2-yl]-acetic acid;
{6-Fluoro-4-[4-(piperidine-1-sulfonyl)-benzoyl]-naphthalen-2-yl}-acetic acid;
[4-(4-Diethylsulfamoyl-benzoyl)-6-fluoro-naphthalen-2-yl]-acetic acid;
{6-Fluoro-4-[2-methyl-4-(morpholine-4-sulfonyl)-benzoyl]-naphthalen-2-yl}-acetic acid;
[4-(4-Dimethylsulfamoyl-2-methyl-benzoyl)-6-fluoro-naphthalen-2-yl]-acetic acid;
[6-Fluoro-4-(2-methyl-4-methylsulfamoyl-benzoyl)-naphthalen-2-yl]-acetic acid;
(6-Fluoro-4-{4-[4-(2-fluoro-phenyl)-piperazine-1-sulfonyl]-benzoyl}-naphthalen-2-yl)-acetic acid;
[6-Chloro-4-(4-methanesulfonyl-benzoyl)naphthalen-2-yl]-acetic acid;
[4-(4-Methanesulfonyl-benzoyl)-6-methyl-naphthalen-2-yl]-acetic acid;
[4-(4-Methanesulfonyl-benzoyl)-6-trifluoromethyl-naphthalen-2-yl]-acetic acid;
[6-Chloro-4-(3-methanesulfonyl-benzoyl)naphthalen-2-yl]-acetic acid;
[6-Fluoro-4-(4-fluoro-3-methanesulfonyl-benzoyl)-naphthalen-2-yl]-acetic acid;
[6-Fluoro-4-(4-methanesulfonyl-benzoyl)-3-methyl-naphthalen-2-yl]-acetic acid;

[6-Chloro-4-(4-methanesulfonyl-benzoyl)-3-methyl-naphthalen-2-yl]-acetic acid;
[4-(4-Ethanesulfonyl-benzoyl)-6-fluoro-3-methyl-naphthalen-2-yl]-acetic acid;
2-[6-Fluoro-4-(4-methanesulfonyl-benzoyl)-naphthalen-2-yl]-propionic acid;
[4-(4-Methanesulfonyl-benzyl)-6-methyl-naphthalen-2-yl]-acetic acid;
[4-(4-Methanesulfonyl-benzyl)-6-trifluoromethyl-naphthalen-2-yl]-acetic acid;
[4-(4-Methanesulfonyl-benzyl)-7-trifluoromethyl-naphthalen-2-yl]-acetic acid;
[6-Fluoro-4-(4-methanesulfonyl-benzyl)naphthalen-2-yl]-acetic acid;
[6-Fluoro-4-(4-methanesulfonyl-2-methyl-benzyl)-naphthalen-2-yl]-acetic acid;
[6-Fluoro-4-(4-methanesulfonyl-3-trifluoromethyl-benzyl)-naphthalen-2-yl]-acetic acid;
[4-(4-Ethanesulfonyl-2-methyl-benzyl)-6-fluoro-naphthalen-2-yl]-acetic acid;
[4-(4-Dimethylsulfamoyl-benzyl)-6-fluoro-naphthalen-2-yl]-acetic acid;
[4-(4-Ethanesulfonyl-benzyl)-6-fluoro-naphthalen-2-yl]-acetic acid;
[6-Fluoro-4-(4-methylsulfamoyl-benzyl)naphthalen-2-yl]-acetic acid;
[6-Fluoro-4-(4-methanesulfonyl-benzyl)-3-methyl-naphthalen-2-yl]-acetic acid;
[6-Fluoro-4-(3-methanesulfonyl-benzyl)-3-methyl-naphthalen-2-yl]-acetic acid;
[6-Fluoro-3-methyl-4-(4-trifluoromethanesulfonyl-benzyl)-naphthalen-2-yl]-acetic acid;
[6-Fluoro-3-methyl-4-(3-trifluoromethanesulfonyl-benzyl)-naphthalen-2-yl]-acetic acid;
[6-Fluoro-3-methyl-4-(4-phenylmethanesulfonyl-benzyl)-naphthalen-2-yl]-acetic acid;
[4-(4-Ethanesulfonyl-benzyl)-6-fluoro-3-methyl-naphthalen-2-yl]-acetic acid;
{4-[(2-Chloro-4-methanesulfonyl-phenyl)-hydroxy-methyl]-6-fluoro-naphthalen-2-yl}-acetic acid;
{4-[Hydroxy-(4-methanesulfonyl-phenyl)-methyl]-6-methyl-naphthalen-2-yl}-acetic acid;
{6-Chloro-4-[hydroxy-(4-methanesulfonyl-phenyl)-methyl]-naphthalen-2-yl}-acetic acid;
{6-Fluoro-4-[hydroxy-(4-methanesulfonyl-2-methyl-phenyl)-methyl]-naphthalen-2-yl}-acetic acid;
{6-Fluoro-4-[hydroxy-(4-methanesulfonyl-phenyl)-methyl]-naphthalen-2-yl}-acetic acid;
{4-[Hydroxy-(4-methanesulfonyl-phenyl)-methyl]-naphthalen-2-yl}-acetic acid;
{4-[(4-Ethanesulfonyl-phenyl)-hydroxy-methyl]-6-fluoro-naphthalen-2-yl}-acetic acid;
{4-[(4-Ethanesulfonyl-2-methyl-phenyl)-hydroxy-methyl]-6-fluoro-naphthalen-2-yl}-acetic acid;
{4-[(2-Chloro-4-methanesulfonyl-phenyl)-difluoro-methyl]-6-fluoro-naphthalen-2-yl}-acetic acid;
{4-[Difluoro-(4-methanesulfonyl-phenyl)-methyl]-6-fluoro-naphthalen-2-yl}-acetic acid;
{4-[(4-Ethanesulfonyl-phenyl)-difluoro-methyl]-6-fluoro-naphthalen-2-yl}-acetic acid;
{6-Fluoro-4-[(4-methanesulfonyl-phenyl)-methoxy-methyl]-naphthalen-2-yl}-acetic acid;
{6-Fluoro-4-[hydroxy-(4-methanesulfonyl-phenyl)-methyl]-3-methyl-naphthalen-2-yl}-acetic acid;
(6-Fluoro-4-{hydroxy-[4-(morpholine-4-sulfonyl)-phenyl]-methyl}-naphthalen-2-yl)-acetic acid;
{6-Fluoro-4-[hydroxy-(4-methylsulfamoyl-phenyl)-methyl]-naphthalen-2-yl}-acetic acid;
{6-Fluoro-4-[4-(piperazine-1-sulfonyl)-benzoyl]-naphthalen-2-yl}-acetic acid;
4-[4-(3-Carboxymethyl-7-fluoro-naphthalene-1-carbonyl)-benzenesulfonyl]-piperazine-1-carboxylic acid ethyl ester;
4-[4-(3-Carboxymethyl-7-fluoro-naphthalene-1-carbonyl)-benzenesulfonyl]-piperazine-1-carboxylic acid tert-butyl ester;
{6-Fluoro-4-[4-(4-methyl-piperazine-1-sulfonyl)-benzoyl]-naphthalen-2-yl}-acetic acid;
[4-(2-Benzenesulfonyl-benzyl)-6-fluoro-3-methyl-naphthalen-2-yl]-acetic acid;
[4-(4-Benzenesulfonyl-benzyl)-6-fluoro-3-methyl-naphthalen-2-yl]-acetic acid;
[6-Chloro-4-(4-methanesulfonyl-benzyl)-3-methyl-naphthalen-2-yl]-acetic acid;
[6-Chloro-4-(4-methanesulfonylmethyl-benzyl)-3-methyl-naphthalen-2-yl]-acetic acid; and
[4-(4-Methanesulfonyl-benzoyl)-7-trifluoromethyl-naphthalen-2-yl]-acetic acid.

18. A pharmaceutically acceptable salt of a compound of claim 17.

19. A pharmaceutically acceptable ester of a compound of claim 17.

20. A compound of claim 8 selected from the group consisting of:
[6-Fluoro-3-methyl-4-(4-pyrazol-1-yl-benzyl)-naphthalen-2-yl]-acetic acid;
{6-Fluoro-3-methyl-4-[3-(1-methyl-1H-tetrazol-5-yl)-benzyl]-naphthalen-2-yl}-acetic acid;
[4-(3-Cyano-benzyl)-6-Fluoro-3-methyl-naphthalen-2-yl]-acetic acid;
[4-(4-Cyano-benzyl)-6-Fluoro-3-methyl-naphthalen-2-yl]-acetic acid;
[6-Fluoro-3-methyl-4-(4-methyl-benzyl)-naphthalen-2-yl]-acetic acid;
[4-(4-Benzyloxy-benzyl)-6-fluoro-3-methyl-naphthalen-2-yl]-acetic acid;
[4-(4-Bromo-benzyl)-6-fluoro-3-methyl-naphthalen-2-yl]-acetic acid;
[4-(3-Chloro-benzyl)-6-fluoro-3-methyl-naphthalen-2-yl]-acetic acid;
[6-Fluoro-4-(4-fluoro-benzyl)-3-methyl-naphthalen-2-yl]-acetic acid;
[6-Fluoro-3-methyl-4-(4-trifluoromethoxy-benzyl)-naphthalen-2-yl]-acetic acid;
3-(3-Carboxymethyl-7-fluoro-2-methyl-naphthalen-1-ylmethyl)-benzoic acid methyl ester;
{6-Fluoro-3-methyl-4-[4-(1-methyl-1H-tetrazol-5-yl)-benzyl]-naphthalen-2-yl}-acetic acid;
[6-Fluoro-3-methyl-4-(4-pyrimidin-5-yl-benzyl)-naphthalen-2-yl]-acetic acid;
[6-Fluoro-4-(4'-methanesulfonyl-biphenyl-4-ylmethyl)-3-methyl-naphthalen-2-yl]-acetic acid; and
[4-(4-Benzylsulfanyl-benzyl)-6-fluoro-3-methyl-naphthalen-2-yl]-acetic acid.

21. A compound of claim 1 which is [6-fluoro-4-(4-methanesulfonyl-benzoyl)-3-methyl-naphthalen-2-yl]-acetic acid.

22. A compound of claim 1 which is [4-(3-ethyl-4-methanesulfonyl-benzoyl)-6-fluoro-naphthalen-2-yl]-acetic acid.

23. A compound of claim 1 which is [4-(4-dimethylsulfamoyl-benzoyl)-6-fluoro-naphthalen-2-yl]-acetic acid.

24. A compound of claim 1 which is [6-fluoro-4-(4-methanesulfonyl-2-methyl-benzoyl)-naphthalen-2-yl]-acetic acid.

25. A compound of claim 1 which is [6-fluoro-4-(4-methanesulfonyl-benzyl)-3-methyl-naphthalen-2-yl]-acetic acid.

26. A compound of claim 1 which is [6-fluoro-4-(4-methanesulfonyl-2-methyl-benzyl)-naphthalen-2-yl]-acetic acid.

27. A compound of claim 1 which is [4-(4-ethanesulfonyl-benzoyl)-6-fluoro-3-methyl-naphthalen-2-yl]-acetic acid.

28. A compound of claim 1 which is [6-fluoro-4-(4-methanesulfonyl-benzoyl)-naphthalen-2-yl]-acetic acid.

29. A compound of claim 1 which is [6-chloro-4-(4-methanesulfonyl-benzoyl)-3-methyl-naphthalen-2-yl]-acetic acid.

30. A compound of claim 1 which is [6-fluoro-4-(4-methanesulfonyl-benzyl)-naphthalen-2-yl]-acetic acid.

31. A compound of claim 1 which is {6-fluoro-4-[hydroxy-(4-methanesulfonyl-phenyl)-methyl]-3-methyl-naphthalen-2-yl}-acetic acid.

32. A compound of claim 1 which is [4-(4-ethanesulfonyl-benzyl)-6-fluoro-3-methyl-naphthalen-2-yl]-acetic acid.

\* \* \* \* \*

UNITED STATES PATENT AND TRADEMARK OFFICE
CERTIFICATE OF CORRECTION

PATENT NO. : 8,124,629 B2
APPLICATION NO. : 12/614478
DATED : February 28, 2012
INVENTOR(S) : Firooznia et al.

Page 1 of 1

It is certified that error appears in the above-identified patent and that said Letters Patent is hereby corrected as shown below:

Claim 12, column 183, line 22, delete "claim 1 $R^7$" and insert -- claim 1 wherein $R^7$ --

Signed and Sealed this
First Day of May, 2012

David J. Kappos
*Director of the United States Patent and Trademark Office*